(12) United States Patent
Thotapally et al.

(10) Patent No.: US 9,000,175 B2
(45) Date of Patent: Apr. 7, 2015

(54) BICYCLIC GPR119 MODULATORS

(75) Inventors: Rajesh Thotapally, Pune (IN); Onkar Gangaram Kachi, Pune (IN); Atish Harishchandra Rodge, Pune (IN); Ashok Bhau Pathak, Pune (IN); Bhavana Shrirang Kardile, Pune (IN); Milind Dattatraya Sindkhedkar, Pune (IN); Venkata P. Palle, Pune (IN); Rajender Kumar Kamboj, Pune (IN)

(73) Assignee: Lupin Limited, Mumbai, Maharashtra (IN)

( * ) Notice: Subject to any disclaimer, the term of this patent is extended or adjusted under 35 U.S.C. 154(b) by 0 days.

(21) Appl. No.: 13/989,611

(22) PCT Filed: Nov. 24, 2011

(86) PCT No.: PCT/IB2011/002814
§ 371 (c)(1),
(2), (4) Date: May 24, 2013

(87) PCT Pub. No.: WO2012/069917
PCT Pub. Date: May 31, 2012

(65) Prior Publication Data
US 2013/0245000 A1    Sep. 19, 2013

(30) Foreign Application Priority Data

Nov. 26, 2010  (IN) .............. 1335/KOL/2010
Apr. 14, 2011  (IN) .............. 539/KOL/2011

(51) Int. Cl.
| | |
|---|---|
| C07D 401/14 | (2006.01) |
| C07D 401/12 | (2006.01) |
| C07D 471/04 | (2006.01) |
| A61K 31/506 | (2006.01) |
| A61K 31/5377 | (2006.01) |
| A61K 31/454 | (2006.01) |
| A61K 31/437 | (2006.01) |
| A61K 31/4545 | (2006.01) |
| A61K 31/155 | (2006.01) |
| C07D 413/14 | (2006.01) |
| C07D 417/14 | (2006.01) |
| C07D 491/08 | (2006.01) |
| A61K 45/06 | (2006.01) |

(52) U.S. Cl.
CPC .......... *C07D 471/04* (2013.01); *C07D 401/12* (2013.01); *C07D 401/14* (2013.01); *C07D 413/14* (2013.01); *C07D 417/14* (2013.01); *C07D 491/08* (2013.01); *A61K 31/155* (2013.01); *A61K 31/437* (2013.01); *A61K 31/454* (2013.01); *A61K 31/4545* (2013.01); *A61K 31/506* (2013.01); *A61K 31/5377* (2013.01); *A61K 45/06* (2013.01)

(58) Field of Classification Search
USPC ......... 514/318; 546/201
See application file for complete search history.

(56) References Cited

U.S. PATENT DOCUMENTS

2010/0292259 A1 *  11/2010  Kaneko et al. ............ 514/269

FOREIGN PATENT DOCUMENTS

| | | |
|---|---|---|
| EP | 2 399 914 | 12/2011 |
| JP | 2011-136942 | 7/2011 |
| WO | WO 2004/065380 | 8/2004 |
| WO | WO 2004/076413 | 9/2004 |
| WO | WO 2005/007647 | 1/2005 |
| WO | WO 2005/121121 | 12/2005 |
| WO | WO 2006/070208 | 7/2006 |
| WO | WO 2006/076243 | 7/2006 |
| WO | WO 2006/083491 | 8/2006 |
| WO | WO 2007/035355 | 3/2007 |
| WO | WO 2007/116230 | 10/2007 |
| WO | WO 2007/120689 | 10/2007 |
| WO | WO 2008/005569 | 1/2008 |
| WO | WO 2008/005576 | 1/2008 |
| WO | WO 2008/025800 | 3/2008 |
| WO | WO 2008/054675 | 5/2008 |
| WO | WO 2008/070692 | 6/2008 |

(Continued)

OTHER PUBLICATIONS

Dorwald; "Side Reactions in Organic Synthesis: A Guide to Successful Synthesis Design" 2005 Wiley-VCH Verlag GmbH & Co. KGaA, Wienheim, chapter 1.*

(Continued)

*Primary Examiner* — John Mabry
*Assistant Examiner* — Daniel Carcanague
(74) *Attorney, Agent, or Firm* — Merchant & Gould P.C.

(57) ABSTRACT

The present invention relates to compounds of Formula (I) that are useful for treating, preventing and/or managing the diseases, disorders, syndromes or conditions associated with the modulation of GPR119 receptor activity. The invention also relates to the process for preparation of the compounds, pharmaceutical compositions thereof. The invention further relates to methods of treating, preventing and/or managing diseases, disorders syndromes or conditions associated with the modulation of GPR119 receptor by using either alone or in combinations of Formula (I).

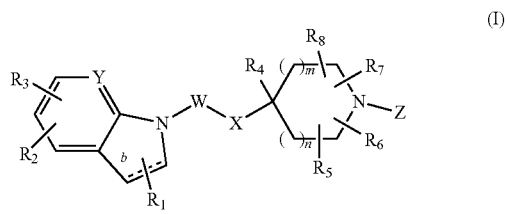

11 Claims, No Drawings

(56) References Cited

FOREIGN PATENT DOCUMENTS

| WO | WO 2009/050522 |   | 4/2009 |
|----|----------------|---|--------|
| WO | WO 2009/050523 |   | 4/2009 |
| WO | WO 2009/051119 |   | 4/2009 |
| WO | WO 2009/126245 |   | 10/2009 |
| WO | WO 2009/141238 |   | 11/2009 |
| WO | WO 2010/008739 |   | 1/2010 |
| WO | WO 2010009195  | * | 1/2010 |
| WO | WO 2010/075269 |   | 7/2010 |
| WO | WO 2010/075271 |   | 7/2010 |
| WO | WO 2010/095663 |   | 8/2010 |
| WO | WO 2010/119881 |   | 10/2010 |
| WO | WO 2010/128414 |   | 11/2010 |
| WO | WO 2010/128425 |   | 11/2010 |
| WO | WO 2010/149685 |   | 12/2010 |

OTHER PUBLICATIONS

Arbeeny et al., "The Metabolic Syndrome: From Pathophysiology to Novel Treatment Strategies", *Curr. Med. Chem.-Imm., Endoc. & Metab. Agents*, vol. 1, 2001, pp. 1-24.

Boonen et al., "Osteoporosis management: impact of fracture type on cost and quality of life in patients at risk for fracture I", *Current Medical Research and Opinion*, vol. 24, No. 6, 2008, pp. 1781-1788.

Chiasson et al., "The Efficacy of Acarbose in the Treatment of Patients with Non-Insulin-dependent Diabetes Mellitus", *Ann Intern Med*, vol. 121, 1994, pp. 928-935.

Cole et al., "Osteoporosis Epidemiology Update", *Current Rheumatology Reports*, vol. 10, 2008, pp. 92-96.

Coniff et al., "Multicenter, Placebo-Controlled Trial Comparing Acarbose (BAY g 5421) With Placebo, Tolbutamide, and Tolbutamide-Plus-Acarbose in Non-Insulin-Dependent Diabetes Mellitus", *The American Journal of Medicine*, vol. 98, 1995, pp. 443-451.

Coniff et al., "Acarbose: A Review of US Clinical Experience", *Clinical Therapeutics*, vol. 19, No. 1, 1997, pp. 16-26.

Cornicelli et al., "15-Lipoxygenase and Its Inhibition: A Novel Therapeutic Target for Vascular Disease", *Current Pharmaceutical Design*, vol. 5, 1999, pp. 11-20.

Ford et al., "Prevalence of the Metabolic Syndrome Among US Adults, Findings From the Third National Health and Nutrition Examination Survey", *J. Am. Med. Assoc.*, vol. 287, No. 3, 2002, pp. 356-359.

Steven M. Haffner, "Management of Dyslipidemia in Adults With Diabetes", *Diabetes Care*, vol. 21, No. 1, 1998, pp. 160-178.

Seijiro Hara, "Ileal $Na^+$/bile acid cotransporter inhibitors", *Drugs of the Future*, vol. 24, No. 4, 1999, pp. 425-430.

International Search Report and Written Opinion from International Application No. PCT/IB2011/002814 mailed May 2, 2012.

Iwamoto et al., "Effect of Combination Therapy of Troglitazone and Sulphonylureas in Patients with Type 2 Diabetes Who Were Poorly Controlled by Sulphonylurea Therapy Alone", *Diabetic Medicine*, vol. 13, 1996, pp. 365-370.

Jones et al., "GPR119 agonists for the treatment of type 2 diabetes", *Expert Opin. Ther. Patents*, vol. 19, No. 10, 2009, pp. 1339-1359.

Peter O. Kwiterovich, "State-of-the-Art Update and Review: Clinical Trials of Lipid-Lowering Agents", *The American Journal of Cardiology*, vol. 82, No. 12A, 1998, pp. 3U-17U.

Laakso et al., "Epidemiology of macrovascular disease in diabetes", *Diabetes Reviews*, vol. 5, No. 4, 1997.

Li et al., "The macrophage foam cell as a target for therapeutic intervention", *Nature Medicine*, vol. 8, No. 11, 2007, pp. 1235-1242.

Mahler et al., "Type 2 Diabetes Mellitus: Update on Diagnosis, Pathophysiology, and Treatment", *The Journal of Clinical Endocrinology & Metabolism*, vol. 84, No. 4, 1999, pp. 1165-1171.

Overton et al., "GPR119, a novel G protein-coupled receptor target for the treatment of type 2 diabetes and obesity", *British Journal of Pharmacology*, vol. 153, 2008, S76-S81.

Reginster et al., "Osteoporosis: A still increasing prevalence", *Bone*, vol. 38, 2006, S4-S9.

Ritter et al., "The voltage-gated sodium Nav1.9 is required for inflammation-based urinary bladder dysfunction", *Neuroscience Letters*, vol. 452, 2009, pp. 28-32.

Zaverio M. Ruggeri, "Platelets in atherothrombosis", *Nature Medicine*, vol. 8, No. 11, 2002, 1227-1234.

Sendobry et al., "Attenuation of diet-induced atherosclerosis in rabbits with a highly selective 15-lipoxygenase inhibitor lacking significant antioxidant properties", *British Journal of Pharmacology*, vol. 120, 1997, pp. 1199-1206.

Turner et al., "Insulin resistance, impaired glucose tolerance and non-insulin-dependent diabetes, pathologic mechanisms and treatment: Current status and therapeutic possibilities", *Progress in Drug Research*, vol. 51, 1998, pp. 33-94.

Who Scientific Group, "Prevention and Management of Osteoporosis", *Who Technical Report Series 921*, 2003.

Wright et al., "UKPDS 28: A Randomized Trial of Efficacy of Early Addition of Metformin in Sulfonylurea-Treated Type 2 Diabetes", *Diabetes Care*, vol. 21, No. 1, 1998, 87-92.

Bardin CW, *Current Therapy in Endocrinology and Metabolism*, Sixth Edition, Mosby-Year Book, Inc., St. Louis, MO, pp. 509-519.

Wuts et al., *Greene's Protective Groups in Organic Synthesis*, Fourth Edition, John Wiley & Sons, Inc., 2007 (in 4 parts).

* cited by examiner

BICYCLIC GPR119 MODULATORS

RELATED APPLICATIONS

This application is a National Stage Application of PCT/IB2011/002814, filed 24 Nov. 2011, which claims benefit of Indian patent applications No. 1335/KOL/2010, filed on Nov. 26, 2010 and 0539/KOL/2011, filed on Apr. 14 2011 and which applications are incorporated herein by reference. To the extent appropriate, a claim of priority is made to each of the above disclosed applications.

FIELD OF THE INVENTION

The invention relates to heterocyclic compounds and their stereoisomers or pharmaceutically acceptable salts thereof. The invention also relates to a process for the preparation of the compounds of invention. The invention also relates to methods of treating, preventing and/or managing diseases, disorders, syndromes or conditions associated with the modulation of the GPR119 receptor. The invention also relates to combination therapy for treating, preventing and/or managing diseases and disorders associated with the modulation of GPR119 receptors.

BACKGROUND OF THE INVENTION

Diabetes mellitus can be classified into two types: Type I (also referred to as insulin dependent diabetes mellitus) and Type II (also referred to as non-insulin dependent diabetes mellitus). Type I diabetes is an autoimmune disease wherein there is an extensive loss of the insulin producing β-cells of the pancreas. The resulting insulin deficiency leads to hyperglycemia (abnormally high glucose levels in the blood).

Type II diabetes mellitus develops as a result of non-responsiveness of muscle, fat and liver cells to insulin. This phenomenon is referred to as insulin resistance and could arise due to a reduced number of insulin receptors on the surface of these cells, or a defective insulin-mediated signaling, or a combination of both. Chronic Type II diabetes leads to pancreatic β-cell dysfunction. Surprisingly, there is no cure for diabetes. The current treatments focus on disease management, by controlling blood glucose levels and delaying complications that arise due to hyperglycemia. Treatments that target insulin resistance include metformin and TZDs (Thiazolidinediones), and those that stimulate insulin secretion, such as sulfonylureas and GLP-1 agonists. Sulfonylureas often lead to hypoglycemia due to excessive insulin secretion. Moreover, the insulin secretion, in this case, is independent of the blood glucose concentration. GLP-1 agonists stimulate insulin secretion only in the presence of glucose, but it is not orally bioavailable and has to be given intravenously. DPP-IV inhibitors work by increasing the levels of GLP-1 which in turn leads to insulin secretion. (Jones R M, et al., *Expert Opin. Ther. Patents* (2009) 19(10):1339-1359).

GPR119 (G protein-coupled receptor) is a member of the rhodopsin family of GPCRs and is a $G_{\alpha s}$ coupled receptor. It is expressed predominantly in the pancreas (β-cells) and gastrointestinal tract (enteroendocrine cells) in humans (Overton H A, et al., *British Journal of Pharmacology* (2008) 153 S76-S81). GPR119 activation by endogenous ligands (e.g., oleoylethanolamide, OEA) leads to an increase in the intracellular concentrations of cAMP, which subsequently leads to increased secretion of glucose-dependent insulinotropic peptide (GIP) and glucagon-like peptide (GLP-1). This mechanism is responsible for the glucose stimulated insulin secretion (GSIS) from the β-cells of the pancreas. Treatments that increase GLP-1 secretion may be useful for various conditions and disorders including, but not limited to, metabolic disorders, gastrointestinal disorders, inflammatory diseases, psychosomatic, depressive and neuropsychiatric diseases.

GPR119 is reported to be involved in various diseases in addition to Type 2 diabetes. These include but are not limited to obesity (Overton H A, et al., *British Journal of Pharmacology* (2008) 153 S76-S81) and osteoporosis (WO2007/120689 A2).

As reported in the literature, the agonists of GPR119 receptors are useful as therapeutic agents for treating or preventing a condition modulated by PYY(peptide YY), such as a condition modulated by stimulation of NPY Y2 receptor (Y2R). Conditions modulated by PYY include but are not limited to bone-related conditions, metabolic disorders, angiogenesis-related conditions, ischemia-related conditions, convulsive disorders, malabsorptive disorders, cancers, and inflammatory disorders. PCT application WO 2009/126245 A1 discloses GPR119 receptors to be involved in inflammation, inflammatory bowel disease and atherosclerosis.

Obesity is a condition in which individuals have high body mass index (BMI). Overweight conditions and obesity are closely linked to Type 2 diabetes, heart disease, increased cholesterol, dislipidemia, high blood pressure, insulin resistance, glucose intolerance, hyperinsulinemia, coronary heart disease, angina pectoris, congestive heart failure, strokes, gallstones, cholecystitis, cholelithiasis, gout, osteoarthritis, obstructive sleep apnea, respiratory problems, certain forms of cancers (endometrial, breast, prostate and colon) and psychological disorders (e.g., depression, eating disorder, low self-esteem).

Osteoporosis is characterized by the loss of bone mass and the deterioration of skeletal structure leading to decreased bone strength. Patients have an enhanced risk of fractures. Osteoporosis leads to morbidity, mortality and decreased quality of life. Osteoporotic fractures therefore cause substantial mortality, morbidity, and economic cost. With an ageing population, the number of osteoporotic fractures and their costs will at least double in the next 50 years unless effective preventive strategies are developed. (Cole et al., *Curr. Rheum. Reports* (2008); 10; 92-96; Reginster, *Bone* (2006) 38:S4-S9); Boonen, *Curr. Med. Res. Opin.* (2008); 24; 1781-1788).

Atherosclerosis is a condition involving inflammation, lipid accumulation, cell death (necrosis) and fibrosis. Foam cell formation results from monocyte infiltration and cholesterol deposition in the subendothelial space. Complications of atherosclerosis lead to myocardial infarction and stroke. Atherosclerosis is one of the major causes of death in many countries (Ruggeri, *Nat. Med.* (2002); 8; 1227-1234; Li, *Nat. Med.* (2002); 8; 1234-1242).

Inflammatory bowel disease (IBD) is a term that includes diseases leading to inflammation of intestine. The diseases that are classified under this category are Crohn's disease, ulcerative colitis and ulcerative proctitis.

Several patent applications disclose compounds that modulate GPR119 receptor activity and their use in the treatment of various diseases and disorders. Some of the patent applications disclosing compounds modulating GPR119 receptor activity are PCT publications JP 2011136942, WO 2010/119881, WO 2010/149685, WO 2010/128425, WO 2010/128414, WO 2010/095663, WO 2010/075271, WO 2010/075269, WO 2010/008739, WO 2009/050523, WO 2009/050522, WO 2008/054675, WO 2008/025800, WO 2007/116230, WO 2008/005576, WO 2008/005569, WO 2008/070692, WO 2007/035355, WO 2006/076243, WO 2004/065380, WO 2006/083491, WO 2006/070208, WO 2005/007647, WO 2005/121121, WO 2004/076413. Pyrimidyl indoline compounds having hypoglycemic effect are disclosed in WO 2009/051119 and WO 2009/141238.

SUMMARY OF THE INVENTION

In accordance with one aspect, the invention provides the compounds of Formula (I):

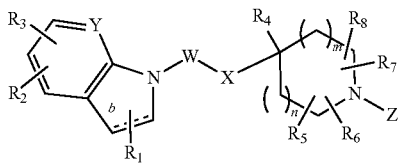

wherein, $\underset{=\!=\!=}{b}$ is a single or double bond; provided that when $\underset{=\!=\!=}{b}$ a double bond W is selected from group A and group B, and, when $\underset{=\!=\!=}{b}$ is a single bond W is selected from group A;

group A is selected from the group consisting of a 6-membered aromatic ring, wherein the 6-membered aromatic ring is selected from the group consisting of

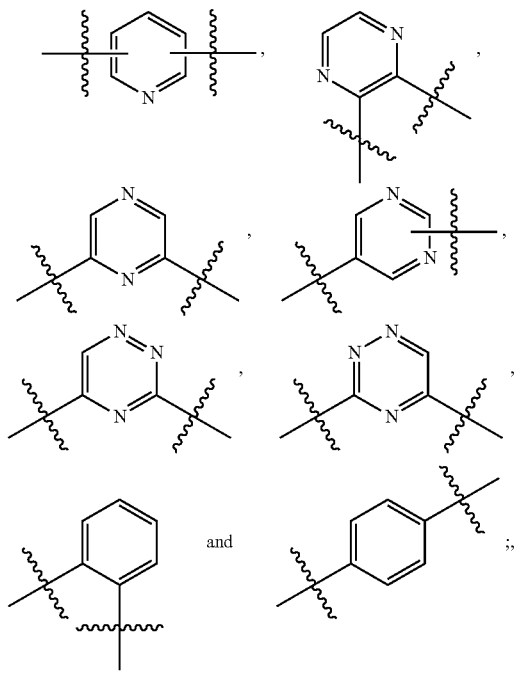

a 5-membered heteroaryl, a cycloalkyl, a heterocyclyl, a bicyclic aryl and a bicyclic heteroaryl, and a member of group A may be optionally substituted with one or more $R_{12}$;

group B is selected from the group consisting of

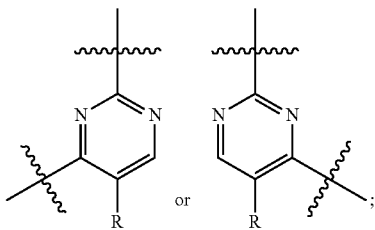

wherein, R at each occurrence is selected from the group consisting of haloalkyl, alkoxy, cycloalkyl and $NR_aR_b$;

$R_1$, $R_2$, are each independently selected from the group consisting of hydrogen, alkyl, alkenyl, alkynyl, cycloalkyl, halo, hydroxyalkyl, haloalkyl, —$NR_aR_b$, —$C(O)OR_a$ and —$C(O)NR_aR_b$;

or when 'b' is single bond, $R_1$ may be oxo (=O);

$R_3$ is selected from the group consisting of —$S(O)_pR_a$, —$C(O)OR_a$, —$(CH_2)_qC(O)NR_aR_b$, —$(CH_2)_qN(R_a)C(O)R_b$, —$N(R_a)C(O)OR_b$, —$N(R_a)C(O)NR_aR_b$, —$S(O)_2NR_aR_b$, —$N(R_a)S(O)_2R_b$, —CN, alkoxy, hydroxyalkyl, heterocyclyl and heteroaryl;

Y is N or C;

$R_a$ and $R_b$ are each independently selected from the group consisting of hydrogen, alkyl, halo, haloalkyl, hydroxy, alkenyl, alkynyl, cycloalkyl, hydroxyalkyl, alkoxyalkyl, aryl, heteroaryl, arylalkyl, and heterocyclyl; or $R_a$ and $R_b$ may join together with the nitrogen atom to which they are attached to form a heterocyclic ring;

$R_4$ is selected from the group consisting of hydrogen, alkyl, halo, haloalkyl, cyano and —$OR_a$;

Z is selected from the group consisting of hydrogen, alkyl, alkenyl, alkynyl, cycloalkyl, heterocyclyl, aryl, heteroaryl, cycloalkylalkyl, heterocyclylalkyl, heteroarylalkyl, arylalkyl, haloalkyl, hydroxyalkyl, —$(CH_2)_qC(O)OR_a$, —$(CH_2)_qC(O)OR_cR_dR_e$, —$(CH_2)_qC(O)R_a$, —$C(O)(CH_2)_qNR_aR_b$, —$(CH_2)_qC(O)NR_aR_b$, —$S(O)_2R_a$, $S(O)_2NR_aR_b$, —$C(O)CR_cR_dR_e$ and —$(CH_2)_qCR_cR_dR_e$;

$R_c$, $R_d$ and $R_e$ are each independently selected from the group consisting of hydrogen, halogen, hydroxyl, alkyl, haloalkyl, alkenyl, alkynyl, cycloalkyl, aryl, heteroaryl, arylalkyl, and heterocyclyl; or $R_c$ and $R_d$ may join together with the carbon atom to which they are attached to form a 3 to 7 membered carbocyclic or heterocyclic ring;

$R_5$, $R_6$, $R_7$, $R_8$ are each independently selected from the group consisting of hydrogen, alkyl, alkenyl, alkynyl, cylcoalkyl, heterocyclyl, aryl, heteroaryl, cyano, hydroxy, haloalkyl, alkoxy, —$C(O)OR_a$, —$OC(O)R_a$, —$C(O)NR_aR_b$, —$N(R_a)C(O)R_b$, —$S(O)_pR_a$, —$S(O)_2NR_aR_b$, and —$N(R_a)S(O)_2R_b$; wherein $R_5$, $R_6$, $R_7$, and $R_8$ may be present on same or different carbon atom; or any two of $R_4$, $R_5$, $R_6$, $R_7$, $R_8$ and Z may join together to form a cycloalkyl or heterocyclyl ring; or any two of $R_5$, $R_6$, $R_7$ and $R_8$, when they are attached to the same carbon, may together form oxo (=O);

X is selected from the group consisting of —$(CR_{10}R_{11})_qO(CR_{10}R_{11})_r$—, —$(CR_{10}R_{11})_qS(O)_p(CR_{10}R_{11})_r$ and —$(CR_{10}R_{11})_qNR_9(CR_{10}R_{11})_r$—;

$R_9$ is hydrogen or alkyl;

$R_{10}$ and $R_{11}$ are each independently selected from the group consisting of hydrogen, halogen, alkyl and haloalkyl; or $R_{10}$ and $R_{11}$ may join together with the carbon atom to which they are attached to form a 3 to 7 membered carbocyclic ring;

$R_{12}$ at each occurrence is independently selected from hydrogen, alkyl, halogen, haloalkyl, alkoxy, cycloalkyl and $NR_aR_b$;

'm', 'n' and 'p' are each independently selected from 0, 1 or 2;

'q' is an integer ranging from 0 to 4, both inclusive;

't' is an integer ranging from 0 to 4, both inclusive;

with the proviso that when $\overset{b}{=\!=\!=}$ is double bond and W is

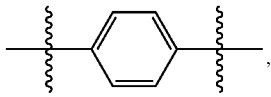

then X is not —NH— or —NHCH($R_{11}$);

and wherein, alkyl, alkenyl, alkynyl, cycloalkyl, aryl, heteroaryl, heterocyclyl wherever they occur may optionally be substituted with one or more substituents independently selected from hydroxy, halo, cyano, nitro, oxo (=O), thio (=S), alkyl, haloalkyl, alkenyl, alkynyl, aryl, arylalkyl, cycloalkyl, cycloalkylalkyl, cycloalkenyl, heteroaryl, heterocyclic ring, heterocyclylalkyl, heteroarylalkyl, —C(O)O$R^x$, —C(O)$R^x$, —C(S)$R^x$, —C(O)N$R^xR^y$, —N$R^x$(O)N$R^yR^z$, —N($R^x$)S(O)$R^y$, —N($R^x$)S(O)$_2R^y$, —N$R^y$, —N$R^x$(O)$R^y$, —N$R^x$C(S)$R^y$, —N$R^x$C(S)N$R^yR^z$, —S(O)N$R^x_R{}^y$, —S(O)$_2$N$^xR^y$, —OC(O)$R^x$, —OC(O)N$R^xR^y$, —$R^x$(O)O$R^y$, —$R^x$(O)N$R^yR^z$, —$R^x$(O)$R^y$, —S$R^x$, —S(O)$R^x$, and —S(O)$_2R^x$; wherein each occurrence of $R^x$, $R^y$ and $R^Z$ are independently selected from hydrogen, alkyl, haloalkyl, alkenyl, alkynyl, aryl, arylalkyl, cycloalkyl, cycloalkenyl, heteroaryl, heterocyclic ring, heterocyclylalkyl ring and heteroarylalkyl;

or pharmaceutically acceptable salt thereof.

The below embodiments are illustrative in nature only and are not intended to limit the scope of the invention.

According to one embodiment there are provided compounds of Formula (I):

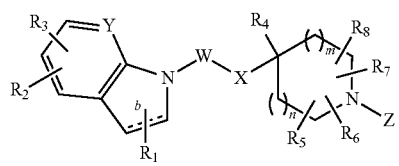

(I)

or pharmaceutically acceptable salt thereof;

wherein, $\overset{b}{=\!=\!=}$ is a single or double bond;

W is selected from 6-membered aromatic ring selected from the group consisting of:

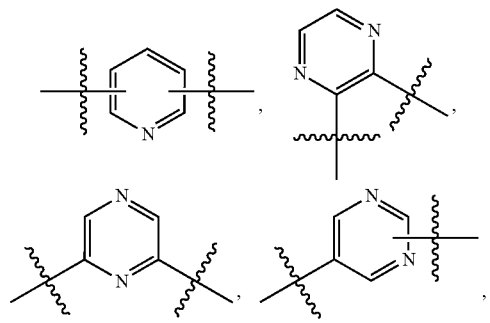

-continued

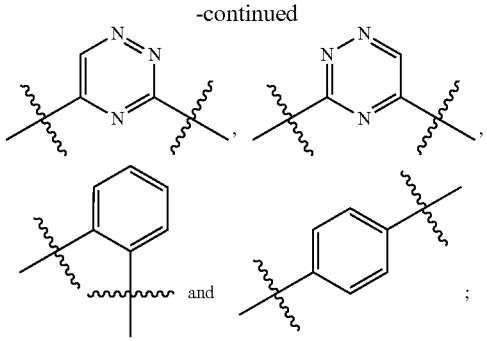

X, Z, $R_1$, $R_2$, $R_3$, $R_4$, $R_5$, $R_6$, $R_7$, $R_8$, 'n' and 'm' are as defined herein above.

According to another embodiment there are provided compounds of Formula (I) in which $\overset{b}{=\!=\!=}$ is a double bond and W is selected from 6-membered aromatic ring selected from the group consisting of:

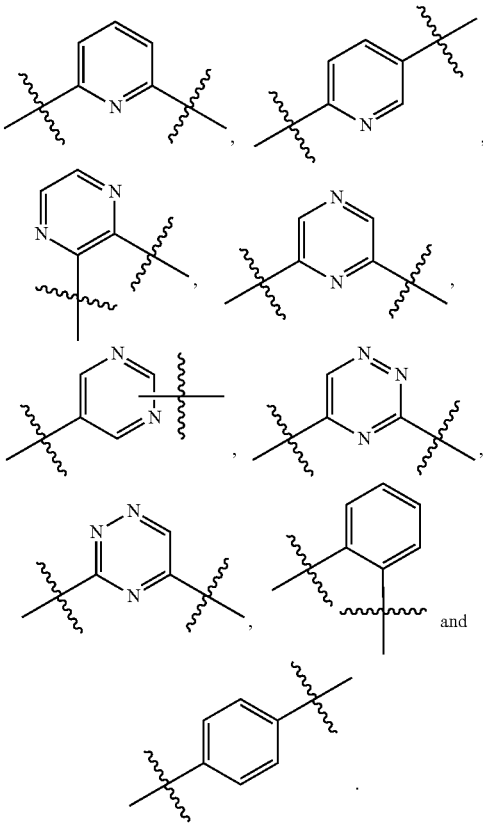

According to another embodiment there are provided compounds of Formula (II):

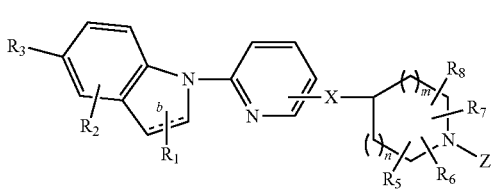

(II)

or pharmaceutically acceptable salt thereof;

wherein, b is a single or double bond;

X, Z, $R_2$, $R_3$, $R_5$, $R_6$, $R_7$, $R_8$, 'n' and 'm' are as defined herein above.

According to another embodiment there are provided compounds of Formula (III):

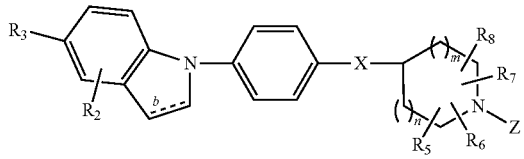

(III)

or pharmaceutically acceptable salt thereof;
wherein, b is a single or double bond;

$R_3$ is selected from the group consisting of —S(O)$_p$R$_a$, —C(O)OR$_a$, —(CH$_2$)$_q$C(O)NR$_a$R$_b$, —(CH$_2$)$_q$N(R$_a$)C(O)R$_b$, —N(R$_a$)C(O)OR$_b$, —N(R$_a$)C(O)NR$_a$R$_b$, —S(O)$_2$NR$_a$R$_b$, —N(R$_a$)S(O)$_2$R$_b$, hydroxyalkyl and heterocyclyl;

X, Z, $R_2$, $R_5$, $R_6$, $R_7$, $R_8$, 'n' and 'in' are as defined herein above.

According to another embodiment there are provided compounds of Formula (IV):

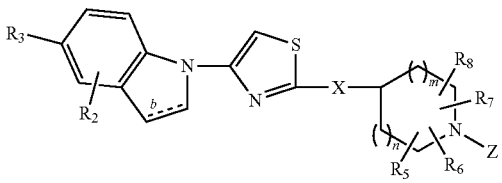

(IV)

or pharmaceutically acceptable salt thereof;
wherein, b is a single or double bond;

X, Z, $R_2$, $R_3$, $R_5$, $R_6$, $R_7$, $R_8$, 'n' and 'm' are as defined herein above.

According to another embodiment there are provided compounds of Formula (V):

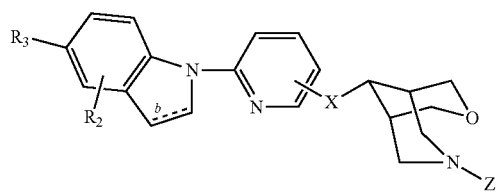

(V)

or pharmaceutically acceptable salt thereof;
wherein, b is a single or double bond;

X, Z, $R_2$, and $R_3$ are as defined herein above.

It should be understood that Formula (I), (II), (III), (IV) and (V) structurally encompass all N-oxides, tautomers, stereoisomers and pharmaceutically acceptable salts that may be contemplated from the chemical structures described herein.

According to one sub embodiment there are provided a compound of Formula (I) in which W is selected from

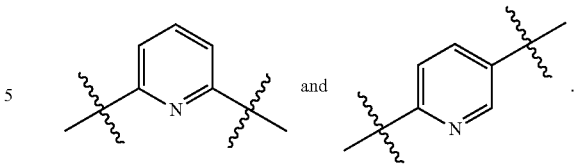

and

According to another sub embodiment there are provided a compound of Formula (II), (III), (IV) and/or (V) in which X is —(CR$_{10}$R$_{11}$)$_q$O(CR$_{10}$R$_{11}$)$_t$— and —(CR$_{10}$R$_{11}$)$_q$NR$_9$ (CR$_{10}$R$_{11}$)$_t$—; wherein 'q' is 0 or 1; 't' is 0 or 1; and each of R$_{10}$ and R$_{11}$ are independently selected from hydrogen, halogen or alkyl.

According to another sub embodiment there are provided a compound of Formula (II), (III), (IV) and/or (V) in which $R_2$ is hydrogen or halogen.

According to another sub embodiment there are provided a compound of Formula (II), (IV) and/or (V) in which $R_3$ is CN, alkoxy, hydroxyalkyl, C(O)OR$_a$, —S(O)$_2$R$_a$, —C(O)NR$_a$R$_b$, —N(R$_a$)C(O)R$_b$, —CH$_2$N(R$_a$)C(O)R$_b$, —N(R$_a$)C(O)OR$_b$, —S(O)$_2$NR$_a$R$_b$, —N(R$_a$)S(O)$_2$R$_b$, heterocyclyl or heteroaryl wherein R$_a$ and R$_b$ are each and independently a hydrogen, alkyl, haloalkyl, cycloalkyl, hydroxyalkyl, aryl, heteroaryl or heterocyclyl; or R$_a$ and R$_b$ may join together with the nitrogen atom to which they are attached to form a heterocyclic ring.

According to another sub embodiment there are provided a compound of Formula (III) in which $R_3$ is hydroxyalkyl, C(O)OR$_a$, —S(O)$_2$R$_a$, —C(O)NR$_a$R$_b$, —N(R$_a$)C(O)R$_b$, —CH$_2$N(R$_a$)C(O)R$_b$, —N(R$_a$)C(O)OR$_b$, —S(O)$_2$NR$_a$R$_b$, —N(R$_a$)S(O)$_2$R$_b$, heterocyclyl wherein R$_a$ and R$_b$ are each and independently a hydrogen, alkyl, haloalkyl, cycloalkyl, hydroxyalkyl, aryl, heteroaryl or heterocyclyl; or R$_a$ and R$_b$ may join together with the nitrogen atom to which they are attached to form a heterocyclic ring.

According to another sub embodiment there are provided a compound of Formula (II), (III), (IV) and/or (V) in which Z is hydrogen, alkyl, haloalkyl, cycloalkyl, heterocyclyl, aryl, heteroaryl, heterocyclylalkyl, heteroarylalkyl, arylalkyl, hydroxyalkyl, —C(O)OR$_a$, —C(O)R$_a$, —C(O)CR$_c$R$_d$R$_e$, —(CH$_2$)$_q$CR$_c$R$_d$R$_e$, —S(O)$_2$R$_a$ or S(O)$_2$NR$_a$R$_b$ wherein R$_a$, R$_b$, R$_c$, R$_d$ and R$_e$ are each and independently a hydrogen, alkyl, halo, haloalkyl, hydroxy, cycloalkyl, hydroxyalkyl, aryl, heteroaryl, arylalkyl, and heterocyclyl; or R$_a$ and R$_b$ may join together with the nitrogen atom to which they are attached to form a heterocyclic ring; or R$_c$ and R$_d$ may join together with the carbon atom to which they are attached to form a 3 to 7 membered carbocyclic or heterocyclic ring.

According to another sub embodiment there are provided a compound of Formula (II), (III) and/or (IV) in which 'm' is 0 or 1; and 'n' is 0 or 1.

According to another sub embodiment there are provided a compound of Formula (II), (III) and/or (IV) in which $R_5$, $R_6$, $R_7$ and $R_8$ are each and independently selected from the group consisting of hydrogen, alkyl, cyano, hydroxy, haloalkyl or alkoxy; or any two of $R_4$, $R_5$, $R_6$, $R_7$, $R_8$ and Z may join together to form a cycloalkyl or heterocyclyl ring; or any two of $R_5$, $R_6$, $R_7$ and $R_8$, when they are attached to the same carbon, may together form oxo (=O).

According to another sub embodiment there are provided a compound of Formula (I), (II), (III), (IV) and/or (V) in which b is a single or double bond; W is selected from group A as defined herein above or 5-membered heteroaryl; $R_2$ is hydrogen or halogen; $R_3$ is —S(O)$_2$R$_a$, —C(O)NR$_a$R$_b$, —N(R$_a$)C (O)R$_b$, —N(R$_a$)C(O)OR$_b$, heterocyclyl, heterocyclylalkyl or heteroaryl wherein $R_a$ and $R_b$ are each independently a hydrogen, alkyl; X is —O—, —NH—; Z is alkyl, haloalkyl, heteroaryl, heterocyclyl, —C(O)Oalkyl, —C(O)CR$_c$R$_d$R$_e$, —(CH$_2$)$_q$R$_c$R$_d$R$_e$; $R_5$, $R_6$, $R_7$ and $R_8$ are hydrogen or halogen or any two of $R_4$, $R_5$, $R_6$, $R_7$, $R_8$ and Z may join together to form a cycloalkyl or heterocyclyl ring; $R_c$, $R_d$, and $R_e$ are as defined herein above; 'm' is 1; and 'n' is 1.

In another embodiment of the invention there is provided a pharmaceutical composition comprising at least one compound of Formula (I) and one or more pharmaceutically acceptable excipients such as a carrier or a diluent. Preferably, the pharmaceutical composition comprises a therapeutically affective amount of at least one compound of Formula (I).

In another embodiment of the invention there is provided a pharmaceutical composition comprising a compound of Formula (I) for treating, preventing, and/or managing diseases, disorders, syndromes or conditions associated with the modulation of the GPR119 receptor.

In another embodiment of the invention, the compounds of Formula (I) may be used either alone or in combination with one or more therapeutically active agents described herein for treating, preventing, managing diseases, disorders, syndromes or conditions associated with the modulation of the GPR119 receptor.

In another embodiment, the invention further provides methods of treating, preventing, and/or managing diseases, disorders, syndromes or conditions associated with the modulation of the GPR119 receptor.

In another embodiment, the invention is related to a pharmaceutical composition comprising a therapeutically effective amount of at least one of the compound of Formula (I) or its stereoisomers, or pharmaceutically acceptable salts thereof, and one or more pharmaceutically acceptable carriers or diluents for treating, preventing, managing diseases, disorders, syndromes or conditions associated with the modulation of the GPR119 receptor.

In another embodiment of the invention there are provided processes for the preparation of compounds of the invention having the structure of Formula (I):

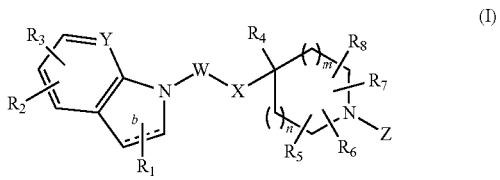

(I)

comprising,
a) reacting a compound of formula (2) where L is a leaving group, with a compound of formula (7), where L' is a leaving group PG is protecting group, in the presence of suitable base to give a compound of formula (8),

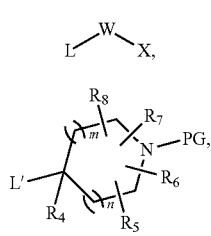

(2)

(7)

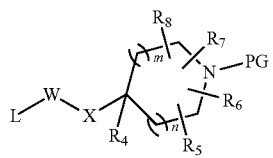

(8)

b) treating the compound of formula (8) with a compound of formula (5) in the presence of palladium catalyst to give a compound of formula (9),

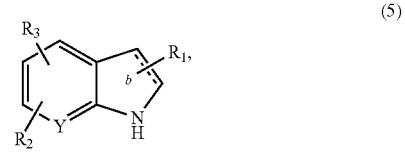

(5)

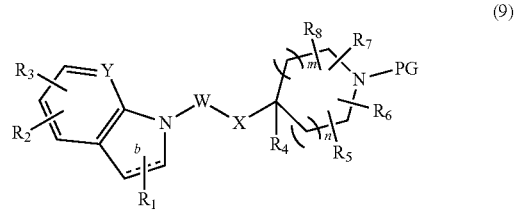

(9)

c) deprotecting the compound of formula (9) with a suitable reagent to give a compound of formula (10), and

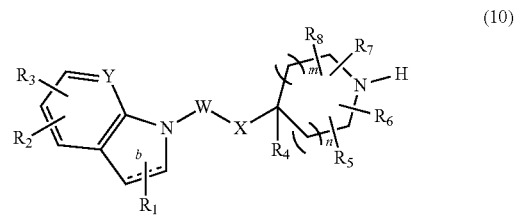

(10)

d) coupling the compound of formula (10) with Z-L where L is a leaving group, to obtain the compound of formula (I).

The details of one or more embodiments of the inventions are set forth in the description below. Other features, objects and advantages of the inventions will be apparent from the description and claims.

DETAILED DESCRIPTION OF THE INVENTION

Unless otherwise stated, the following terms used in the specification and claims have the meanings given below:

For purposes of interpreting this specification, the following definitions will apply and whenever appropriate, terms used in the singular will also include the plural and vice versa.

The terms "halogen" or "halo" means fluorine, chlorine, bromine, or iodine.

The term "oxo" means the C(=O) group. Such an oxo group may be a part of either a cycle or a chain in the compounds of the present invention.

The term "alkyl" refers to an alkane derived hydrocarbon radical that includes solely carbon and hydrogen atoms in the backbone, containing no unsaturation, having from one to six carbon atoms, and which is attached to the rest of the molecule by a single bond, e.g., methyl, ethyl, n-propyl, 1-methylethyl (isopropyl), n-butyl, n-pentyl, 1,1-dimethylethyl (t-butyl) and the like. Unless set forth or recited to the contrary, all alkyl groups described or claimed herein may be straight chain or branched, substituted or unsubstituted.

The term "alkenyl" refers to a hydrocarbon radical containing from 2 to 10 carbon atoms and including at least one carbon-carbon double bond. Non-limiting Examples of alkenyl groups include ethenyl, 1-propenyl, 2-propenyl (allyl), iso-propenyl, 2-methyl-1-propenyl, 1-butenyl, 2-butenyl and the like. Unless set forth or recited to the contrary, all alkenyl groups described or claimed herein may be straight chain or branched, substituted or unsubstituted.

The term "alkynyl" refers to a hydrocarbon radical containing at least one carbon-carbon triple bond, and having 2 to about 10 carbon atoms. Non-limiting examples of alkynyl groups include ethynyl, propynyl, butynyl and the like. Unless set forth or recited to the contrary, all alkynyl groups described or claimed herein may be straight chain or branched, substituted or unsubstituted.

The term "alkoxy" denotes an alkyl group attached via an oxygen linkage to the rest of the molecule. Representative examples of such groups are —OCH$_3$ and —OC$_2$H$_5$. Unless set forth or recited to the contrary, all alkoxy groups described or claimed herein may be straight chain or branched, substituted or unsubstituted.

The term "cycloalkyl" refers to a non-aromatic mono or multicyclic ring system of 3 to about 12 carbon atoms, such as cyclopropyl, cyclobutyl, cyclopentyl, cyclohexyl and the like. Examples of multicyclic cycloalkyl groups include, but are not limited to, perhydronapththyl, adamantyl and norbornyl groups, bridged cyclic groups or spirobicyclic groups, e.g., spiro(4,4)non-2-yl and the like. Unless set forth or recited to the contrary, all cycloalkyl groups described or claimed herein may be substituted or unsubstituted.

The term "cycloalkylalkyl" refers to a cycloalkyl group as defined above, directly bonded to an alkyl group as defined above, e.g., cyclopropylmethyl, cyclobutylmethyl, cyclopentylmethyl, cyclohexylmethyl, cyclohexylethyl etc. Unless set forth or recited to the contrary, all cycloalkylalkyl groups described or claimed herein may be substituted or unsubstituted.

The term "cycloalkenyl" refers to a monocyclic or bicyclic nonaromatic carbocyclic radical containing at least one double bond and having from 3 to 10 ring members, and refers in particular cyclobutenyl, cyclopentenyl or cyclohexenyl radicals. Unless set forth or recited to the contrary, all cycloalkyl groups described or claimed herein may be substituted or unsubstituted.

The term "haloalkyl" refers to an alkyl, as defined herein, that is substituted by one or more halogen groups as defined herein. Preferably, the haloalkyl may be monohaloalkyl, dihaloalkyl or polyhaloalkyl including perhaloalkyl. A monohaloalkyl can have one iodine, bromine, chlorine or fluorine substituent. Dihaloalkyl and polyhaloalkyl groups can be substituted with two or more of the same halogen atoms or a combination of different halogen groups. Preferably, a polyhaloalkyl is substituted with up to 12, 10, 8, 6, 4, 3, or 2 halogen groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl and the like. A perhaloalkyl refers to an alkyl having all hydrogen atoms replaced with halogen atoms.

The term "hydroxyalkyl" refers to an alkyl, as defined herein, that is substituted by one or more hydroxy groups. Preferably the hydroxyalkyl can be monohydroxyalkyl or dihydroxyalkyl. Non-limiting examples of hydroxyalkyl include 2-hydroxyethyl, 3-hydroxypropyl, 2-hydroxypropyl, and the like.

The term "aryl" refers to an aromatic radical having 6 to 14 carbon atoms, including monocyclic, bicyclic and tricyclic aromatic systems, such as phenyl, naphthyl, tetrahydronaphthyl, indanyl, and biphenyl and the like. Unless set forth or recited to the contrary, all aryl groups described or claimed herein may be substituted or unsubstituted.

The term "arylalkyl" refers to an aryl group as defined above, directly bonded to an alkyl group as defined above, e.g., —CH$_2$C$_6$H$_5$ and —C$_2$H$_4$C$_6$H$_5$. Unless set forth or recited to the contrary, all arylalkyl groups described or claimed herein may be substituted or unsubstituted.

The term "heterocyclic ring" or "heterocyclyl ring" or "heterocyclyl", unless otherwise specified, refers to substituted or unsubstituted non-aromatic 3- to 15-membered ring which consists of carbon atoms and with one or more heteroatom(s) independently selected from N, O or S. The heterocyclic ring may be a mono-, bi- or tricyclic ring system, which may include fused, bridged or Spiro ring systems and the nitrogen, carbon, oxygen or sulfur atoms in the heterocyclic ring may be optionally oxidized to various oxidation states. In addition, the nitrogen atom may be optionally quaternized, the heterocyclic ring or heterocyclyl may optionally contain one or more olefinic bond(s), and one or two carbon atoms(s) in the heterocyclic ring or heterocyclyl may be interrupted with —C(O)—, —C(=N-alkyl)-, or C(=N-cycloalkyl), etc. In addition the heterocyclic ring may be fused with aromatic ring. Non-limiting examples of heterocyclic rings include azepinyl, azetidinyl, benzodioxolyl, benzodioxanyl, benzopyranyl, chromanyl, dioxolanyl, dioxaphospholanyl, decahydroisoquinolyl, indanyl, indolinyl, isoindolinyl, isochromanyl, isothiazolidinyl, isoxazolidinyl, morpholinyl, oxazolinyl, oxazolidinyl, 2-oxopiperazinyl, 2-oxopiperidinyl, 2-oxopyrrolidinyl, 2-oxoazepinyl, octahydroindolyl, octahydroisoindolyl, perhydroazepinyl, piperazinyl, 4-piperidonyl, pyrrolidinyl, piperidinyl, phenothiazinyl, phenoxazinyl, quinuclidinyl, tetrahydroisquinolyl, tetrahydrofuryl, tetrahydropyranyl, thiazolinyl, thiazolidinyl, thiamorpholinyl, thiamorpholinyl sulfoxide, thiamorpholinyl sulfone and the like. The heterocyclic ring may be attached to the main structure at any heteroatom or carbon atom that results in the creation of a stable structure. Unless set forth or recited to the contrary, all heterocyclyl groups described or claimed herein may be substituted or unsubstituted.

A "carbocyclic ring" or "carbocycle" as used herein refers to a 3- to 10-membered saturated or unsaturated, monocyclic, fused bicyclic, spirocyclic or bridged polycyclic ring containing carbon atoms, which may optionally be substituted, for example, carbocyclic rings include but are not limited to cyclopropyl, cyclobutyl, cyclopentyl, cyclohexyl, cyclopropylene, cyclohexanone, aryl, naphthyl, adamentyl etc. Unless set forth or recited to the contrary, all carbocyclic groups or rings described or claimed herein may be aromatic or non aromatic.

The term "heteroaryl" unless otherwise specified, refers to substituted or unsubstituted 5 to 14 membered aromatic heterocyclic ring radical with one or more heteroatom(s) independently selected from N, O or S. The heteroaryl may be a mono-, bi- or tricyclic ring system. The heteroaryl ring radical may be attached to the main structure at any heteroatom or carbon atom that results in the creation of a stable structure. Examples of such heteroaryl ring radicals include, but are not limited to, oxazolyl, isoxazolyl, imidazolyl, furyl, indolyl, isoindolyl, pyrrolyl, triazolyl, triazinyl, tetrazoyl, thienyl, thiazolyl, isothiazolyl, pyridyl, pyrimidinyl, pyrazinyl, pyridazinyl, benzofuranyl, benzothiazolyl, benzoxazolyl, benzimidazolyl, benzothienyl, benzopyranyl, carbazolyl, quinolinyl, isoquinolinyl, quinazolinyl, cinnolinyl, naphthyridinyl, pteridinyl, purinyl, quinoxalinyl, quinolyl, isoquinolyl, thiadiazolyl, indolizinyl, acridinyl, phenazinyl, phthalazinyl and the like. Unless set forth or recited to the contrary, all heteroaryl groups described or claimed herein may be substituted or unsubstituted.

The term "heterocyclylalkyl" refers to a heterocyclic ring radical directly bonded to an alkyl group. The heterocyclylalkyl radical may be attached to the main structure at any carbon atom in the alkyl group that results in the creation of a stable structure. Unless set forth or recited to the contrary, all heterocyclylalkyl groups described or claimed herein may be substituted or unsubstituted.

The term "heteroarylalkyl" refers to a heteroaryl ring radical directly bonded to an alkyl group. The heteroarylalkyl radical may be attached to the main structure at any carbon atom in the alkyl group that results in the creation of a stable structure. Unless set forth or recited to the contrary, all heteroarylalkyl groups described or claimed herein may be substituted or unsubstituted.

Unless otherwise specified, the term "substituted" as used herein refers to a group or moiety having one or more substituents attached to the structural skeleton of the group or moiety. Such substituents include, but are not limited to hydroxy, halo, carboxyl, cyano, nitro, oxo (=O), thio (=S), alkyl, haloalkyl, alkenyl, alkynyl, aryl, arylalkyl, cycloalkyl, cycloalkylalkyl, cycloalkenyl, amino, heteroaryl, heterocyclic ring, heterocyclylalkyl, heteroarylalkyl, —C(O)OR$^x$, —C(O)R$^x$, —C(S)R$^x$, —C(O)NR$^x$R$^y$, —NR$^x$C(O)NR$^y$R$^z$, —N(R$^x$)S(O)R$^y$, —N(R$^x$)S(O)$_2$R$^y$, —NR$^x$R$^y$, —NR$^x$C(O)R$^y$, —NR$^x$C(S)R$^y$, —NR$^x$C(S)NR$^y$R$^z$, —S(O)NR$^x$R$^y$, —S(O)$_2$NR$^x$R$^y$, —OR$^x$, —OC(O)R$^x$, —OC(O)NR$^x$R$^y$, —R$^x$C(O)OR$^y$, —R$^x$C(O)NR$^y$R$^z$, —R$^x$C(O)R$^y$, —SR$^x$, —S(O)R$^x$, and —S(O)$_2$R$^x$; wherein each occurrence of R$^x$, R$^y$ and R$^z$ are independently selected from hydrogen, alkyl, haloalkyl, alkenyl, alkynyl, aryl, arylalkyl, cycloalkyl, cycloalkenyl, heteroaryl, heterocyclic ring, heterocyclylalkyl ring and heteroarylalkyl.

"May optionally be substituted" means that the moiety or group may or may not be substituted. For example, "optionally substituted aryl" means that the aryl radical may or may not be substituted and that the description includes both substituted aryl radicals and aryl radicals having no substitution.

Unless otherwise stated, in the present application "protecting group" (PG) refers to the groups intended to protect an otherwise labile group, e.g., an amino group, a carboxy group and the like, under specific reaction conditions. Various protecting groups along with the methods of protection and deprotection are generally known to a person of ordinary skilled in the art. Incorporated herein in this regard as reference is *Greene's Protective Groups in Organic Synthesis,* 4th Edition, John Wiley & Sons, New York. In the present invention, preferred amino protecting groups are t-butoxycarbonyl, benzyloxycarbonyl, acetyl and the like; while preferred carboxy protecting groups are esters, amides and the like.

A "stereoisomer" refers to a compound made up of the same atoms bonded by the same bonds but having different three-dimensional structures, which are not interchangeable. The invention contemplates various stereoisomers and mixtures thereof and includes "enantiomers", which refers to two stereoisomers whose molecules are non-superimposable mirror images of one another.

The term "treating" or "treatment" of a state, diseases, disorders, syndromes or conditions includes: (a) preventing or delaying the appearance of clinical symptoms of the state, disease, disorder, condition or syndrome developing in a subject that may be afflicted with or predisposed to the state, disease, disorder, condition or syndrome but does not yet experience or display clinical or subclinical symptoms of the state, disease, disorder, condition or syndrome; (b) inhibiting the state, disease, disorder, condition or syndrome, i.e., arresting or reducing the development of the disease or at least one clinical or subclinical symptom thereof and/or (c) slowing the progression of a disease, disorder, condition or syndrome or at least one of its clinical or subclinical symptoms thereof.

The term "modulate" or "modulating" or "modulation" refers to an increase or decrease in the amount, quality, or effect of a particular activity, function or molecule; by way of illustration and not limitation, agonists, partial agonists, inverse agonists, and antagonists of a G protein-coupled receptor are modulators of the receptor. For example, the compounds of invention are useful as modulators of the GPR119 receptor.

The term "subject" includes mammals preferably humans and other animals, such as domestic animals; e.g., household pets including cats and dogs and non-domestic animals.

A "therapeutically effective amount" means the amount of a compound that, when administered to a subject for treating a state, disease, disorder, condition or syndrome, is sufficient to cause the effect in the subject which is the purpose of the administration. The "therapeutically effective amount" will vary depending on the compound, the disease and its severity and the age, weight, physical condition and responsiveness of the subject to be treated.

The compounds of the invention may form salts. Non-limiting examples of pharmaceutically acceptable salts forming part of this invention include salts derived from inorganic bases, salts of organic bases, salts of chiral bases, salts of natural amino acids and salts of non-natural amino acids. With respect to the overall compounds described by the Formula (I), the invention extends to these stereoisomeric forms and to mixtures thereof. The different stereoisomeric forms of the present patent application may be separated from one another by the method known in the art, or a given isomer may be obtained by stereospecific or asymmetric synthesis. Tautomeric forms and mixtures of compounds described herein are also contemplated.

Screening of compounds of invention for GPR119 receptor modulation activity may be achieved by using various in-vitro and in-vivo protocols mentioned herein below or methods known in the art.

Pharmaceutical Compositions

The invention relates to pharmaceutical compositions containing the compounds of the Formula (I) disclosed herein. In particular, pharmaceutical compositions containing a therapeutically effective amount of at least one compound of Formula (I) described herein and at least one pharmaceutically acceptable excipient such as a carrier or diluent. Preferably, the contemplated pharmaceutical compositions include the compound(s) described herein in an amount sufficient to modulate GPR119 receptor mediated diseases described herein when administered to a subject.

The compounds of the invention may be associated with a pharmaceutically acceptable excipient such as a carrier or a diluent or be diluted by a carrier, or enclosed within a carrier which can be in the form of a capsule, sachet, paper or other container. The pharmaceutically acceptable excipient includes pharmaceutical agents that do not induce the production of antibodies harmful to the individual receiving the composition, and which may be administered without undue toxicity.

Examples of suitable carriers include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, salicylic acid, fatty acids, fatty acid amines, fatty acid monoglycerides and diglycerides, pentaerythritol fatty acid esters, polyoxyethylene, hydroxymethylcellulose and polyvinylpyrrolidone.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, stabilizers, surfactants, colorants, or any combination of the foregoing. The pharmaceutical composition of the invention may be formulated so as to provide quick, sustained, or delayed release of the active ingredient after administration to the subject by employing procedures known in the art.

The pharmaceutical compositions described herein may be prepared by conventional techniques known in the art. For example, the active compound of Formula (I) can be mixed with a carrier, or diluted by a carrier, or enclosed within a carrier, which may be in the form of an ampoule, capsule, sachet, paper, or other container. When the carrier serves as a diluent, it may be a solid, semi-solid, or liquid material that acts as a vehicle, excipient, or medium for the active compound. The active compound can be adsorbed on a granular solid container, for example, in a sachet.

The pharmaceutical compositions may be in conventional forms, for example, capsules, tablets, aerosols, solutions, suspensions or products for topical application.

The route of administration may be any route which effectively transports the active compound of the invention, to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment).

Solid oral formulations include, but are not limited to, tablets, capsules (soft or hard gelatin), dragees (containing the active ingredient in powder or pellet form), troches and lozenges. Tablets, dragees, or capsules having talc and/or a carbohydrate carrier or binder or the like are particularly suitable for oral application. Liquid formulations include, but are not limited to, syrups, emulsions, soft gelatin and sterile injectable liquids, such as aqueous or non-aqueous liquid suspensions or solutions. For parenteral application, particularly suitable are injectable solutions or suspensions formulation.

The pharmaceutical preparation is preferably in unit dosage form. In such form, the preparation is subdivided into unit doses containing appropriate quantities of the active component. The unit dosage form can be a packaged preparation; the package containing discrete quantities of preparation, such as pocketed tablets, capsules, and powders in vials or ampoules. Also, the unit dosage form can be a capsule, tablet, cachet, or lozenge itself, or it can be the appropriate number of any of these in packaged form.

For administration to subject patients, the total daily dose of the compounds of the invention depends, of course, on the mode of administration. For example, oral administration may require a higher total daily dose, than an intravenous (direct into blood). The quantity of active component in a unit dose preparation may be varied or adjusted from 0.1 mg to 10000 mg, according to the potency of the active component or mode of administration.

Suitable doses of the compounds, for use in treating the diseases and disorders described herein, can be determined by those skilled in the relevant art. Therapeutic doses are generally identified through a dose ranging study in subject based on preliminary evidence derived from the animal studies. Doses must be sufficient to result in a desired therapeutic benefit without causing unwanted side effects for the patient. For example, the daily dosage of the GPR119 modulator can range from about 0.1 to about 30.0 mg/kg. Mode of administration, dosage forms, suitable pharmaceutical excipients, diluents or carriers can also be well used and adjusted by those skilled in the art. All changes and modifications are envisioned within the scope of the invention.

In one embodiment of the invention, the compound of Formula (I) and/or the pharmaceutical compositions of Formula (I) may be used either alone or in combination with one or more additional therapeutic agents for treating, preventing, managing diseases, disorders, syndromes or conditions associated with the modulation of the GPR119 receptor.

The compounds and compositions of the invention and the additional therapeutic agent as described herein may be administered simultaneously, sequentially or separately.

The combination of the compound of Formula (I) with any one or more additional therapeutic agent may be given to the subject in the same or separate dosage formulation.

Where separate dosage formulations are used, the compound of Formula (I) and one or more additional therapeutic agents can be administered at essentially the same time i.e., concurrently, or at separately staggered times i.e., sequentially. Combination therapy is understood to include all these regimens. Selection of additional therapeutic agents will, in large part, depend on the desired target therapy. Turner N, et al, Prog. Drug Res. (1998) 51: 33-94; Haffner S, Diabetes Care (1998) 21:160-178; and DeFronzo R, et al. (eds.), Diabetes Reviews (1997) Vol. 5 No. 4. A number of studies have investigated the benefits of combination therapies with oral agents {see, e.g., Mahler R, *J. Clin. Endocrinol. Metab.* (1999) 84:1165-71; United Kingdom Prospective Diabetes Study Group: UKPDS 28, Diabetes Care (1998) 21:87-92; Bardin C W (ed.), *Current Therapy in Endocrinology and Metabolism,* 6th Ed. (Mosby—Year Book, Inc., St. Louis, Mo. 1997); Chiasson J, et al., Ann. Intern. Med. (1994) 121: 928-935; Coniff R, et al., *Clin. Ther.* (1997) 19:16-26; Coniff R, et al., *Am. J. Med.* (1995) 98:443-451; and Iwamoto Y, et al, *Diabet. Med.* (1996) 13:365-370; Kwiterovich P, *Am. J. Cardiol.* (1998) 82(12A):3U-17U).

The additional therapeutic agent which can be used in combination with the compounds of invention include, but not limited to, anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, anti-pancreatic agents, anti-metabolic syndrome agents, lipid lowering agents, anti-lipodystrophy agents, appetite suppressants, treatments for heart failure, treatments for peripheral arterial disease and anti-inflammatory agents.

A combination therapy may be used in modulating, including preventing, the onset of the symptoms or complications associated with diabetes or treating, preventing or reducing the risk of developing diabetes and its related symptoms, complications, and disorders, wherein the compounds of the invention can be effectively used in combination with, one or more additional therapeutic agents. One or more additional therapeutic agents for diabetes includes but not limited to insulin and insulin analogs; insulin secretagogues such as sulfonylureas and analogs; meglitinides; insulin sensitizers such as biguanides; thiazolidinediones (PPAR); PPAR alpha/gamma dual agonists; alpha-glucosidase inhibitors; dipeptidyl peptidase-IV (DPP4) inhibitors; glucagon-like peptide-1 (GLP-1) receptor agonists including glucagon-like peptides and its analogues, amylin agonists; glucagon antagonists; alpha2-antagonists and imidazolines; SGLT2 inhibitors; insulin signaling agonists, insulin mimetics, aldose reductase inhibitors; 11-beta-hydroxysteroid dehydrogenase Type I inhibitors; RXR agonists; fatty acid oxidation inhibitors; beta-agonists; phosphodiesterase inhibitors, both cAMP and cGMP type; lipoxygenase inhibitors; PTP1B inhibitors; gluconeogenesis inhibitors; somatostatin and its analogs and antagonists; antilipolytic agents; glucose transport stimulating agents; glucose synthase kinase inhibitors; galanin receptor agonists; chemokine receptor antagonist; glucokinase activators; GDIR agonists; GPR40 modulators and other GPR119 modulators.

Insulin and its analogs include insulin from animal source and recombinant insulin and its derivatives, for e.g., short acting derivatives Lispro, aspart, glulisine and their protamine solutions and mixtures thereof, or the long acting derivatives, for e.g., glargine, detemir, and their modified formulations, for e.g., inhaled formulations comprising insulin, insulin via buccal route and the like. Sulfonylureas and analogs includes, but not limited to, chlorpropamide, glibenclamide, tolbutamide, tolazamide, acetohexamide, glipizide, glimepiride and the like. Meglitinides such as repaglinide, mitiglinide and the like. Biguanides includes, but not limited to, metformin, phenformin, buformin and the like. Thiazolidinediones for e.g., ciglitazone, pioglitazone, troglitazone, rosiglitazone and the like. PPAR-alpha agonists for e.g., fenofibrate, gemfibrozil and the like. PPAR alpha/gamma dual agonists, for e.g., muraglitazar, peliglitazar, and the like. Dipeptidyl peptidase-IV (DPP4) inhibitors includes saxagliptin, sitagliptin, vildagliptin, denagliptin and the like. Glucagon-like peptide-1 (GLP-1) receptor agonists, for e.g., Exenatide, Liraglutide, AVE0010, R1583, SUN E7001, GSK-716155 and Exendin-4 (PC-DACTM) and the like. Alpha2-antagonists and imidazolines include, but are not limited to, midaglizole, isaglidole, deriglidole, idazoxan, efaroxan, fluparoxan and the like. SGLT2 inhibitors include, but are not limited to, dapagliflozin, sergliflozin, canagliflozin, LX4211, BI-10773, BI-44847, ASP-1941, TS-071 and the like. Alpha-glucosidase inhibitors include, but are not limited to, acarbose, miglitol, voglibose and the like. Amylin analogs such as pramlintide and its derivatives. Other insulin secretagogues, for e.g., linogliride, insulinotropin, exendin-4, N,N-dimethyl-N'-[2-(4-morpholinyl)phenyl]guanidine (E)-2-butenedioate salt (BTS-675820), (−)—N-(trans-4-isopropylcyclohexanecarbonyl)-D-phenylalanine (A-4166)) and the like.

In another embodiment, the compound of Formula (I) may be used in combination therapy for treating obesity or obesity-related disorders, wherein the compound of Formula (I) can be effectively used in combination with one or more therapeutic agents having synergistic effects such as anti-obesity agents, anorectic agents, appetite suppressant and related agents. Diet and/or exercise can also have synergistic effects.

Anti-obesity agents include but are not limited to β-3 adrenoceptor agonist agents; gastrointestinal lipase inhibitors, leptins, cannabinoid-1 ("CB-1") receptor antagonists (such as rimonabant); PPAR delta agonists or partial agonists; dual PPAR alpha, PPAR delta agonists or partial agonists; dual PPAR delta, PPAR gamma agonists or partial agonists; pan PPAR agonists or partial agonists; neuropeptide Y; enterostatin; cholecytokinin; bombesin; amylin; histamine H3 receptors; serotonin 2C receptor agonists (5HT2c), dopamine D2 receptors; melanocyte stimulating hormone; corticotrophin releasing factor; galanin; gamma amino butyric acid (GABA), apolipoprotein-B secretion/microsomal triglyceride transfer protein (apo-B/mTP) inhibitors, MCR-4 agonists, MCR-4 antagonists; cholescystokinin-A (CCK-A) agonists, serotonin, galanin receptor antagonists; urocortin mimetics, CRF antagonists, CRF binding proteins and norepinephrine reuptake inhibitors (for example, sibutramine), sympathomimetic agents, β3 adrenergic receptor agonists, dopamine agonists (for example, bromocriptine), melanocyte-stimulating hormone receptor analogs, melanin concentrating hormone antagonists, leptons (the OB protein), leptin analogues, leptin receptor agonists, galanin antagonists, lipase inhibitors (such as tetrahydrolipstatin, i.e., Orlistat), anorectic agents (such as a bombesin agonist), europeptide-Y antagonists, thyromimetic agents, dehydroepiandrosterone or an analogue thereof, glucocorticoid receptor agonists or antagonists, orexin receptor antagonists, urocortin binding protein antagonists, glucagon-like peptide-1 receptor agonists, ciliary neurotrophic factors (such as AXOKINE, human agouti-related proteins (AGRP), ghrelin receptor antagonists, histamine 3 receptor antagonists or reverse agonists, neuromedin U receptor agonists, noradrenergic anorectic agents (for example, phentermine, mazindol and the like) and appetite suppressants (for example, bupropion). Some of the compounds that can be used in combination with the compounds of the invention include, but are not limited to, phenylpropanolamine, phentermine; orlistat, rimonabant, dexamphetamine, diethylpropion, mazindol, fenfluramine, dexfenfluramine, sibutramine, QNEXA (combination of phentermine and topiramate), Lorcaserin, CONTRAVE (combination of naltrexone and bupropion) and the like.

In a further embodiment, the compound of Formula (I) may be used in combination therapy for treating, preventing, and/or managing lipodystrophy including HIV protease associated lipodystrophy. Accordingly, the compound of Formula (I) may be used in combination with HIV protease inhibitors, including but not limited to, REYATAZ and KALETRA and the like.

In a further embodiment, the compound of Formula (I) may be used in combination therapy for modulating metabolic syndrome for e.g., treating metabolic syndrome and its related symptoms, complications and disorders, wherein the compound of Formula (I) may be effectively used in combination with, for example, the active agents discussed above for modulating or treating diabetes, obesity, hyperlipidemia, atherosclerosis, and/or their respective related symptoms, complications and disorders. Metabolic Syndrome or "Syndrome X" is described in Ford et al., J. Am. Med. Assoc., 287:356-359 (2002) and Arbeeny et al., Curr. Med. Chem.-Imm., Endoc. & Metab. Agents, 1:1-24 (2001).

In a further embodiment, the compound of Formula (I) may be used in combination therapy in modulating hyperlipidemia. Examples of suitable lipid lowering agents and anti-atherosclerotic agents, for use in combination with the compounds of Formula (I) include one or more MTP/ApoB secretion inhibitors (e.g., dirlopatide, N-(2,2,2-trifluoroethyl)-9-[4-[4-[[[4'-(trifluoromethyl)[1,1'-biphenyl]-2-yl]carbonyl-]amino]-1-piperidinyl]butyl]-9H-fluorene-9-carboxamide methane sulfonate, CP-741952, SLx-4090; HMG CoA reductase inhibitors (e.g., atorvastatin, rosuvastatin, simvastatin, pravastatin, lovastatin, fluvastatin); squalene synthetase inhibitors, PPAR alpha agonists and fibric acid derivatives (e.g., fenofibrate, gemfibrozil); ACAT inhibitors; lipoxygenase inhibitors; cholesterol absorption inhibitors (e.g., ezetimibe); Ileal Na+/bile acid cotransporter inhibitors (e.g., compounds as disclosed in Drugs of the Future, 24:425-430 (1999); upregulators of LDL receptor activity (e.g., (3R)-3-[(13R)-β-hydroxy-10-oxotetradecyl]-5,7-dimethoxy-1(3H)-isobenzofuranone and (3alpha,4alpha,5alpha)-4-(2-propenyl)-cholestan-3-ol; bile acid sequestrants (e.g., WELCHOL, COLESTID, LOCHOLEST and QUESTRAN; and fibric acid derivatives, such as ATROMID, LOPID and TRICOT); cholesterol ester transfer protein inhibitors (e.g., torcetrapib and (2R)-3-{[3-(4-chloro-3-ethyl-phenoxy)-phenyl]-[[3-(1,1,2,2-tetrafluoro ethoxy)phenyl]methyl]amino}-1,1,1-trifluoro-2-propanol); nicotinic acid and derivatives thereof (e.g., niacin, acipimox); PCSK9 inhibitors; LXR agonists; lipoxygenase inhibitors as disclosed by Sendobry et al., "Attenuation of diet-induced atherosclerosis in rabbits with a highly selective 15-lipoxygenase inhibitor lacking significant antioxidant properties", Brit. J. Pharmacology, 120:1199-1206 (1997), and Cornicelli et al., "15-Lipoxygenase and its Inhibition: A Novel Therapeutic Target for Vascular Disease", Current Pharmaceutical Design, 5:11-20 (1999)). Preferred hypolipidemic agents are pravastatin, lovastatin, simvastatin, atorvastatin, fluvastatin, cerivastatin, atavastatin, and rosuvastatin.

Examples of suitable anti-hypertensive agents for use in combination with the compounds of the invention include beta adrenergic blockers, calcium channel blockers (L-type and T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors (e.g., aliskiren), ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists, Dual ET/AII antagonist, neutral endopeptidase (NEP) inhibitors, vasopeptidase inhibitors (dual NEP-ACE inhibitors) (e.g., omapatrilat and gemopatrilat), nitrates, central alpha agonists (e.g., clonidine), alpha1 blockers (e.g., prazosine), arterial vasodilators (e.g., minoxidil), sympatolytics (e.g., resperine), renin inhibitors (e.g., Aliskiren).

In a further embodiment, the compound of Formula (I) may be used in combination therapy with therapeutic agents showing therapeutic benefits of GPR 119 activity modulators derived from increasing levels of GIP and PPY.

In a further embodiment, the compound of Formula (I) may be used either alone or in combination with one or more therapeutically active drug for treating, preventing and/or managing a disease or disorder caused by low bone mass such as osteoporosis, and for increasing bone mass in an individual. WO 2007/120689A2 discloses that administration of a GPR119 agonist to an individual, such as by oral administration, can act at the GPR119 receptor to increase the GIP level in the individual. One or more therapeutically active drugs can be selected from the group consisting of calcium, vitamin D, estrogen, tibolone, selective estrogen receptor modulator (SERM; e.g., raloxifene, tamoxifen), biphosphonate (e.g., etidronate, alendronate, risedronate), calcitonin, 1α-hydroxylated metabolite of vitamin D, fluoride, thiazide, anabolic steroids, ipriflavone, vitamin K, parathyroid hormone (PTH), strontium, statin, osteoprotererin, EP4 receptor selective agonists, cannabinoid receptor type 2 (CB2) selective agonists, and p38 MAP kinase inhibitors. (World Health Organization Technical Report Series 921 (2003), Prevention and Management of Osteoporosis).

In a further embodiment, the compound of Formula (I) may be used either alone or in combination with one or more therapeutically active drug for treating, preventing and/or managing a disease or disorder associated with inflammation. Examples of suitable anti-inflammatory agents for use in combination with the compounds of the invention include, but are not limited to, NSAIDS, prednisone, acetaminophen, aspirin, codeine, fentanyl, ibuprofen, indomethacin, ketorolac, morphine, naproxen, phenacetin, piroxicam, sufentanyl, sunlindac, prednisolone, methylprednisolone, dexamethazone, flucatisone, betamethasone, hydrocortisone, and beclomethasone.

The above other therapeutic agents, when employed in combination with the compounds of the invention may be used, for example, in those amounts indicated in the Physicians' Desk Reference, or as otherwise determined by one of ordinary skill in the art.

In one embodiment, the compounds of the invention can be administered in therapeutically effective amounts in combination with one or more therapeutic active agents (pharmaceutical combinations) as described above. Where compounds of the invention are administered in conjunction with other therapies, dosages of the co-administered compounds will of course vary, depending on the type of co-drug employed, on the specific drug employed, on the condition being treated and so forth. In general, compounds of the invention will be administered in therapeutically effective amounts via one or more acceptable modes known in the art, either alone or in combination with one or more therapeutic agents. A therapeutically effective amount can vary widely depending on the severity of the disease, the age and relative health of the subject, the potency of the compound used and other factors.

Method of Treatment

In one embodiment, the invention provides a compound of Formula (I) and pharmaceutical compositions thereof that are useful in treating diseases, disorders or conditions associated with the modulation of GPR119 receptors which includes, but are not limited to, treating, preventing, managing and/or slowing the progression of diabetes and related conditions, microvascular complications associated with diabetes, macrovascular complications associated with diabetes, obesity, cardiovascular diseases, and metabolic syndrome and its component conditions.

The invention further provides methods of treating diseases, disorders syndromes or conditions associated with the modulation of the GPR119 receptor in a subject in need thereof by administering to the subject a therapeutically effective amount of a compound of Formula (I) or a pharmaceutical composition thereof.

In a further embodiment the diseases, disorders or conditions associated with the modulation of the GPR119 receptors include Type 2 diabetes, Type 1 diabetes, hyperglycemia, impaired glucose tolerance, insulin resistance, hyperinsulinemia, wound healing, retinopathy, neuropathy, nephropathy, obesity, Metabolic Syndrome, lipodystrophy including HIV protease associated lipodystrophy, lipid disorders, hypertension, dyslipidemia, hyperlipidemia, hypertriglyceridemia, hypercholesterolemia, low HDL, high LDL, vascular restenosis, peripheral arterial disease, and its sequela for example acute coronary syndrome, myocardial infarction, angina pectoris, peripheral vascular disease, intermittent claudication, myocardial ischemia, stroke and heart failure.

In a further embodiment the diseases, disorders or conditions associated with the modulation of GPR119 receptor includes inflammatory diseases such as psoriasis, rheumatoid arthritis and osteoarthritis, inflammatory bowel diseases, atherosclerosis and bone diseases including osteoporosis.

General Methods of Preparation

The compounds described herein may be prepared by techniques known in the art. In addition, the compounds described herein may be prepared by following the reaction sequence as depicted in Schemes 1 to 3. Further, in the following schemes, where specific bases, acids, reagents, solvents, coupling agents, etc., are mentioned, it is understood that other bases, acids, reagents, solvents, coupling agents etc., known in the art may also be used and are therefore included within the scope of the present invention. Variations in reaction conditions, for example, temperature and/or duration of the reaction, which may be used as known in the art are also within the scope of the present invention. All the isomers of the compounds described are these schemes, unless otherwise specified, are also encompassed within the scope of this invention.

Compounds of Formula (I) may be prepared as shown in the following reaction schemes and the brief description thereof. Exemplary reagents and procedures for these reactions appear hereinafter and in the working examples. Protection and deprotection, in the schemes below, may be carried out by procedures generally known in the art (for example, Greene, T. W. and Wuts, P.G.M., Protecting Groups in Organic Synthesis, 3rd Edition, 1999 [Wiley]).

As shown in Scheme 1 wherein $\stackrel{b}{=\!=\!=}$, W, X, Z, $R_1$, $R_2$, $R_3$, $R_4$, $R_5$, $R_6$, $R_7$, $R_8$, 'n' and 'm' are as defined herein above, the compounds of formula (I) may be obtained by treating substituted compound (2) where L is a leaving group, with a piperidine compound of formula (3), where L' is a leaving group, in the presence of a base to give a compound of formula (4). This compound of formula (4) is further treated with the compound of formula (5) in the presence of palladium catalyst to give a compound of formula (I).

Scheme 1

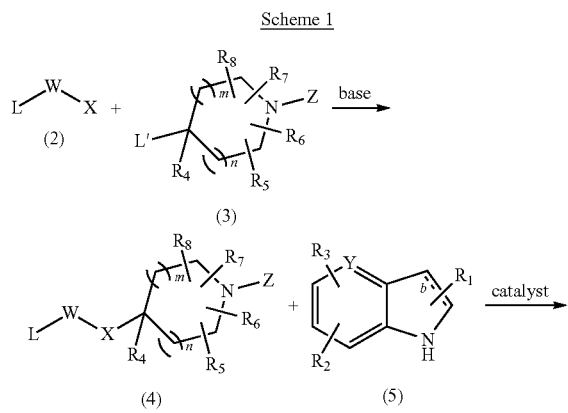

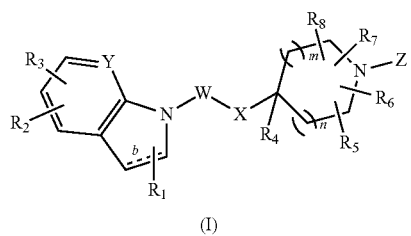

(I)

Alternatively, compounds of formula (I) may also be prepared by following the procedure as depicted in Scheme 2 wherein $\stackrel{b}{=\!=\!=}$, W, X, Z, $R_1$, $R_2$, $R_3$, $R_4$, $R_5$, $R_6$, $R_7$, $R_8$, and 'm' are as defined herein above. The compound (2) can be reacted with the compound of formula (5) in the presence of palladium catalyst to give a compound of formula (6), which on further reaction with a compound of formula (3) in the presence of a base results in a compound of formula (I).

Scheme 2

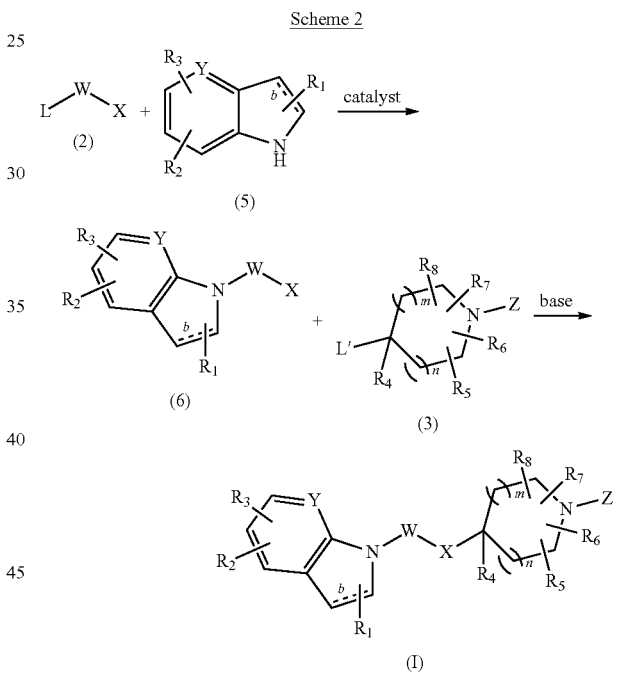

Another alternative approach to prepare the compound of formula (I), wherein $\stackrel{b}{=\!=\!=}$, W, X, Z, $R_1$, $R_2$, $R_3$, $R_4$, $R_5$, $R_6$, $R_7$, $R_8$, 'n' and 'm' are as defined herein above, is depicted in Scheme 3. A compound of formula (2) can be reacted with a piperidine compound of formula (7) in the presence of a base to give a compound of formula (8). This compound of formula (8), where PG is a protecting group, is further treated with the compound of formula (5) in presence of palladium catalyst to give a compound of formula (9). Deprotection of intermediate (9) can be carried out with appropriate reagents known to a person skilled in the art of organic synthesis.

The deprotected compound of formula (10) is then treated with Z-L where L is a leaving group such as halide, mesylate, triflate etc., by methods known in the art of organic synthesis to give compounds of formula (I).

Scheme 3

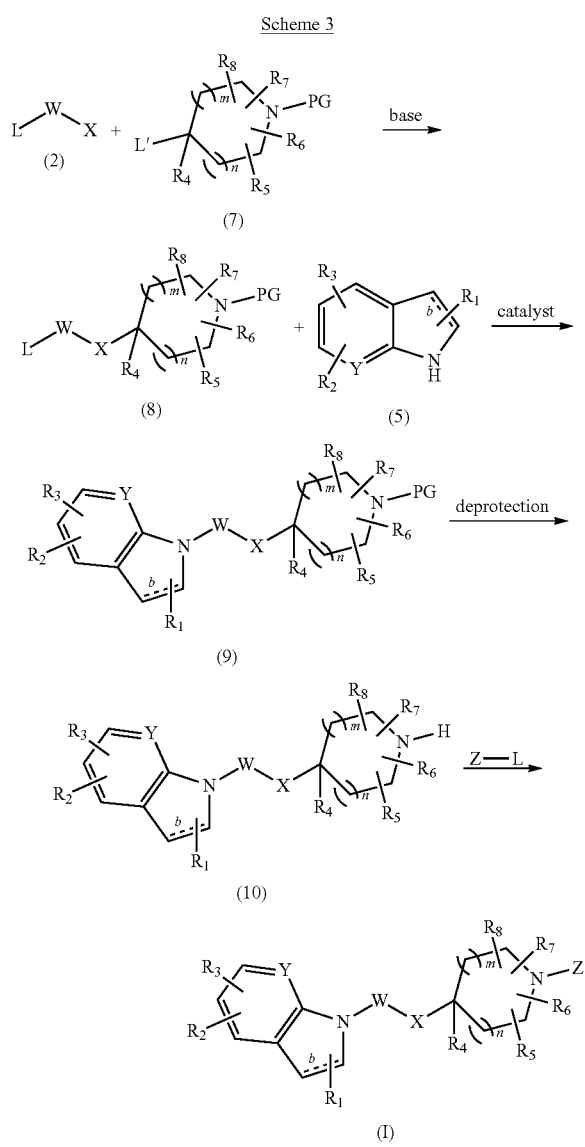

EXPERIMENTAL

Some of the representative examples of the present invention were prepared by following one or more reaction schemes as described above.

The invention is further illustrated by the following examples which are provided merely to be exemplary of the invention and do not limit the scope of the invention. The examples set forth below demonstrate the synthetic procedures for the preparation of the relative compounds. Certain modifications and equivalents will be apparent to those skilled in the art and are intended to be included within the scope of the invention. The aforementioned patents and patent applications are incorporated herein by reference.

Nomenclature of the compounds of the invention is according to ChemBioDraw version 12. Structures of the intermediates as well as the final compounds were confirmed by spectral data.

Intermediate-1

N-(1H-indol-5-yl)pivalamide

To a stirred solution of 5-Indole amine (0.6 g, 4.54 mmol) in anhydrous dichloromethane (15 mL), triethylamine (1.3 mL, 9.0 mmol) and pivaloyl chloride (0.45 mL, 5.4 mmol) were added and stirred at room temperature for 2 h. The reaction mixture was diluted with water; the organic layer was separated and concentrated in vacuo. The resultant residue was purified by flash column chromatography to give N-(1H-indol-5-yl)pivalamide (0.88 g, 89%); MS: 217.0 (M+1).

Intermediate-2

N-(1H-indol-5-yl)cyclopropanecarboxamide

The title compound was prepared by following the similar procedure as described in Intermediate-1, using 1H-indol-5-amine and cyclopropanecarbonyl chloride; MS: 201.1 (M+1).

Intermediate-3

N-((1H-indol-5-yl)methyl) isobutyramide

The title compound was prepared by following the similar procedure as described in intermediate-1, using (1H-indol-5-yl)methanamine and isobutyryl chloride (169 mg, 99%); MS: 217.0 (M+1).

Intermediate-4

(2-chloropyridin-4-yl)methyl methanesulfonate

To a stirred solution of (2-chloropyridin-4-yl)methanol (0.500 g, 3.496 mmol) in dichloromethane (15 mL), triethylamine (0.424 g, 4.195 mmol) and methanesulfonylchloride (0.440 g, 3.846 mmol) were added at 0° C. and stirred at room temperature for 2-3 h. The reaction was quenched with water and extracted with dichloromethane. The organic layer was concentrated in vacuo to give (2-chloropyridin-4-yl)methyl methanesulfonate (0.530 g, 68%); MS: 221.9 (M+1).

Intermediate-5 tert-butyl 4-((6-bromopyridin-3-yl)amino)piperidine-1-carboxylate

To a mixture of tert-butyl 4-oxopiperidine-1-carboxylate (1.15 g, 5.78 mmol) and 6-bromopyridin-3-amine (0.5 g, 2.89 mmol) in dichloroethane (20 mL), acetic acid (8 mL, 2.89 mmol) was added and the contents were stirred at room temperature for 3 h. Sodium triacetoxy borohydride (1.225 g, 5.78 mmol) was added and the contents were stirred at room temperature for 12 h. The reaction was diluted with ethyl acetate and washed with brine; the organic layer was separated and concentrated in vacuo. The resulting residue was purified by flash column chromatography to give tert-butyl 4-((6-bromopyridin-3-yl)amino)piperidine-1-carboxylate (0.638 g, 62%); MS: 357.1 (M+1)

Intermediate-6 tert-Butyl 4-((6-chloropyridin-3-yl)oxy)piperidine-1-carboxylate

To a mixture of 4-hydroxy-piperidine-1-carboxylic acid tert-butyl ester (15.5 g, 77 mmol), 2-Chloro-5-hydroxy-pyridine (9.9 g, 77 mmol) and triphenylphosphine (24.24 g, 92.4 mmol) in THF, diisopropylazodicarboxylate (18.6 g, 92.4 mmol) was added at 0° C. and stirred for 18 h. The reaction was quenched with water and the mixture was extracted with ethyl acetate. The organic layer was concentrated in vacuo, resulting residue was purified by flash column chromatography to give tert-butyl 4-((6-chloropyridin-3-yl)oxy)piperidine-1-carboxylate (11 g, 45%); MS: 335.2 (M+23).

Intermediate-7 cis(±)-tert-Butyl-4-((6-chloropyridin-3-yl)oxy)-3-fluoropiperidine-1-carboxylate The title compound was prepared by following the similar procedure as described in Intermediate-1, using 6-chloropyridin-3-ol and trans(±)-tert-butyl 3-fluoro-4-hydroxypiperidine-1-carboxylate (0.490 g, 48%); MS: 332.2 (M+1).

Intermediate-8 tert-Butyl-3-((6-chloropyridin-3-yl)oxy)pyrrolidine-1-carboxylate

The title compound was prepared by following the similar procedure as described in intermediate-6, using 6-chloropyridin-3-ol and tert-butyl 3-hydroxypyrrolidine-1-carboxylate; MS: 299.0 (M+1)

Intermediate-9 tert-Butyl-3-((6-chloropyridin-3-yl)oxy)azetidine-1-carboxylate

The title compound was prepared by following the similar procedure as described inIntermediate-6, using 6-chloropyridin-3-ol and tert-butyl 3-hydroxyazetidine-1-carboxylate (0.319 g, 64.7% yield); MS: 284.9 (M+1).

Intermediate-10

N-(1H-indol-5-yl)isobutyramide

To a stirred solution of 5-Indole amine (0.5 g, 3.78 mmol), 1-ethyl-3(3-dimethylaminopropyl)carbodiimidehydrochloride (1.45 g, 7.56 mmol), 1-hyroxybenzotriazole (0.578 g, 3.78 mmol) in anhydrous DMF (25 mL), triethylamine (1.0 mL, 7.5 mmol) and isobutyric acid (0.31 mL, 3.4 mmol) were added and stirred at room temperature for 12 h. The reaction was quenched with water and the mixture was extracted with ethyl acetate. The organic layer was concentrated in vacuo and the resultant residue was purified by flash column chromatography to give N-(1H-indol-5-yl)isobutyramide (0.596 g, 77.8%); MS: 203.1 (M+1)

Intermediate-11

N-Cyclopropyl-1H-indole-5-carboxamide

The title compound was prepared by following the similar procedure as described in Intermediate-10, using 1H-indole-5-carboxylic acid and cyclopropanamine (0.34 g, 92%); MS: 201.1 (M+1).

Intermediate-12

N,N-dimethyl-1H-indole-5-carboxamide

The title compound was prepared by following the similar procedure as described in Intermediate-10, using 1H-indole-5-carboxylic acid and dimethylamine (0.330 g, 56.6%); MS: 189.1 (M+1).

Intermediate-13

N,N-dimethylindoline-5-carboxamide

The title compound was prepared by following the similar procedure as described in Intermediate-10, using indoline-5-carboxylic acid and dimethylamine; MS: 191.1 (M+1).

Intermediate-14

N-methyl-1H-indole-5-carboxamide

The title compound was prepared by following the similar procedure as described in Intermediate-10, using 1H-indole-5-carboxylic acid and methylamine (0.320 g, 59%); MS: 175(M+1).

Intermediate-15

N-ethyl-1H-indole-5-carboxamide

The title compound was prepared by following the similar procedure as described in Intermediate-10, using 1H-indole-5-carboxylic acid and ethylamine; MS: 189.1 (M+1).

Intermediate-16

N-isopropyl-1H-indole-5-carboxamide

The title compound was prepared by following the similar procedure as described in Intermediate-10, using 1H-indole-5-carboxylic acid and propan-2-amine (0.420 g, 67%).

Intermediate-17

5-(Isopropylsulfonyl)-1H-indole

The title compound was prepared by following the similar procedure as described in Intermediate-20, using 5-iodo-1H-indole (0.610 g, 66%); MS: 224 (M+1)

Intermediate-18

(1H-indol-5-yl)(pyrrolidin-1-yl)methanone

The title compound was prepared by following the similar procedure as described in Intermediate-10, using 1H-indole-5-carboxylic acid and pyrrolidine (0.210 g, 70%).

Intermediate-19

N-(2-hydroxyethyl)-1H-indole-5-carboxamide

The title compound was prepared by following the similar procedure as described in Intermediate-10, using 1H-indole-5-carboxylic acid and 2-aminoethanol; MS: 205 (M+1).

Intermediate-20

3,3-difluoro-5-(methylsulfonyl)indolin-2-one

To a stirred solution of 5-bromo-3,3-difluoroindolin-2-one (5.0 g, 20 mmol) in DMSO (50 mL), sodium methanesulfinate (3.0 g, 30 mmol), copper(I) trifluoromethane-sulfonate benzene complex (1.52 g, 3.022 mmol) and N,N'-dimethylethylenediamine (0.33 mL, 3.022 mmol) were added and stirred at 120° C. for 14 h. The reaction was quenched with water and the mixture was extracted with ethyl acetate. The organic layer was concentrated in vacuo and resulting residue was purified by flash column chromatography to give the title product (2.9 g, 58.2%); MS: 247.9 (M+1).

Intermediate-21

5-(Methylsulfonyl)-1H-indole

The title compound was prepared by following the similar procedure as described in Intermediate-20, using 5-Iodo-1H-indole. (9.200 g, 57%); MS: 196 (M+1).

Intermediate-22

7-Fluoro-5-(methylsulfonyl)-1H-indole

The title compound was prepared by following the similar procedure as described in Intermediate-20 using 7-fluoro-5-iodo-1H-indole (0.109 g, 67%); MS: 214 (M+1).

Intermediate-23

3-Methyl-5-(methylsulfonyl)-1H-indole

The title compound was prepared by following the similar procedure as described in Intermediate-20 using 5-bromo-3-methyl-1H-indole (0.227 g, 57%); MS: 210 (M+1).

Intermediate-24

5-(Cyclopropylsulfonyl)-1H-indole

The title compound was prepared by following the similar procedure as described in Intermediate-20 using 5-iodo-1H-indole (0.400 g, 44%); MS: 222 (M+1).

Intermediate-25

5-(Methylsulfonyl)-1H-pyrrolo[2,3-b]pyridine

The title compound was prepared by following the similar procedure as described in Intermediate-20 using 5-bromo-1H-pyrrolo[2,3-b]pyridine; MS: 196.02 (M+1).

Intermediate-26

5-(Methylsulfonyl)indoline

The title compound was prepared by following the similar procedure as described in Intermediate-20, using 5-iodoindoline (0.630, 87%); MS: 198 (M+1).

Intermediate-27 tert-Butyl 5-(2-oxopyrrolidin-1-yl)-1H-indole-1-carboxylate

To a stirred mixture of tert-butyl 5-iodo-1H-indole-1-carboxylate (1.5 g, 4.3 mmol), Xant Phos (0.25 g, 0.43 mmol) and 2-pyrrolidinone (0.74 g, 8.7 mmol) in anhydrous dioxane (15 mL), cesium carbonate (2.8 g, 8.7 mmol) was added and the contents were stirred for 5 minutes. Tris(dibenzylideneacetone)-dipalladium (0)chloroform adduct (0.452 g, 0.437 mmol) was added and the reaction mixture was stirred at 110-115° C. for 6 h. The reaction mixture was cooled to room temperature and filtered over celite and filtrate was extracted with ethyl acetate. The organic layer was concentrated in vacuo and the residue was purified by flash column chromatography to yield tert-butyl 5-(2-oxopyrrolidin-1-yl)-1H-indole-1-carboxylate (0.80 g, 61%); MS: 301 (M+1).

Intermediate-28

Ethyl-1-(5-((1-(tert-butoxycarbonyl)piperidin-4-yl)oxy)pyridin-2-yl)-1H-indole-5-carboxylate The title compound was prepared by following the similar procedure as described in Intermediate-27 using tert-butyl 4-((6-chloropyridin-3-yl)oxy)piperidine-1-carboxylate and ethyl 1H-indole-5-carboxylate (0.21 g, 36%); MS: 466.2 (M+1).

Intermediate-29 tert-butyl 4-(((6-chloropyridin-3-yl)oxy)methyl)piperidine-1-carboxylate

The title compound was prepared by following the similar procedure as described in Intermediate-6 using tert-butyl 4-(hydroxymethyl)piperidine-1-carboxylate and 6-chloropyridin-3-ol (0.10 g, 54%); MS: 271 (M−56).

Intermediate-30 tert-Butyl 4-((6-(5-pivalamido-1H-indol-1-yl)pyridin-3-yl)oxy)piperidine-1-carboxylate The title compound was prepared by following the similar procedure as described in Intermediate-27, using tert-butyl 4-((6-chloropyridin-3-yl)oxy)piperidine-1-carboxylate and N-(1H-indol-5-yl)pivalamide; MS: 437.6 (M−56).

Intermediate-31 tert-Butyl 4-((6-(5-(methylsulfonyl)-1H-indol-1-yl)pyridin-3-yl)amino)-piperidine-1-carboxylate The title compound was prepared by following the similar procedure as described in Intermediate-27 using tert-butyl 4-((6-bromopyridin-3-yl)amino)piperidine-1-carboxylate and 5-(methylsulfonyl)-1H-indole; MS: 415.2 (M−56).

Intermediate-32 tert-Butyl 4-((6-(5-(methylsulfonyl)indolin-1-yl)pyridin-3-yl)amino)-piperidine-1-carboxylate The title compound was prepared by following the similar procedure as described in Intermediate-27 using tert-butyl 4-((6-bromopyridin-3-yl)amino)piperidine-1-carboxylate and 5-(methyl-sulfonyl)indoline; MS: 473.3 (M+1).

Intermediate-33 tert-Butyl 3-((6-(5-((2-hydroxyethyl)carbamoyl)-1H-indol-1-yl)pyridin-3-yl)oxy)pyrrolidine-1-carboxylate The title compound was prepared by following the similar procedure as described in Intermediate-27 using tert-butyl 3-((6-chloropyridin-3-yl)oxy)pyrrolidine-1-carboxylate and N-(2-hydroxyethyl)-1H-indole-5-carboxamide; MS: 466.5 (M+)

Intermediate-34

1-(2-((1-(5-ethylpyrazin-2-yl)piperidin-4-yl)oxy)thiazol-4-yl)-1H-indol-5-amine

The title compound was prepared by following the similar procedure as described in Intermediate-27 using 4-bromo-2-((1-(5-ethylpyrazin-2-yl)piperidin-4-yl)oxy)thiazole and tert-butyl-1H-indol-5-ylcarbamate (0.092 g, 40%); MS: 421.2 (M+1).

Intermediate-35 tert-Butyl 4-((4-(5-amino-1H-indol-1-yl)thiazol-2-yl)oxy)-piperidine-1-carboxylate The title compound was prepared by following the similar procedure as described in Intermediate-27 using tert-butyl 4((4-bromothiazol-2-yl)oxy)piperidine-1-carboxylate and tert-butyl 1H-indol-5-ylcarbamate; MS: 415.1 (M+1).

Intermediate-36

4-((6-(5-(Methylsulfonyl)-1H-indol-1-yl)pyridin-3-yl)oxy)piperidine-1-carbonitrile To a stirred solution of tert-butyl 4-((6-(5-(methylsulfonyl)-1H-indol-1-yl)pyridin-3-yl)oxy)-piperidine-1-carboxylate (0.3 g, 0.63 mmol) in dichloromethane (5 mL) trifluoroacetic acid (2.0 mL) was added at 0° C. and stirred at room temperature for 2-3 h. The solvent was removed in vacuo and the resulting residue was dissolved in dichloromethane (5 mL), triethylamine (0.193 g, 1.91 mmol) and the cyanogen bromide (0.101 g, 0.95 mmol) were added at 0° C. and stirred at room temperature for 2-3 h. The reaction was quenched with water and the mixture was extracted with ethyl acetate. The organic layer was concentrated in vacuo and the residue was purified by flash column chromatography to give 4-((6-(5-(methylsulfonyl)-1H-indol-1-yl)pyridin-3-yl)oxy)piperidine-1-carbonitrile (0.160 g, 63%); MS: 397 (M+1).

Intermediate-37

4-((6-(5-(Isopropylsulfonyl)-1H-indol-1-yl)pyridin-3-yl)oxy)piperidine-1-carbonitrile The title compound was prepared by following the similar procedure as described in Intermediate-36 using tert-butyl 4-((6-(5-(isopropylsulfonyl)-1H-indol-1-yl)pyridin-3-yl)oxy)piperidine-1-carboxylate; MS: 425.3 (M+1).

Intermediate-38

4-((6-(5-(Methylsulfonyl)-1H-indol-1-yl)pyridin-3-yl)methoxy) piperidine-1-carbonitrile The title compound was prepared by following the similar procedure as described in Intermediate-36 using tert-butyl 4-((6-(5-(methylsulfonyl)-1H-indol-1-yl)pyridin-3-yl)methoxy)piperidine-1-carboxylate (0.18 g, 93%); MS: 411.2 (M+1).

Intermediate-39

4-((6-(5-(Methylsulfonyl)indolin-1-yl)pyridin-3-yl)methoxy)piperidine-1-carbonitrile The title compound was prepared by following the similar procedure as described in Intermediate-36 using tert-butyl 4-((6-(5-(methylsulfonyl)indolin-1-yl)pyridin-3-yl) methoxy)piperidine-1-carboxylate (0.16 g, 79%); MS: 413.2 (M+1).

Intermediate-40

4-((6-(5-(Methylsulfonyl)indolin-1-yl)pyridin-3-yl)oxy)piperidine-1-carbonitrile The title compound was prepared by following the similar procedure as described in Intermediate-36 using tert-butyl 4-((6-(5-(methylsulfonyl)indolin-1-yl)pyridin-3-yl)oxy)piperidine-1-carboxylate (0.070 g, 83%); MS: 399.2 (M+1).

Intermediate-41

4-Hydroxypiperidine-1-carbonitrile

The title compound was prepared by following the described in Intermediate-36 using tert-butyl 4-hydroxypiperidine-1-carboxylate (0.340 g, 54%).

Intermediate-42 tert-Butyl 4-((6-chloropyridin-2-yl)oxy)piperidine-1-carboxylate

To a stirred solution of 4-Hydroxy-piperidine-1-carboxylic acid tert-butyl ester (1.63 g, 8.1 mmol) in THF (20 mL), NaH (0.40 g, 10.1 mmol)) was added and stirred at 60° C. for 0.5 h. 2,6-dichloropyridine (1.0 g, 6.75 mmol) was added and stirred at room temperature for 3-4-h. The reaction was quenched with water and extracted with ethyl acetate. The organic layer was concentrated in vacuo and the resultant residue was purified by flash column chromatography to yield tert-butyl 4-((6-chloropyridin-2-yl)oxy)piperidine-1-carboxylate as a pale yellow solid (0.98 g, 48%); MS: 335.1 (M+23)

Intermediate-43 tert-Butyl 4-((6-chloropyridin-3-yl)methoxy)piperidine-1-carboxylate

The title compound was prepared by following the similar procedure as described in Intermediate-42 using 4-hydroxypiperidine-1-carboxylic acid tert-butyl ester and (6-chloropyridin-3-yl)methyl methanesulfonate; MS: 227 (M−100).

Intermediate-44 tert-Butyl 4-((2-chloropyridin-4-yl)methoxy)piperidine-1-carboxylate

The title compound was prepared by following the similar procedure as described in Intermediate-42 using (2-chloropyridin-4-yl)methylmethanesulfonate (Intermediate-4) and 4-hydroxy-piperidine-1-carboxylic acid tert-butyl ester (0.215 g, 29%); MS: 327.2 (M+1).

Intermediate-45

4-Bromo-2-((1-(5-ethylpyrazin-2-yl)piperidin-4-yl)oxy)thiazole

The title compound was prepared by following the similar procedure as described in Intermediate-42 using 1-(5-ethylpyrazin-2-yl)piperidin-4-ol and 2,4-dibromothiazole (0.480 g, 54%); MS: 369.2 (M+1).

Intermediate-46 tert-Butyl 4-((4-bromothiazol-2-yl)oxy)piperidine-1-carboxylate

The title compound was prepared by following the similar procedure as described in Intermediate-42 using tert-butyl 4-hydroxypiperidine-1-carboxylate and 2,4-dibromothiazole (0.1 g, 25%); MS: 363.2 (M+1).

Intermediate-47 tert-Butyl 4-(((4-bromothiazol-2-yl)oxy)methyl)piperidine-1-carboxylate

The title compound was prepared by following the similar procedure as described in Intermediate-42, using tert-butyl 4-(hydroxymethyl)piperidine-1-carboxylate and 2,4-dibromothiazole (0.124 g, 39%); MS: 377.3 (M+1).

Intermediate-48

(6-Chloropyridin-3-yl)methyl methanesulfonate

The title compound was prepared by following the similar procedure as described in Intermediate-42 using (6-chloropyridin-3-yl)methanol; MS: 222 (M+1).

Intermediate-49

1-(3-Isopropyl-1,2,4-oxadiazol-5-yl)piperidin-4-ol

To a stirred solution of 4-hydroxypiperidine-1-carbonitrile (0.4 g, 3.1 mmol) in THF (10 mL), (E)-N'-hydroxyisobutyrimidamide (0.35 g, 35 mmol) and $ZnCl_2$ (1M solution in THF) (4.7 mL) were added and stirred at room temperature for 10 h. The reaction mixture was concentrated in vacuo and the resulting crude was dissolved in 4N HCl in ethanol-water (1:1) and stirred at 60-70° C. for 2-3 h. The reaction was quenched by saturated $NaHCO_3$ and the organic layer was separated and concentrated. The residue on column chromatography gave the title compound. (0.280 g, 41.8%)

Intermediate-50

N-(Indolin-5-yl)isobutyramide

To a stirred solution of N-(1H-indol-5-yl)isobutyramide (0.42 g, 2.9 mmol) in acetic acid (10 mL), sodium cynoborohydride (0.29 g, 4.6 mmol) was added at 0° C., and the reaction mixture was stirred at room temperature for 2-3 h. The reaction was quenched with water and neutralized by 50% NaOH solution, extracted with diethyl ether. The organic layer was separated and concentrated in vacuo to give N-(indolin-5-yl)isobutyramide (0.122 g, 28.5%); MS: 205.1 (M+1).

Intermediate-51

5-Iodoindoline

The title compound was prepared by following the similar procedure as described in Intermediate-50 using 5-iodo-1H-indole. (0.9 g, 89%); MS: 245.9 (M+1).

Intermediate-52

Ethyl 1H-indol-5-ylcarbamate

To a stirred solution of 1H-indol-5-amine (11 g, 83.2 mmol) and triethyl amine (25.22 g, 250 mmol) in dichloromethane (110 mL) at –10° C., ethyl-chloro-formate (13.5 g 124.8 mmol) was added dropwise and stirred at 0° C. for 2-3 h. The reaction was quenched with water and the mixture was extracted with ethyl acetate. The organic layer was concentrated in vacuo and the resultant residue was purified by flash column chromatography to give ethyl-1H-indol-5-ylcarbamate (5.980 g, 35.2%); MS: 205 (M+1).

Intermediate-53

1-(4-((6-Chloropyridin-3-yl)oxy)piperidin-1-yl)-2-methylpropan-2-ol

To a stirred solution of tert-butyl 4-((6-chloropyridin-3-yl)oxy)piperidine-1-carboxylate (1.0 g, 3.2 mmol) in dichloromethane (10 mL), trifluoroacetic acid (3 mL) was added at 0° C. and stirred for 3 h. The reaction mixture was concentrated in vacuo and resultant residue was dissolved in MeOH (5 mL), 2,2-dimethyloxirane (0.246 g, 3.2 mmol) was added and stirred at room temperature for 10-12 h. The reaction mixture was concentrated in vacuo to give the title product (0.775, 85%); MS: 285.0 (M+1).

Intermediate-54

2-Chloro-5-((1-(2-fluoro-2-methylpropyl)piperidin-4-yl)oxy)pyridine

To a stirred solution 1-(4-((6-chloropyridin-3-yl)oxy)piperidin-1-yl)-2-methylpropan-2-ol (0.775 g, 2.7 mmol) in dichloromethane (15 mL), deoxofluor (0.71 mL, 3.2 mmol) was added and stirred for 3 h. The reaction was quenched by saturated $NaHCO_3$ and the mixture was extracted with dichloromethane. The organic layer was separated, concentrated in vacuo and the resulting residue was purified by flash column chromatography to yield 2-chloro-5-((1-(2-fluoro-2-methylpropyl)piperidin-4-yl)oxy)pyridine; MS: 287.02 (M+1)

Intermediate-55

5-Bromo-3,3-difluoroindolin-2-one

To an ice-cooled solution of 5-Bromo isatin (7.0 g, 31.0 mmol) in dichloromethane (200 mL) in acetonitrile (20 mL), diethylaminosulfur triflouride (10.2 mL, 77.4 mmol) was added and stirred at room temperature for 20 h. The reaction mixture was cooled to 0° C.; methanol (15 mL) was added dropwise. Water (100 mL) was added to the reaction mixture and the organic layer was extracted with dichloromethane. The organic layer was concentrated in vacuo and the resulting residue was purified by flash column chromatography to yield title compound (6.1 g, 79.4%); MS: 249.53 (M+1).

Intermediate-56

3-Fluoro-5-(methylsulfonyl)-1H-indole

To a stirring solution of 3,3-difluoro-5-(methylsulfonyl) indolin-2-one (1.0 g, 4.0 mmol) in anhydrous THF (25 mL), a solution of "BH$_2$F.THF" (nominal concentration 1.3 M, 13 ml) was added at 0° C. The reaction mixture was stirred at room temperature for 16 h. The reaction mixture was brought to 0° C., aqueous HCl (3 M, 13 mL) was added dropwise. The reaction mixture was subsequently neutralized with aqueous NaOH (2.5M). The mixture was extracted with ethyl acetate, separated and concentrated in vacuo. The residue was purified by flash column chromatography to give the title compound (0.450 g, 52.3%); MS: 213.9 (M+1).

Intermediate-57

5-(1H-tetrazol-1-yl)-1H-indole

To a stirring solution of 1H-indol-5-amine (0.6 g, 4.52 mmol) in acetic acid (9 mL), sodium azide (0.42 g, 6.2 mmol) and triethoxy ethane (1.0 mL, 6.2 mmol) were added and stirred at 100° C. for 3 h. The reaction was brought to room temperature and stirred for 10-12 h. The reaction was quenched with saturated NaHCO$_3$ and the mixture was extracted with ethyl acetate. The organic layer was separated, washed with brine, dried over anhydrous NaSO$_4$ and concentrated in vacuo. Resultant residue was purified by flash column chromatography to yield 5-(1H-tetrazol-1-yl)-1H-indole. (0.174 g, 21%); MS: 186 (M+1).

Intermediate-58

5-(1H-1,2,4-triazol-1-yl)-1H-indole

To a stirred solution of 5-iodo-1H-indole (2.0 g, 8.2 mmol), 1H-1,2,4-triazole (0.511 g, 7.4 mmol), CuI (0.15 g, 0.82 mmol), K$_2$CO$_3$ (2.27 g, 16.46 mmol) and L-proline (0.511 g, 7.4 mmol) in DMF (20 mL), N,N'-dimethylethylenediamine (2.375 g 16.46 mmol) was added and stirred at 120° C. for 2-3 h. The reaction was quenched with water and the mixture was extracted with ethyl acetate. The organic layer was separated, concentrated in vacuo and the residue was purified by flash column chromatography to give 5-(1H-1,2,4-triazol-1-yl)-1H-indole (0.790 g, 52%); MS: 185 (M+1).

Intermediate-59

3-(1H-indol-5-yl)oxazolidin-2-one

The title compound was prepared by following the similar procedure as described in Intermediate-58 (0.348 g, 41%); MS: 202.8 (M+1).

Intermediate-60 tert-Butyl-4-((trimethylsilyl)oxy)-5,6-dihydropyridine-1(2H)-carboxylate

To a stirred solution of tert-butyl 4-oxopiperidine-1-carboxylate (5.0 g, 25.0 mmol) in anhydrous DMF (50 mL), trimethylsilyl chloride (3 mL, 30.1 mmol) and triethylamine (8.3 mL, 60.2 mmol) were added at 80° C. and stirred for 10-12 h. The reaction mixture was cooled to room temperature, diluted with hexane and washed with saturated NaHCO$_3$. Combined organic layers were dried over anhydrous Na$_2$SO$_4$, filtered and concentrated in vacuo and the residue was purified by flash column chromatography to give tert-butyl 4-((trimethylsilyl)oxy)-5,6-dihydropyridine-1 (2H)-carboxylate as a pale yellow oil (2.16 g, 32%); MS: 271 (M$^+$).

Intermediate-61 tert-Butyl-3-fluoro-4-oxopiperidine-1-carboxylate

To a stirred solution of tert-butyl 4-((trimethylsilyl)oxy)-5,6-dihydropyridine-1(2H)-carboxylate (2.15 g, 7.92 mmol) in anhydrous acetonitrile (20 mL), selectfluor (3.08 g, 8.71 mmol) was added and stirred at room temperature for 1-2 h. The reaction mixture was diluted with ethyl acetate and washed with saturated NaHCO$_3$ solution. The organic layer was separated, concentrated in vacuo and the residue was purified by flash column chromatography to yield tert-butyl 3-fluoro-4-oxopiperidine-1-carboxylate as a white solid (1.34 g, 78%). $^1$H NMR (400 MHz, CDCl$_3$) δ; 1.50 (s, 9H), 2.49-2.63 (m, 2H), 3.20-3.27 (m, 2H), 4.11-4.21 (m, 2H), 4.76-4.80 (m, 0.5H), 4.88-4.92 (m, 0.5H).

Intermediate-62 cis (±) and trans (±)-tert-Butyl-3-fluoro-4-hydroxypiperidine-1-carboxylate

To a stirred solution of tert-butyl-3-fluoro-4-oxopiperidine-1-carboxylate (1.3 g, 6.0 mmol) in methanol (15 mL), NaBH$_4$ (0.29 g, 7.7 mmol) was added at 0° C. and stirred for 2-3 h. Methanol was removed in vacuo and the residue was diluted with ethyl acetate and washed with water. The organic layer was separated, concentrated in vacuo and the residue was purified by flash column chromatography to give cis(±)-tert-butyl 3-fluoro-4-hydroxypiperidine-1-carboxylate (0.850 g, 65%) and trans(±)-tert-butyl 3-fluoro-4-hydroxypiperidine-1-carboxylate (0.315 g, 24%); MS: 242.1 (M+23).

Intermediate-63 trans(±)-tert-butyl-4-((6-chloropyridin-3-yl)oxy)-3-fluoropiperidine-1-carboxylate The title compound was prepared by following the similar procedure as described in Intermediate-6 using 6-chloropyridin-3-ol and cis(±)tert-butyl-3-fluoro-4-hydroxypiperidine-1-carboxylate; MS: 353.2 (M+23).

Intermediate-64

N-isopropylindoline-5-carboxamide

The title compound was prepared by following the similar procedure as described in Intermediate-10 using indoline-5-carboxylic acid and propan-2-amine (0.315 g, 31%); MS: 205 (M+1).

Intermediate-65 tert-Butyl-44(5-bromopyridin-2-yl)oxy)piperidine-1-carboxylate

The title compound was prepared by following the similar procedure as described in Intermediate-6 using 5-bromopyridin-2-ol and tert-butyl 4-hydroxypiperidine-1-carboxylate (1.49 g, 56%); MS: 357 (M+).

Intermediate-66 tert-Butyl-5-(pyrrolidin-1-yl)-1H-indole-1-carboxylate

To a stirred solution of pyrrolidine (1.43 mL, 17.47 mmol) in DMSO (15 mL), CuI (33.3 mg, 0.174 mmol)), L-proline (0.20 g, 1.75 mmol) and cesium carbonate (1.14 mg, 3.5 mmol) were added and stirred at 120° C. for 18 h. The reaction was quenched with water and the mixture was extracted with ethyl acetate. The organic layer was separated, washed with brine and dried over anhydrous sodium sulphate. The organic layer was concentrated in vacuo and the resulting residue was triturated with diethyl ether to give the title compound. (0.41 g, 82%); MS: 287.2 (M+1).

Intermediate-67

2-(1H-indol-5-yl)oxazole

To a stirred solution oxazole (0.1 g, 1.45 mmol) in anhydrous THF (3 mL), n-BuLi (1.6 mL, 1.6 mmol) was added at −78° C. and stirred for 30 minutes. The reaction mixture was brought to 0° C., $ZnCl_2.Et_2O$ (4.35 mL, 4.35 mmol) was added and stirred for 1 h. 5-iodo-1H-indole (0.352 g, 1.45 mmol) and $(Ph_3P)PdCl_2$ (0.050 g, 0.072 mmol) were added and stirred at 80° C. for 1 h. The reaction mixture was quenched with water and the mixture was extracted with ethyl acetate. The organic layer was concentrated in vacuo and the residue was purified by flash column chromatography to give 2-(1H-indol-5-yl)oxazole (0.060 g, 22%); MS: 185.0 (M+1).

Intermediate-68

N-(2,2,2-trifluoroethyl)-1H-indole-5-carboxamide

The title compound was prepared by following the similar procedure as described in Intermediate-10 using 1H-indole-5-carboxylic acid and 2,2,2-trifluoroethanamine (0.93 g, 62%); MS: 243 (M+).

Intermediate-69: tert-Butyl 1H-indol-5-ylcarbamate

To a stirred solution 1H-indol-5-amine (0.5 g, 3.78 mmol) in dichloromethane (10 mL), triethylamine (0.95 g, 9.4 mmol) and di-tert-butyl dicarbonate (0.908 g, 4.166 mmol) were added at 0° C. The reaction contents were stirred at room temperature for 4 h. The reaction was quenched with water and the mixture was extracted with ethyl acetate. The organic layer was concentrated in vacuo and the residue was purified by flash column chromatography to give tert-butyl 1H-indol-5-ylcarbamate (0.380 g, 43%); MS: 233.5 (M+1).

Intermediate-70

1-(2-((1-(3-Isopropyl-1,2,4-oxadiazol-5-yl)piperidin-4-yl)oxy)thiazol-4-yl)-1H-indol-5-amine The title compound was prepared by following the similar procedure as described in Intermediate-17 using 5-(44(4-bromothiazol-2-yl)oxy)piperidin-1-yl)-3-isopropyl-1,2,4-oxadiazole and tert-butyl 1H-indol-5-ylcarbamate.

Intermediate-71

2-chloro-1-(pyrrolidin-1-yl)ethanone

To an ice-cooled solution of pyrrolidine (0.4 g, 5.62 mmol) in dichloromethane (4 mL), triethylamine (1.176 mL, 8.44 mmol) and chloroacetyl chloride (0.451 mL, 5.62 mmol) was added. The resulting mixture was stirred at room temperature for 2 h. The reaction mixture was diluted with dichloromethane and washed with water. The organic layer was concentrated in vacuo and residue was purified by column chromatography to give title compound (0.5 g, 60.2%); MS: 147.10 (M+).

Intermediate-72

5-(4((4-Bromothiazol-2-yl)oxy)piperidin-1-yl)-3-isopropyl-1,2,4-oxadiazole

The title compound was prepared by following the similar procedure as described in Intermediate-42, using 1-(3-isopropyl-1,2,4-oxadiazol-5-yl)piperidin-4-ol and 2,4-dibromothiazole

Intermediate-73 anti-tert-Butyl-9-((6-chloropyridin-3-yl)oxy)-3-oxa-7-azabicyclo[3.3.1]-nonane-7-carboxylate The title compound was prepared by following the similar procedure as described in Intermediate-5, using tert-butyl 9-hydroxy-3-oxa-7-azabicyclo[3.3.1]nonane-7-carboxylate and 6-chloropyridin-3-ol (0.015 g, 11%); MS: 355(M+1)

Intermediate-74 syn-tert-Butyl-9-((6-chloropyridin-3-yl)oxy)-3-oxa-7-azabicyclo[3.3.1]-nonane-7-carboxylate The title compound was prepared by following the similar procedure as described in Intermediate-5, using tert-butyl 9-hydroxy-3-oxa-7-azabicyclo[3.3.1]nonane-7-carboxylate and 6-chloropyridin-3-ol (0.020 g, 14%); MS: 355(M+1)

Intermediate-75 tert-Butyl-4-((6-(5-(methylsulfonyl)-1H-indol-1-yl)pyridin-3-yl) methoxy)piperidine-1-carboxylate The title compound was prepared by following a procedure described in Intermediate-27 by using tert-butyl 4-((6-chloropyridin-3-yl)methoxy)piperidine-1-carboxylate and 5-(methylsulfonyl)-1H-indole (0.410 g, 27.70%); MS: 386.32 (M−100).

Intermediate-76 tert-Butyl-4-((6-(5-methoxy-1H-pyrrolo[2,3-b]pyridin-1-yl)pyridin-3-yl)oxy)-piperidine-1-carboxylate The title compound was prepared by following the similar procedure as described in Intermediate-27 using 5-methoxy- 1H-pyrrolo[2,3-b]pyridine and tert-butyl 4-((6-chloropyridin-3-yl)oxy)piperidine-1-carboxylate. (0.09 g, 45%); MS: 425(M+1).

Intermediate-77 tert-Butyl-4-(4-bromophenoxy)piperidine-1-carboxylate

The title compound was prepared by following the similar procedure as described in Intermediate-5 using tert-butyl 4-hydroxypiperidine-1-carboxylate and 4-bromophenol (0.65 g, 36%); MS: 256 (M−100).

Intermediate-78

Isopropyl 1H-indol-5-ylcarbamate

The title compound was prepared by following the similar procedure as described in Intermediate-52, using 1H-indol-5-amine and isopropyl-chloro-formate (0.72 g, 52%); MS: 219(M+1).

Intermediate-79 tert-Butyl-4-((((6-chloropyridin-3-yl)methyl)amino)piperidine-1-carboxylate

The title compound was prepared by following the similar procedure as described in Intermediate-5 using tert-butyl-4-oxopiperidine-1-carboxylate and tert-butyl 4-oxopiperidine-1-carboxylate (0.15 g, 36%); MS: 326.4 (M+1).

Intermediate-80 tert-Butyl-4-(4-(5-(methylsulfonyl)indolin-1-yl)phenoxy)piperidine-1-carboxylate The title compound was prepared by following the similar procedure as described in Intermediate-27 using tert-butyl-4-(4-bromophenoxy)piperidine-1-carboxylate and 5-(methylsulfonyl)indoline (0.11 g, 35%); MS: 373 (M−100).

Intermediate-81

5-(Ethylsulfonyl)-1H-indole

The title compound was prepared by following the similar procedure as described in Intermediate-20 using 5-iodo-1H-indole (0.347 g, 40%); MS: 210 (M+1).

EXAMPLES

Example-1 tert-Butyl-4-((6-(5-(methylsulfonyl)-1H-indol-1-yl)pyridin-3-yl)oxy) piperidine-1-carboxylate

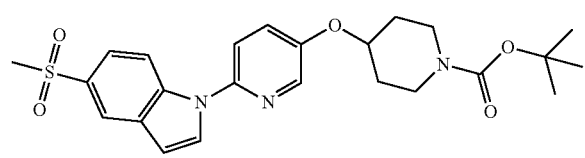 [SMILES: CC(C)(C)OC(=O)N1CCC(Oc2ccc(-n3ccc4cc(S(C)(=O)=O)ccc43)nc2)CC1]

To a mixture of 4-((6-chloropyridin-3-yl)oxy)piperidine-1-carboxylate (intermediate-6) (0.440 g, 1.4 mmol) and 5-(methylsulfonyl)-1H-indole (intermediate-21) (0.261 g, 1.3 mmol) in anhydrous dioxane (5 mL), 2-(2'-Di-tert-butylphosphine) biphenylpalladium(II)acetate (0.130 g, 0.281 mmol) and NaO$^t$Bu (sodium tert.butoxide) (0.312 g, 0.960 mmol) were added. The resultant reaction mixture was refluxed for 4-5 h. The reaction mixture was filtered over celite and filtrate was concentrated in vacuo. The residue was purified by flash column chromatography to give tert-butyl 4-((6-(5-(methylsulfonyl)-1H-indol-1-yl)pyridin-3-yl)oxy) piperidine-1-carboxylate (0.337 g, 50%).
$^1$H NMR (400 MHz, CDCl$_3$) δ; 1.47 (s, 9H), 1.82 (bs, 2H), 1.98-2.08 (m, 2H), 3.08 (s, 3H), 3.37 (bs, 2H), 3.73 (bs, 2H), 4.55 (bs, 1H), 6.82 (bs, 1H), 7.42 (bs, 2H), 7.71 (bs, 1H), 7.79 (d, J=9.2 Hz, 1H), 8.18 (d, J=8.4 Hz, 1H), 8.29 (bs, 2H); MS: 416 (M−56).

Example-2

1-(5-((1-(5-Ethylpyrimidin-2-yl)piperidin-4-yl)oxy)pyridin-2-yl)-5-(methyl sulfonyl)-1H-indole

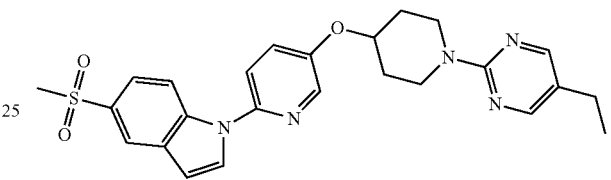

To a stirred solution of example-1 (0.1 g, 0.212 mmol) in dichloromethane (5 mL) trifluoroacetic acid (0.5 mL) was added at 0° C. and stirred at room temperature for 2-3 h. The solvent was removed in vacuo and the resulting salt was dissolved in 2-propanol (3 mL), diisopropylethylamine (0.082 g, 0.635 mmol) and 2-chloro-5-ethylpyrimidine (0.039 g, 0.275 mmol) were added and stirred at 160° C. for 3 h. The suspension was passed through celite, the filtrate was concentrated and the resulting residue was purified by flash column chromatography to give 1-(6-((1-(5-ethylpyrimidin-2-yl)piperidin-4-yl)oxy)pyridin-2-yl)-5-(methylsulfonyl)-1H-indole as white solid (0.054 g, 24%).
$^1$H NMR (400 MHz, CDCl$_3$) δ; 1.20 (t, J=7.2 Hz, 3H), 1.87-1.89 (m, 2H), 2.04-2.09 (m, 2H), 2.48 (q, J=7.6 Hz, 2H) 3.09 (s, 3H), 3.65-3.70 (m, 2H), 4.21-4.24 (m, 2H), 4.65 (bs, 1H), 6.83 (s, 1H), 7.41-7.48 (m, 2H), 7.73 (s, 1H), 7.81 (d, J=8.4 Hz, 1H), 8.20 (bs, 3H), 8.31 (bs, 2H); MS: 478 (M+1).

Example-3 tert-Butyl-4-(4-(5-(methylsulfonyl)-1H-indol-1-yl)phenoxy)-piperidine-1-carboxylate

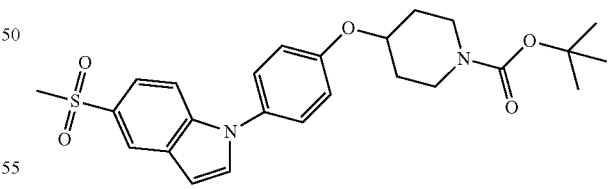

The title compound was prepared by following the similar procedure as described in Example-1 by using 5-(methylsulfonyl)-1H-indole (intermediate-21) and tert-butyl-4-(4-bromophenoxy)piperidine-1-carboxylate (intermediate-77) (0.130 g, 24%).
$^1$H NMR (400 MHz, CDCl$_3$) δ; 1.49 (s, 9H), 1.85-1.86 (m, 2H), 1.96-2.01 (m, 2H), 3.09 (s, 3H), 3.36-3.43 (m, 2H), 3.71-3.77 (m, 2H), 4.54-4.56 (m, 1H), 6.80 (dd, J=3.2, 0.4 Hz, 1H), 7.07, (dd, J=6.8, 2.4 Hz, 2H), 7.38 (dd, J=6.8, 2.0 Hz, 2H), 7.42 (d, J=3.2 Hz, 1H), 7.54 (d, J=8.8 Hz, 1H), 7.74 (dd, J=1.6, 8.4 Hz, 1H), 8.33 (d, J=4 Hz, 1H); MS: 471 (M+1).

Example-4

3-Isopropyl-5-(4-((6-(5-(methylsulfonyl)-1H-indol-1-yl)pyridin-3-yl)oxy) piperidin-1-yl)-1,2,4-oxadiazole

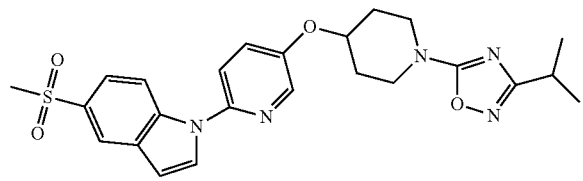 [SMILES: CC(C)c1noc(N2CCC(Oc3ccc(-n4ccc5cc(S(C)(=O)=O)ccc54)nc3)CC2)n1]

Step A: 4-((6-(5-(Methylsulfonyl)-1H-indol-1-yl)pyridin-3-yl)oxy)piperidine-1-carbonitrile To a stirred solution of example-1 (0.3 g, 0.63 mmol) in dichloromethane (5 mL) trifluoroacetic acid (2.0 mL) was added at 0° C. and stirred at room temperature for 2-3 h. The solvent was removed in vacuo and the resulting salt was dissolved in dichloromethane (5 mL). Triethylamine (0.193 g, 1.91 mmol) and the cyanogen bromide (0.101 g, 0.95 mmol) were added at 0° C. and stirred at room temperature for 2-3 h. The reaction mixture was quenched with water and the mixture was extracted with ethyl acetate. The organic layer was concentrated in vacuo and purified by flash column chromatography to give 4-((6-(5-(methylsulfonyl)-1H-indol-1-yl)pyridin-3-yl)oxy)piperidine-1-carbonitrile (intermediate-36) (0.160 g, 63%); MS: 397.46 (M+1).

Step B: 3-Isopropyl-5-(4-((6-(5-(methylsulfonyl)-1H-indol-1-yl)pyridin-3-yl) oxy)-piperidin-1-yl)-1,2,4-oxadiazole To a mixture of 4-((6-(5-(methylsulfonyl)-1H-indol-1-yl)pyridin-3 yl)oxy)piperidine-1-carbonitrile (intermediate-36) (0.110 g, 0.27 mmol) and N-hydroxy-isobutyramidine (0.05 g, 0.5 mmol) in anhydrous THF (15 mL), 1M solution of zinc chloride in THF (0.56 mL, 0.56 mmol) was added. The suspension was stirred at room temperature for 18 h. Solvent was concentrated in vacuo, the resulting crude was dissolved in 4N HCl in ethanol, water (1:1) and stirred at 60-70° C. for 2-3 h. The reaction was quenched by saturated NaHCO$_3$ and the organic layer was separated and concentrated. The residue was purified by flash column chromatography to give 3-isopropyl-5-(4-((6-(5-(methylsulfonyl)-1H-indol-1-yl)pyridin-3-yl)oxy)piperidin-1-yl)-1,2,4-oxadiazole (0.041 g, 30%)

$^1$H NMR (400 MHz, CDCl$_3$) δ; 1.29 (d, J=6.8 Hz, 6H), 1.98-2.01 (m, 2H), 2.07-2.10 (s, 2H), 2.88-2.92 (m, 1H), 3.09 (s, 3H), 3.65-3.69 (m, 2H), 3.84-3.88 (m, 2H), 4.66 (bs, 1H), 6.82-6.83 (d, J=2.8 Hz, 1H), 7.44 (bs, 2H), 7.72 (d, J=2.8 Hz, 1H), 7.80 (d, J=8.8 Hz, 1H), 8.20 (d, J=8.8 Hz, 1H), 8.30 (bs, 2H); MS: 482 (M+1).

Example-5 tert-Butyl-4-(((6-(5-(methylsulfonyl)-1H-indol-1-yl)pyridin-3-yl)oxy)methyl)piperidine-1-carboxylate

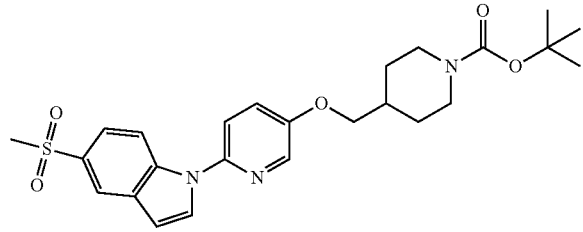 [SMILES: CC(C)(C)OC(=O)N1CCC(COc2ccc(-n3ccc4cc(S(C)(=O)=O)ccc43)nc2)CC1]

The title compound was prepared by following the similar procedure as described in Example-1 using 5-(methylsulfonyl)-1H-indole (intermediate-21) and tert-butyl 4-(((6-chloropyridin-3-yl)oxy)methyl)piperidine-1-carboxylate (intermediate-29) (0.188 g, 11%).

$^1$H NMR (400 MHz, CDCl$_3$) δ; 1.23-1.29 (m, 2H), 1.45 (s, 9H), 1.83-1.86 (m, 2H), 2.00 (bs, 1H), 2.73-2.79 (m, 2H), 3.07 (s, 3H), 3.90-3.91 (m, 2H), 4.17 (m, 2H), 6.81 (s, 1H), 7.39 (s, 2H), 7.69 (bs, 1H), 7.77-7.79 (m, 2H), 8.14-8.16 (m, 1H), 8.24-8.28 (m, 1H); MS: 430 (M–56).

Example-6

1-(5-(((1-(5-Ethylpyrimidin-2-yl)piperidin-4-yl)methoxy)pyridin-2-yl)-5-(methylsulfonyl)-1H-indole

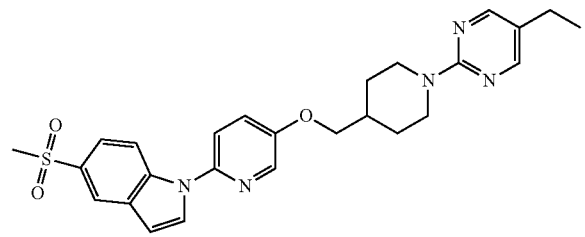 [SMILES: CCc1cnc(N2CCC(COc3ccc(-n4ccc5cc(S(C)(=O)=O)ccc54)nc3)CC2)nc1]

The title compound was prepared by following the similar procedure as described in Example-2 by using Example-5 (0.012 g, 11%).

$^1$H NMR (400 MHz, CDCl$_3$) δ; 1.22 (t, J=7.6 Hz, 3H), 1.37-1.46 (m, 2H), 1.97-2.06 (m, 2H), 2.11-2.17 (m 1H), 2.49 (q, J=7.6 Hz, 2H), 2.92-2.96 (m, 2H), 3.11 (s, 3H), 3.97 (d, J=6.4 Hz, 2H), 4.83 (m, 2H), 6.84 (dd, J=2.8, 0.4 Hz, 1H), 7.43 (d, J=2.0 Hz, 2H), 7.74 (d, J=3.6 Hz, 1H), 7.82 (dd, J=7.2, 1.6 Hz, 1H), 8.17 (s, 1H), 8.20 (s, 1H), 8.21 (bs 1H), 8.29 (t, J=2.0, 1.6 Hz, 1H), 8.32 (d, J=1.6 Hz, 1H); MS: 492 (M+1).

Example-7

3-Isopropyl-5-(4-(((6-(5-(methylsulfonyl)-1H-indol-1-yl)pyridin-3-yl)oxy) methyl)piperidin-1-yl)-1,2,4-oxadiazole

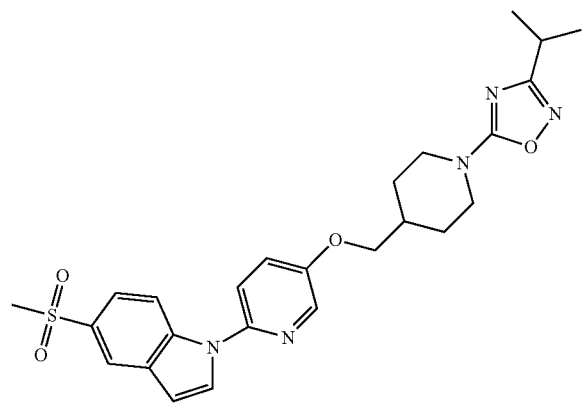 [SMILES: CC(C)c1noc(N2CCC(COc3ccc(-n4ccc5cc(S(C)(=O)=O)ccc54)nc3)CC2)n1]

The title compound was prepared by following the similar procedure as described in Example-4 by using Example-5 (0.012 g, 12%).

$^1$H NMR (400 MHz, CDCl$_3$) δ; 1.30 (d, J=7.2 Hz, 6H), 1.49-1.56 (m, 2H), 1.97-2.00 (m, 2H), 2.05-2.14 (m, 1H), 2.87-2.94 (m, 1H), 3.09 (s, 3H), 3.10-3.17 (m, 2H), 3.96 (d,

J=6.4 Hz, 2H), 4.23-4.27 (m, 2H), 6.83 (dd, J=3.2, 0.4 Hz, 1H), 7.42 (d, J=1.6 Hz, 2H), 7.72 (d, J=3.6 Hz, 1H), 7.80 (dd, J=6.8, 2.0 Hz, 1H), 8.17 (d, J=8.8 Hz, 1H), 8.27 (m, 1H), 8.30 (d, J=1.6 Hz, 1H); MS: 496 (M+1).

Example-8 tert-Butyl-4-((6-(5-((ethoxycarbonyl)amino)-1H-indol-1-yl)pyridin-3-yl)oxy)piperidine-1-carboxylate

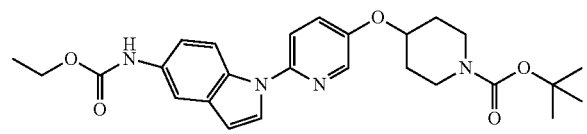 [SMILES: CCOC(=O)Nc1ccc2c(ccn2-c2ccc(OC3CCN(C(=O)OC(C)(C)C)CC3)cn2)c1]

The title compound was prepared by following the similar procedure as described in Example-1 using tert-butyl 4-((6-chloropyridin-3-yl)oxy)piperidine-1-carboxylate (intermediate-06) and ethyl 1H-indol-5-ylcarbamate (intermediate-52) (6.0 g, 35%).

¹H NMR (400 MHz, CDCl₃) δ: 1.32 (t, J=7.2 Hz, 3H), 1.48 (s, 9H), 1.76-1.84 (m, 2H), 1.95-2.00 (m, 2H), 3.33-3.39 (m, 2H), 3.71-3.77 (m, 2H), 4.21 (q, J=7.2 Hz, 2H), 4.49-4.52 (m, 1H), 6.59 (bs, 1H), 6.63 (d, J=3.2 Hz, 1H), 7.18 (d, J=9.2 Hz, 1H), 7.38 (dd, J=10.4, 8.0 Hz, 2H), 7.60 (d, J=3.2 Hz, 1H), 7.75 (bs, 1H), 7.99 (d, J=8.8 Hz, 1H), 8.23 (d, J=2 Hz, 1H); MS: 481 (M+1).

Example-9

Ethyl(1-(5-((1-(5-ethylpyrimidin-2-yl)piperidin-4-yl)oxy)pyridin-2-yl)-1H-indol-5-yl)carbamate

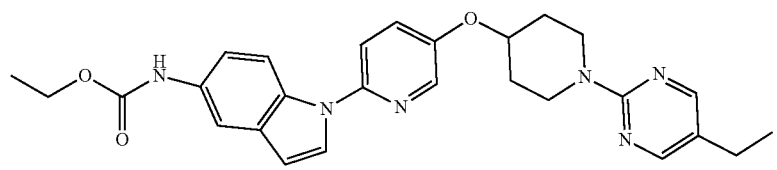 [SMILES: CCOC(=O)Nc1ccc2c(ccn2-c2ccc(OC3CCN(c4ncc(CC)cn4)CC3)cn2)c1]

The title compound was prepared by following the similar procedure as described in Example-2 by using Example-8 (1.4 g, 23%).

¹H NMR (400 MHz, CDCl₃) δ: 1.21 (t, J=7.6 Hz, 3H), 1.33 (t, J=6.8 Hz, 3H), 1.86-1.89 (m, 2H), 2.06-2.09 (m, 2H), 2.78 (q, J=7.6 Hz, 2H), 3.63-3.70 (m, 2H), 4.20-4.28 (m, 2H), 4.60 (bs, 1H), 6.59 (bs, 1H), 6.64 (d, J=3.2 Hz, 1H), 7.18 (d, J=8.8 Hz, 1H), 7.41 (bs, 2H), 7.62 (d, J=3.2 Hz, 1H), 7.76 (bs, 1H), 8.01 (d, J=8.8 Hz, 1H), 8.20 (bs, 2H), 8.27 (d, J=1.2 Hz, 1H); MS: 487 (M+1).

Example-10 tert-Butyl-4-((6-(5-(ethylsulfonyl)-1H-indol-1-yl)pyridin-3-yl)oxy)piperidine-1-carboxylate

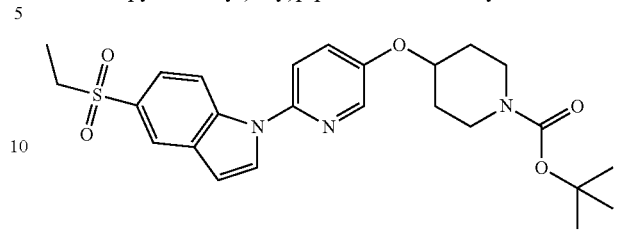

The title compound was prepared by following the similar procedure as described in Example-1 by using tert-butyl-4-((6-chloropyridin-3-yl)oxy)piperidine-1-carboxy late (intermediate-6) and 5-(ethylsulfonyl)-1H-indole (intermediate-81).

¹H NMR (400 MHz, CDCl₃) δ: 1.27 (t, J=7.2 Hz, 3H), 1.48 (s, 9H), 1.79-1.83 (m, 2H), 1.97-2.02 (m, 2H), 3.15 (q, J=7.2 Hz, 2H), 3.36-3.40 (m, 2H), 3.71-3.77 (m, 2H), 4.55-4.57 (m, 1H), 6.82 (dd, J=3.6, 0.8 Hz, 1H), 7.40-7.45 (m, 2H), 7.71 (d, J=3.6 Hz, 1H), 7.75 (dd, J=8.8, 2.0 Hz, 1H), 8.18 (d, J=8.8 Hz, 1H), 8.25-8.28 (m, 2H); MS: 430.1 (M–56).

Example-11

1-(5-((1-(5-Ethylpyrimidin-2-yl)piperidin-4-yl)oxy)pyridin-2-yl)-5-(ethyl sulfonyl)-1H-indole

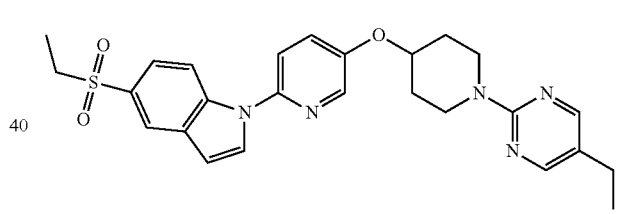

The title compound was prepared by following the similar procedure as described in Example-2 by using Example-10.

¹H NMR (400 MHz, CDCl₃) δ: 1.19 (t, J=7.2 Hz, 3H), 1.24 (t, J=7.6 Hz, 3H), 1.86-1.89 (m, 2H), 2.06-2.09 (m, 2H), 2.47 (q, J=7.6 Hz, 2H), 3.15 (q, J=7.6 Hz, 2H), 3.65-3.70 (m, 2H), 4.18-4.24 (m, 2H), 4.63 (bs, 1H), 6.82 (dd, J=3.6, 0.8 Hz, 1H), 7.43-7.47 (m, 2H), 7.71-7.72 (d, J=3.6 Hz, 1H), 7.75 (dd, J=8.8, 2.0 Hz, 1H), 8.18-8.20 (m, 3H), 8.25 (d, J=1.2 Hz, 1H), 8.30 (m, 1H); MS: 492.1 (M+1).

Example-12

2-Methyl-1-(4-((6-(5-(methylsulfonyl)-1H-indol-1-yl)pyridin-3-yl)oxy) piperidin-1-yl)propan-2-ol

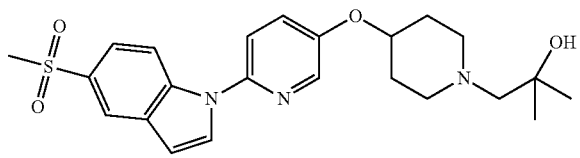 [SMILES: CC(C)(O)CN1CCC(Oc2ccc(-n3ccc4cc(S(C)(=O)=O)ccc43)nc2)CC1]

To a stirred solution of Example-1 (0.4 g, 0.848 mmol) in dichloromethane (5 mL) trifluoroacetic acid (0.065 mL, 0.848 mmol) was added at 0° C. and stirred for 3 h. The reaction mixture was concentrated in vacuo and the resultant residue was dissolved in methanol (5 mL), 2,2-dimethyloxirane (0.061 g, 0.85 mmol) was added and stirred at room temperature for 18 h. Methanol was concentrated in vacuo and the resultant residue was purified by flash column chromatography to give 2-methyl-1-(4-((6-(5-(methylsulfonyl)-1H-indol-1-yl)pyridin-3-yl)oxy)piperidin-1-yl)propan-2-ol (0.279 g, 74%).

$^1$H NMR (400 MHz, CDCl$_3$) δ; 1.20 (s, 6H), 1.88-1.92 (m, 2H), 2.06 (bs, 2H), 2.39 (s, 2H), 2.59-2.63 (m, 2H), 2.93-2.95 (m, 2H), 3.10 (s, 3H), 4.43 (bs, 1H), 6.840-6.849 (m, 1H), 7.41-7.43 (m, 2H), 7.73 (d, J=3.6 Hz, 1H), 7.81 (dd, J=8.8, 1.6 Hz, 1H), 8.20 (d, J=8.8 Hz, 1H), 8.28-8.31 (m, 2H); MS: 444.2 (M+1).

Example-13

1-(4-((6-(5-(Ethylsulfonyl)-1H-indol-1-yl)pyridin-3-yl)oxy)piperidin-1-yl)-2-methylpropan-2-ol

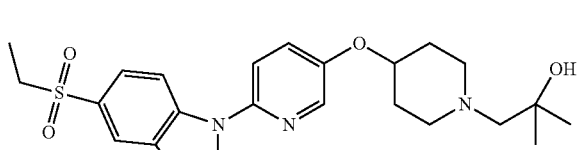

The title compound was prepared by following the similar procedure as described in Example-12 by using Example-10.

$^1$H NMR (400 MHz, CDCl$_3$) δ; 1.20 (s, 6H), 1.27 (t, J=7.2 Hz, 3H), 1.92 (bs, 2H), 2.06 (bs, 2H), 2.35-2.39 (bs, 2H), 2.61-2.63 (m, 2H), 2.95 (bs, 2H), 3.17 (q, J=7.6 Hz, 2H), 4.43 (bs, 1H), 6.83-6.84 (m, 1H), 7.41-7.46 (m, 2H), 7.73 (d, J=3.6 Hz, 1H), 7.77 (dd, J=8.8, 2.0 Hz, 1H), 8.19 (d, J=8.8 Hz, 1H), 8.27-8.29 (m, 2H); MS: 458.08 (M+1).

Example-14

1-(5-((1-(2-Fluoro-2-methylpropyl)piperidin-4-yl)oxy)pyridin-2-yl)-5-(methylsulfonyl)-1H-indole

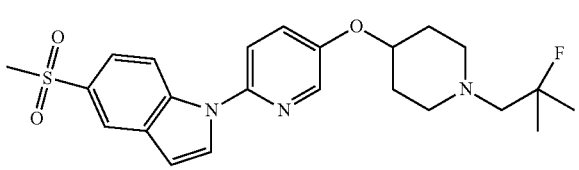 [SMILES: CC(C)(F)CN1CCC(Oc2ccc(-n3ccc4cc(S(C)(=O)=O)ccc43)nc2)CC1]

To a stirred solution of example-12 (0.25 g, 0.564 mmol) in dichloromethane (15 mL) deoxofluor (0.11 mL, 0.62 mmol) was added at 20° C. and stirred for 3 h. The reaction was quenched by the addition of saturated. NaHCO$_3$ solution. The mixture was extracted with dichloromethane, concentrated in vacuo and the residue was purified by flash column chromatography to give 1-(5-((1-(2-fluoro-2-methylpropyl)piperidin-4-yl)oxy)pyridin-2-yl)-5-(methylsulfonyl)-1H-indole (0.170 g, 67%).

$^1$H NMR (400 MHz, CDCl$_3$) δ; 1.37 (d, J=21.6 Hz, 6H), 1.85-1.90 (m, 2H), 2.03 (bs, 2H), 2.42-2.50 (m, 4H), 2.88-2.90 (m, 2H), 3.08 (s, 3H), 4.35-4.39 (m, 1H), 6.81 (d, J=2.8 Hz, 1H), 7.38-7.43 (m, 2H), 7.71 (d, J=3.6 Hz, 1H), 7.79 (dd, J=8.8, 2.0 Hz, 1H), 8.17 (d, J=8.8 Hz, 1H), 8.26-8.29 (m, 2H); MS: 446.2 (M+1).

Example-15

5-(Ethylsulfonyl)-1-(5-((1-(2-fluoro-2-methylpropyl)piperidin-4-yl)oxy) pyridin-2-yl)-1H-indole

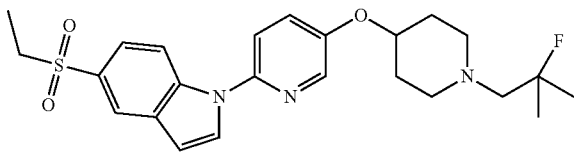 [SMILES: CCS(=O)(=O)c1ccc2c(ccn2-c2ccc(OC3CCN(CC(C)(C)F)CC3)cn2)c1]

The title compound was prepared by following the similar procedure as described in Example-14 by using Example-13.

$^1$H NMR (400 MHz, CDCl$_3$) δ; 1.27 (t, J=7.2 Hz, 3H), 1.38 (d, J=21.6 Hz, 6H), 1.83-1.91 (m, 2H), 2.01-2.03 (m, 2H), 2.42-2.51 (m, 4H), 2.87-2.90 (m, 2H), 3.15 (q, J=7.2 Hz, 2H), 4.36-4.40 (m, 1H), 6.82 (d, J=3.2 Hz, 1H), 7.39-7.44 (m, 2H), 7.71 (d, J=3.2 Hz, 1H), 7.75 (dd, J=8.8, 2.0 Hz, 1H), 8.18 (d, J=8.8 Hz, 1H), 8.25-8.27 (m, 2H); MS: 460.2 (M+1).

Example-16 tert-Butyl-4-((6-(5-(isopropylsulfonyl)-1H-indol-1-yl)pyridin-3-yl)oxy) piperidine-1-carboxylate

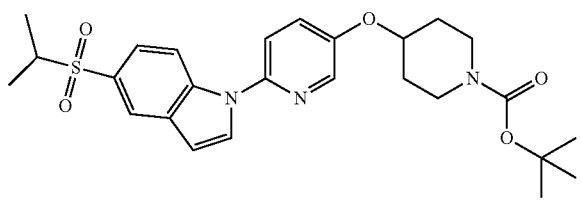 [SMILES: CC(C)S(=O)(=O)c1ccc2c(ccn2-c2ccc(OC3CCN(C(=O)OC(C)(C)C)CC3)cn2)c1]

The title compound was prepared by following the similar procedure as described in Example-1, using tert-Butyl 4-((6-chloropyridin-3-yl)oxy)piperidine-1-carboxylate (intermediate-6) and 5-(Isopropylsulfonyl)-1H-indole (intermediate-17).

$^1$H NMR (400 MHz, CDCl$_3$) δ; 1.30-1.33 (m, 6H), 1.59 (s, 9H), 1.82-1.85 (m, 2H), 1.98-2.00 (m, 2H), 3.23-3.26 (m, 1H), 3.36-3.43 (m, 2H), 3.73-3.78 (m, 2H), 4.58 (bs, 1H), 6.83-6.84 (m, 1H), 7.44-7.45 (m, 2H), 7.72 (d, J=3.6 Hz, 1H), 7.75 (dd, J=8.8, 2.0 Hz, 1H), 8.19 (d, J=8.8 Hz, 1H), 8.24 (d, J=1.6 Hz, 1H), 8.29-8.30 (m, 1H); MS: 500.09 (M+1).

Example-17

1-(5-((1-(5-Ethylpyrimidin-2-yl)piperidin-4-yl)oxy)pyridin-2-yl)-5-(iso propylsulfonyl)-1H-indole

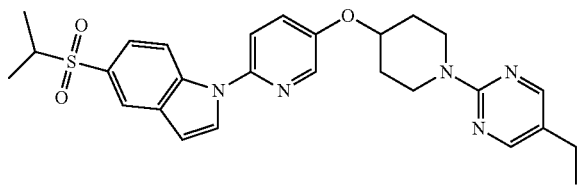 [SMILES: CCc1cnc(N2CCC(Oc3ccc(-n4ccc5cc(S(=O)(=O)C(C)C)ccc54)nc3)CC2)nc1]

The title compound was prepared by following the similar procedure as described in Example-2 by using Example-16.

$^1$H NMR (400 MHz, CDCl$_3$) δ; 1.22 (t, J=7.6 Hz, 3H), 1.32 (d, J=6.8 Hz, 6H), 1.87-1.93 (m, 2H), 2.09-2.14 (m, 2H), 2.50 (q, J=7.6 Hz, 2H), 3.25-3.27 (m, 1H), 3.66-3.72 (m, 2H), 4.21-4.27 (m, 2H), 4.64-4.67 (m, 1H), 6.84 (d, J=3.2 Hz, 1H), 7.43-7.50 (m, 2H), 7.73-7.77 (m, 2H), 8.19-8.25 (m, 4H), 8.32 (s, 1H); MS: 506.09 (M+1).

Example-18

5-(4-((6-(5-(Isopropylsulfonyl)-1H-indol-1-yl)pyridin-3-yl)oxy)piperidin-1-yl)-3-methyl-1,2,4-oxadiazole

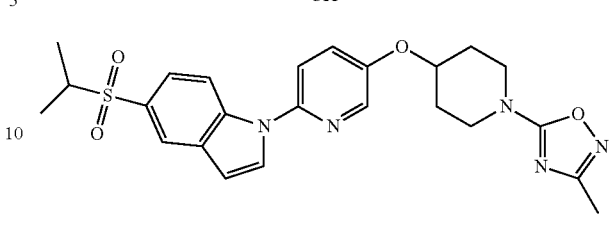

The title compound was prepared by following the similar procedure as described in Example-4 by using Example-16 (0.027 g, 12%).

$^1$H NMR (400 MHz, CDCl$_3$) δ; 1.29 (d, J=7.2 Hz, 6H), 2.02-2.18 (m, 4H), 2.25 (s, 3H), 3.23-3.26 (m, 1H), 3.67-3.73 (m, 2H), 3.84-3.90 (m, 2H), 4.69-4.70 (m, 1H), 6.84 (d, J=3.6 Hz, 1H), 7.46-7.47 (m, 2H), 7.73 (d, J=3.6 Hz, 1H), 7.76 (dd, J=8.8, 1.6 Hz, 1H), 8.21 (d, J=8.8 Hz, 1H), 8.24 (d, J=1.6 Hz, 1H), 8.31-8.32 (m, 1H); MS: 482.17 (M+1).

Example-19 tert-Butyl-4-((6-(5-((2-hydroxyethyl)carbamoyl)-1H-indol-1-yl)pyridin-3-yl)amino)piperidine-1-carboxylate

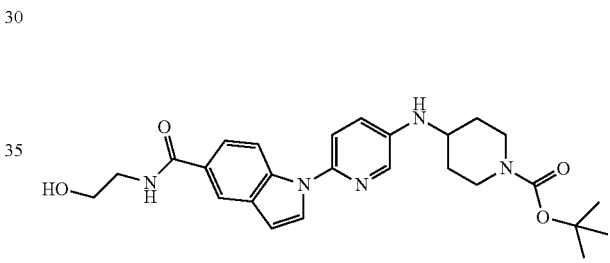

The title compound was prepared by following the similar procedure as described in Example-1 by using tert-butyl 4-((6-bromopyridin-3-yl)amino)piperidine-1-carboxylate (intermediate-5) and N-(2-hydroxyethyl)-1H-indole-5-carboxamide (intermediate-19)

$^1$H NMR (400 MHz, CDCl$_3$) δ; 1.29-1.49 (m, 2H), 1.52 (s, 9H), 2.10 (d, J=10.8 Hz, 2H), 2.97 (t, J=12 Hz, 2H), 3.46-3.51 (m, 1H), 3.66-3.70 (m, 2H), 3.87-3.89 (m, 2H), 4.10 (m, 2H), 6.70-6.74 (m, 2H), 7.09 (dd, J=8.8, 3.2 Hz, 1H), 7.31 (d, J=8.8 Hz, 1H), 7.62 (d, J=3.6 Hz, 1H), 7.70 (dd, J=8.8, 2.0 Hz, 1H), 7.93-7.99 (m, 2H), 8.14 (d, J=1.2 Hz, 1H); MS: 482.3 (M+1).

Example-20

1-(5-((1-(5-Ethylpyrimidin-2-yl)piperidin-4-yl)amino)pyridin-2-yl)-N-(2-hydroxyethyl)-1H-indole-5-carboxamide

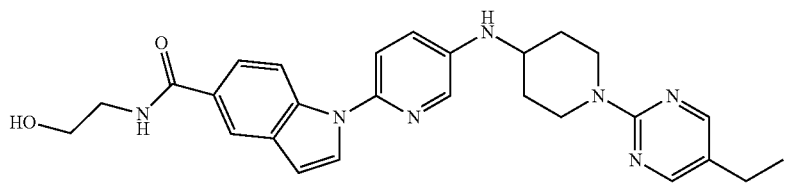 [SMILES: CCc1cnc(N2CCC(Nc3ccc(-n4ccc5cc(C(=O)NCCO)ccc54)nc3)CC2)nc1]

The title compound was prepared by following the similar procedure as described in Example-2 by using Example-19.

¹H NMR (400 MHz, CDCl₃) δ: 1.22 (t, J=7.6 Hz, 3H), 1.44-1.54 (m, 2H), 2.21 (d, J=10.8 Hz, 2H), 2.50 (q, J=7.6 Hz, 2H), 3.19 (t, J=11.6 Hz, 2H), 3.62 (m, 1H), 3.67-3.71 (m, 2H), 3.87-3.90 (m, 2H), 4.68-4.71 (m, 2H), 6.68 (s, 1H), 6:74 (d, J=3.6 Hz, 1H), 7.12 (dd, J=8.8, 2.8 Hz, 1H), 7.32 (d, J=8.4 Hz, 1H), 7.63 (d, J=3.6 Hz, 1H), 7.69-7.71 (m. 1H), 7.96 (d, J=8.8 Hz, 1H), 8.01 (d, J=2.8 Hz, 1H), 8.14 (d, J=1.2 Hz, 1H), 8.22 (s, 2H); MS: 486.05 (M+1).

Example-21 tert-Butyl 4-((6-(5-(dimethylcarbamoyl)-1H-indol-1-yl)pyridin-3-yl) amino)piperidine-1-carboxylate

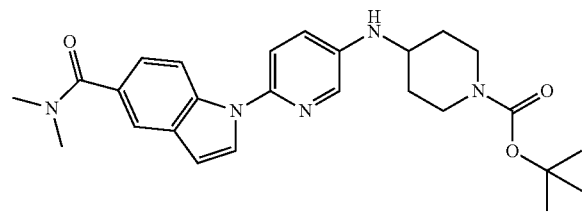 [SMILES: CN(C)C(=O)c1ccc2c(ccn2-c2ccc(NC3CCN(C(=O)OC(C)(C)C)CC3)cn2)c1]

The title compound was prepared by following the similar procedure as described in Example-1 by using tert-butyl 4-((6-bromopyridin-3-yl)amino)piperidine-1-carboxylate (intermediate-5) and N,N-dimethyl-1H-indole-5-carboxamide (intermediate-12).

¹H NMR (400 MHz, DMSO-d₆) δ; 1.24-1.28 (m, 2H), 1.41 (s, 9H), 1.93 (m, J=10.8 Hz, 2H), 2.89 (s, 1H), 2.99 (s, 6H), 3.53 (s, 1H), 3.89 (d, J=11.2 Hz, 2H), 5.94 (d, J=8 Hz, 1H), 6.70 (d, J=3.2 Hz, 1H), 7.20-7.25 (m, 2H), 7.45 (d, J=8.8 Hz, 1H), 7.68 (s, 1H), 7.84 (d, J=3.2 Hz, 1H), 7.95-7.97 (m, 1H), 8.02 (d, J=8.8 Hz, 1H); MS: 464.2 (M+1).

Example-22

1-(5-((1-(5-Ethylpyrimidin-2-yl)piperidin-4-yl)amino)pyridin-2-yl)-N,N-dimethyl-1H-indole-5-carboxamide

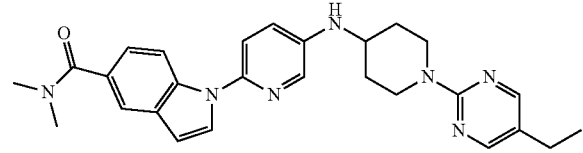 [SMILES: CCc1cnc(N2CCC(Nc3ccc(-n4ccc5cc(C(=O)N(C)C)ccc54)nc3)CC2)nc1]

The title compound was prepared by following the similar procedure as described in Example-2 by using Example-21.

¹H NMR (400 MHz, DMSO-d₆) δ; 1.16 (t, J=7.6 Hz, 3H), 1.29-1.38 (m, 2H), 2.00 (d, J=9.6 Hz, 2H), 2.43 (q, J=7.6 Hz, 2H), 2.99 (s, 6H), 3.14 (t, J=11.2 Hz, 2H), 3.57-3.65 (m, 1H), 4.52 (d, J=13.6 Hz, 2H), 5.95 (d, J=8.4 Hz, 1H), 6.71 (d, J=3.2 Hz, 1H), 7.22-7.26 (m, 2H), 7.46 (d, J=8.8 Hz, 1H), 7.68 (d, J=1.2 Hz, 1H), 7.84 (d, J=3.2 Hz, 1H), 7.98-8.04 (m, 2H), 8.25 (m, 2H); MS: 470.2 (M+1).

Example-23

2-Methyl-1-(4-((6-(5-(methylsulfonyl)-1H-indol-1-yl)pyridin-3-yl)oxy) piperidin-1-yl)propan-1-one

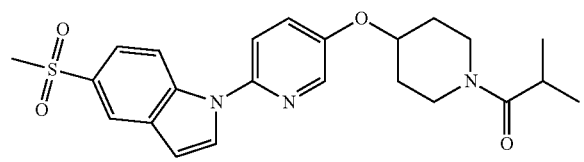 [SMILES: CC(C)C(=O)N1CCC(Oc2ccc(-n3ccc4cc(S(C)(=O)=O)ccc43)nc2)CC1]

To a stirred solution of Example-1 (0.120 g, 0.254 mmol) in dichloromethane (5 mL), trifluoroacetic acid (1 mL) was added at 0° C. and stirred for 2-3 h. The reaction mixture was concentrated in vacuo and the resultant residue was dissolved in dichloromethane (10 mL), triethylamine (0.3 mL, 2.036 mmol), N-Ethyl-N'-(3-dimethylaminopropyl) carbodiimide hydrochloride (0.073 g, 0.38 mmol) and isobutyric acid (0.025 g, 0.28 mmol) were added sequentially and stirred at room temperature for 2 h. The reaction was quenched with water and the organic layer was extracted with ethyl acetate, separated dried over Na₂SO₄ and concentrated in vacuo. The resultant residue was purified by flash column chromatography to give 2-methyl-1-(4-((6-(5-(methylsulfonyl)-1H-indol-1-yl)pyridin-3-yl)oxy)piperidin-1-yl)propan-1-one (41 mg, 36%).

¹H NMR (400 MHz, CDCl₃) δ; 1.14 (d, J=6.8 Hz, 6H), 1.86-2.20 (m, 4H), 2.80-2.86 (m, 1H), 3.07 (s, 3H), 3.45-3.51 (m, 1H), 3.63-3.66 (m, 1H), 3.76-3.87 (m, 2H), 4.60-4.64 (m, 1H), 6.81 (d, J=3.2 Hz, 1H), 7.41 (dd, J=3.6, 2.8 Hz, 2H), 7.71 (d, J=3.2 Hz, 1H), 7.78 (dd, J=8.8, 2.0 Hz, 1H), 8.18 (d, J=8.8 Hz, 1H), 8.27 (dd, J=4.0, 1.6 Hz, 2H); MS: 442 (M+1).

Example-24

(±)-tert-Butyl-34(6-(5-(methylsulfonyl)-1H-indol-1-yl)pyridin-3-yl)oxy) pyrrolidine-1-carboxylate

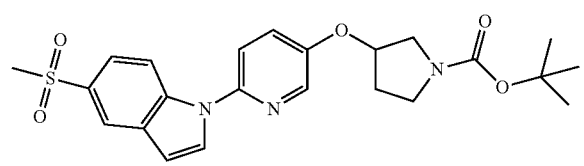 [SMILES: CC(C)(C)OC(=O)N1CCC(Oc2ccc(-n3ccc4cc(S(C)(=O)=O)ccc43)nc2)C1]

The title compound was prepared by following the similar procedure as described in Example-1 by using (±)-tert-butyl 3-((6-chloropyridin-3-yl)oxy)pyrrolidine-1-carboxylate (intermediate-8) and 5-(methylsulfonyl)-1H-indole (intermediate-21).

¹H NMR (400 MHz, CDCl₃) δ; 1.45 (s, 9H), 2.16-2.21 (m, 2H), 3.06 (s, 3H), 3.53-3.67 (m, 4H), 4.96 (s, 1H), 6.80 (s, 1H), 7.38 (s, 2H), 7.69-7.78 (m, 2H), 8.17-8.27 (m, 3H); MS: 480.05 (M+23).

Example-25

(±)-1-(5-((1-(5-Ethylpyrimidin-2-yl)pyrrolidin-3-yl)oxy)pyridin-2-yl)-5-(methylsulfonyl)-1H-indole

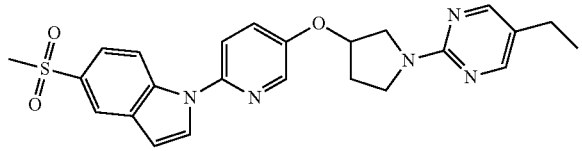 [SMILES: CCc1cnc(N2CCC(Oc3ccc(-n4ccc5cc(S(C)(=O)=O)ccc54)nc3)C2)nc1]

The title compound was prepared by following the similar procedure as described in Example-2 by using Example-24.

$^1$H NMR (400 MHz, CDCl$_3$) δ; 1.18 (t, J=7.6 Hz, 3H), 2.32-2.50 (m, 4H), 3.08 (s, 3H), 3.72-3.79 (m, 1H), 3.85-3.88 (m, 3H), 5.12-5.14 (m, 1H), 6.82 (d, J=3.2 Hz, 1H), 7.412-7.417 (m, 2H), 7.71 (d, J=3.6 Hz, 1H), 7.79 (dd, J=8.8, 2.0 Hz, 1H), 8.17 (d, J=8.8 Hz, 1H), 8.20 (s, 2H), 8.26-8.29 (m, 2H); MS: 464.11 (M+1).

Example-26

(±)-5-(Methylsulfonyl)-1-(5-((1-(4-(trifluoromethyl)benzyl)pyrrolidin-3-yl)oxy)pyridin-2-yl)-1H-indole

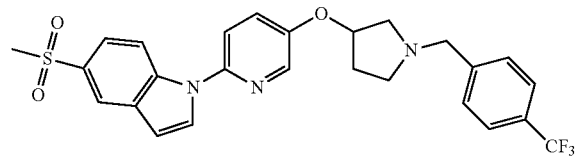 [SMILES: CS(=O)(=O)c1ccc2c(ccn2-c2ccc(OC3CCN(Cc4ccc(C(F)(F)F)cc4)C3)cn2)c1]

To a stirred solution of Example-24 (0.100 g, 0.218 mmol) in dichloromethane (4 mL) trifluoroacetic acid (1 mL) was added at 0° C. and stirred for 2 h. The reaction contents were concentrated in vacuo and the resultant residue was dissolved in N,N'-dimethylformamide (5 mL), triethylamine (0.283 mL, 2.1 mmol), K$_2$CO$_3$ (0.283 g, 2.1 mmol) and 1-(chloromethyl)-4-(trifluoromethyl)benzene (0.081 g, 0.42 mmol) were added, stirred at 65° C. for 7 h. The reaction contents were cooled to room temperature, quenched with water and the organic layer was extracted with dichloromethane. The organic layer was separated, concentrated in vacuo and the resultant residue was purified by flash column chromatography to give 5-(methylsulfonyl)-1-(5-((1-(4-(trifluoromethyl)benzyl)pyrrolidin-3-yl)oxy)pyridin-2-yl)-1H-indole (0.023 g, 20%).

$^1$H NMR (400 MHz, CDCl$_3$) δ; 2.09 (bs, 1H), 2.37-2.43 (m, 1H), 2.63 (bs, 1H), 2.87 (bs, 2H), 3.00 (bs, 1H), 3.10 (s, 3H), 3.76-3.78 (m, 2H), 4.94 (bs, 1H), 6.84 (d, J=2.8 Hz, 1H), 7.37-7.43 (m, 2H), 7.49-7.51 (m, 2H), 7.60-7.62 (m, 2H), 7.72-7.73 (m, 1H), 7.80-7.82 (m, 1H), 8.18-8.22 (m, 2H), 8.31 (s, 1H); MS: 515.9 (M$^+$).

Example-27 tert-Butyl-3-((6-(5-(methylsulfonyl)-1H-indol-1-yl)pyridin-3-yl)oxy)-azetidine-1-carboxylate

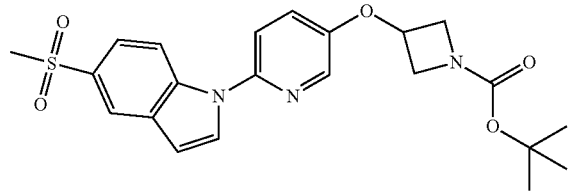 [SMILES: CC(C)(C)OC(=O)N1CC(Oc2ccc(-n3ccc4cc(S(C)(=O)=O)ccc43)nc2)C1]

The title compound was prepared by following the similar procedure as described in Example-1 by using tert-butyl 3-((6-chloropyridin-3-yl)oxy)azetidine-1-carboxylate (intermediate-9) and 5-(methylsulfonyl)-1H-indole (intermediate-21).

$^1$H NMR (400 MHz, CDCl$_3$) δ; 1.48 (s, 9H), 3.10 (s, 3H), 4.07-4.11 (m, 2H), 4.37-4.41 (m, 2H), 4.99-5.02 (m, 1H), 6.85 (d, J=3.6 Hz, 1H), 7.32 (dd, J=8.8, 2.8 Hz, 1H), 7.45 (d, J=8.8 Hz, 1H), 7.74 (d, J=3.2 Hz, 1H), 7.82 (dd, J=8.8, 2.0 Hz, 1H), 8.14 (d, J=2.8 Hz, 1H), 8.22 (d, J=8.8 Hz, 1H), 8.31 (d, J=1.6 Hz, 1H); MS: 466.0 (M+23).

Example-28

1-(5-((1-(5-Ethylpyrimidin-2-yl)azetidin-3-yl)oxy)pyridin-2-yl)-5-(methylsulfonyl)-1H-indole

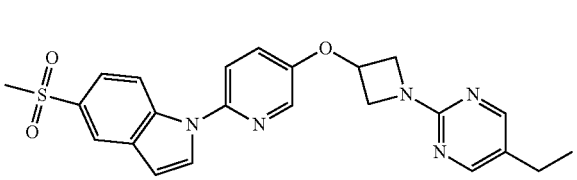 [SMILES: CCc1cnc(N2CC(Oc3ccc(-n4ccc5cc(S(C)(=O)=O)ccc54)nc3)C2)nc1]

The title compound was prepared by following the similar procedure as described in Example-2 by using Example-27.

$^1$H NMR (400 MHz, CDCl$_3$) δ; 1.22 (t, J=7.6 Hz, 3H), 2.52 (q, J=7.6 Hz, 2H), 3.11 (s, 3H), 4.26-4.29 (m, 2H), 4.59-4.63 (m, 2H), 5.17-5.20 (m, 1H), 6.85 (dd, J=3.2, 0.4 Hz, 1H), 7.35-7.38 (m, 1H), 7.46 (d, J=8.8 Hz, 1H), 7.74 (d, J=3.6 Hz, 1H), 7.82 (dd, J=8.8, 1.6 Hz, 1H), 8.19-8.21 (m, 2H), 8.23 (s, 2H), 8.31 (d, J=1.6 Hz, 1H); MS: 450.0 (M+1).

Example-29

5-(Methylsulfonyl)-1-(5-((1-(4-(trifluoromethyl)benzyl)azetidin-3-yl)oxy)pyridin-2-yl)-1H-indole

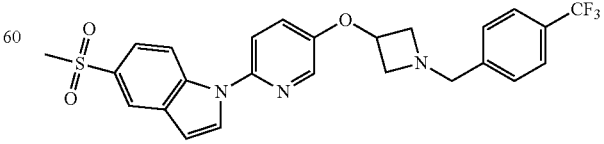

The title compound was prepared by following the similar procedure as described in Example-26 by using Example-27.

¹H NMR (400 MHz, CDCl₃) δ; 3.10 (s, 3H), 3.27-3.30 (m, 2H), 3.80 (s, 2H), 3.87-3.91 (m, 2H), 4.92-4.95 (m, 1H), 6.84 (d, J=3.6 Hz, 1H), 7.30-7.33 (m, 1H), 7.41-7.46 (m, 3H), 7.60-7.62 (m, 2H), 7.72 (d, J=3.6 Hz, 1H), 7.81 (dd, J=8.8, 2.0 Hz, 1H), 8.16 (d, J=2.8 Hz, 1H), 8.19 (d, J=8.8 Hz, 1H), 8.31 (d, J=1.2 Hz, 1H); MS: 502.0 (M+1).

Example-30

1-(5-((1-Isobutylpiperidin-4-yl)oxy)pyridin-2-yl)-5-(methylsulfonyl)-1H-indole

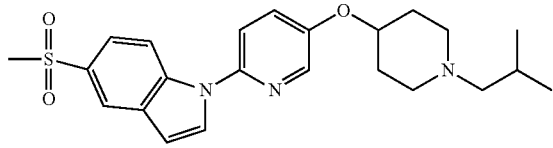 [SMILES: CC(C)CN1CCC(Oc2ccc(-n3ccc4cc(S(C)(=O)=O)ccc43)nc2)CC1]

To a stirred solution of Example-23 (0.350 g, 0.8 mmol) in THF (15 mL), LiAlH₄ (0.060 g, 1.585 mmol) was added at 0° C. and stirred at room temperature for 18 h. The reaction contents were poured into ice cold water and the organic layer was extracted with ethyl acetate, separated and concentrated in vacuo. The resultant residue was purified by flash column chromatography to give 1-(5-((1-isobutylpiperidin-4-yl)oxy)pyridin-2-yl)-5-(methylsulfonyl)-1H-indole (0.025 g, 7.38%).

¹H NMR (400 MHz, CDCl₃) δ; 0.95 (d, J=6.4 Hz, 6H), 1.93 (m, 4H), 2.13 (m, 5H), 2.83 (m, 2H), 3.10 (s, 3H), 4.48 (m, 1H), 6.84 (d, J=3.2 Hz, 1H), 7.40-7.45 (m, 2H), 7.73 (d, J=3.2 Hz, 1H), 7.81 (dd, J=8.8, 2.0 Hz, 1H), 8.19 (d, J=8.8 Hz, 1H), 8.28-8.31 (m, 2H); MS: 428.2 (M+1).

Example-31 tert-Butyl-4-((6-(5-(methylsulfonyl)-1H-pyrrolo[2,3-b]pyridin-1-yl)-pyridin-3-yl)oxy)piperidine-1-carboxylate

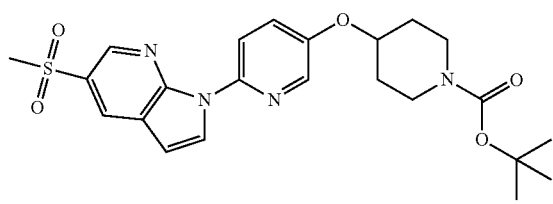 [SMILES: CC(C)(C)OC(=O)N1CCC(Oc2ccc(-n3ccc4cc(S(C)(=O)=O)cnc43)nc2)CC1]

The title compound was prepared by following the similar procedure as described in Example-1 by using tert-Butyl 4-((6-chloropyridin-3-yl)oxy)piperidine-1-carboxylate (intermediate-6) and 5-(methylsulfonyl)-1H-pyrrolo[2,3-b]pyridine (intermediate-25).

¹H NMR (400 MHz, CDCl₃) δ; 1.49 (s, 9H), 1.78-1.86 (m, 2H), 1.97-2.06 (m, 2H), 3.16 (s, 3H), 3.35-3.41 (m, 2H), 3.72-3.78 (m, 2H), 4.54-4.58 (m, 1H), 6.80 (d, J=4.0 Hz, 1H), 7.48 (dd, J=9.2, 2.8 Hz, 1H), 8.21 (d, J=2.8 Hz, 1H), 8.42 (d, J=3.6 Hz, 1H), 8.53 (d, J=2.4 Hz, 1H), 8.68 (d, J=8.8 Hz, 1H), 8.93 (d, J=2.0 Hz, 1H); MS: 417 (M−56).

Example-32

1-(5-((1-(5-Ethylpyrimidin-2-yl)piperidin-4-yl)oxy)pyridin-2-yl)-5-(methyl sulfonyl)-1H-pyrrolo[2,3-b]pyridine

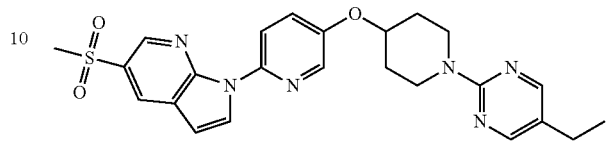

The title compound was prepared by following the similar procedure as described in Example-2 by using Example-31.

¹H NMR (400 MHz, CDCl₃) δ; 1.23 (t, J=7.6 Hz, 3H), 1.82-1.92 (m, 2H), 2.07-2.12 (m, 2H), 2.49 (q, J=7.6 Hz, 2H), 3.16 (s, 3H), 3.67-3.72 (m, 2H), 4.19-4.25 (m, 2H), 4.63-4.66 (m, 1H), 6.80 (d, J=4.0 Hz, 1H), 7.51 (dd, J=8.8, 2.8 Hz, 1H), 8.21 (s, 2H), 8.24 (d, J=2.8 Hz, 1H), 8.43 (d, J=3.6 Hz, 1H), 8.53 (d, J=1.2 Hz, 1H), 8.68 (d, J=8.8 Hz, 1H), 8.93 (d, J=2.0 Hz, 1H); MS: 479 (M+1)

Example-33

1-(5-((1-(2-Fluoro-2-methylpropyl)piperidin-4-yl)oxy)pyridin-2-yl)-5-(methylsulfonyl)-1H-pyrrolo[2,3-b]pyridine

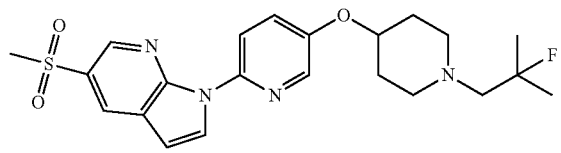 [SMILES: CC(C)(F)CN1CCC(Oc2ccc(-n3ccc4cc(S(C)(=O)=O)cnc43)nc2)CC1]

The title compound was prepared by following the similar procedure as described in Example-12 and Example-14 by using Example-31.

¹H NMR (400 MHz, CDCl₃) δ; 1.39 (d, J=21.2 Hz, 6H), 1.89 (bs, 2H), 2.04 (bs, 2H), 2.46-2.52 (m, 4H), 2.89 (bs, 2H), 3.16 (s, 3H), 4.38 (bs, 1H), 6.80 (d, J=3.6 Hz, 1H), 7.47 (dd, J=8.8, 2.8 Hz, 1H), 8.21 (d, J=2.8 Hz, 1H), 8.41 (d, J=4.0 Hz, 1H), 8.52 (d, J=2.0 Hz, 1H), 8.64 (d, J=8.8 Hz, 1H), 8.93 (d, J=2.4 Hz, 1H); MS: 447.4 (M+1)

Example-34

2,2-Dimethyl-1-(4-((6-(5-(methylsulfonyl)-1H-indol-1-yl)pyridin-3-yl) oxy)piperidin-1-yl)propan-1-one

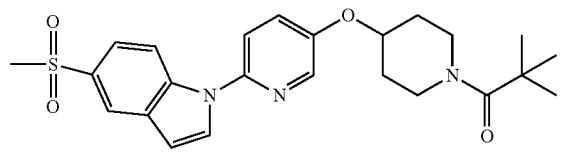 [SMILES: CC(C)(C)C(=O)N1CCC(Oc2ccc(-n3ccc4cc(S(C)(=O)=O)ccc43)nc2)CC1]

The title compound was prepared by following the similar procedure as described in Example-23 by using Example-1.

$^1$H NMR (400 MHz, CDCl$_3$) δ; 1.33 (s, 9H), 1.86-1.92 (m, 2H), 2.02-2.07 (m, 2H), 3.10 (s, 3H), 3.62-3.68 (m, 2H), 3.89-3.95 (m, 2H), 4.64-4.67 (m, 1H), 6.85 (d, J=3.2 Hz, 1H), 7.45 (d, J=2.4 Hz, 2H), 7.74 (d, J=3.2 Hz, 1H), 7.82 (dd, J=9.2, 2.0 Hz, 1H), 8.21 (d, J=8.8 Hz, 1H), 8.30-8.32 (m, 2H); MS: 456.2 (M+1).

Example-35

5-(Methylsulfonyl)-1-(5-((1-neopentylpiperidin-4-yl)oxy)pyridin-2-yl)-1H-indole

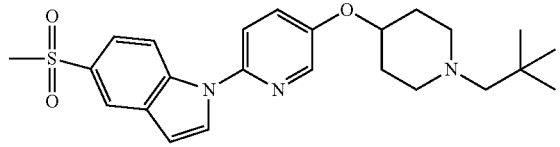 [SMILES: CC(C)(C)CN1CCC(Oc2ccc(-n3ccc4cc(S(C)(=O)=O)ccc43)nc2)CC1]

The title compound was prepared by following the similar procedure as described in Example-30 by using Example-34.

$^1$H NMR (400 MHz, CDCl$_3$) δ; 0.89 (s, 9H), 1.84-1.90 (m, 2H), 2.01-2.04 (m, 2H), 2.11 (s, 2H), 2.43-2.49 (m, 2H), 2.80-2.85 (m, 2H), 3.10 (s, 3H), 4.34-4.38 (m, 1H), 6.84 (d, J=3.2 Hz, 1H), 7.42-7.43 (m, 2H), 7.73 (d, J=3.6 Hz, 1H), 7.81 (dd, J=8.8, 1.6 Hz, 1H), 8.19 (d, J=8.8 Hz, 1H), 8.28-8.31 (m, 2H); MS: 442.2 (M+1).

Example-36 tert-Butyl-4-((6-(5-(methylsulfonyl)indolin-1-yl)pyridin-3-yl)oxy)-piperidine-1-carboxylate

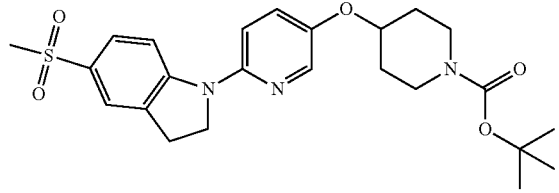 [SMILES: CC(C)(C)OC(=O)N1CCC(Oc2ccc(N3CCc4cc(S(C)(=O)=O)ccc43)nc2)CC1]

The title compound was prepared by following the similar procedure as described in Example-1 by using tert-butyl 4-((6-chloropyridin-3-yl)oxy)piperidine-1-carboxylate (intermediate-6) and 5-(methylsulfonyl)indoline (intermediate-26) (0.160 g, 48.0%).

$^1$H NMR (400 MHz, CDCl$_3$) δ; 1.49 (s, 9H), 1.71-1.79 (m, 2H), 1.91-1.96 (m, 2H), 3.02 (s, 3H), 3.24-3.34 (m, 4H), 3.70-3.76 (m, 2H), 4.12 (t, J=2.4 Hz, 2H), 4.38-4.41 (m, 1H), 6.79 (d, J=9.2 Hz, 1H), 7.28 (dd, J=9.2, 3.2 Hz, 1H), 7.65 (d, J=1.6 Hz, 1H), 7.72 (dd, J=8.8, 2.0 Hz, 1H), 8.11 (d, J=3.2 Hz, 1H), 8.16 (d, J=8.4 Hz, 1H); MS: 474 (M+1).

Example-37

1-(5-((1-(5-Ethylpyrimidin-2-yl)piperidin-4-yl)oxy)pyridin-2-yl)-5-(methyl sulfonyl)indoline

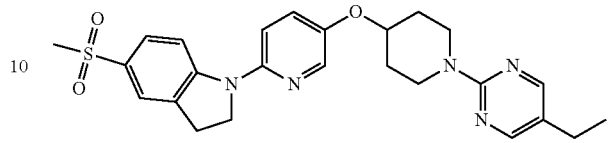

The title compound was prepared by following the similar procedure as described in Example-2 by using Example-36 (0.15 g, 25%)

$^1$H NMR (400 MHz, CDCl$_3$) δ; 1.92 (t, J=7.6 Hz, 3H), 1.79-1.83 (m, 2H), 2.01-2.04 (m, 2H), 2.47 (q, J=7.6 Hz, 2H), 3.02 (s, 3H), 3.26 (t, J=17.2 Hz, 2H), 3.57-3.63 (m, 2H), 4.12 (t, J=17.6 Hz, 2H), 4.18-4.23 (m, 2H), 4.48-4.49 (m, 1H), 6.80 (d, J=8.8 Hz, 1H), 7.32 (dd, J=8.8, 3.2 Hz, 1H), 7.65 (d, J=1.6 Hz, 1H), 7.72 (dd, J=8.4, 2.0 Hz, 1H), 8.13-8.18 (m, 4H); MS: 480.2 (M+1).

Example-38

3-Isopropyl-5-(4-((6-(5-(methylsulfonyl)indolin-1-yl)pyridin-3-yl)oxy)-piperidin-1-yl)-1,2,4-oxadiazole

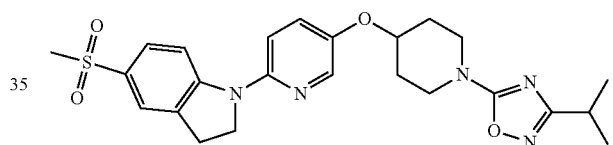

The title compound was prepared by following the similar procedure as described in Example-4 by using Example-36 (0.017 g, 20%).

$^1$H NMR (400 MHz, CDCl$_3$) δ; 1.32 (d, J=2.8 Hz, 6H), 1.93-1.97 (m, 2H), 1.98-2.08 (m, 2H), 2.80-2.95 (m, 1H), 3.05 (s, 3H), 3.29 (t, J=17.2 Hz, 2H), 3.61-3.67 (m, 2H), 3.83-3.90 (m, 2H), 4.14 (t, J=17.6 Hz, 2H), 4.51-4.55 (m, 1H), 6.82 (d, J=9.2 Hz, 1H), 7.33 (dd, J=8.8, 2.8 Hz, 1H), 7.68 (d, J=1.6 Hz, 1H), 7.75 (dd, J=8.4, 2.0 Hz, 1H), 8.15 (dd, J=8.4, 2.8 Hz, 1H), 8.22 (d, J=8.4 Hz, 1H); MS: 484.2 (M+1).

Example-39 tert-Butyl-4-((6-(5-(dimethylcarbamoyl)-1H-indol-1-yl)pyridin-3-yl)oxy) piperidine-1-carboxylate

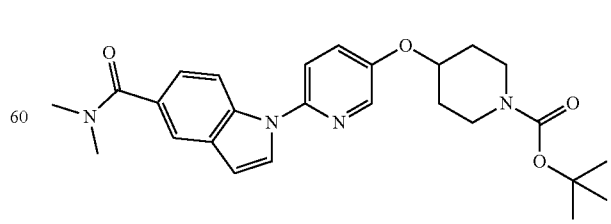

The title compound was prepared by following the similar procedure as described in Example-1 by using tert-butyl 4-((6-chloropyridin-3-yl)oxy)piperidine-1-carboxylate (intermediate-6) and N,N-dimethyl-1H-indole-5-carboxamide (intermediate-12).

¹H NMR (400 MHz, DMSO-d₆) δ; 1.41 (s, 9H), 1.53-1.61 (m, 2H), 1.94-1.98 (m, 2H), 2.99 (s, 6H), 3.17-3.20 (m, 2H), 3.67-3.73 (m, 2H), 4.67-4.72 (m, 1H), 6.77 (d, J=3.2 Hz, 1H), 7.28 (dd, J=8.4, 1.6 Hz, 1H), 7.70 (d, J=1.2 Hz, 3H), 7.99 (d, J=3.6 Hz, 1H), 8.22 (d, J=8.4 Hz, 1H), 8.33 (t, J=1.6, 1H); MS: 465.3 (M+1).

Example-40

1-(5-((1-(5-Ethylpyrimidin-2-yl)piperidin-4-yl)oxy)pyridin-2-yl)-N,N-dimethyl-1H-indole-5-carboxamide

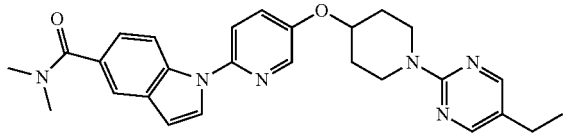

The title compound was prepared by following the similar procedure as described in Example-2 by using Example-39.

¹H NMR (400 MHz, CDCl₃) δ; 1.20 (t, J=7.6 Hz, 3H), 1.85-1.89 (m, 2H), 2.07-2.11 (m, 2H), 2.48 (q, J=7.6 Hz, 2H), 3.08 (s, 6H), 3.65-3.70 (m, 2H), 4.19-4.25 (m, 2H), 4.60-4.63 (m, 1H), 6.72 (d, J=2.8 Hz, 1H), 7.36 (dd, J=8.4, 1.6 Hz, 1H), 7.44 (m, 2H), 7.65 (d, J=3.6 Hz, 1H), 7.76 (d, J=0.8 Hz, 1H), 8.06 (d, J=8.8 Hz, 1H), 8.20 (s, 2H), 8.29 (t, J=2 Hz, 1H); MS: 471.3 (M+1).

Example-41 tert-Butyl-4-((6-(5-(methylsulfonyl)-1H-indol-1-yl)pyridin-3-yl)-methoxy) piperidine-1-carboxylate The title compound was prepared by following the similar procedure as described in Example-1 by using 5-(methylsulfonyl)-1H-indole (intermediate-21) and tert-butyl 4-((6-chloropyridin-3-yl)methoxy)piperidine-1-carboxylate (intermediate-43).

¹H NMR (400 MHz, CDCl₃) δ; 1.44 (s, 9H), 1.58-1.63 (m, 2H), 1.88 (bs, 2H), 3.07 (s, 3H), 3.08-3.15 (m, 2H), 3.61-3.63 (m, 1H), 3.76 (bs, 2H), 4.61 (s, 2H), 6.82-6.83 (m, 1H), 7.45 (d, J=8.4 Hz, 1H), 7.77-7.81 (m, 2H), 7.87 (dd, J=8.0, 2.0 Hz, 1H), 8.27 (d, J=1.6 Hz, 1H), 8.35 (d, J=8.8 Hz, 1H), 8.53 (bs, 1H); MS: 484.3 (M+1).

Example-42

1-(5-(((1-(5-Ethylpyrimidin-2-yl)piperidin-4-yl)oxy)methyl)pyridin-2-yl)-5-(methylsulfonyl)-1H-indole

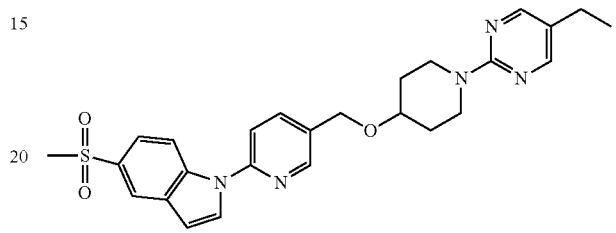

The title compound was prepared by following the similar procedure as described in Example-2 by using Example-41.

¹H NMR (400 MHz, CDCl₃) δ; 1.20 (t, J=7.6 Hz, 3H), 1.64-1.73 (m, 2H), 2.00-2.04 (m, 2H), 2.46 (q, J=7.6 Hz, 2H), 3.09 (s, 3H), 3.36-3.42 (m, 2H), 3.72-3.76 (m, 1H), 4.29-4.35 (m, 2H), 4.67 (s, 2H), 6.85 (d, J=3.6 Hz, 1H), 7.48 (d, J=8.4 Hz, 1H), 7.80-7.83 (m, 2H), 7.91 (dd, J=8.8, 2.0 Hz, 1H), 8.17 (s, 2H), 8.29 (s, 1H), 8.37 (d, J=8.8 Hz, 1H), 8.57 (s, 1H); MS: 492.2 (M+1).

Example-43 tert-Butyl-4-((6-(5-(dimethylcarbamoyl)indolin-1-yl)pyridin-3-yl)oxy)-piperidine-1-carboxylate

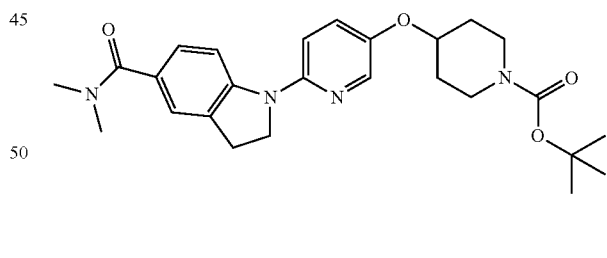

The title compound was prepared by following the similar procedure as described in Example-1 by using tert-butyl 4-((6-chloropyridin-3-yl)oxy)piperidine-1-carboxylate (intermediate-6) and N,N-dimethylindoline-5-carboxamide (intermediate-13).

¹H NMR (400 MHz, CDCl₃) δ; 1.46 (s, 9H), 1.70-1.78 (m, 2H), 1.90-1.95 (m, 2H), 3.07 (s, 6H), 3.21 (t, J=8.8 Hz, 2H), 3.26-3.32 (m, 2H), 3.70-3.76 (m, 2H), 4.03 (t, J=8.4 Hz, 2H), 4.33-4.37 (m, 1H), 6.75 (d, J=8.8, 1H), 7.22-7.30 (m, 3H), 8.03 (d, J=8.4 Hz, 1H), 8.08 (d, J=2.8 Hz, 1H); MS: 467.3 (M+1).

Example-44 tert-Butyl-4-(((6-(5-(methylsulfonyl)indolin-1-yl)pyridin-3-yl)oxy)-methyl)piperidine-1-carboxylate

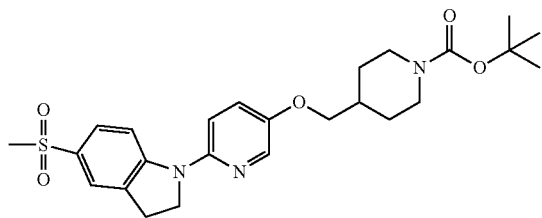 [SMILES: CC(C)(C)OC(=O)N1CCC(COc2ccc(N3CCc4cc(S(C)(=O)=O)ccc43)nc2)CC1]

The title compound was prepared by following the similar procedure as described in Example-1 by using 5-(methylsulfonyl)indoline (intermediate-26) and tert-butyl 4-(((6-chloropyridin-3-yl)oxy)methyl)piperidine-1-carboxylate (intermediate-29).

$^1$H NMR (400 MHz, CDCl$_3$) δ; 1.26-1.33 (m, 2H), 1.49 (s, 9H), 1.83-1.87 (m, 2H), 1.99-2.07 (m, 1H), 2.77 (m, 2H), 3.04 (s, 3H), 3.28 (t, J=8.4 Hz, 2H), 3.86 (d, J=6.4 Hz, 2H), 4.11-4.19 (m, 4H), 6.81 (d, J=9.2 Hz, 1H), 7.27-7.30 (m, 1H), 7.67 (bs, 1H), 7.74 (dd, J=8.4, 2.0 Hz, 1H), 8.10 (d, J=2.8 Hz, 1H), 8.17 (d, J=8.8 Hz, 1H); MS: 432.2 (M−56).

Example-45 tert-butyl 4-(((6-(5-(dimethylcarbamoyl)-1H-indol-1-yl)pyridin-3-yl)oxy) methyl)piperidine-1-carboxylate

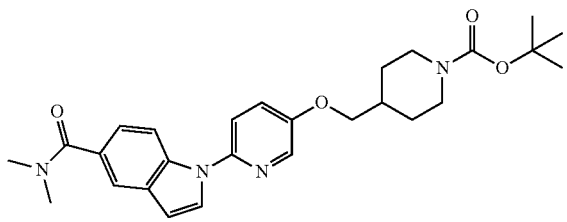 [SMILES: CN(C)C(=O)c1ccc2c(ccn2-c2ccc(OCC3CCN(C(=O)OC(C)(C)C)CC3)cn2)c1]

The title compound was prepared by following the similar procedure as described in Example-1 by using N,N-dimethyl-1H-indole-5-carboxamide (intermediate-12) and tert-butyl-4-(((6-chloropyridin-3-yl)oxy)methyl)piperidine-1-carboxylate (Intermediate 29).

$^1$H NMR (400 MHz, CDCl$_3$) δ; 1.66-1.23 (m, 2H), 1.40 (s, 9H), 1.76-1.80 (m, 2H), 1.97 (bs, 1H), 2.66-2.67 (m, 2H), 2.99 (s, 6H), 3.99 (d, J=6.4 Hz, 4H), 6.77 (d, J=3.2 Hz, 1H), 7.28 (dd, J=8.8, 1.6 Hz, 1H), 7.62-7.72 (m, 3H), 7.98 (d, J=3.2 Hz, 1H), 8.20 (d, J=8.4 Hz, 1H), 8.29 (d, J=2.8 Hz, 1H); MS: 479.3 (M+1).

Example-46 tert-Butyl-4-((6-(5-(methylsulfonyl)indolin-1-yl)pyridin-3-yl)methoxy) piperidine-1-carboxylate

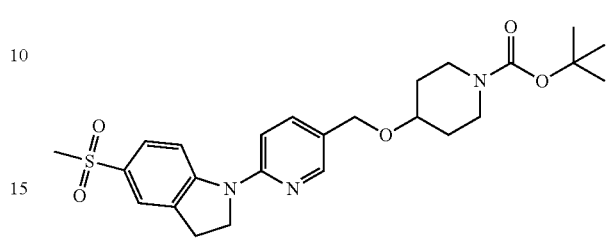

The title compound was prepared by following the similar procedure as described in Example-1 using 5-(methylsulfonyl)indoline (intermediate-26) and tert-butyl 4-((6-chloropyridin-3-yl)methoxy)piperidine-1-carboxylate (intermediate-43) (462 mg, 34%).

$^1$H NMR (400 MHz, CDCl$_3$) δ; 1.48 (s, 9H), 1.59-1.63 (m, 2H), 1.88 (bs, 2H), 3.05 (s, 3H), 3.09-3.15 (m, 2H), 3.31 (t, J=8.8 Hz, 2H), 3.57-3.63 (m, 1H), 3.77-3.79 (bs, 2H), 4.16 (t, J=8.8 Hz, 2H), 4.54 (s, 2H), 6.82 (d, J=8.8 Hz, 1H), 7.69-7.71 (bs, 2H), 7.77 (dd, J=8.8, 2.0 Hz, 1H), 8.36-8.41 (m, 2H); MS: 488.2 (M+1).

Example-47

1-(5-((1-(5-Ethylpyrimidin-2-yl)piperidin-4-yl)oxy)methyl)pyridin-2-yl)-N,N-dimethyl-1H-indole-5-carboxamide

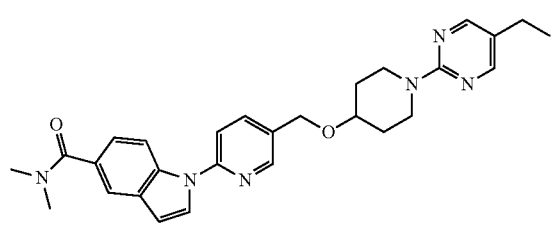 [SMILES: CCc1cnc(N2CCC(OCc3ccc(-n4ccc5cc(C(=O)N(C)C)ccc54)nc3)CC2)nc1]

The title compound was prepared by following the similar procedure as described in Example-2.

$^1$H NMR (400 MHz, CDCl$_3$) δ; 1.19 (t, J=7.6 Hz, 3H), 1.22-1.45 (m, 2H), 1.95-1.98 (m, 2H), 2.13-2.17 (m, 1H), 2.47 (q, J=7.6 Hz, 2H), 2.90-2.97 (m, 2H), 3.08 (s, 6H), 3.94 (d, J=6.4 Hz, 2H), 4.79-4.83 (m, 2H), 6.70-6.71 (m, 1H), 7.34-7.40 (m, 3H), 7.64 (d, J=3.2 Hz, 1H), 7.75 (m, 1H), 8.02 (d, J=8.4 Hz, 1H), 8.18-8.25 (m, 3H); MS: 485.3 (M+1).

Example-48

(syn)-tert-Butyl-9-((6-(5-(methylsulfonyl)-1H-indol-1-yl)pyridin-3-yl)oxy)-3-oxa-7-azabicyclo[3.3.1]nonane-7-carboxylate

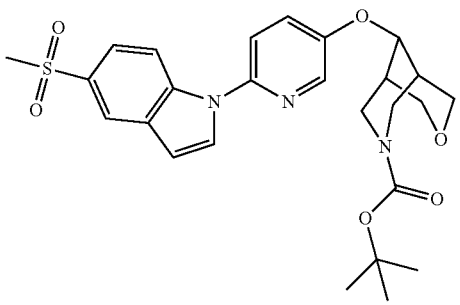 [SMILES: CC(C)(C)OC(=O)N1CC2COCC(C1)C2Oc1ccc(-n2ccc3cc(S(C)(=O)=O)ccc32)nc1]

The title compound was prepared by following the similar procedure as described in Example-1 by using 5-(methylsulfonyl)-1H-indole (intermediate-21) and anti-tert-Butyl-9-((6-chloropyridin-3-yl)oxy)-3-oxa-7-azabicyclo[3.3.1]-nonane-7-carboxylate (intermediate-73).

$^1$H NMR (400 MHz, CDCl$_3$) δ; 1.46 (s, 9H), 1.92-1.97 (m, 2H), 3.08-3.15 (m, 4H), 3.24-3.27 (m, 1H), 3.84-3.93 (m, 2H), 4.12-4.20 (m, 2H), 4.44-4.48 (m, 1H), 4.59-4.66 (m, 2H), 6.82-6.83 (m, 1H), 7.42-7.49 (m, 2H), 7.72 (d, J=1.6 Hz, 1H), 7.80 (dd, J=8.8, 1.6 Hz, 1H), 8.20 (d, J=8.8 Hz, 1H), 8.29-8.31 (m, 2H); MS: 514.2 (M+1).

Example-49

(anti) tert-Butyl-9-((6-(5-(methylsulfonyl)-1H-indol-1-yl)pyridin-3-yl) oxy)-3-oxa-7-azabicyclo[3.3.1]nonane-7-carboxylate

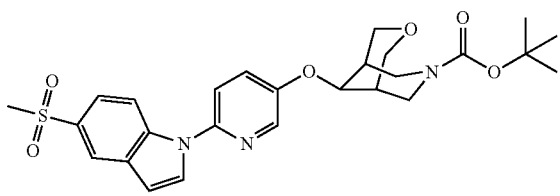 [SMILES: CC(C)(C)OC(=O)N1CC2COCC(C1)C2Oc1ccc(-n2ccc3cc(S(C)(=O)=O)ccc32)nc1]

The title compound was prepared by following the similar procedure as described in Example-1 by using 5-(methylsulfonyl)-1H-indole (intermediate-21) and syn-tert-Butyl-9-((6-chloropyridin-3-yl)oxy)-3-oxa-7-azabicyclo[3.3.1]-nonane-7-carboxylate (intermediate-74).

$^1$H NMR (400 MHz, CDCl$_3$) δ; 1.46 (s, 9H), 2.00-2.06 (m, 2H), 3.09 (s, 3H), 3.40-3.56 (m, 2H), 3.77-3.86 (m, 2H), 4.12-4.32 (m, 4H), 4.46-4.67 (m, 1H), 6.84-6.85 (m, 1H), 7.43-7.52 (m, 2H), 7.73 (d, J=3.2 Hz, 1H), 7.81 (dd, J=8.8, 2.0 Hz, 1H), 8.21 (d, J=8.8 Hz, 1H), 8.30-8.33 (m, 2H); MS: 458.1 (M−56).

Example-50 syn 7-(5-Ethylpyrimidin-2-yl)-9-((6-(5-(methylsulfonyl)-1H-indol-1-yl) pyridin-3-yl)oxy)-3-oxa-7-azabicyclo[3.3.1]nonane

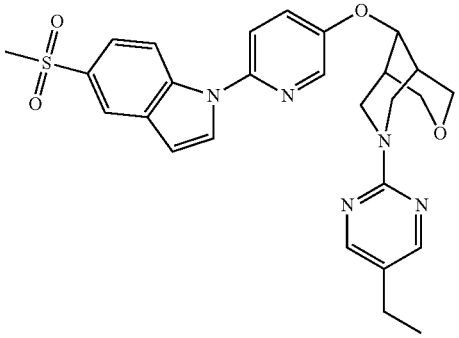 [SMILES: CCc1cnc(N2CC3COCC(C2)C3Oc2ccc(-n3ccc4cc(S(C)(=O)=O)ccc43)nc2)nc1]

The title compound was prepared by following the similar procedure as described in Example-2 by using Example-48.

$^1$H NMR (400 MHz, CDCl$_3$) δ; 1.18 (t, J=7.6 Hz, 3H), 2.03 (s, 2H), 2.46 (q, J=7.6 Hz, 2H), 3.08 (s, 3H), 3.25-3.38 (m, 2H), 3.87 (d, J=11.2 Hz, 2H), 4.19 (d, J=11.6 Hz, 2H), 4.75 (t, J=3.2 Hz, 1H), 5.11 (d, J=12.8 Hz, 2H), 6.83-6.84 (m, 1H), 7.47-7.52 (m, 2H), 7.73 (d, J=3.6 Hz, 1H), 7.80 (dd, J=8.8, 2.0 Hz, 1H), 8.20-8.23 (m, 2H), 8.29-8.36 (m, 2H); MS: 520.2 (M+1).

Example-51 anti 7-(5-Ethylpyrimidin-2-yl)-9-((6-(5-(methylsulfonyl)-1H-indol-1-yl) pyridin-3-yl)oxy)-3-oxa-7-azabicyclo[3.3.1]nonane

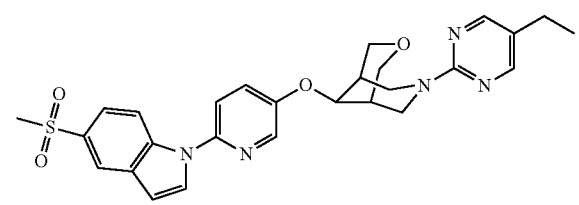 [SMILES: CCc1cnc(N2CC3COCC(C2)C3Oc2ccc(-n3ccc4cc(S(C)(=O)=O)ccc43)nc2)nc1]

The title compound was prepared by following the similar procedure as described in Example-2 by using Example-49.

$^1$H NMR (400 MHz, CDCl$_3$) δ; 1.81 (t, J=7.6 Hz, 3H), 2.20 (bs, 2H), 2.46 (q, J=7.6 Hz, 2H), 3.09 (s, 3H), 3.46-3.48 (m, 1H), 3.57-3.60 (m, 2H), 3.82 (d, J=12.0 Hz, 2H), 4.20 (d, J=11.6 Hz, 2H), 4.71-4.74 (m, 2H), 6.83-6.84 (m, 1H), 7.43-7.50 (m, 3H), 7.73 (d, J=3.6 Hz, 1H), 7.81 (dd, J=8.8, 2.0 Hz, 1H), 8.18-8.23 (m, 2H), 8.30-8.36 (m, 2H); MS: 520.2 (M+1).

Example-52 tert-Butyl-4-((6-(5-cyano-1H-indol-1-yl)pyridin-3-yl)oxy)piperidine-1-carboxylate

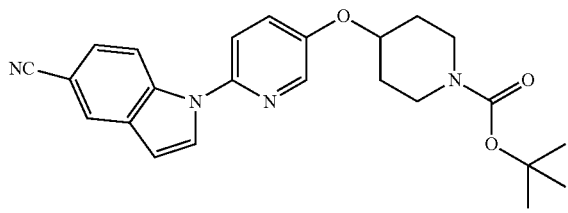 [SMILES: CC(C)(C)OC(=O)N1CCC(Oc2ccc(-n3ccc4cc(C#N)ccc43)nc2)CC1]

The title compound was prepared by following the similar procedure as described in Example-1 by using tert-Butyl 4-((6-chloropyridin-3-yl)oxy)piperidine-1-carboxylate (intermediate-6) and 1H-indole-5-carbonitrile $^1$H NMR (400 MHz, CDCl$_3$) δ; 1.48 (s, 9H), 1.77-1.85 (m, 2H), 1.96-2.01 (m, 2H), 3.34-3.41 (m, 2H), 3.71-3.77 (m, 2H), 4.25-4.57 (m, 1H), 6.75-6.73 (m, 1H), 7.38-7.44 (m, 2H), 7.49 (dd, J=8.0, 1.6 Hz, 1H), 7.68 (d, J=3.6 Hz, 1H), 8.00 (d, J=1.2 Hz, 1H), 8.12 (d, J=8.8 Hz, 1H), 8.26-8.27 (m, 1H); MS: 463.2 (M−56).

Example-53 tert-Butyl-4-((6-(5-(cyclopropylcarbamoyl)-1H-indol-1-yl)pyridin-3-yl)oxy)piperidine-1-carboxylate

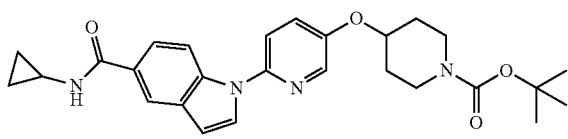 [SMILES: CC(C)(C)OC(=O)N1CCC(Oc2ccc(-n3ccc4cc(C(=O)NC5CC5)ccc43)nc2)CC1]

The title compound was prepared by following the similar procedure as described in Example-1 by using tert-butyl 4-((6-chloropyridin-3-yl)oxy)piperidine-1-carboxylate (intermediate-6) and N-cyclopropyl-1H-indole-5-carboxamide (intermediate-11).

1H NMR (400 MHz, CDCl$_3$) δ; 0.64-0.67 (m, 2H), 0.86-0.91 (m, 2H), 1.48 (s, 9H), 1.79-1.83 (m, 2H), 1.96-2.01 (m, 2H), 2.92-2.97 (m, 1H), 3.34-3.40 (m, 2H), 3.76-3.78 (m, 2H), 4.52-4.55 (m, 1H), 6.74 (dd, J=3.2, 0.4 Hz, 1H), 7.41-7.42 (m, 2H), 7.65-7.66 (m, 1H), 7.68 (d, J=1.6 Hz, 1H), 8.04 (d, J=8.8 Hz, 1H), 8.07 (d, J=1.6 Hz, 1H), 8.26-8.26 (m, 1H); MS: 477 (M+1).

Example-54

N-Cyclopropyl-1-(5-((1-(5-ethylpyrimidin-2-yl)piperidin-4-yl)oxy)pyridin-2-yl)-1H-indole-5-carboxamide

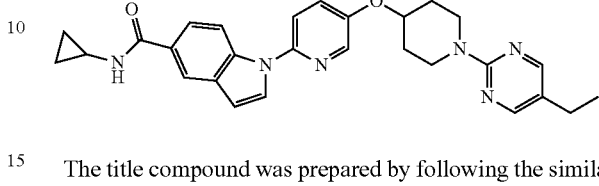

The title compound was prepared by following the similar procedure as described in Example-2 by using Example-53.

$^1$H NMR (400 MHz, CDCl$_3$) δ; 0.62-0.64 (m, 2H), 0.85-0.87 (m, 2H), 1.18 (t, J=7.6 Hz, 3H), 1.83-1.88 (m, 2H), 2.04-2.09 (m, 2H), 2.70 (q, J=7.6 Hz, 2H), 2.91-2.94 (m, 1H), 3.62-3.68 (m, 2H), 4.17-4.23 (m, 2H), 4.60 (m, 1H), 6.27 (bs, 1H), 6.71-6.72 (m, 1H), 7.41-7.42 (m, 2H), 7.63-7.66 (m, 2H), 8.01-8.05 (m, 2H), 8.27 (s, 2H), 8.27 (s, 1H); MS: 483.3 (M+1).

Example-55 tert-Butyl-4-((6-(5-(oxazol-2-yl)-1H-indol-1-yl)pyridin-3-yl)oxy)-piperidine-1-carboxylate

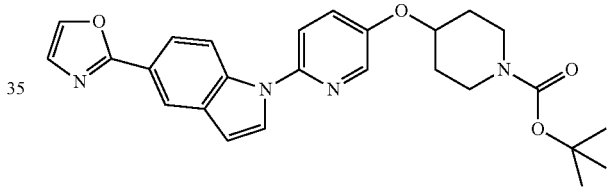

The title compound was prepared by following the similar procedure as described in Example-1 by using tert-butyl 4-((6-chloropyridin-3-yl)oxy)piperidine-1-carboxylate (intermediate-6) and 2-(1H-indol-5-yl)oxazole (intermediate-67).

$^1$H NMR (400 MHz, CDCl$_3$) δ; 1.48 (s, 9H), 1.79-1.85 (m, 2H), 1.96-2.02 (m, 2H), 3.34-3.40 (m, 2H), 3.72-3.78 (m, 2H), 4.52-4.56 (m, 1H), 6.76-6.77 (m, 1H), 7.23 (s, 1H), 7.39-7.45 (m, 2H), 7.66 (d, J=3.6 Hz, 1H), 7.71 (s, 1H), 7.98 (dd, J=8.8, 1.6 Hz, 1H), 8.10 (d, J=8.8 Hz, 1H), 8.27 (s, 1H), 8.29 (s, 1H); MS: 461.2 (M+1).

Example-56 tert-Butyl-4-((6-(5-isobutyramido-1H-indol-1-yl)pyridin-3-yl)oxy)-piperidine-1-carboxylate

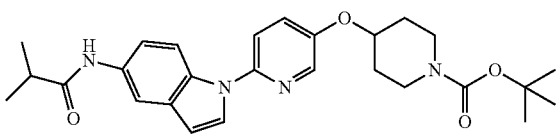

The title compound was prepared by following the similar procedure as described in Example-1 by using tert-butyl 4-((6-chloropyridin-3-yl)oxy)piperidine-1-carboxylate (intermediate-6) and N-(1H-indol-5-yl)isobutyramide (intermediate-10).

¹H NMR (400 MHz, CDCl₃) δ; 1.29 (d, J=7.2 Hz, 6H), 1.48 (s, 9H), 1.81-1.81 (m, 2H), 1.95-2.01 (m, 2H), 2.50-2.57 (m, 1H), 3.33-3.39 (m, 2H), 3.71-3.77 (m, 2H), 4.50-4.52 (m, 1H), 6.64 (d, J=3.2 Hz, 1H), 7.22 (s, 1H), 7.24 (d, J=2.4 Hz, 1H), 7.38-7.39 (m, 2H), 7.61 (d, J=3.6 Hz, 1H), 7.96 (d, J=2 Hz, 1H), 8.00 (d, J=8.8 Hz, 1H), 8.23-8.24 (m, 1H); MS: 481 (M+1).

Example-57

N-(1-(5-((1-(3-Isopropyl-1,2,4-oxadiazol-5-yl)piperidin-4-yl)oxy)pyridin-2-yl)-1H-indol-5-yl)isobutyramide

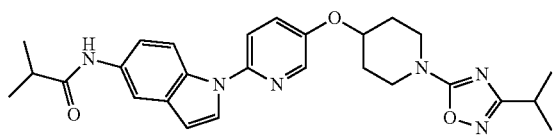 [SMILES: CC(C)C(=O)Nc1ccc2c(ccn2-c2ccc(OC3CCN(c4nc(C(C)C)no4)CC3)cn2)c1]

The title compound was prepared by following the similar procedure as described in Example-4 by using Example-56.

¹H NMR (400 MHz, CDCl₃) δ; 1.30 (d, J=0.8 Hz, 12H), 1.96-2.02 (m, 2H), 2.05-2.11 (m, 2H), 2.11-2.55 (m, 1H), 2.86-2.92 (m, 1H), 3.63-3.69 (m, 2H), 3.82-3.89 (m, 2H), 4.61-4.63 (m, 1H), 6.64 (d, J=3.6 Hz, 1H), 7.19 (m, 1H), 7.26-7.29 (m, 1H), 7.38-7.43 (m, 2H), 7.61 (d, J=3.2 Hz, 1H), 7.95 (d, J=2.0 Hz, 1H), 8.01 (d, J=9.2 Hz, 1H), 8.25 (s, 1H); MS: 489.3 (M+1).

Example-58

1-(5-((1-(5-Ethylpyrimidin-2-yl)piperidin-4-yl)oxy)pyridin-2-yl)-1H-indole-5-carbonitrile

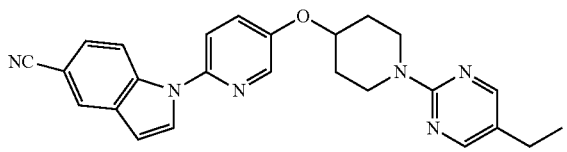 [SMILES: CCc1cnc(N2CCC(Oc3ccc(-n4ccc5cc(C#N)ccc54)nc3)CC2)nc1]

The title compound was prepared by following the similar procedure as described in Example-2 by using Example-52.

¹H NMR (400 MHz, CDCl₃) δ; 1.21 (t, J=7.6 Hz, 3H), 1.85-1.89 (m, 2H), 2.06-2.10 (m, 2H), 2.47 (q, J=7.6 Hz, 2H), 3.64-3.70 (m, 2H), 4.18-4.24 (m, 2H), 4.62-4.63 (m 1H), 6.75-6.76 (m, 1H), 7.39-7.51 (m, 3H), 7.69 (d, J=3.6 Hz, 1H), 8.00 (s, 1H), 8.12 (d, J=8.8 Hz, 1H), 8.19 (s, 2H), 8.29 (s, 1H); MS: 425.3 (M+1).

Example-59

2-(1-(5-((1-(5-Ethylpyrimidin-2-yl)piperidin-4-yl)oxy)pyridin-2-yl)-1H-indol-5-yl)oxazole

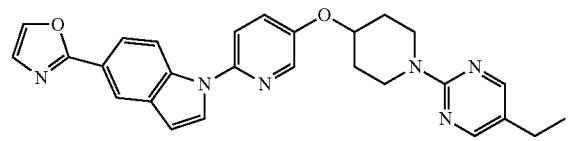 [SMILES: CCc1cnc(N2CCC(Oc3ccc(-n4ccc5cc(-c6ncco6)ccc54)nc3)CC2)nc1]

The title compound was prepared by following the similar procedure as described in Example-2 by using Example-55.

¹H NMR (400 MHz, CDCl₃) δ; 1.18 (t, J=7.6 Hz, 3H), 1.85-1.91 (m, 2H), 2.05-2.11 (m, 2H), 2.47 (q, J=7.6 Hz, 2H), 3.63-3.69 (m, 2H), 4.19-4.61 (m, 2H), 4.62-4.63 (m, 1H), 6.76 (d, J=3.2 Hz, 1H), 7.22-7.25 (m, 1H), 7.44 (d, J=2.0 Hz, 2H), 7.66 (d, J=3.2 Hz, 1H), 7.70 (s, 1H), 7.98 (dd, J=8.8, 1.6 Hz, 1H), 8.11 (d, J=8.8 Hz, 1H), 8.19 (s, 2H), 8.29-8.30 (m, 1H), 8.35 (s, 1H); MS: 467.2 (M+1).

Example-60 tert-Butyl-4-((6-(5-(methylcarbamoyl)-1H-indol-1-yl)pyridin-3-yl)-oxy) piperidine-1-carboxylate

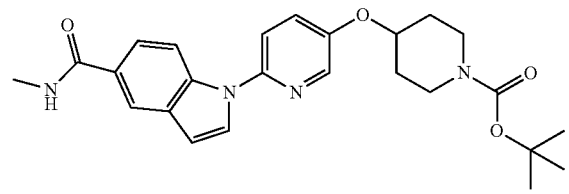 [SMILES: CNC(=O)c1ccc2c(ccn2-c2ccc(OC3CCN(C(=O)OC(C)(C)C)CC3)cn2)c1]

The title compound was prepared by following the similar procedure as described in Example-1 by using tert-butyl 4-((6-chloropyridin-3-yl)oxy)piperidine-1-carboxylate (intermediate-6) and N-methyl-1H-indole-5-carboxamide (intermediate-14).

¹H NMR (400 MHz, CDCl₃) δ; 1.45 (s, 9H), 1.79-1.83 (m, 2H), 1.96-2.00 (m, 2H), 3.04 (s, 3H), 3.33-3.40 (m, 2H), 3.71-3.76 (m, 2H), 4.52-4.54 (m, 1H), 6.19 (bs, 1H), 6.73-6.74 (m, 1H), 7.41 (s, 2H), 7.65-7.69 (m, 2H), 8.03-8.10 (m, 2H), 8.25-8.26 (m, 1H); MS: 451.2 (M+1).

Example-61 tert-Butyl-4-((6-(5-(ethylcarbamoyl)-1H-indol-1-yl)pyridin-3-yl)oxy)-piperidine-1-carboxylate

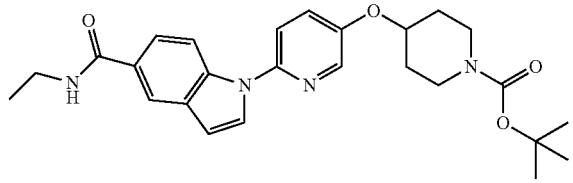 [SMILES: CCNC(=O)c1ccc2c(ccn2-c2ccc(OC3CCN(C(=O)OC(C)(C)C)CC3)cn2)c1]

The title compound was prepared by following the similar procedure as described in Example-1 by using tert-butyl 4-((6-chloropyridin-3-yl)oxy)piperidine-1-carboxylate (intermediate-6) and N-ethyl-1H-indole-5-carboxamide (intermediate-15).

$^1$H NMR (400 MHz, CDCl$_3$) δ; 1.28 (t, J=7.2 Hz, 3H), 1.47 (s, 9H), 1.81 (m, 2H), 1.98 (m, 2H), 3.48 (m, 2H), 3.52-3.55 (m, 2H), 3.74 (m, 2H), 4.51 (m, 1H), 6.14 (bs, 1H), 6.74 (d, J=2.8 Hz, 1H), 7.41 (s, 2H), 7.65-7.70 (m, 2H), 8.03-8.09 (m, 2H), 8.26 (s, 1H); MS: 465.2 (M+1).

Example-62 tert-Butyl-4-(((6-(5-(isopropylcarbamoyl)-1H-indol-1-yl)pyridin-3-yl)oxy) piperidine-1-carboxylate

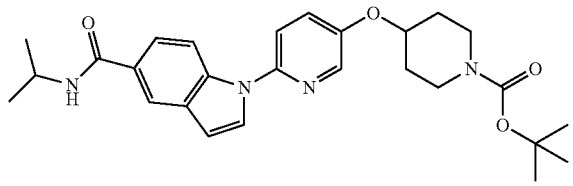 [SMILES: CC(C)NC(=O)c1ccc2c(ccn2-c2ccc(OC3CCN(C(=O)OC(C)(C)C)CC3)cn2)c1]

The title compound was prepared by following the similar procedure as described in Example-1 by using tert-butyl 4-((6-chloropyridin-3-yl)oxy)piperidine-1-carboxylate (intermediate-6) and N-isopropyl-1H-indole-5-carboxamide (intermediate-16).

$^1$H NMR (400 MHz, CDCl$_3$) δ; 1.23-1.29 (m, 6H), 1.41 (s, 9H), 1.80-1.82 (m, 2H), 1.96-1.97 (m, 2H), 3.34-3.40 (m, 2H), 3.72-3.75 (m, 2H), 4.34 (m, 1H), 4.53 (m, 1H), 5.97 (bs, 1H), 6.74 (d, J=3.2 Hz, 1H), 7.39-7.43 (m, 2H), 7.65-7.69 (m, 2H), 8.02-8.07 (m, 2H), 8.26 (s, 1H); MS: 479.3 (M+1).

Example-63

1-(5-(((1-(5-Ethylpyrimidin-2-yl)piperidin-4-yl)oxy) pyridin-2-yl)-N-methyl-1H-indole-5-carboxamide

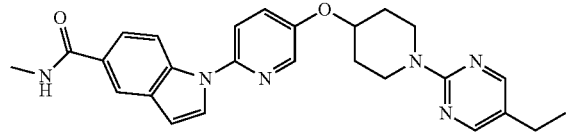 [SMILES: CCc1cnc(N2CCC(Oc3ccc(-n4ccc5cc(C(=O)NC)ccc54)nc3)CC2)nc1]

The title compound was prepared by following the similar procedure as described in Example-2 by using Example-60.

$^1$H NMR (400 MHz, CDCl$_3$) δ; 1.20 (t, J=7.6 Hz, 3H), 1.85-1.89 (m, 2H), 2.06-2.10 (m, 2H), 2.47 (q, J=7.6 Hz, 2H), 3.05 (s, 3H), 3.64-3.69 (m, 2H), 4.19-4.25 (m, 2H), 4.61-4.62 (m, 1H), 6.19 (bs, 1H), 6.74-6.75 (m, 1H), 7.43 (s, 2H), 7.66-7.69 (m, 2H), 8.03 (d, J=8.8 Hz, 1H), 8.10 (s, 1H), 8.19 (s, 2H), 8.29 (s, 1H); MS: 457.3 (M+1).

Example-64

N-Ethyl-1-(5-((1-(5-ethylpyrimidin-2-yl)piperidin-4-yl)oxy)pyridin-2-yl)-1H-indole-5-carboxamide

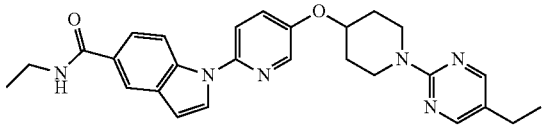 [SMILES: CCNC(=O)c1ccc2c(ccn2-c2ccc(OC3CCN(c4ncc(CC)cn4)CC3)cn2)c1]

The title compound was prepared by following the similar procedure as described in Example-2 by using Example-61.

$^1$H NMR (400 MHz, CDCl$_3$) δ; 1.21 (t, J=7.6 Hz, 3H), 1.30 (t, J=7.2 Hz, 3H), 1.87-1.91 (m, 2H), 2.08-2.13 (m, 2H), 2.49 (q, J=7.6 Hz, 2H), 3.54-3.57 (m, 2H), 3.66-3.71 (m, 2H), 4.21-4.27 (m, 2H), 4.64 (m, 1H), 6.16 (bs, 1H), 6.76-6.77 (m, 1H), 7.45 (m, 2H), 7.68-7.72 (m, 2H), 8.06-8.12 (m, 2H), 8.21 (s, 2H), 8.30 (m, 1H); MS: 471.3 (M+1).

Example-65

1-(5-((1-(5-Ethylpyrimidin-2-yl)piperidin-4-yl)oxy) pyridin-2-yl)-N-isopropyl-1H-indole-5-carboxamide

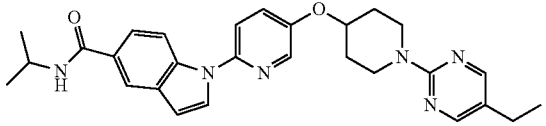 [SMILES: CCc1cnc(N2CCC(Oc3ccc(-n4ccc5cc(C(=O)NC(C)C)ccc54)nc3)CC2)nc1]

The title compound was prepared by following the similar procedure as described in Example-2 using Example-62.

$^1$H NMR (400 MHz, CDCl$_3$) δ; 1.23 (t, J=7.6 Hz, 3H), 1.30 (d, J=6.4 Hz, 6H), 1.88-1.91 (m, 2H), 2.07-2.12 (m, 2H), 2.49 (q, J=7.6 Hz, 2H), 3.69 (m, 2H), 4.20-4.26 (m, 2H), 4.32-4.37 (m, 1H), 4.63-4.65 (m, 1H), 5.98 (bs, 1H), 6.76 (d, J=3.6 Hz, 1H), 7.45 (m, 2H), 7.67-7.71 (m, 2H), 8.05-8.09 (m, 2H), 8.30 (s, 2H), 8.31 (m, 1H); MS: 485.3 (M+1).

Example-66 tert-Butyl-4-(((6-(5-(methylcarbamoyl)-1H-indol-1-yl)pyridin-3-yl)-oxy)methyl)piperidine-1-carboxylate

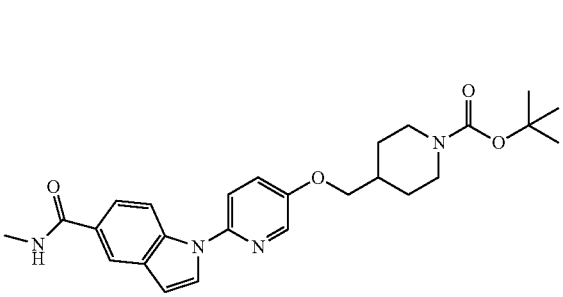 [SMILES: CNC(=O)c1ccc2c(ccn2-c2ccc(OCC3CCN(C(=O)OC(C)(C)C)CC3)cn2)c1]

The title compound was prepared by following the similar procedure as described in Example-1 by using N-methyl-1H-indole-5-carboxamide (intermediate-14) and tert-butyl 4-(((6-chloropyridin-3-yl)oxy)methyl)piperidine-1-carboxylate (intermediate-29).

¹H NMR (400 MHz, CDCl₃) δ; 1.25-1.38 (m, 2H), 1.46 (s, 9H), 1.85-1.88 (m, 2H), 2.02-2.04 (m, 1H), 2.76-2.81 (m, 2H), 3.06 (s, 3H), 3.92 (d, J=6.4 Hz, 2H), 4.74 (bs, 2H), 6.75 (d, J=3.2 Hz, 1H), 7.37-7.44 (m, 2H), 7.66-7.70 (m, 2H), 8.03 (d, J=8.8 Hz, 1H), 8.11 (s, 1H), 8.26 (s, 1H); MS: 465.08 (M+1).

Example-67

1-(5-((1-(5-Ethylpyrimidin-2-yl)piperidin-4-yl)methoxy)pyridin-2-yl)-N-methyl-1H-indole-5-carboxamide

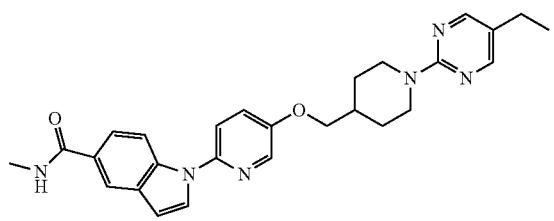

The title compound was prepared by following the similar procedure as described in Example-2 using Example-66.

¹H NMR (400 MHz, CDCl₃) δ; 1.21 (t, J=7.6 Hz, 3H), 1.34-1.44 (m, 2H), 1.94-1.98 (m, 2H), 2.14-2.16 (m, 1H), 2.46 (q, J=7.6 Hz, 2H), 2.89-2.96 (m, 2H), 3.05 (s, 3H), 3.93 (d, J=6.4 Hz, 2H), 4.80 (d, J=13.2 Hz, 2H), 6.18 (d, J=4.4 Hz, 1H), 6.74 (d, J=3.2 Hz, 1H), 7.39-7.42 (m, 2H), 7.65-7.69 (m, 2H), 8.03 (d, J=8.8 Hz, 1H), 8.18 (s, 1H), 8.25 (s, 3H); MS: 471.2 (M+1).

Example-68

1-(5-((1-(3-Isopropyl-1,2,4-oxadiazol-5-yl)piperidin-4-yl)oxy)pyridin-2-yl)-N-methyl-1H-indole-5-carboxamide

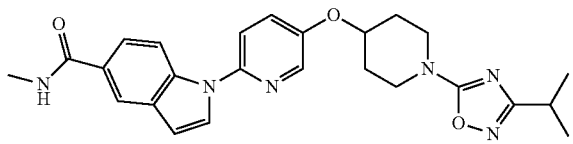 [SMILES: CNC(=O)c1ccc2c(ccn2-c2ccc(OC3CCN(c4nc(C(C)C)no4)CC3)cn2)c1]

The title compound was prepared by following the similar procedure as described in Example-4 using Example-60.

¹H NMR (400 MHz, CDCl₃) δ; 1.29 (d, J=6.8 Hz, 6H), 1.96-2.09 (m, 2H), 2.06-2.10 (m, 2H), 2.88-2.92 (m, 1H), 3.06 (s, 3H), 3.63-3.70 (m, 2H), 3.83-3.89 (m, 2H), 4.65 (bs, 1H), 6.18 (bs, 1H), 6.75 (s, 1H), 7.43 (bs 2H), 7.66-7.70 (m, 2H), 8.05-8.10 (m, 2H), 8.28 (bs, 1H); MS: 461.2 (M+1).

Example-69 tert-Butyl-4-((6-(5-(pyrrolidine-1-carbonyl)-1H-indol-1-yl)pyridin-3-yl)oxy)piperidine-1-carboxylate

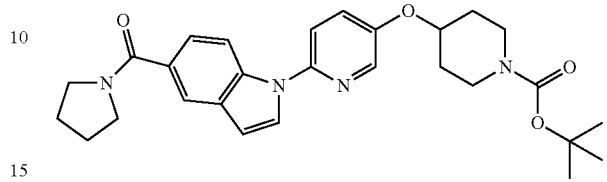

The title compound was prepared by following the similar procedure as described in Example-1 by using tert-butyl-4-((6-chloropyridin-3-yl)oxy)piperidine-1-carboxylate (intermediate-6) and (1H-indol-5-yl)(pyrrolidin-1-yl)methanone (intermediate-18).

¹H NMR (400 MHz, CDCl₃) δ; 1.48 (s, 9H), 1.79-1.88 (m, 4H), 1.96-1.99 (m, 4H), 3.34-3.40 (m, 2H), 3.47-3.69 (m, 2H), 3.71-3.78 (m, 4H), 4.52-4.55 (m, 1H), 6.67 (bs, 1H), 7.41-7.42 (m, 2H), 7.47 (dd, J=8.4, 1.2 Hz, 1H), 7.65 (d, J=3.6 Hz, 1H), 7.86 (s, 1H), 8.04 (d, J=8.4 Hz, 1H), 8.26 (m, 1H); MS: 491.3 (M+1).

Example-70

Isopropyl 4-((6-(5-(pyrrolidine-1-carbonyl)-1H-indol-1-yl)pyridin-3-yl)oxy)piperidine-1-carboxylate

To a stirred solution of Example-69 (0.050 g, 0.102 mmol) in dichloromethane (3 mL) trifluoroacetic acid (0.2 mL) was added and stirred for 1 h. The reaction contents were concentrated in vacuo and the residue was dissolved in dichloromethane (3 mL), triethylamine (0.015 g, 0.153 mmol), isopropylchloroformate (0.012 g, 0.102 mmol) were added at 0° C. and stirred for 1 h. The reaction was quenched by water and the organic layer was extracted with dichloromethane. The organic layer was concentrated in vacuo and the resultant residue was purified by flash column chromatography to give isopropyl 4-((6-(5-(pyrrolidine-1-carbonyl)-1H-indol-1-yl)pyridin-3-yl)oxy)piperidine-1-carboxylate (0.012 g, 25%).

¹H NMR (400 MHz, CDCl₃) δ; 1.24 (d, J=6.0 Hz, 6H), 1.80-1.87 (m, 4H), 1.94-1.99 (m, 4H), 3.38-3.44 (m, 2H), 3.49-3.52 (m, 2H), 3.65-3.74 (m, 2H), 3.75-3.78 (m, 2H), 4.51-4.91 (m, 1H), 4.92-4.94 (m, 1H), 6.69-6.70 (m, 1H), 7.37-7.40 (m, 2H), 7.44-7.50 (m, 1H), 7.63 (d, J=3.6 Hz, 1H), 7.84 (d, J=1.2 Hz, 1H), 8.02 (d, J=8.4 Hz, 1H), 8.24-8.25 (m, 1H); MS: 476.3 (M⁺).

Example-71

(1-(5-((1-(5-Ethylpyrimidin-2-yl)piperidin-4-yl)oxy)pyridin-2-yl)-1H-indol-5-yl)(pyrrolidin-1-yl)methanone

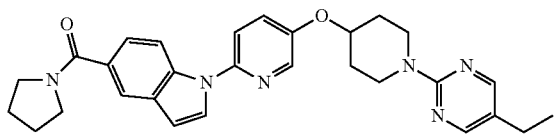 [SMILES: CCc1cnc(N2CCC(Oc3ccc(-n4ccc5cc(C(=O)N6CCCC6)ccc54)nc3)CC2)nc1]

The title compound was prepared by following the similar procedure as described in Example-2 by using Example-69.

¹H NMR (400 MHz, CDCl₃) δ; 1.19 (t, J=7.6 Hz, 3H), 1.85-1.91 (m, 4H), 1.96-2.00 (m, 2H), 2.07-2.08 (m, 2H), 2.48 (q, J=7.6 Hz, 2H), 3.51-3.55 (m, 2H), 3.62-3.70 (m, 4H), 4.21-4.25 (m, 2H), 4.62 (m, 1H), 6.72 (d, J=3.2 Hz, 1H), 7.43-7.49 (m, 3H), 7.66 (d, J=3.2 Hz, 1H), 7.87 (s, 1H), 8.05 (d, J=8.8 Hz, 1H), 8.20 (s, 2H), 8.29 (s, 1H); MS: 497.2 (M+1).

Example-72

Isopropyl 4-((6-(5-(isopropylcarbamoyl)-1H-indol-1-yl)pyridin-3-yl)oxy) piperidine-1-carboxylate

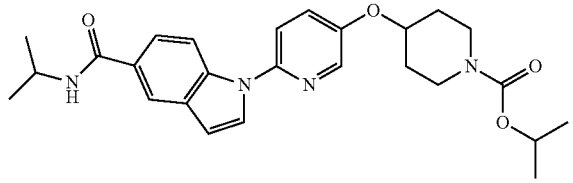 [SMILES: CC(C)NC(=O)c1ccc2c(ccn2-c2ccc(OC3CCN(C(=O)OC(C)C)CC3)cn2)c1]

The title compound was prepared by following the similar procedure as described in Example-70 using Example-62.

¹H NMR (400 MHz, CDCl₃) δ; 1.19-1.28 (m, 12H), 1.80-1.83 (m, 2H), 1.96-2.00 (m, 2H), 3.38-3.45 (m, 2H), 3.73-3.78 (m, 2H), 4.27-4.34 (m, 1H), 4.52-4.56 (m, 1H), 4.89-4.95 (m, 1H), 6.73 (d, J=3.2 Hz, 1H), 7.37-7.43 (m, 2H), 7.64-7.69 (m, 2H), 8.02-8.06 (m, 2H), 8.25 (s, 1H); MS: 465.2 (M+1).

Example-73

Ethyl-4-((6-(5-(isopropylcarbamoyl)-1H-indol-1-yl)pyridin-3-yl)oxy)-piperidine-1-carboxylate

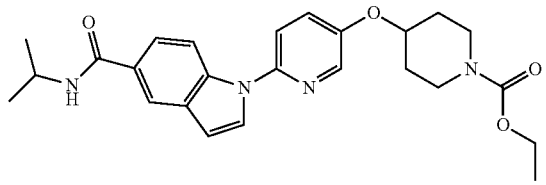 [SMILES: CCOC(=O)N1CCC(Oc2ccc(-n3ccc4cc(C(=O)NC(C)C)ccc43)nc2)CC1]

The title compound was prepared by following the similar procedure as described in Example-70 using Example-62.

¹H NMR (400 MHz, CDCl₃) δ; 1.21-1.28 (m, 9H), 1.82-1.86 (m, 2H), 1.98-2.03 (m, 2H), 3.42-3.49 (m, 2H), 3.75-3.81 (m, 2H), 4.16 (q, J=7.2 Hz, 2H), 4.31-4.36 (m, 1H), 4.54-4.57 (m, 1H), 5.99 (bs, 1H), 6.74-6.75 (m, 1H), 7.39-7.45 (m, 2H), 7.66-7.07 (m, 2H), 8.04-8.08 (m, 2H), 8.27 (m, 1H); MS: 451.2 (M+1).

Example-74

Isopropyl 4-((6-(5-(dimethylcarbamoyl)-1H-indol-1-yl)pyridin-3-yl)oxy) piperidine-1-carboxylate

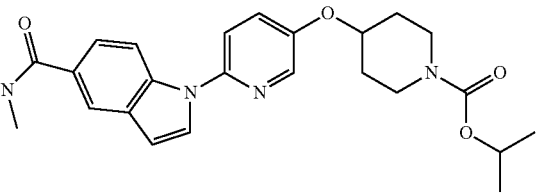

The title compound was prepared by following the similar procedure as described in Example-70 using Example-39.

¹H NMR (400 MHz, CDCl₃) δ; 1.28 (d, J=6.4 Hz, 6H), 1.81-1.86 (m, 2H), 1.99-2.03 (m, 2H), 3.09 (s, 6H), 3.41-3.52 (m, 2H), 3.77-3.82 (m, 2H), 4.54-4.59 (m, 1H), 4.92-4.98 (m, 1H), 6.72-6.73 (m, 1H), 7.37 (dd, J=8.4, 6.4 Hz, 1H), 7.42-7.43 (m, 2H), 7.66 (d, J=3.6 Hz, 1H), 7.77 (s, 1H), 8.06 (d, J=8.4 Hz, 1H), 8.27-8.28 (m, 1H); MS: 451.2 (M+1).

Example-75

Ethyl-4-((6-(5-(dimethylcarbamoyl)-1H-indol-1-yl)pyridin-3-yl)oxy)-piperidine-1-carboxylate

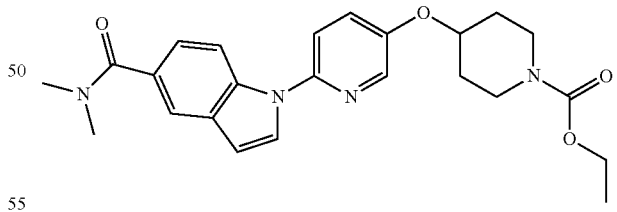

The title compound was prepared by following the similar procedure as described in Example-70 using Example-39.

¹H NMR (400 MHz, CDCl₃) δ; 1.29 (t, J=7.2 Hz, 3H), 1.82-1.89 (m, 2H), 1.98-2.04 (m, 2H), 3.10 (s, 6H), 3.43-3.50 (m, 2H), 3.76-3.82 (m, 2H), 4.17 (q, J=7.2 Hz, 2H), 4.55-4.59 (m, 1H), 6.72-6.73 (m, 1H), 7.36-7.43 (m, 3H), 7.65 (d, J=3.2 Hz, 1H), 7.77 (s, 1H), 8.06 (d, J=8.8 Hz, 1H), 8.28 (m, 1H); MS: 437.2 (M+1).

Example-76 tert-Butyl-4-((6-(5-((2-hydroxyethyl)carbamoyl)-1H-indol-1-yl)-pyridin-3-yl)oxy)piperidine-1-carboxylate

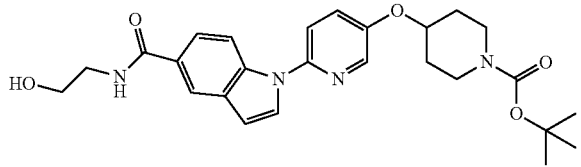 [SMILES: CC(C)(C)OC(=O)N1CCC(Oc2ccc(-n3ccc4cc(C(=O)NCCO)ccc43)nc2)CC1]

The title compound was prepared by following the similar procedure as described in Example-1 by using tert-butyl 4-((6-chloropyridin-3-yl)oxy)piperidine-1-carboxylate (intermediate-6) and N-(2-hydroxyethyl)-1H-indole-5-carboxamide (intermediate-19) (0.110 g, 48.0%).

$^1$H NMR (400 MHz, CDCl$_3$) δ; 1.46 (s, 9H), 1.80-1.84 (m, 2H), 1.98-2.02 (m, 2H), 2.96 (bs, 2H), 3.35-3.41 (m, 2H), 3.66-3.74 (m, 2H), 3.76-3.89 (m, 2H), 4.54-4.56 (m, 2H), 6.66 (bs, 1H), 6.75-6.76 (m, 1H), 7.42 (bs, 2H), 7.66-7.73 (m, 2H), 8.07 (d, J=8.8 Hz, 1H), 8.14 (s, 1H), 8.27 (m, 1H); MS: 481.2 (M+1).

Example-77

1-(5-((1-(5-Ethylpyrimidin-2-yl)piperidin-4-yl)oxy)pyridin-2-yl)-N-(2-hydroxyethyl)-1H-indole-5-carboxamide

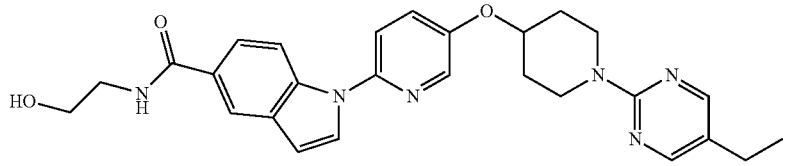 [SMILES: CCc1cnc(N2CCC(Oc3ccc(-n4ccc5cc(C(=O)NCCO)ccc54)nc3)CC2)nc1]

The title compound was prepared by following the similar procedure as described in Example-2 using Example-76.

$^1$H NMR (400 MHz, CDCl$_3$) δ; 1.20 (t, J=4.8 Hz, 3H), 1.87-1.91 (m, 2H), 2.08-2.12 (m, 2H), 2.49 (q, J=22.8 Hz, 2H), 2.84 (bs, 1H), 3.67-3.71 (m, 4H), 3.87-3.90 (m, 2H), 4.21-4.27 (m, 2H), 4.63-4.65 (m, 1H), 6.82 (t, J=10.8 Hz, 1H), 6.77 (d, J=3.2 Hz, 1H), 7.43-7.46 (s, 2H), 7.68-7.74 (m, 2H), 8.09 (d, J=8.4 Hz, 1H), 8.15 (s, 1H), 8.21 (s, 2H), 8.31 (m, 1H); MS: 487.0 (M+1).

Example-78 trans(±)-tert-Butyl-3-fluoro-4-((6-(5-(methylsulfonyl)-1H-indol-1-yl)pyridin-3-yl)oxy)piperidine-1-carboxylate

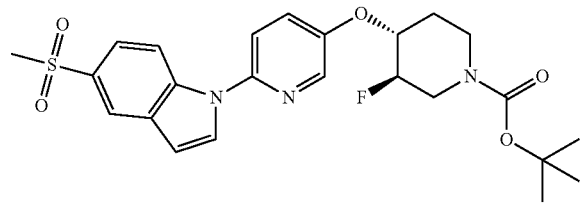 [SMILES: CC(C)(C)OC(=O)N1CC[C@@H](Oc2ccc(-n3ccc4cc(S(C)(=O)=O)ccc43)nc2)[C@H](F)C1]

The title compound was prepared by following the similar procedure as described in Example-1 by using 5-(methylsulfonyl)-1H-indole (intermediate-21) and trans(±)-tert-butyl-4-((6-chloropyridin-3-yl)oxy)-3-fluoropiperidine-1-carboxylate (intermediate-63) (0.220 g, 37%).

$^1$H NMR (400 MHz, CDCl$_3$) δ; 1.51 (s, 9H), 1.78-1.82 (m, 1H), 2.14-2.20 (m, 1H), 3.07 (s, 3H), 3.32 (bs, 1H), 3.43-3.49 (m, 1H), 3.70-3.74 (m, 1H), 4.00 (bs, 1H), 4.47-4.58 (m, 1H), 4.70 (bs, 1H), 6.82 (d, J=3.2 Hz, 1H), 7.41 (d, J=8.8 Hz, 1H), 7.47-7.48 (m, 1H), 7.71 (d, J=3.6 Hz, 1H), 7.78-7.80 (m, 1H), 8.20 (d, J=8.8 Hz, 1H), 8.28 (d, J=2.0 Hz, 1H), 8.32 (d, J=2.8 Hz, 1H); MS: 434.1 (M−56).

Example-79

3-Ethyl-5-((4-((6-(5-(methylsulfonyl)-1H-indol-1-yl)pyridin-3-yl)oxy)-piperidin-1-yl)methyl)-1,2,4-oxadiazole

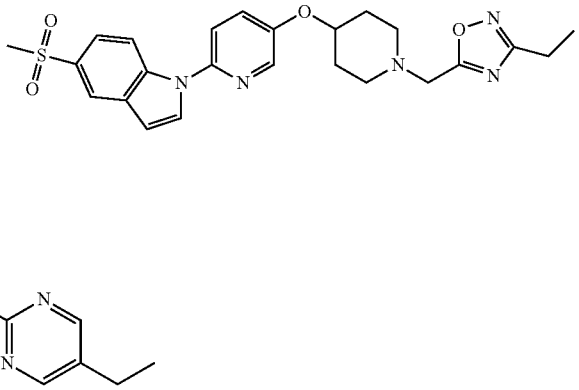

To a solution of tert-butyl 4-((6-chloropyridin-3-yl)oxy)piperidine-1-carboxylate (0.150 g, 0.318 mmol) in dichloromethane (15 mL), trifluoroacetic acid (0.2 mL) was added and the reaction mixture was stirred for 1 h. The reaction mixture was concentrated in vacuo, the resultant residue was dissolved in NMP (3 mL), 5-(chloromethyl)-3-ethyl-1,2,4-oxadiazole (0.051 g 0.350 mmol) and DIPEA (0.123 g, 0.955 mmol) were added and stirred at 60° C. for 3 h. The reaction was quenched by water and the organic layer was extracted with ethyl acetate. The organic layer was separated, concentrated in vacuo and the resultant residue was purified by flash column chromatography to give 3-ethyl-54(4-((6-(5-(methylsulfonyl)-1H-indol-1-yl)pyridin-3-yl)oxy)piperidin-1-yl)methyl)-1,2,4-oxadiazole (0.012 g, 8%).

$^1$H NMR (400 MHz, CDCl$_3$) δ; 1.36 (t, J=7.6 Hz, 3H), 1.99 (m, 2H), 2.11 (m, 2H), 2.59 (m, 2H), 2.82 (q, J=6.4 Hz, 2H), 2.89 (m, 2H), 3.12 (s, 3H), 3.90 (s, 2H), 4.46 (bs, 1H), 6.83 (d, J=3.2 Hz, 1H), 7.42 (d, J=2 Hz, 2H), 7.74 (d, J=3.2 Hz, 1H), 7.80 (dd, J=8.8, 1.6 Hz, 1H), 8.19 (d, J=8.8 Hz, 1H), 8.27-8.30 (m, 2H); MS: 482.0 (M+1).

Example-80

3-Isopropyl-5-((4-((6-(5-(methylsulfonyl)-1H-indol-1-yl)pyridin-3-yl)oxy) piperidin-1-yl)methyl)-1,2,4-oxadiazole

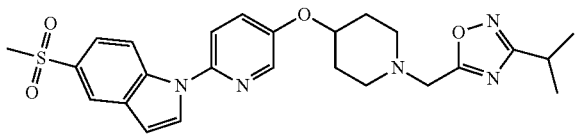 [SMILES: CC(C)c1noc(CN2CCC(Oc3ccc(-n4ccc5cc(S(C)(=O)=O)ccc54)nc3)CC2)n1]

The title compound was prepared by following the similar procedure as described in Example-79 by using Example-1 and 5-(chloromethyl)-3-isopropyl-1,2,4-oxadiazole.

$^1$H NMR (400 MHz, CDCl$_3$) δ; 1.38 (d, J=6.8 Hz, 6H), 1.86-1.90 (m, 2H), 2.02-2.03 (m, 2H), 2.68 (bs, 2H), 2.95-2.98 (m, 2H), 3.10-3.18 (m, 4H), 3.97 (s, 2H), 4.91 (bs, 1H), 6.84 (d, J=3.6 Hz, 1H), 7.43 (d, J=1.2 Hz, 2H), 7.73 (d, J=3.6 Hz, 1H), 7.81 (dd, J=8.8, 1.6 Hz, 1H), 8.19 (d, J=8.8 Hz, 1H), 8.28 (s, 1H), 8.32 (s, 1H); MS: 496.1 (M+1).

Example-81

1-(5-((1-(4-Fluorophenyl)piperidin-4-yl)oxy)pyridin-2-yl)-5-(methyl sulfonyl)-1H-indole

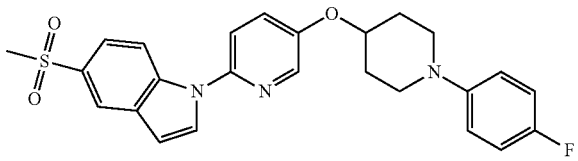 [SMILES: CS(=O)(=O)c1ccc2c(ccn2-c2ccc(OC3CCN(c4ccc(F)cc4)CC3)cn2)c1]

To a stirred solution of example-1 (0.250 g, 0.53 mmol) in dichloromethane (5 mL) trifluoroacetic acid (0.5 mL) was added at 0° C. and stirred at room temperature for 2-3 h. The solvent was removed in vacuo and the resulting salt was dissolved in anhydrous dioxane (10 mL), and 1-bromo-4-florobenzene (0.074 g, 0.424 mmol), 2-(2'-Di-tert-butylphosphine)biphenylpalladium(II) acetate (0.049 g, 0.106 mmol) and NaO$^t$Bu (0.120 g, 1.318 mmol) were added. The resultant reaction mixture was refluxed for 4-5 h. The reaction mixture was filtered over celite and concentrated in vacuo. The residue was purified by flash column chromatography to give the title compound.

$^1$H NMR (400 MHz, CDCl$_3$) δ; 2.03-2.07 (m, 2H), 2.19-2.23 (m, 2H), 3.06-3.10 (m, 5H), 3.43-3.52 (m, 2H), 4.55-4.58 (m, 1H), 6.85 (d, J=3.6 Hz, 1H), 6.93-7.02 (m, 4H), 7.43-7.49 (m, 2H), 7.63 (d, J=3.2 Hz, 1H), 7.82 (dd, J=8.8, 1.6 Hz, 1H), 8.21 (d, J=8.8 Hz, 1H), 8.32 (s, 2H); MS: 466.1 (M+1).

Example-82

1-(5-((1-(4-Fluorobenzyl)piperidin-4-yl)oxy)pyridin-2-yl)-5-(methyl sulfonyl)-1H-indole

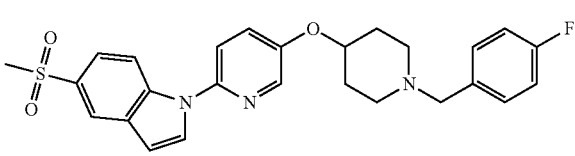 [SMILES: CS(=O)(=O)c1ccc2c(ccn2-c2ccc(OC3CCN(Cc4ccc(F)cc4)CC3)cn2)c1]

To a stirred solution of Example-1 (0.200 g, 0.424 mmol) in dichloromethane (10 mL) trifluoroacetic acid (0.2 mL) was added and stirred for 1 h. The reaction mixture was concentrated in vacuo and the residue was dissolved in DMF (5 mL), Et$_3$N (0.050 g, 0.5 mmol) was added and stirred for 15 minutes. 4-Fluoro benzaldehyde (0.057 g, 0.467 mmol), sodium triacetoxyborohydride (0.134 g, 0.636 mmol) were added and stirred for 10 h. The reaction was quenched by water and the organic layer was extracted with ethyl acetate. The organic layer was concentrated in vacuo and the residue was purified by flash column chromatography to give 1-(5-((1-(4-fluorobenzyl)piperidin-4-yl)oxy)pyridin-2-yl)-5-(methylsulfonyl)-1H-indole (0.012 g, 6%).

$^1$H NMR (400 MHz, CDCl$_3$) δ; 1.92 (bs, 2H), 2.06 (bs, 2H), 2.36 (bs, 2H), 2.78 (bs, 2H), 3.10 (s, 3H), 3.48-3.54 (m, 2H), 4.44 (bs, 1H), 6.84 (d, J=3.6 Hz, 1H), 7.03 (t, 8.4 Hz, 2H), 7.32 (bs, 2H), 7.42-7.3-43 (m, 2H), 7.73 (d, J=3.6 Hz, 1H), 7.81 (dd, J=8.8, 1.6 Hz, 1H), 8.19 (d, J=8.8 Hz, 1H), 8.28-8.31 (m, 2H); MS: 481.1 (M+1).

Example-83

1-(5-((1-((4-Ethyloxazol-2-yl)methyl)piperidin-4-yl)oxy)pyridin-2-yl)-N,N-dimethyl-1H-indole-5-carboxamide

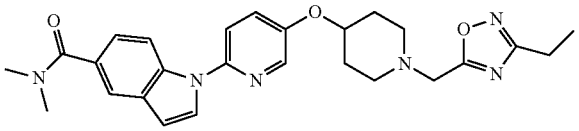 [SMILES: CC(C)c1noc(CN2CCC(Oc3ccc(-n4ccc5cc(C(=O)N(C)C)ccc54)nc3)CC2)n1]

The title compound was prepared by following the similar procedure as described in Example-79 by using Example-39.

$^1$H NMR (400 MHz, CDCl$_3$) δ; 1.24 (t, J=7.6 Hz, 3H), 1.66-1.73 (m, 2H), 2.00-2.28 (m, 2H), 2.42-2.50 (m, 2H), 2.68 (q, J=7.6 Hz, 2H), 2.79-2.90 (m, 2H), 2.99 (s, 6H), 3.91 (s, 2H), 4.50-4.55 (m, 1H), 6.76 (d, J=3.6 Hz, 1H), 7.28 (dd, J=8.4, 1.6 Hz, 1H), 7.66-7.70 (m, 3H), 7.98 (d, J=3.6 Hz, 1H), 8.21 (d, J=8.8 Hz, 1H), 8.29 (m, 1H); MS: 475.2 (M+1).

Example-84

1-(5-((1-((4-Isopropyloxazol-2-yl)methyl)piperidin-4-yl)oxy)pyridin-2-yl)-N,N-dimethyl-1H-indole-5-carboxamide

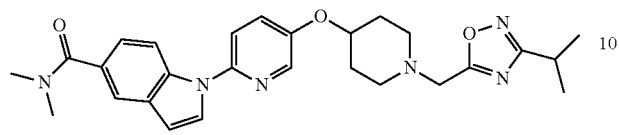

The title compound was prepared by following the similar procedure as described in Example-79 by using Example-39.

$^1$H NMR (400 MHz, CDCl$_3$) δ; 1.27 (d, J=6.8 Hz, 6H), 1.69-1.71 (m, 2H), 2.00-2.02 (m, 2H), 2.41-2.50 (m, 2H), 2.79-2.81 (m, 2H), 2.99 (s, 6H), 3.03-3.37 (m, 1H), 3.91 (s, 2H), 4.52 (bs, 1H), 6.76 (d, J=3.6 Hz, 1H), 7.28 (dd, J=8.8, 2.0 Hz, 1H), 7.37-7.70 (m, 3H), 7.98 (d, J=3.2 Hz, 1H), 8.21 (d, J=8.8 Hz, 1H), 8.29 (s, 1H); MS: 489.1 (M+1).

Example-85

3-Cyclopropyl-5-(4-((6-(5-(methylsulfonyl)-1H-indol-1-yl)pyridin-3-yl)oxy)piperidin-1-yl)-1,2,4-oxadiazole

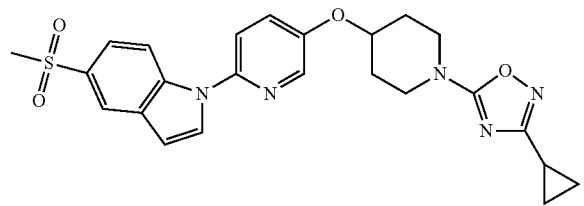 [SMILES: CS(=O)(=O)c1ccc2c(ccn2-c2ccc(OC3CCN(c4nc(C5CC5)no4)CC3)cn2)c1]

The title compound was prepared by following the similar procedure as described in Example-4 by using Example-1 and (Z)—N-hydroxycyclopropanecarbimidic acid.

$^1$H NMR (400 MHz, CDCl$_3$) δ; 0.92-0.95 (m, 4H), 1.84-188 (m, 1H), 1.93-1.99 (m, 2H), 2.03-2.09 (m, 2H), 3.07 (s, 3H), 3.59-3.65 (m, 2H), 3.78-3.84 (m, 2H), 4.62-4.64 (m, 1H), 6.81 (d, J=3.2 Hz, 1H), 7.42 (bs, 2H), 7.70 (d, J=3.6 Hz, 1H), 7.78 (dd, J=8.8, 2.0 Hz, 1H), 8.18 (d, J=8.8 Hz, 1H), 8.28 (s, 2H); MS: 480.1 (M+1).

Example-86

4-Cyclopropyl-2-((4-((6-(5-(methylsulfonyl)-1H-indol-1-yl)pyridin-3-yl)oxy)piperidin-1-yl)methyl)oxazole

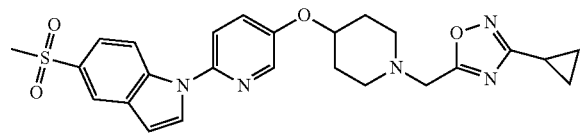 [SMILES: CS(=O)(=O)c1ccc2c(ccn2-c2ccc(OC3CCN(Cc4nc(C5CC5)no4)CC3)cn2)c1]

The title compound was prepared by following the similar procedure as described in Example-79 by using Example-1.

$^1$H NMR (400 MHz, CDCl$_3$) δ; 1.08-1.10 (m, 4H), 1.97 (bs, 2H), 2.10-2.16 (m, 3H), 2.56 (bs, 2H), 2.86-2.88 (m, 2H), 3.10 (s, 3H), 3.85 (s, 2H), 4.45 (bs, 1H), 6.84 (d, J=3.2 Hz, 1H), 7.42 (s, 2H), 7.73 (d, J=3.6 Hz, 1H), 7.81 (dd, J=8.8, 1.6 Hz, 1H), 8.20 (d, J=8.8 Hz, 1H), 8.27-8.31 (m, 2H); MS: 494.1 (M+1).

Example-87 tert-Butyl-4-((6-(5-((2,2,2-trifluoroethyl)carbamoyl)-1H-indol-1-yl)-pyridin-3-yl)oxy)piperidine-1-carboxylate

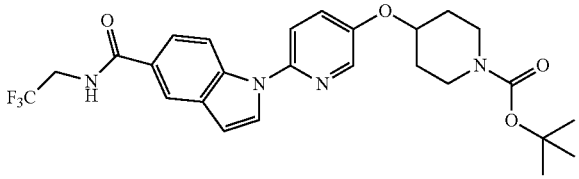 [SMILES: CC(C)(C)OC(=O)N1CCC(Oc2ccc(-n3ccc4cc(C(=O)NCC(F)(F)F)ccc43)nc2)CC1]

The title compound was prepared by following the similar procedure as described in Example-1 by using tert-butyl 4-((6-chloropyridin-3-yl)oxy)piperidine-1-carboxylate (intermediate-06) and tert-butyl 4-((6-chloropyridin-3-yl)oxy)piperidine-1-carboxylate (intermediate-68).

$^1$H NMR (400 MHz, CDCl$_3$) δ; 1.49 (d, J=9.0 Hz, H), 1.81-1.87 (m, 2H). 1.98-2.03 (m, 2H), 3.36-3.42 (m, 2H), 3.73-3.78 (m, 2H), 4.15-4.24 (m, 2H), 4.54 (bs, 1H), 6.79 (d, J=3.2 Hz, 1H), 7.44 (s, 2H), 7.69 (d, J=3.6 Hz, 1H), 7.73 (dd, J=8.8, 1.6 Hz, 1H), 8.10 (d, J=8.4 Hz, 1H), 8.16 (s, 1H), 8.29 (bs, 1H); MS: 519.3 (M+1).

Example-88

1-(5-((1-(5-Ethylpyrimidin-2-yl)piperidin-4-yl)oxy)pyridin-2-yl)-N-(2,2,2-trifluoroethyl)-1H-indole-5-carboxamide

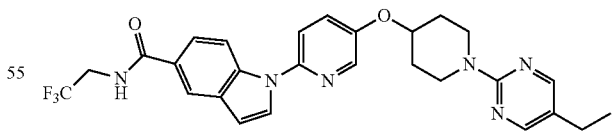

The title compound was prepared by following the similar procedure as described in Example-2 by using Example-87.

$^1$H NMR (400 MHz, CDCl$_3$) δ; 1.92 (t, J=4.8 Hz, 3H), 1.86-1.92 (m, 2H), 2.06-2.12 (m, 2H), 2.31 (q, J=7.6 Hz, 2H), 3.66-3.70 (m, 2H), 4.14-4.25 (m, 4H), 4.63-4.64 (m, 1H), 6.41 (t, J=6.4 Hz, 1H), 6.77 (d, J=3.2 Hz, 1H). 7.44-7.45 (m, 2H), 7.68-7.73 (m, 2H), 8.10 (d, J=8.8 Hz, 2H), 8.14-8.20 (m, 2H), 8.30 (m, 1H); MS: 525.2 (M+1).

Example-89

Isopropyl 4-((6-(5-((2-hydroxyethyl)carbamoyl)-1H-indol-1-yl)pyridin-3-yl)oxy)piperidine-1-carboxylate

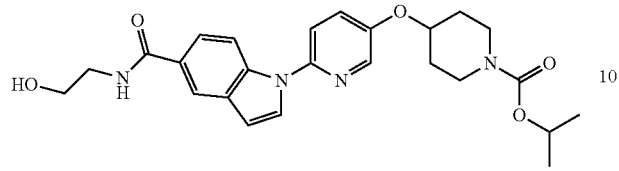

The title compound was prepared by following the similar procedure as described in Example-70 by using Example-76.

$^1$H NMR (400 MHz, CDCl$_3$) δ: 1.25 (d, J=6.0 Hz, 6H), 1.80-1.83 (m, 2H), 1.98-1.99 (m, 2H), 3.39-3.46 (m, 2H), 3.64-3.68 (m, 2H), 3.74-3.78 (m, 2H), 3.84-3.86 (m, 2H), 4.54-4.56 (m, 1H), 4.91-4.94 (m, 1H), 6.74 (d, J=3.6 Hz, 1H), 7.41 (s, 2H), 7.65-7.71 (m, 2H), 8.05 (d, J=8.4 Hz, 1H), 8.12 (s, 1H), 8.25 (s, 1H); MS: 467.1 (M+1).

Example-90

Ethyl 4-((6-(5-((2-hydroxyethyl)carbamoyl)-1H-indol-1-yl)pyridin-3-yl)oxy)piperidine-1-carboxylate

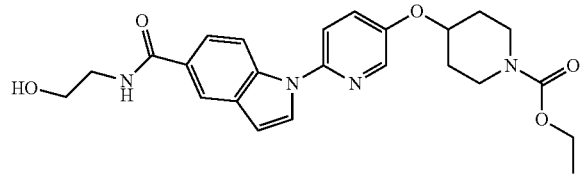 [SMILES: CCOC(=O)N1CCC(Oc2ccc(-n3ccc4cc(C(=O)NCCO)ccc43)nc2)CC1]

The title compound was prepared by following the similar procedure as described in Example-70 by using Example-76.

$^1$H NMR (400 MHz, CDCl$_3$) δ: 1.26 (t, J=7.2 Hz, 3H), 1.79-1.85 (m, 2H), 1.96-2.00 (m, 2H), 3.40-3.46 (m, 2H), 3.64-3.68 (m, 2H), 3.73-3.78 (m, 2H), 3.85 (t, J=4.8 Hz, 2H), 4.14 (q, J=7.2 Hz, 2H), 4.52-4.56 (m, 1H), 6.64-6.66 (m, 1H), 6.73 (d, J=3.6 Hz, 1H), 7.40 (s, 2H), 7.64-7.70 (m, 2H), 8.04 (d, J=8.8 Hz, 1H), 8.11 (s, 1H), 8.25 (bs, 1H); MS: 453.2 (M+1).

Example-91 tert-Butyl-4-((6-(7-fluoro-5-(methylsulfonyl)-1H-indol-1-yl)pyridin-3-yl)oxy)piperidine-1-carboxylate

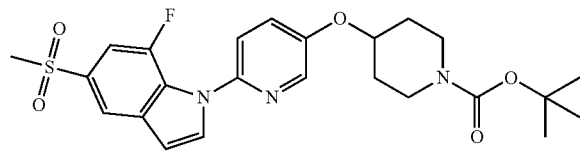 [SMILES: CC(C)(C)OC(=O)N1CCC(Oc2ccc(-n3ccc4cc(S(C)(=O)=O)cc(F)c43)nc2)CC1]

The title compound was prepared by following the similar procedure as described in Example-1 using tert-butyl 4-((6-chloropyridin-3-yl)oxy)piperidine-1-carboxylate (intermediate-06) and 7-Fluoro-5-(methylsulfonyl)-1H-indole (intermediate-22) (0.060 g, 23%).

$^1$H NMR (400 MHz, CDCl$_3$) δ; 1.30 (s, 9H), 1.59 (bs, 2H), 1.86 (bs, 2H), 3.11 (s, 3H), 3.38-3.44 (m, 2H), 3.74-3.80 (m, 2H), 4.58-4.62 (m, 1H), 6.88 (dd, J=3.6, 2.4 Hz, 1H), 7.41 (s, 1H), 7.41 (d, J=1.6 Hz, 1H), 7.52 (dd, J=11.2, 1.6 Hz, 1H), 7.70 (d, J=3.2 Hz, 1H), 8.13 (d, J=1.6 Hz, 1H), 8.25 (d, J=2.0 Hz, 1H); MS: 434 (M−56).

Example-92

3-Methyl-5-(4-((6-(5-(methylsulfonyl)-1H-indol-1-yl)pyridin-3-yl) oxy) piperidin-1-yl)-1,2,4-oxadiazole

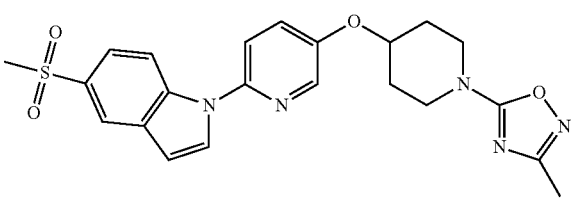 [SMILES: Cc1noc(N2CCC(Oc3ccc(-n4ccc5cc(S(C)(=O)=O)ccc54)nc3)CC2)n1]

The title compound was prepared by following the similar procedure as described in Example-4 using Example-1 (0.010 g, 5.84%).

$^1$H NMR (400 MHz, CDCl$_3$) δ; 1.95-2.01 (m, 2H), 2.05-2.10 (m, 2H), 2.20 (s, 3H), 3.07 (s, 3H), 3.63-3.69 (m, 2H), 3.79-3.86 (m, 2H), 4.65 (bs, 1H), 6.80 (d, J=3.2 Hz, 1H), 7.36-7.44 (m, 2H), 7.69-7.70 (m, 1H), 7.76-7.84 (m, 1H), 8.16-8.19 (m, 1H), 8.20-8.30 (m, 2H); MS: 454.1 (M+1).

Example-93

Methyl-1-(5-((1-(tert-butoxycarbonyl)piperidin-4-yl)oxy)pyridin-2-yl)-1H-indole-5-carboxylate

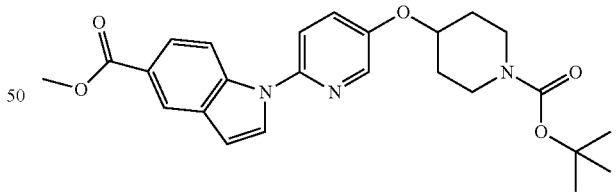

The title compound was prepared by following the similar procedure as described in Example-1 using tert-butyl 4-((6-chloropyridin-3-yl)oxy)piperidine-1-carboxylate (intermediate-6) and methyl 1H-indole-5-carboxylate (0.615 g, 21%).

$^1$H NMR (400 MHz, CDCl$_3$) δ; 1.46 (s, 9H), 1.80 (bs, 2H), 1.97 (bs, 2H), 3.34-3.38 (m, 2H), 3.73 (bs, 2H), 3.93 (s, 3H), 4.53 (bs, 1H), 6.76 (s, 1H), 7.40 (s, 2H), 7.65 (s, 1H), 7.98 (dd, J=8.8, 2.8 Hz, 2H), 8.26 (s, 1H), 8.39 (s, 1H); MS: 452.1 (M+1).

Example-94 tert-Butyl-4-((6-(5-(hydroxymethyl)-1H-indol-1-yl)pyridin-3-yl)oxy)piperidine-1-carboxylate

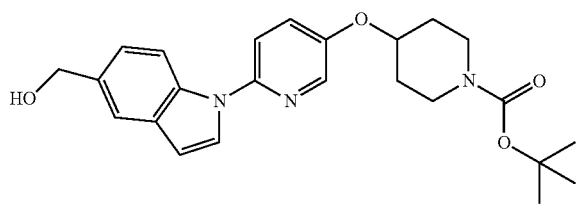 [SMILES: CC(C)(C)OC(=O)N1CCC(Oc2ccc(-n3ccc4cc(CO)ccc43)nc2)CC1]

To a stirred solution of Example-96 (0.3 g, 0.665 mmol) in dry THF, LiAlH$_4$ in THF (0.2 ml, 0.996 mmol) was added at 0° C. and stirred for 20 minutes. The reaction was quenched with methanol at 0° C., the reaction mixture was concentrated in vacuo and the residue was diluted with ethyl acetate and washed with water. The organic layer was separated, concentrated in vacuo and the resulting residue was purified by flash column chromatography to give the title compound (0.198 g, 70.46%).

$^1$H NMR (400 MHz, CDCl$_3$) δ; 1.45 (s, 9H), 1.73-1.81 (m, 2H), 1.95-2.00 (m, 2H), 3.33-3.39 (m, 2H), 3.71-3.77 (m, 2H), 4.50-4.54 (m, 1H), 4.78 (s, 2H), 6.67 (d, J=3.2 Hz, 1H), 7.29 (dd, J=8.8, 1.6 Hz, 2H), 7.37-7.43 (m, 2H), 7.63 (d, J=3.2 Hz, 1H), 7.65 (s, 1H), 8.02 (d, J=8.4 Hz, 1H), 8.24 (bs, 1H); MS: 424.23 (M+1).

Example-95

Methyl-1-(5-((1-(5-ethylpyrimidin-2-yl)piperidin-4-yl)oxy)pyridin-2-yl)-1H-indole-5-carboxylate

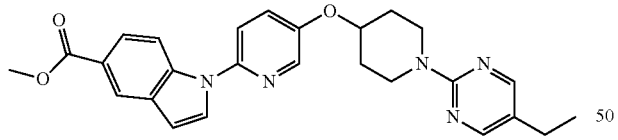

The title compound was prepared by following the similar procedure as described in Example-2 by using Example-93 (0.220 g, 74.82%).

$^1$H NMR (400 MHz, CDCl$_3$) δ; 1.19 (t, J=7.6 Hz, 3H), 1.83-1.90 (m, 2H), 2.04-2.11 (m, 2H), 2.47 (q, J=7.6 Hz, 2H), 3.63-3.69 (m, 2H), 3.93 (s, 1H), 4.18-4.24 (m, 2H), 4.59-4.61 (m, 1H), 6.76 (d, J=3.2 Hz, 1H), 7.43 (d, J=1.6 Hz, 2H), 7.66 (d, J=3.6 Hz, 2H), 7.95 (dd, J=8.8, 2.0 Hz, 2H), 8.03 (d, J=8.8 Hz, 1H), 8.18 (s, 2H), 8.28 (s, 1H), 8.40 (s, 1H); MS: 458.1 (M+1).

Example-96

(1-(5-((1-(5-Ethylpyrimidin-2-yl)piperidin-4-yl)oxy)pyridin-2-yl)-1H-indol-5-yl)methanol

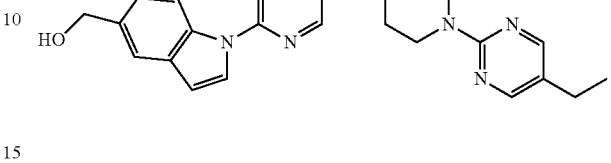

The title compound was prepared by following the similar procedure as described in Example-2 by using Example-94 (0.008 g, 7.14%).

$^1$H NMR (400 MHz, CDCl$_3$) δ; 1.19 (t, J=7.6 Hz, 3H), 1.84-1.88 (m, 2H), 2.05-2.11 (m, 2H), 2.47 (q, J=7.6 Hz, 2H), 3.63-3.69 (m, 2H), 4.19-4.25 (m, 2H), 4.58-4.62 (m, 1H), 4.79 (s, 2H), 6.67 (d, J=3.2 Hz, 1H), 7.29 (dd, J=8.8, 1.6 Hz, 2H), 7.42 (bs, 2H), 7.63-7.65 (m, 2H), 8.03 (d, J=8.4 Hz, 1H), 8.19 (s, 2H). 8.27 (s, 1H); MS: 430.2 (M+1).

Example-97 tert-Butyl-4-((6-(5-(isobutyramidomethyl)-1H-indol-1-yl)pyridin-3-yl) oxy)piperidine-1-carboxylate

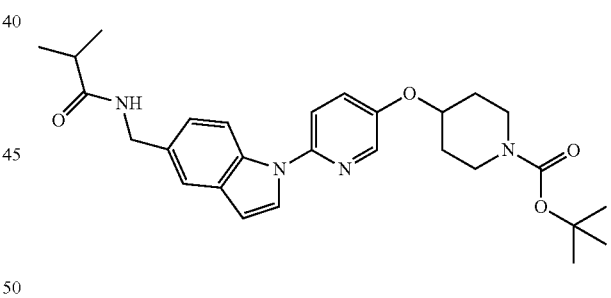

The title compound was prepared by following the similar procedure as described in Example-1 using N-((1H-indol-5-yl)methyl) isobutyramide (intermediate 3) and tert-butyl 4-((6-chloropyridin-3-yl)oxy)piperidine-1-carboxylate (intermediate 6) (0.103 g, 21.77%).

$^1$H NMR (400 MHz, CDCl$_3$) δ; 1.18 (d, J=4 Hz, 6H), 1.47 (s, 9H), 1.77-1.82 (m, 2H), 1.95-1.99 (m, 2H), 2.35-2.38 (m, 1H), 3.33-3.39 (m, 2H), 3.70-3.76 (m, 2H), 4.51-4.53 (m, 3H), 5.67 (s, 1H), 6.65 (d, J=3.2 Hz, 1H), 7.18 (dd, J=8.8, 1.6 Hz, 1H), 7.36-7.41 (m, 2H), 7.55 (s, 1H), 7.61 (d, J=3.6 Hz, 1H), 7.99 (d, J=8.4 Hz, 1H), 8.24 (s, 1H); MS: 452.1 (M+1).

Example-98

N-((1-(5-((1-(5-Ethylpyrimidin-2-yl)piperidin-4-yl)oxy)pyridin-2-yl)-1H-indol-5-yl)methyl)isobutyramide

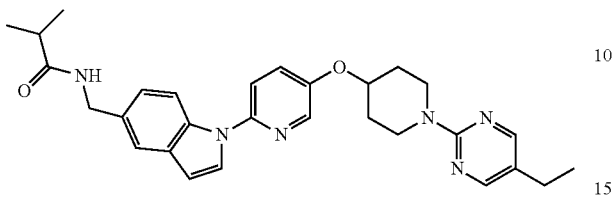

The title compound was prepared by following the similar procedure as described in Example-2 by using Example-97 (0.070 g, 83.57%).

$^1$H NMR (400 MHz, CDCl$_3$) δ; 1.1-1.23 (m, 9H), 1.84-1.87 (m, 2H), 2.04-2.07 (m, 2H), 2.34-2.37 (m, 1H), 2.46 (q, J=7.6 Hz, 2H), 3.61-3.68 (m, 2H), 4.17-4.22 (m, 2H), 4.52 (d, J=5.6 Hz, 2H), 4.58-4.60 (m, 1H), 5.67 (s, 1H), 6.64 (dd, J=3.2, 0.4 Hz, 1H), 7.18 (dd, J=8.8, 2.0 Hz, 1H), 7.40 (bs, 2H), 7.55 (bs, 1H), 7.62 (d, J=3.6 Hz, 1H), 7.98-8.00 (m, 1H), 8.18 (s, 2H), 8.25-8.26 (m, 1H); MS: 522 (M+23).

Example-99 tert-Butyl-4-((6-(5-(3-isopropyl-1,2,4-oxadiazol-5-yl)-1H-indol-1-yl) pyridin-3-yl) oxy)piperidine-1-carboxylate

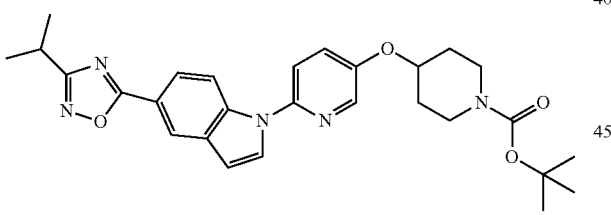

To a stirred solution of N'-hydroxyisobutyrimidamide (0.10 g, 1.0 mmol) in dry THF (10 mL), NaH (0.078 g, 3.26 mmol) was added and stirred at 60° C. for 2 h. The reaction contents were brought to room temperature, Ethyl-1-(5-((1-(tert-butoxycarbonyl)piperidin-4-yl) oxy) pyridin-2-yl)-1H-indole-5-carboxylate (0.205 g, 0.440 mmol) was added and stirred at 60° C. for 3 h. The reaction was quenched by methanol at 0° C. and concentrated in vacuo. The resultant residue was dissolved with ethyl acetate and washed with water, the organic layer was separated, concentrated in vacuo and the resulting residue was purified by flash column chromatography to give the title compound (0.050 g, 10.16%).

$^1$H NMR (400 MHz, CDCl$_3$) δ; 1.44 (d, J=7.2 Hz, 6H), 1.50 (s, 9H), 1.81-1.86 (m, 2H), 1.99-2.04 (m, 2H), 3.15-3.22 (s, 1H), 3.36-3.42 (m, 2H), 3.73-3.79 (m, 2H), 4.55-4.59 (m, 1H), 6.82 (dd, J=3.2, 0.4 Hz, 1H), 7.45 (bs, 2H), 7.69 (d, J=3.6 Hz, 1H), 8.03 (dd, J=8.8, 1.6 Hz, 1H), 8.13-8.16 (m, 1H), 8.30 (bs, 1H), 8.49 (bs, 1H); MS: 504.2 (M+1).

Example-100

5-(1-(5-((1-(5-Ethylpyrimidin-2-yl)piperidin-4-yl)oxy)pyridin-2-yl)-1H-indol-5-yl)-3-isopropyl-1,2,4-oxadiazole

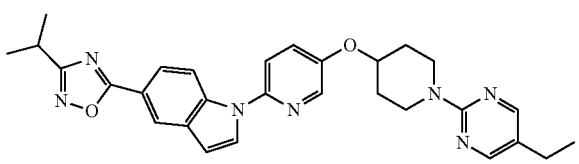 [SMILES: CCc1cnc(N2CCC(Oc3ccc(-n4ccc5cc(-c6nc(C(C)C)no6)ccc54)nc3)CC2)nc1]

The title compound was prepared by following the similar procedure as described in Example-2 by using Example-99 (0.052 g, 55.60%).

$^1$H NMR (400 MHz, CDCl$_3$) δ; 1.22 (t, J=7.2 Hz, 3H), 1.44 (d, J=7.2 Hz, 6H), 1.87-1.92 (m, 2H), 2.09-2.13 (m, 2H), 2.50 (q, J=7.6 Hz, 2H), 3.17-3.21 (m, 1H), 3.66-3.72 (m, 2H), 4.21-4.27 (m, 2H), 4.64-4.66 (m, 1H), 6.82 (dd, J=3.2, 0.4 Hz, 1H), 7.47-7.46 (m, 2H), 7.70 (d, J=3.6 Hz, 1H), 8.04 (dd, J=8.8, 2.0 Hz, 1H), 8.15-8.17 (m, 1H), 8.21 (s, 2H), 8.32-8.33 (m, 1H), 8.49 (s, 1H).

Example-101

Isopropyl 4-((6-(5-(3-isopropyl-1,2,4-oxadiazol-5-yl)-1H-indol-1-yl) pyridin-3-yl) oxy)piperidine-1-carboxylate

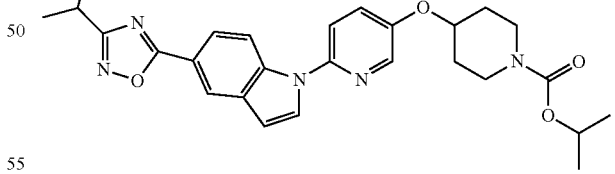

The title compound was prepared by following the similar procedure as described in Example-70 by using Example-99 (0.035 g, 43%).

$^1$H NMR (400 MHz, CDCl$_3$) δ; 1.28 (d, J=6.0 Hz, 6H), 1.44 (d, J=7.2 Hz, 6H), 1.82-1.87 (m, 2H), 1.99-2.03 (m, 2H), 3.15-3.21 (s, 1H), 3.42-3.48 (m, 2H), 3.76-3.82 (m, 2H), 4.57-4.60 (m, 1H), 4.93-4.99 (m, 1H), 6.82 (d, J=3.2 Hz, 1H), 7.45 (s, 2H), 7.69 (d, J=3.2 Hz, 1H), 8.03 (dd, J=8.8, 1.2 Hz, 1H), 8.14-8.16 (m, 1H), 8.29-8.30 (m, 1H), 8.49 (bs, 1H); MS: 490.2 (M+1).

Example-102 tert-Butyl-4-((6-(5-(3-methyl-1,2,4-oxadiazol-5-yl)-1H-indol-1-yl)pyridin-3-yl)oxy)piperidine-1-carboxylate

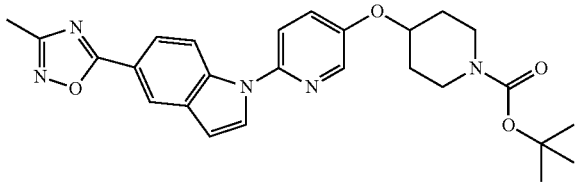 [SMILES: Cc1noc(-c2ccc3c(ccn3-c3ccc(OC4CCN(C(=O)OC(C)(C)C)CC4)cn3)c2)n1]

The title compound was prepared by following the similar procedure as described in Example-99 using Ethyl-1-(5-((1-(tert-butoxycarbonyl)piperidin-4-yl)oxy)pyridin-2-yl)-1H-indole-5-carboxylate (intermediate 28) (0.615 g, 21.30%).

$^1$H NMR (400 MHz, CDCl$_3$) δ; 1.46 (s, 9H), 1.55-1.83 (m, 2H), 1.95-2.00 (m, 2H), 2.46 (s, 3H), 3.33-3.39 (m, 2H), 3.70-3.76 (m, 2H), 4.51-4.56 (m, 1H), 6.78 (dd, J=3.6, 0.8 Hz, 1H), 7.41 (s, 2H), 7.66 (d, J=3.6 Hz, 1H), 7.99 (dd, J=8.8, 1.6 Hz, 1H), 8.12 (d, J=8.8 Hz, 1H), 8.26-8.27 (m, 1H), 8.44 (s, 1H); MS: 476.2 (M+1).

Example-103

5-(1-(5-((1-(5-Ethylpyrimidin-2-yl)piperidin-4-yl)oxy)pyridin-2-yl)-1H-indol-5-yl)-3-methyl-1,2,4-oxadiazole

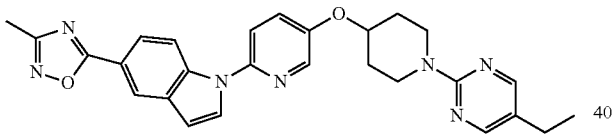

The title compound was prepared by following the similar procedure as described in Example-2 by using Example-102.

$^1$H NMR (400 MHz, CDCl$_3$) δ; 1.20 (t, J=7.6 Hz, 3H), 1.86-1.90 (m, 2H), 2.07-2.12 (m, 2H), 2.45-2.51 (m, 5H), 3.64-3.70 (m, 2H), 4.19-4.26 (m, 2H), 4.63-4.64 (m, 1H), 6.80 (d, J=3.2 Hz, 1H), 7.45 (s, 1H), 7.69 (d, J=3.2 Hz, 1H), 8.01 (dd, J=8.8, 1.6 Hz, 2H), 8.15 (d, J=8.8 Hz, 1H), 8.20 (s, 2H), 8.31-8.32 (m, 1H), 8.46 (s, 1H); MS: 482.2 (M+1).

Example-104 tert-Butyl-4-((6-(5-(pyrrolidin-1-yl)-1H-indol-1-yl)pyridin-3-yl) oxy) piperidine-1-carboxylate

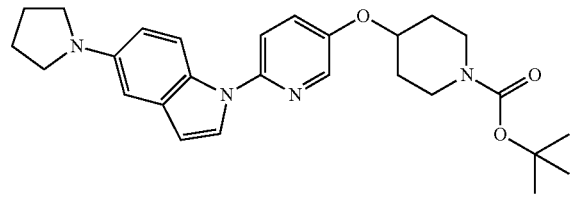 [SMILES: CC(C)(C)OC(=O)N1CCC(Oc2ccc(-n3ccc4cc(N5CCCC5)ccc43)nc2)CC1]

The title compound was prepared by following the similar procedure as described in Example-1 using tert-butyl 4-((6-chloropyridin-3-yl)oxy)piperidine-1-carboxylate (intermediate 6) and tert-butyl-5-(pyrrolidin-1-yl)-1H-indole-1-carboxylate (intermediate 66) (0.030 g, 10.16%).

$^1$H NMR (400 MHz, CDCl$_3$) δ; 1.49 (s, 9H), 1.81 (s, 2H), 1.97 (s, 2H), 2.04 (s, 4H), 3.20-3.50 (m, 6H), 3.75 (s, 2H), 4.50 (s, 1H), 6.55 (s, 1H), 6.70 (d, J=8.8 Hz, 1H), 6.79 (s, 1H), 7.35-7.41 (m, 2H), 7.57 (s, 1H), 7.96 (d, J=8.8 Hz, 1H), 8.22 (s, 1H); MS: 463.3 (M+1).

Example-105

1-(5-(((1-(5-Ethylpyrimidin-2-yl)piperidin-4-yl)oxy)pyridin-2-yl)-5-(pyrrolidin-1-yl)-1H-indole

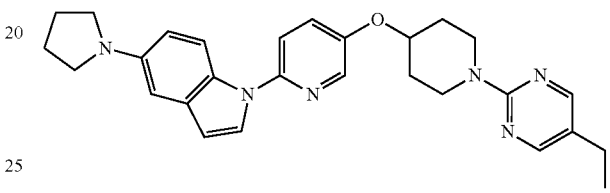

The title compound was prepared by following the similar procedure as described in Example-2 by using Example-104 (0.060 g, 64%).

$^1$H NMR (400 MHz, CDCl$_3$) δ; 1.20 (t, J=7.6 Hz, 3H), 1.56-1.87 (m, 2H), 2.01-2.10 (m, 6H), 2.47 (q, J=7.6 Hz, 2H), 3.32-3.35 (m, 4H), 3.61-3.68 (m, 2H), 4.19-4.25 (m, 2H), 4.55-4.57 (m, 1H), 6.55 (d, J=3.2 Hz, 1H), 6.69 (dd, J=8.8, 2.0 Hz, 1H), 6.78 (s, 1H), 7.39-7.41 (m, 2H), 7.57 (d, J=3.6 Hz, 1H), 7.96 (d, J=9.2 Hz, 1H), 8.19 (s, 2H), 8.24 (s, 1H); MS: 469.3 (M+1).

Example-106

1-(5-(((1-(5-Ethylpyrimidin-2-yl)piperidin-4-yl)oxy)methyl)pyridin-2-yl)-5-(methylsulfonyl)-1H-indole

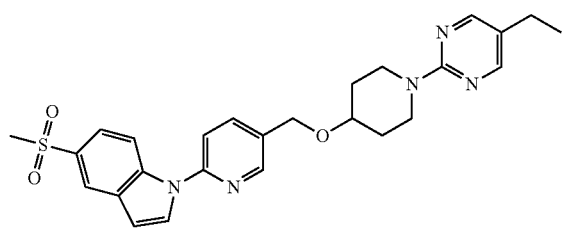 [SMILES: CCc1cnc(N2CCC(OCc3ccc(-n4ccc5cc(S(C)(=O)=O)ccc54)nc3)CC2)nc1]

The title compound was prepared by following the similar procedure as described in Example-2 using tert-butyl-4-((6-(5-(methylsulfonyl)-1H-indol-1-yl)pyridin-3-yl)methoxy)piperidine-1-carboxylate (intermediate 75) (0.055 g, 58%).

$^1$H NMR (400 MHz, CDCl$_3$) δ; 1.20 (t, J=7.6 Hz, 3H), 1.64-1.73 (m, 2H), 2.00-2.04 (m, 2H), 2.46 (q, J=7.6 Hz, 2H), 3.09 (s, 3H), 3.36-3.42 (m, 2H), 3.72-3.76 (m, 1H), 4.29-4.35 (m, 2H), 4.67 (s, 2H), 6.85 (d, J=3.6 Hz, 1H), 7.48 (d, J=8.4 Hz, 1H), 7.80-7.83 (m, 2H), 7.91 (dd, J=8.8, 2.0 Hz, 1H), 8.17 (s, 2H), 8.29 (s, 1H), 8.37 (d, J=8.8 Hz, 1H), 8.57 (s, 1H); MS: 492.2 (M+1).

Example-107

Ethyl 4-(((6-(5-(methylsulfonyl)-1H-indol-1-yl)pyridin-3-yl)methoxy) piperidine-1-carboxylate

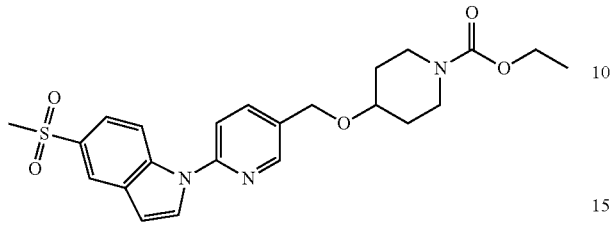

The title compound was prepared by following the similar procedure as described in Example-70 using tert-butyl-4-((6-(5-(methylsulfonyl)-1H-indol-1-yl)pyridin-3-yl) methoxy) piperidine-1-carboxylate (intermediate 75) (0.038 g, 41%).
$^1$H NMR (400 MHz, CDCl$_3$) δ; 1.26 (t, J=7.2 Hz, 3H), 1.53-1.69 (m, 2H), 1.91 (bs, 2H), 3.09 (s, 3H), 3.19-3.25 (m, 2H), 3.64-3.68 (m, 1H), 3.82 (bs, 2H), 4.13 (q, J=7.2 Hz, 2H), 4.63 (s, 2H), 6.85 (dd, J=3.2, 0.4 Hz, 1H), 7.48 (d, J=8.4 Hz, 1H), 7.80-7.83 (m, 2H), 7.89 (dd, J=8.4, 2.4 Hz, 1H), 8.29 (d, J=1.6 Hz, 1H), 8.38 (d, J=8.8 Hz, 1H), 8.56 (bs, 1H); MS: 458.1 (M+1).

Example-108

Isopropyl 4-((6-(5-(methylsulfonyl)-1H-indol-1-yl)pyridin-3-yl)methoxy)piperidine-1-carboxylate

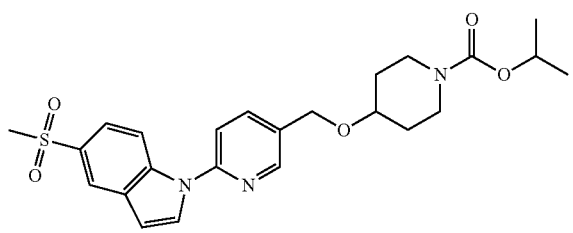 [SMILES: CC(C)OC(=O)N1CCC(OCc2ccc(-n3ccc4cc(S(C)(=O)=O)ccc43)nc2)CC1]

The title compound was prepared by following the similar procedure as described in Example-70 using tert-butyl-4-((6-(5-(methylsulfonyl)-1H-indol-1-yl)pyridin-3-yl) methoxy) piperidine-1-carboxylate (intermediate 75) (0.075 g, 80%).
$^1$H NMR (400 MHz, CDCl$_3$) δ; 1.24 (d, J=6.4 Hz, 6H), 1.64-1.67 (m, 2H), 1.92 (bs, 2H), 3.11 (s, 3H), 3.18-3.24 (m, 2H), 3.65-3.71 (m, 1H), 3.84 (bs, 2H), 4.65 (s, 2H), 4.90-4.96 (m, 1H), 6.87 (dd, J=3.6, 0.8 Hz, 1H), 7.52 (d, J=9.2 Hz, 1H), 7.82-7.85 (m, 2H), 7.91 (dd, J=8.4, 2.4 Hz, 1H), 8.31 (d, J=1.6 Hz, 1H), 8.39 (d, J=8.8 Hz, 1H), 8.56 (bs, 1H); MS: 472.08 (M+1).

Example-109

2-Methyl-1-(4-((6-(5-(methylsulfonyl)-1H-indol-1-yl)pyridin-3-yl) methoxy)piperidin-1-yl) propan-2-ol

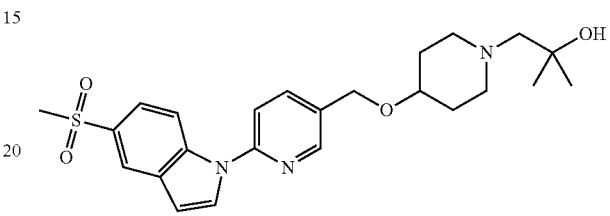

The title compound was prepared by following the similar procedure as described in Example-12 using tert-butyl-4-((6-(5-(methylsulfonyl)-1H-indol-1-yl)pyridin-3-yl) methoxy) piperidine-1-carboxylate (intermediate 75) (0.133 g, 48%).
$^1$H NMR (400 MHz, CDCl$_3$) δ; 1.14 (s, 6H), 1.70 (bs, 2H), 1.92 (bs, 2H), 2.30 (s, 2 H), 2.45(bs, 2H), 2.88 (bs, 2H), 3.07(s, 3H), 3.48 (bs, 1H), 4.60 (s, 2H), 6.83(d, J=3.6 Hz, 1H), 7.46 (d, J=8 Hz, 1H), 7.78-7.80 (m, 1H), 7.81 (d, J=2.0 Hz, 1H), 7.88 (dd, J=8.4, 2.4 Hz, 1H), 8.28 (d, J=1.6 Hz, 1H), 8.35 (d, J=8.8 Hz, 1H), 8.54 (d, J=2 Hz, 1H); MS: 458.1 (M+1).

Example-110

1-(5-(((1-(2-Fluoro-2-methylpropyl)piperidin-4-yl)oxy)methyl)pyridin-2-yl)-5-(methylsulfonyl)-1H-indole The title compound was prepared by following the similar procedure as described in Example-14 by using Example-109 (0.030 g, 27%).
$^1$H NMR (400 MHz, CDCl$_3$) δ; 1.31 (s, 3H), 1.37 (s, 3H), 1.64-1.72 (m, 2H), 1.91-1.94(m, 2H), 2.28 (t, J=9.6 Hz, 2H), 2.39 (s, 1H), 2.44 (s, 1H), 2.82-2.86 (m, 2H), 3.08 (s, 3H), 3.41-3.46 (m, 1H), 4.60 (s, 2H), 6.84 (d, J=2.8 Hz, 1H), 7.45 (d, J=8.4 Hz, 1H), 7.78-7.79 (m, 1H), 7.82 (d, J=2 Hz, 1H), 7.88 (dd, J=8.4, 2.4 Hz, 1H), 8.28 (d, J=1.6 Hz, 1H), 8.35 (d, J=9.2 Hz, 1H), 8.54 (d, J=1.6 Hz, 1H); MS: 496.2 (M+1).

Example-111

3-Isopropyl-5-(4-((6-(5-(methylsulfonyl)-1H-indol-1-yl)pyridin-3-yl) methoxy)piperidin-1-yl)-1,2,4-oxadiazole

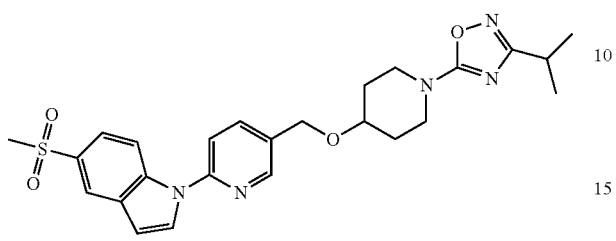

The title compound was prepared by following the similar procedure as described in Example-4 using 4-((6-(5-(methylsulfonyl)-1H-indol-1-yl)pyridin-3-yl)methoxy) piperidine-1-carbonitrile (intermediate 38) and N-hydroxy-isobutyramidine (0.010 g, 5.8%).

¹H NMR (400 MHz, CDCl₃) δ; 1.32 (d, J=6.8 Hz, 6H), 1.82-1.86 (m, 2H), 2.02-2.06 (m, 2H), 2.89-2.93 (m, 1H), 3.12 (s, 3H), 3.48-3.54 (m, 2H), 3.77-3.79 (m, 1H), 3.87-3.88 (m, 2H), 4.68 (s, 2H), 6.88 (dd, J=3.6, 0.4 Hz, 1H), 7.52 (d, J=8.4 Hz, 1H), 7.83-7.86 (m, 2H), 7.92 (dd, J=8.4, 2.4 Hz, 1H), 8.32 (d, J=1.6 Hz, 1H), 8.42 (d, J=8.8 Hz, 1H), 8.60 (d, J=1.6 Hz, 1H); MS: 496.2 (M+1).

Example-112

3-Methyl-5-(4-((6-(5-(methylsulfonyl)-1H-indol-1-yl)pyridin-3-yl)methoxy) piperidin-1-yl)-1,2,4-oxadiazole

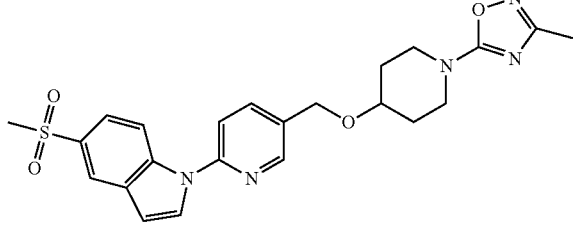

The title compound was prepared by following the similar procedure as described in Example-4 using 4-((6-(5-(methylsulfonyl)-1H-indol-1-yl)pyridin-3-yl)methoxy)piperidine-1-carbonitrile (intermediate 38) and N-hydroxyacetimidamide (0.014 g, 8%).

¹H NMR (400 MHz, CDCl₃) δ; 1.85-1.88 (m, 2H), 1.99-2.07 (m, 2H), 2.23 (s, 3H), 3.11(s, 3H), 3.49-3.55 (m, 2H), 3.77-3.81 (m, 1H), 3.85-3.91 (m, 2H), 4.67 (s, 2H), 6.87 (d, J=3.2 Hz, 1H), 7.45-7.53 (m, 2H), 7.82-7.86 (m, 1H), 7.88-7.93 (m, 1H), 8.31-8.35 (m, 1H), 8.39-8.44 (m, 1H), 8.58 (bs, 1H); MS: 468.08 (M+1).

Example-113

1-(5-(((1-(5-Ethylpyrimidin-2-yl)piperidin-4-yl)oxy)methyl)pyridin-2-yl)-5-(methylsulfonyl)indoline

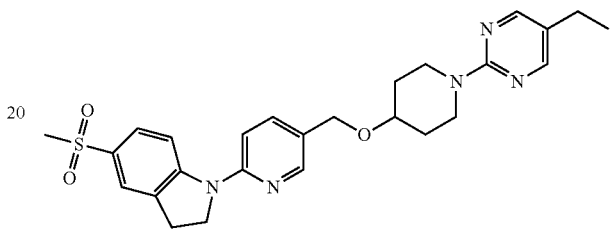

The title compound was prepared by following the similar procedure as described in Example-2 by using Example-46.

¹H NMR (400 MHz, CDCl₃) δ; 1.81 (t, J=7.6 Hz, 3H), 1.309-1.41 (m, 2H), 1.92-1.95 (m, 2H), 2.07-2.13 (m, 1H), 2.46 (q, J=7.6 Hz, 2H), 2.87-2.94 (m, 2H), 3.02 (s, 3H), 3.25 (t, J=17.6 Hz, 2H), 3.86 (d, J=6.4 Hz, 2H), 4.11 (t, J=8.8 Hz, 2H), 4.76-4.80 (m, 2H), 6.78 (d, J=9.2 Hz, 1H), 7.25-7.28 (m, 1H), 7.64 (bs, 1H), 7.71 (dd, J=8.8, 2.0 Hz, 1H), 8.09 (d, J=2.8 Hz, 1H), 8.14 (s, 1H), 8.17 (s, 2H); MS: 494.2 (M+1).

Example-114 tert-Butyl-4-((6-(5-isobutyramido-1H-indol-1-yl)pyridin-3-yl)oxy)-piperidine-1-carboxylate

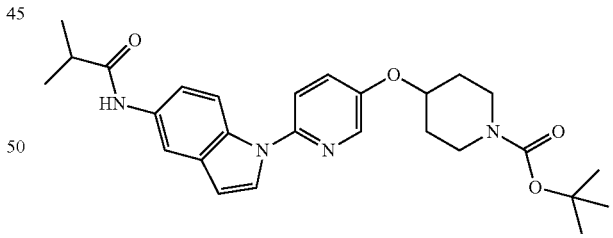

The title compound was prepared by following the similar procedure as described in Example-1 using tert-butyl 4-((6-chloropyridin-3-yl)oxy)piperidine-1-carboxylate (intermediate 06) and N-(1H-indol-5-yl)isobutyramide (intermediate 10).

1H NMR (400 MHz, CDCl₃) δ; 1.29 (d, J=7.2 Hz, 6H), 1.48 (s, 9H), 1.813-1.814 (m, 2H), 1.95-2.00 (m, 2H), 2.50-2.57 (m, 1H), 3.33-3.39 (m, 2H), 3.71-3.77 (m, 2H), 4.50-4.52 (m, 1H), 6.63 (d, J=3.2 Hz, 1H), 7.21 (s, 1H), 7.23 (d, J=2.4 Hz, 1H), 7.38-7.39 (m, 2H), 7.60 (d, J=3.6 Hz, 1H), 7.95 (d, J=2.0 Hz, 1H), 8.00 (d, J=8.8 Hz, 1H), 8.23-8.24 (m, 1H); MS: 481 (M+1).

Example-115

3-Isopropyl-5-(4-((6-(5-(methylsulfonyl)indolin-1-yl)pyridin-3-yl)methoxy)piperidin-1-yl)-1,2,4-oxadiazole

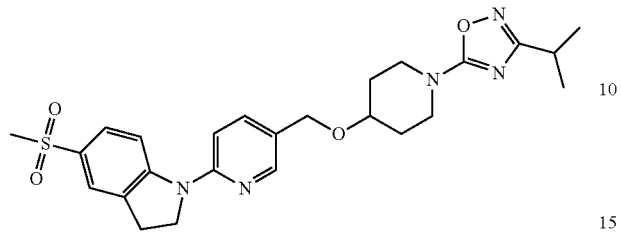

The title compound was prepared by following the similar procedure as described in Example-4 by using Example-46 (0.010 g, 5%).

$^1$H NMR (400 MHz, CDCl$_3$) δ; 1.30 (d, J=6.8 Hz, 6H), 1.75-1.83 (m, 2H), 1.95-2.00 (m, 2H), 2.87-2.94(m, 1H), 3.05 (s, 3H), 3.31(t, J=8.8 Hz, 2H), 3.44-3.50 (m, 2H), 3.69-3.85 (m, 1H), 3.86-3.90 (m, 2H), 4.17 (t, J=8.8 Hz, 2H), 4.56 (s, 2H), 6.82 (d, J=8.4 Hz, 1H), 7.70 (bs, 2H), 7.77 (d, J=8.8 Hz, 1H), 8.37-8.42 (m, 2H); MS: 498.2 (M+1).

Example-116 tert-Butyl-4-((6-(5-(methylsulfonyl)-1H-indol-1-yl)pyridin-2-yl)oxy)-piperidine-1-carboxylate

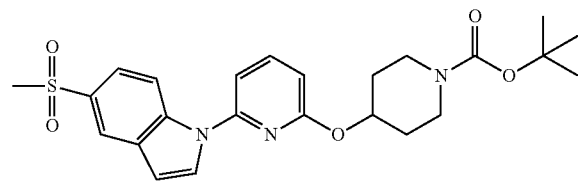 [SMILES: CC(C)(C)OC(=O)N1CCC(Oc2cccc(-n3ccc4cc(S(C)(=O)=O)ccc43)n2)CC1]

The title compound was prepared by following the similar procedure as described in Example-1 by using 5-(methylsulfonyl)-1H-indole (intermediate 21) and tert-butyl 4-((6-chloropyridin-2-yl)oxy)piperidine-1-carboxylate (intermediate 42) (0.19 g, 63%).

$^1$H NMR (400 MHz, CDCl$_3$) δ; 1.48 (s, 9H), 1.79-1.85 (m, 2H), 2.02-2.06 (m, 2H), 3.10 (s, 3H), 3.30-3.36 (m, 2H), 3.78-3.82 (m, 2H), 5.26-5.30 (m, 1H), 6.69 (d, J=8.4 Hz, 1H), 6.83 (d, J=3.2 Hz, 1H), 7.03 (d, J=8 Hz, 1H), 7.73-7.82 (m, 3H), 8.29-8.30 (m, 2H); MS: 372 (M−100)

Example-117

1-(6-((1-(5-Ethylpyrimidin-2-yl)piperidin-4-yl)oxy)pyridin-2-yl)-5-(methylsulfonyl)-1H-indole

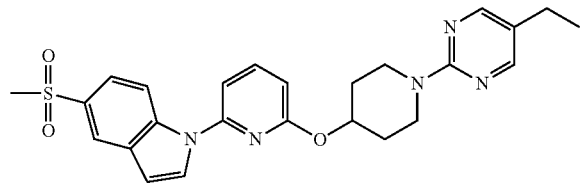 [SMILES: CCc1cnc(N2CCC(Oc3cccc(-n4ccc5cc(S(C)(=O)=O)ccc54)n3)CC2)nc1]

The title compound was prepared by following the similar procedure as described in Example-2 by using Example-116 (0.054 g, 24%).

$^1$H NMR (400 MHz, CDCl$_3$) δ; 1.19 (t, J=7.6 Hz, 3H), 1.85-1.93 (m, 2H), 2.12-2.16 (m, 2H), 2.47 (q, J=7.6 Hz, 2H), 3.10 (s, 3H), 3.61-3.67 (m, 2H), 4.24-4.30 (m, 2H), 5.38-5.40 (m, 1H), 6.70 (d, J=8.0 Hz, 1H), 6.84 (d, J=3.6 Hz, 1H), 7.03 (d, J=7.6 Hz, 1H), 7.74-7.78 (m, 1H), 7.79-7.82 (m, 2H), 8.19 (s, 2H), 8.29 (d, J=1.2 Hz, 1H), 8.35 (d, J=8.8 Hz, 1H); MS: 478 (M+1).

Example-118

N-(1-(5-((1-(5-Ethylpyrimidin-2-yl)piperidin-4-yl)oxy)pyridin-2-yl)-1H-indol-5-yl)pivalamide

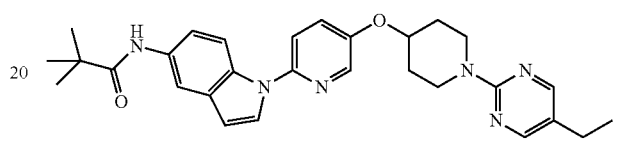

The title compound was prepared by following the similar procedure as described in Example-2 using tert-butyl 4-((6-(5-pivalamido-1H-indol-1-yl)pyridin-3-yl)oxy)piperidine-1-carboxylate (intermediate 30).

$^1$H NMR (400 MHz, CDCl$_3$) δ; 1.2 (t, J=7.6 Hz, 3H), 1.35 (s, 9H), 1.84-1.88 (m, 2H), 2.05-2.10 (m, 2H), 2.47 (q, J=7.6 Hz, 2H), 3.62-3.68 (m, 2H), 4.19-4.25 (m, 2H), 4.58-4.60 (m, 1H), 7.24-7.27 (m, 2H), 7.39-7.41 (m, 3H), 7.61 (d, J=3.2 Hz, 1H), 7.96 (d, J=2.0 Hz, 1H), 8.01 (d, J=8.8 Hz, 1H), 8.19 (s, 2H), 8.26-8.27 (m, 1H); MS: 499 (M+1).

Example-119

N-(1-(5-Ethylpyrimidin-2-yl)piperidin-4-yl)-6-(5-(methylsulfonyl)-1H-indol-1-yl)pyridin-3-amine

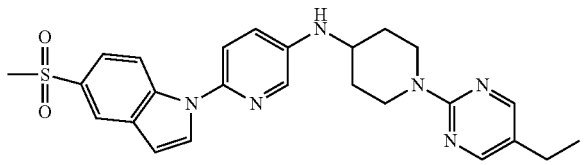 [SMILES: CCc1cnc(N2CCC(Nc3ccc(-n4ccc5cc(S(C)(=O)=O)ccc54)nc3)CC2)nc1]

The title compound was prepared by following the similar procedure as described in Example-2 using tert-butyl 4-((6-(5-(methylsulfonyl)-1H-indol-1-yl)pyridin-3-yl) amino)-piperidine-1-carboxylate (Intermediate 31).

$^1$H NMR (400 MHz, CDCl$_3$) δ; 1.19 (t, J=7.6 Hz, 3H), 1.43-1.53 (m, 2H), 2.17-2.20 (m, 2H), 2.47 (q, J=7.6 Hz, 2H), 3.08 (s, 3H), 3.12-3.19 (m, 2H), 3.60 (bs, 1H), 3.77 (bs, 2H), 4.65-4.70 (m, 2H), 6.79 (dd, J=3.2, 0.8 Hz, 1H), 7.11 (dd, J=8.8, 3.2 Hz, 1H), 7.29 (d, J=8.4 Hz, 1H), 7.67 (d, J=3.6 Hz, 1H), 7.76 (dd, J=8.8, 2.0 Hz, 1H), 8.00 (d, J=2.8 Hz, 1H), 8.06 (d, J=8.8 Hz, 1H), 8.19 (s, 2H), 8.29 (d, J=1.6 Hz, 1H); MS: 477(M+1).

Example-120

N-(1-(3-Isopropyl-1,2,4-oxadiazol-5-yl)piperidin-4-yl)-6-(5-(methyl sulfonyl)-1H-indol-1-yl)pyridin-3-amine

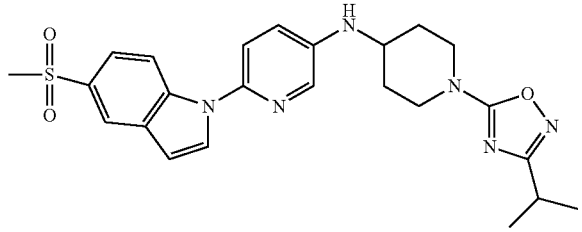 [SMILES: CC(C)c1noc(N2CCC(Nc3ccc(-n4ccc5cc(S(C)(=O)=O)ccc54)nc3)CC2)n1]

The title compound was prepared by following the similar procedure as described in Example-4 using tert-butyl 446-(5-(methylsulfonyl)-1H-indol-1-yl)pyridin-3-yl)amino)-piperidine-1-carboxylate (intermediate 31).

$^1$H NMR (400 MHz, CDCl$_3$) δ; 1.29 (d, J=6.8 Hz, 6H), 1.53-1.54 (m, 2H), 2.19-2.23 (m, 2H), 2.86-2.93 (m, 1H), 3.09 (s, 3H), 3.25-3.32 (m, 2H), 3.57-3.59 (m, 1H), 3.78 (d, J=8.0 Hz, 1H), 4.19-4.15 (m, 2H), 6.80 (dd, J=3.2, 0.4 Hz, 1H), 7.11 (dd, J=8.8, 3.2 Hz, 1H), 7.30 (d, J=8.8 Hz, 1H), 7.67 (d, J=3.6 Hz, 1H), 7.77 (dd, J=8.8 Hz, 1H), 8.00 (d, J=2.8 Hz, 1H), 8.07 (d, J=8.8 Hz, 1H), 8.29 (d, J=1.6 Hz, 1H); MS: 481 (M+1).

Example-121

N-(1-(5-Ethylpyrimidin-2-yl)piperidin-4-yl)-6-(5-(methylsulfonyl)-indolin-1-yl)pyridin-3-amine

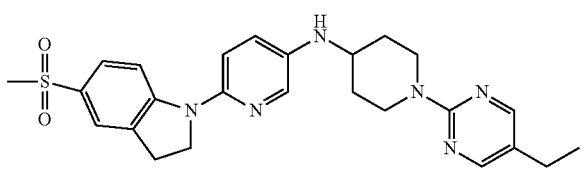

The title compound was prepared by following the similar procedure as described in Example-2 using tert-butyl 4-((6-(5-(methylsulfonyl)indolin-1-yl)pyridin-3-yl)amino)-piperidine-1-carboxylate. (Intermediate 32).

$^1$H NMR (400 MHz, CDCl$_3$) δ; 1.21 (t, J=7.2 Hz, 3H), 1.39-1.45 (m, 2H), 2.15-2.19 (m, 2H), 2.49 (q, J=7.6 Hz, 2H), 3.04 (s, 3H), 3.10-317(m, 2H), 3.25 (t, J=8.8 Hz, 2H), 3.40 (bs, 1H), 3.54 (bs, 1H), 4.12 (t, J=8.8 Hz, 2H), 4.66-4.69 (m, 2H), 6.79 (d, J=8.8 Hz, 1H), 7.07 (dd, J=8.8, 2.8 Hz, 1H), 7.64 (s, 1H), 7.71 (dd, J=8.4, 2.0 Hz, 1H), 7.91 (d, J=2.4 Hz, 1H), 8.02 (d, J=8.8 Hz, 1H), 8.20 (s, 2H); MS: 479 (M+1).

Example-122 tert-Butyl-4-(((6-(5-isobutyramido-1H-indol-1-yl)pyridin-3-yl)oxy)-methyl)piperidine-1-carboxylate

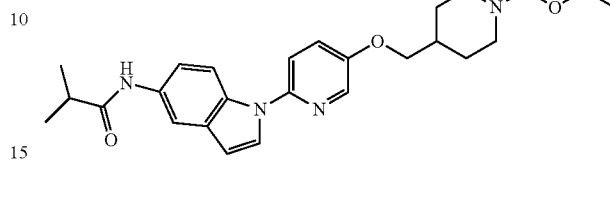

The title compound was prepared by following the similar procedure as described in Example-1 using N-(1H-indol-5-yl)isobutyramide (intermediate 10) and tert-butyl 4-(((6-chloropyridin-3-yl)oxy)methyl)piperidine-1-carboxylate (intermediate 29).

$^1$H NMR (400 MHz, CDCl$_3$) δ; 1.28 (d, J=6.8 Hz, 6H), 1.47 (s, 9H), 1.83-1.86 (m, 2H), 1.96-2.04 (m, 1H), 2.49-2.56 (m, 1H), 2.76 (bs, 2H), 3.89 (d, J=6 Hz, 2H), 4.09-4.18 (m, 2H), 6.63 (d, J=3.2 Hz, 1H), 7.23-7.28 (m, 2H), 7.33-7.39 (m, 2H), 7.59 (d, J=3.6 Hz, 1H), 7.94-7.98 (m, 2H), 8.21 (d, J=2.4 Hz, 1H); MS: 448 (M+1).

Example-123

N-(1-(5-((1-(5-Ethylpyrimidin-2-yl)piperidin-4-yl)oxy)pyridin-2-yl)-1H-indol-5-yl)isobutyramide

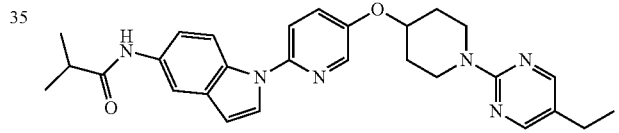

The title compound was prepared by following the similar procedure as described in Example-2 by using Example-114.

$^1$H NMR (400 MHz, CDCl$_3$) δ; 1.20 (t, J=7.6 Hz, 3H), 1.29 (d, J=6.8 Hz, 6H), 1.83-1.90 (m, 2H), 2.04-2.10 (m, 2H), 2.44-2.57 (m, 3H), 3.62-3.68 (m, 2H), 4.19-4.25 (m, 2H), 4.57-4.60 (m, 1H), 6.63 (d, J=3.2 Hz, 1H), 7.21 (s, 1H), 7.40 (s, 2H), 7.61 (d, J=3.2 Hz, 1H), 7.96 (d, J=2 Hz, 1H), 8.00 (d, J=8.8 Hz, 1H), 8.19 (s, 2H), 8.26 (bs, 1H); MS: 485 (M+1).

Example-124

N-(1-(5-((1-(5-Ethylpyrimidin-2-yl)piperidin-4-yl)methoxy)pyridin-2-yl)-1H-indol-5-yl)isobutyramide

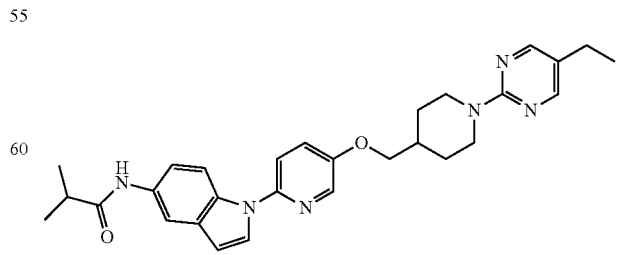

The title compound was prepared by following the similar procedure as described in Example-2 by using Example-122.

¹H NMR (400 MHz, CDCl₃) δ; 1.18 (t, J=7.6 Hz, 3H), 1.28 (d, J=6.8 Hz, 6H), 1.33-1.43 (m, 2H), 1.94-1.97 (m, 2H), 2.10-2.16 (m, 1H), 2.43-2.56 (m, 3H), 2.89-2.96 (m, 2H), 3.92 (d, J=6.4 Hz, 2H), 4.78-4.81 (m, 2H), 6.62 (d, J=3.6 Hz, 1H), 7.21 (s, 1H), 7.24-7.27 (m, 1H), 7.36-7.39 (m, 2H), 7.59 (d, J=3.6 Hz, 1H), 7.95-7.96 (m, 1H), 7.98 (s, 1H), 8.81 (s, 2H), 8.22 (d, J=2.0 Hz, 1H); MS: 499 (M+1).

Example-125 tert-Butyl-4-((6-(5-isobutyramidoindolin-1-yl)pyridin-3-yl)oxy)-piperidine-1-carboxylate

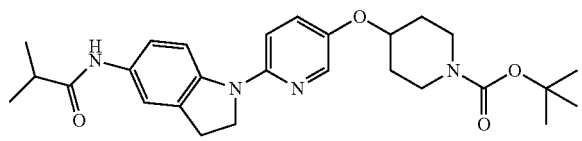 [SMILES: CC(C)C(=O)Nc1ccc2c(c1)CCN2c1ccc(OC2CCN(C(=O)OC(C)(C)C)CC2)cn1]

The title compound was prepared by following the similar procedure as described in Example-1 using tert-butyl 4-((6-chloropyridin-3-yl)oxy)piperidine-1-carboxylate (intermediate 6) and N-(indolin-5-yl)isobutyramide (intermediate 50) (0.017 g, 14%).

¹H NMR (400 MHz, DMSO-d₆) δ; 1.07 (d, J=7.2 Hz, 6H), 1.40 (s, 9H), 1.46-1.55 (m, 2H), 1.85-1.90 (m, 2H), 2.52-2.54 (m, 1H), 3.11-3.15 (m, 4H), 3.64-3.69 (m, 2H), 3.91-3.96 (m, 2H), 4.42-4.46 (m, 1H), 6.78 (d, J=9.2 Hz, 1H), 7.23 (dd, J=8.4, 2.0 Hz, 1H), 7.44 (dd, J=8.8, 2.8 Hz, 1H), 7.49 (d, J=1.6 Hz, 1H), 8.01 (d, J=8.4 Hz, 1H), 8.05 (d, J=3.2 Hz, 1H), 9.62 (s, 1H); MS: 481 (M+1).

Example-126

Isopropyl 4-(((6-(5-isobutyramido-1H-indol-1-yl)pyridin-3-yl)oxy)methyl)piperidine-1-carboxylate

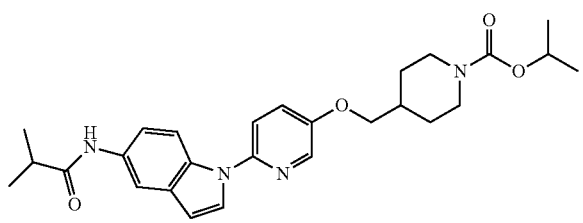 [SMILES: CC(C)OC(=O)N1CCC(COc2ccc(-n3ccc4cc(NC(=O)C(C)C)ccc43)nc2)CC1]

The title compound was prepared by following the similar procedure as described in Example-70 by using Example-122 (0.023 g, 10%).

1H NMR (400 MHz, CDCl₃) δ; 1.24-1.36 (m, 14H), 1.88-1.84 (m, 2H), 2.01-2.04 (m, 1H), 2.50-2.56 (m, 1H), 2.77-2.83 (m, 2H), 3.90 (d, J=6.4 Hz, 2H), 4.23 (bs, 2H), 4.90-4.96 (m, 1H), 6.63 (d, J=3.2 Hz, 1H), 7.22-7.28 (m, 2H), 7.33-7.39 (m, 2H), 7.60 (d, J=3.2 Hz, 1H) 7.94-7.98 (m, 2H), 8.21 (d, J=2.4 Hz, 1H); MS: 479 (M+1).

Example-127

N-(1-(5-((1-Isobutyrylpiperidin-4-yl)oxy)pyridin-2-yl)-1H-indol-5-yl) isobutyramide

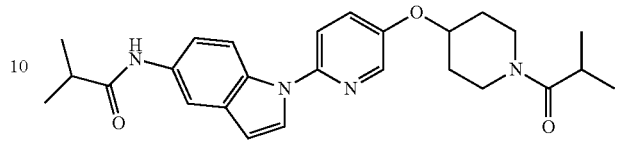

To a stirred solution of Example-114 (0.135 g, 0.282 mmol) in dichloromethane (5 mL), trifluoroacetic acid (1 mL) was added at 0° C. and stirred for 2-3 h. The reaction mixture was concentrated in vacuo and the resultant residue was dissolved in anhydrous DMF (5 mL), DIPEA (0.145 mL, 0.846 mmol), O-Benzotriazole-N,N,N,N'-tetramethyl-uronium-hexafluoro-phosphate (0.213 g, 0.564 mmol), isobutyric acid (0.026 mL, 0.564 mmol) were added and stirred at room temperature for 18 h. The reaction was quenched with water and the organic layer was extracted with ethyl acetate, combined organic layers were dried over Na₂SO₄, filtered and concentrated in vacuo. The resultant residue was purified by flash column chromatography to give N-(1-(5-((1-isobutyrylpiperidin-4-yl)oxy)pyridin-2-yl)-1H-indol-5-yl)isobutyramide (0.035 g, 26.6%).

¹H NMR (400 MHz, CDCl₃)δ; 1.15 (d, J=6.8 Hz, 6H), 1.29 (d, J=6.8 Hz, 6H), 1.86 (bs, 2H), 2.0-2.01 (m, 2H), 2.50-2.55 (m, 1H), 2.81-2.87 (m, 1H), 3.49 (bs, 1H), 3.64-3.70 (m, 1H), 3.79-3.86 (m, 2H), 4.58-4.61 (m, 1H), 6.64 (d, J=3.2 Hz, 1H), 7.20 (s, 1H), 7.29 (d, J=2.0 Hz, 1H), 7.39-7.40 (m, 2H), 7.61 (d, J=3.2 Hz, 1H), 7.95 (d, J=2 Hz, 1H), 8.01 (d, J=8.8 Hz, 1H), 8.24-8.25 (m, 1H); MS: 449 (M+1).

Example-128

2-Chloro-1-(4-((6-(5-(methylsulfonyl)-1H-indol-1-yl)pyridin-3-yl)oxy) piperidin-1-yl)ethanone

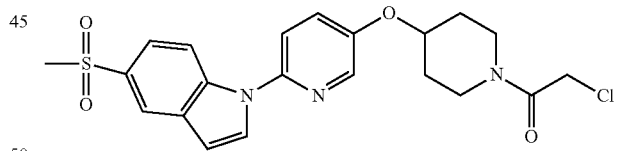

To a stirred solution of example-1 (0.375 g, 0.212 mmol) in dichloromethane (5 mL) trifluoroacetic acid (0.5 mL) was added at 0° C. and stirred at room temperature for 2-3 h. The solvent was removed in vacuo, the resultant residue was dissolved in dichloromethane (3 ml), triethylamine (0.165 ml, 1.190 mmol) and chloroacetyl chloride (0.063 ml, 0.793 mmol) were added and stirred at room temperature for 2 h. The reaction mixture was diluted with dichloromethane (25 ml) and washed with water (10 ml). The organic layer was separated, concentrated under reduced pressure and the resultant residue was purified by flash column chromatography to give 2-chloro-1-(4-((6-(5-(methylsulfonyl)-1H-indol-1-yl)pyridin-3-yl)oxy)piperidin-1-yl)ethanone (0.240 g, 67%).

¹H NMR (400 MHz, CDCl₃) δ; 2.00-2.15 (m, 4H), 3.11 (s, 3H), 3.56-3.61 (m, 1H), 3.77-3.83 (m, 3H), 4.13-4.16 (m,

2H), 4.69-4.72 (m, 1H), 6.85 (d, J=3.2 Hz, 1H), 7.43-7.49 (m, 2H), 7.75 (d, J=3.2 Hz, 1H), 7.82 (dd, J=7.2, 1.6 Hz, 1H), 8.22 (d, J=8.8 Hz, 1H), 8.32 (d, J=1.6 Hz, 1H); MS: 448 (M+).

Example-129

N-(1-(5-((1-(2,2,2-Trifluoroacetyl)piperidin-4-yl)oxy)pyridin-2-yl)-1H-indol-5-yl)isobutyramide

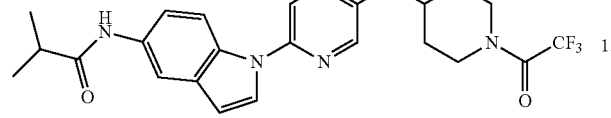

To a stirred solution of Example-117 (0.15 g, 0.313 mmol) in dichloromethane (5 mL), trifluoroacetic acid (2 mL) was added at 0° C. and stirred at room temperature for 1 h. The reaction mixture was concentrated in vacuo, the resultant residue was dissolved in dry dichloromethane (5 mL), triethylamine (0.174 mL, 1.252 mmol) and trifluoroacetic anhydride (0.048 mL, 0.313 mmol) were added at 0° C. and stirred for 1 hr. The reaction was quenched with water and the organic layer was extracted with dichloromethane. The organic layer was separated, concentrated in vacuo, and the residue obtained was purified by flash column chromatography to give N-(1-(5-((1-(2,2,2-trifluoroacetyl)piperidin-4-yl)oxy)pyridin-2-yl)-1H-indol-5-yl)isobutyramide.

$^1$H NMR (400 MHz, CDCl$_3$) δ; 1.28 (d, J=6.8 Hz, 6H), 1.99-2.02 (m, 4H), 2.50-2.55 (m, 1H), 3.65-3.81 (m, 3H), 3.89-3.94 (m, 1H), 4.66-4.68 (m, 1H), 6.64 (d, J=3.2 Hz, 1H), 7.23 (s, 1H), 7.28 (dd, J=8.8, 2.0 Hz, 1H), 7.37-7.40 (m, 2H), 7.60 (d, J=3.2 Hz, 1H), 7.95 (d, J=2.0 Hz, 1H), 8.01 (d, J=8.8 Hz, 1H), 8.24 (d, J=1.6 Hz, 1H); MS: 475 (M+1).

Example-130 tert-Butyl-4-((6-(5-(cyclopropanecarboxamido)-1H-indol-1-yl)pyridine-3-yl)oxy)piperidine-1-carboxylate

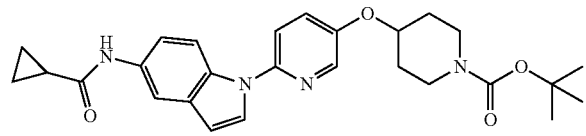 [SMILES: CC(C)(C)OC(=O)N1CCC(Oc2ccc(-n3ccc4cc(NC(=O)C5CC5)ccc43)nc2)CC1]

The title compound was prepared by following the similar procedure as described in Example-1 using N-(1H-indol-5-yl)cyclopropanecarboxamide (intermediate-02) and tert-butyl 4-((6-chloropyridin-3-yl)oxy)piperidine-1-carboxylate (intermediate-06).

$^1$H NMR (400 MHz, CDCl$_3$) δ; 0.82-0.85 (m, 2H), 1.08-1.12 (m, 2H), 1.23-1.27 (m, 1H), 1.47 (s, 9H), 1.77-1.82 (m, 2H), 1.95-1.99 (m, 2H), 3.32-3.39 (m, 2H), 3.70-3.77 (m, 2H), 4.50-4.52 (m, 1H), 6.62 (d, J=3.2 Hz, 1H), 7.28 (s, 1H), 7.38 (s, 2H), 7.44 (s, 1H), 7.59 (d, J=3.2 Hz, 1H), 7.92 (d, J=1.2 Hz, 1H), 7.99 (d, J=8.8 Hz, 1H), 8.23 (bs, 1H); MS: 477 (M+1).

Example-131 tert-Butyl-4-((6-(5-((isopropoxycarbonyl)amino)-1H-indol-1-yl)-pyridin-3-yl)oxy)piperidine-1-carboxylate

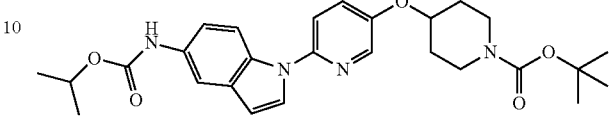

The title compound was prepared by following the similar procedure as described in Example-1 using tert-butyl 4-((6-chloropyridin-3-yl)oxy)piperidine-1-carboxylate (intermediate-06) and Isopropyl 1H-indol-5-ylcarbamate (intermediate 78).

$^1$H NMR (400 MHz, CDCl$_3$) δ; 1.31 (d, J=6.0 Hz, 6H), 1.57 (s, 9H), 1.77-1.83 (m, 2H), 1.95-2.00 (m, 2H), 3.30-3.39 (m, 2H), 3.71-3.77 (m, 2H), 4.49-4.53 (m, 1H), 5.02-5.05 (m, 1H), 6.55 (bs, 1H), 6.62 (dd, J=3.6, 0.8 Hz, 1H), 7.17 (dd, J=8.8, 2.0 Hz, 1H), 7.38-7.38 (m, 2H), 7.60 (d, J=3.2 Hz, 1H), 7.75 (bs, 1H), 7.99 (d, J=8.8 Hz, 1H), 8.22-8.23 (m, 1H); MS: 495 (M+1).

Example-132

Isopropyl(1-(5-((1-(5-ethylpyrimidin-2-yl)piperidin-4-yl)oxy)pyridin-2-yl)-1H-indol-5-yl)carbamate

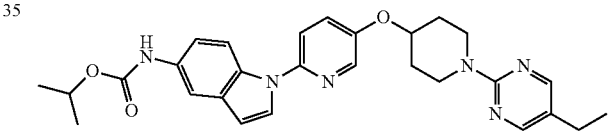

The title compound was prepared by following the similar procedure as described in Example-2 by using Example-131.

$^1$H NMR (400 MHz, CDCl$_3$) δ; 1.19 (t, J=7.6 Hz, 3H), 1.31 (d, J=6.4 Hz, 6H), 1.83-1.88 (m, 2H), 2.05-2.10 (m, 2H), 2.47 (q, J=7.6 Hz, 2H), 3.62-3.68 (m, 2H), 4.19-4.25 (m, 2H), 4.58-4.61 (m, 1H), 5.01-5.07 (m, 1H), 6.56 (bs, 1H), 6.62 (d, J=3.2 Hz, 1H), 7.17 (d, J=8.8 Hz, 1H), 7.40 (s, 2H), 7.60 (d, J=3.6 Hz, 1H), 7.76 (bs, 1H), 7.99 (d, J=8.8 Hz, 1H), 8.19 (s, 2H), 8.26 (s, 1H); MS: 395.48 (M−100).

Example-133 tert-Butyl-4-((6-(5-(N-methylisobutyramido)-1H-indol-1-yl)pyridin-3-yl) oxy)piperidine-1-carboxylate

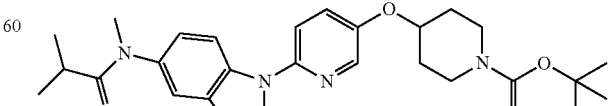

To a solution of Example-131 (0.05 g, 0.104 mmol) in anhydrous DMF (10 mL), sodium hydride (0.006 g, 0.216 mmol) and methyl iodide (0.022 g, 0.156 mmol) were added at 0° C. and stirred at 60° C. for 4-5 h. The reaction was quenched with water and the organic layer was extracted with ethyl acetate. The organic layer was separated, concentrated in vacuo and the resultant residue was purified by flash column chromatography to give tert-butyl 4-((6-(5-(N-methyl-isobutyramido)-1H-indol-1-yl)pyridin-3-yl)oxy)piperidine-1-carboxylate (0.021 g, 41%).

$^1$H NMR (400 MHz, CDCl$_3$) δ; 1.02 (d, J=6.8 Hz, 6H), 1.48 (s, 9H), 1.60-1.83 (m, 2H), 1.96-2.02 (m, 2H), 2.56-2.60 (m, 1H), 3.30 (s, 3H), 3.34-3.44 (m, 2H), 3.71-3.77 (m, 2H), 4.53-4.55 (m, 1H), 6.70 (d, J=3.2 Hz, 1H), 7.70 (dd, J=8.8, 2.0 Hz, 1H), 7.41 (d, J=1.6 Hz, 2H), 7.46 (d, J=2.0 Hz, 1H), 7.65 (d, J=3.2 Hz, 1H), 8.10 (d, J=8.8 Hz, 1H), 8.26-8.26 (m, 1H); MS: 493 (M+1).

Example-134

Isopropyl(1-(5-((1-(3-isopropyl-1,2,4-oxadiazol-5-yl)piperidin-4-yl)oxy) pyridin-2-yl)-1H-indol-5-yl) carbamate

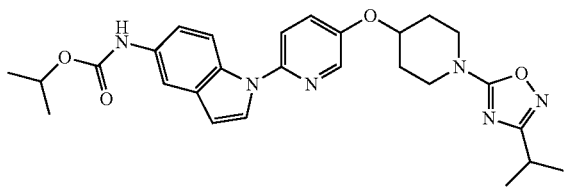 [SMILES: CC(C)OC(=O)Nc1ccc2c(ccn2-c2ccc(OC3CCN(c4nc(C(C)C)no4)CC3)cn2)c1]

The title compound was prepared by following the similar procedure as described in Example-4 by using Example-131.

$^1$H NMR (400 MHz, CDCl$_3$) δ; 1.25-1.30 (m, 12H), 1.93-1.99 (m, 2H), 2.03-2.08 (m, 2H), 2.85-2.92 (m, 1H), 3.60-3.67 (m, 2H), 3.80-3.87 (m, 2H), 4.58-4.60 (m, 1H), 5.00-5.03 (m, 1H), 6.54 (s, 1H), 6.61 (dd, J=3.2, 0.4 Hz, 1H), 7.35-7.38 (m, 2H), 7.58 (d, J=3.2 Hz, 1H), 7.74 (bs, 1H), 7.98 (d, J=8.8 Hz, 1H), 8.22-8.23 (m, 1H); MS: 505 (M+1).

Example-135

N-(1-(5-((1-(5-Ethylpyrimidin-2-yl)piperidin-4-yl)oxy)pyridin-2-yl)-1H-indol-5-yl)-N-methylisobutyramide

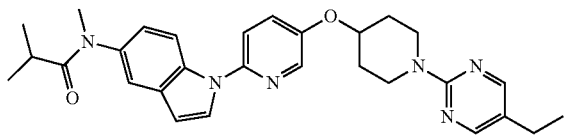 [SMILES: CCc1cnc(N2CCC(Oc3ccc(-n4ccc5cc(N(C)C(=O)C(C)C)ccc54)nc3)CC2)nc1]

The title compound was prepared by following the similar procedure as described in Example-2 by using Example-133.

$^1$H NMR (400 MHz, CDCl$_3$) δ; 1.01 (d, J=6.8 Hz, 6H), 1.19 (t, J=7.6 Hz, 3H), 1.84-1.90 (m, 2H), 2.05-2.11 (m, 2H), 2.47 (q, J=7.6 Hz, 2H), 2.56-2.59 (m, 1H), 3.29 (s, 3H), 3.63-3.69 (m, 2H), 4.18-4.24 (m, 2H), 4.59-4.63 (m, 1H), 6.69 (d, J=3.6 Hz, 1H), 7.06 (dd, J=8.8, 2.4 Hz, 1H), 7.39-7.45 (m, 3H), 7.65 (d, J=3.2 Hz, 1H), 8.09 (d, J=8.8 Hz, 1H), 8.19 (s, 2H), 8.28 (d, J=2.0 Hz, 1H); MS: 499 (M+1).

Example-136 tert-Butyl-4-(((6-(5-(isopropylcarbamoyl)indolin-1-yl)pyridin-3-yl)-oxy) piperidine-1-carboxylate

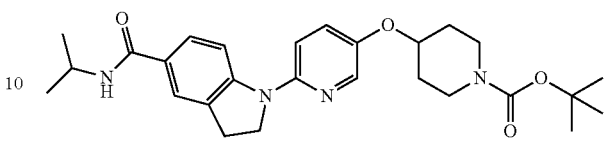

The title compound was prepared by following the similar procedure as described in Example-1 using tert-butyl 4-((6-chloropyridin-3-yl)oxy)piperidine-1-carboxylate (intermediate 06) and N-isopropylindoline-5-carboxamide (Intermediate 64).

$^1$H NMR (400 MHz, CDCl$_3$) δ; 1.26 (d, J=6.4 Hz, 6H), 1.48 (s, 9H), 1.71-1.79 (m, 2H), 1.96-1.96 (m, 2H), 3.23 (t, J=8.8 Hz, 2H), 3.28-3.34 (m, 2H), 3.76-3.77 (m, 2H), 4.07 (t, J=8.8 Hz, 2H), 4.24-4.31 (m, 1H), 4.33-4.36 (m, 1H), 5.81 (d, J=7.6 Hz, 1H), 6.78 (d, J=8.8 Hz, 1H), 7.29 (d, J=3.2 Hz, 1H), 7.54 (dd, J=8.4, 1.6 Hz, 1H), 7.62 (s, 1H), 8.05 (d, J=8.4 Hz, 1H), 8.01 (d, J=3.2 Hz, 1H); MS: 481 (M+1).

Example-137

Isopropyl(1-(5-((1-(3-methyl-1,2,4-oxadiazol-5-yl) piperidin-4-yl)oxy) pyridin-2-yl)-1H-indol-5-yl) carbamate

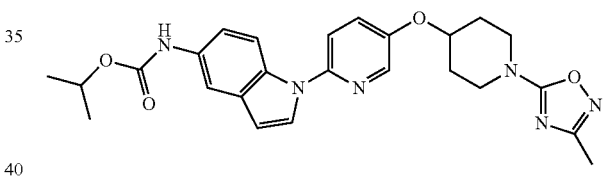

Example-137 was prepared according to procedure described in Example-4 by using Example-131

$^1$H NMR (400 MHz, CDCl$_3$)δ; 1.30 (d, J=6.4 Hz, 6H), 1.95-2.01 (m, 2H), 2.03-2.09 (m, 2H), 2.22 (s, 3H), 3.62-3.69 (m, 2H), 3.80-3.87 (m, 2H), 4.61-4.62 (m, 1H), 5.01-5.04 (m, 1H), 6.55 (bs, 1H), 6.62 (d, J=3.2 Hz, 1H), 7.16 (dd, J=8.8, 1.6 Hz, 1H), 7.39 (s, 2H), 7.59 (d, J=3.6 Hz, 1H), 7.74 (bs, 1H), 7.99 (d, J=8.8 Hz, 1H), 8.23 (m, 1H); MS: 477 (M+1).

Example-138 tert-Butyl-4-((((6-(5-(methylsulfonyl)-1H-indol-1-yl) pyridin-3-yl)methyl)amino)piperidine-1-carboxylate

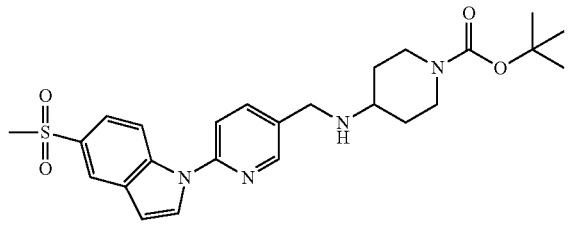 [SMILES: CC(C)(C)OC(=O)N1CCC(NCc2ccc(-n3ccc4cc(S(C)(=O)=O)ccc43)nc2)CC1]

The title compound was prepared by following the similar procedure as described in example-1 using 5-(methylsulfonyl)-1H-indole (intermediate 21) and tert-butyl-4-(((6-chloropyridin-3-yl)methyl)amino)piperidine-1-carboxylate (intermediate 79).

$^1$H NMR (400 MHz, CDCl$_3$) δ; 1.31-1.34 (m, 2H), 1.46 (s, 9H), 1.89-1.92 (m, 2H), 2.69-2.74 (m, 1H), 2.80-2.86 (m, 2H), 3.09 (s, 3H), 3.92 (s, 2H), 4.05 (bs, 2H), 6.85 (d, J=3.2 Hz, 1H), 7.46 (d, J=8.4 Hz, 1H), 7.79-7.83 (m, 2H), 7.91 (dd, J=8.4, 2.0 Hz, 1H), 8.29 (d, J=1.6 Hz, 1H), 8.36 (d, J=8.8 Hz, 1H), 8.54 (d, J=1.6 Hz, 1H); MS: 429 (M−56).

Example-139

1-(5-Ethylpyrimidin-2-yl)-N-((6-(5-(methylsulfonyl)-1H-indol-1-yl)pyridin-3-yl)methyl)piperidin-4-amine

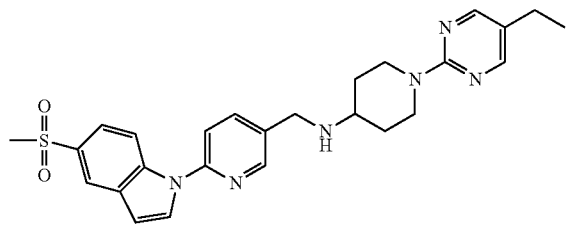 [SMILES: CCc1cnc(N2CCC(NCc3ccc(-n4ccc5cc(S(C)(=O)=O)ccc54)nc3)CC2)nc1]

The title compound was prepared by following the similar procedure as described in Example-2 by using Example-138.

$^1$H NMR (400 MHz, CDCl$_3$) δ; 1.16 (t, J=7.6 Hz, 3H), 1.20-1.28 (m, 2H), 2.02-2.11 (m, 2H), 2.43 (q, J=7.6 Hz, 2H), 2.61-2.66 (m, 2H), 2.81-2.91 (m, 2H), 3.05 (s, 3H), 4.04 (s, 2H), 4.70-4.73 (m, 2H), 6.78 (d, J=3.2 Hz, 1H), 7.43 (d, J=8.0 Hz, 1H), 7.75-7.79 (m, 2H), 8.09-8.14 (m, 2H), 8.21 (s, 1H), 8.41-8.45 (m, 2H), 8.63 (s, 1H); MS: 491 (M+1).

Example-140

Ethyl(1-(5-((1-(3-methyl-1,2,4-oxadiazol-5-yl)piperidin-4-yl)oxy)pyridin-2-yl)-1H-indol-5-yl)carbamate

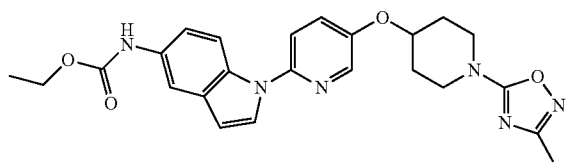 [SMILES: CCOC(=O)Nc1ccc2c(ccn2-c2ccc(OC3CCN(c4nc(C)no4)CC3)cn2)c1]

The title compound was prepared by following the similar procedure as described in Example-4 by using Example-8.

$^1$H NMR (400 MHz, CDCl$_3$) δ; 1.31 (t, J=7.2 Hz, 3H), 1.95-1.99 (m, 2H), 2.04-2.09 (m, 2H), 2.22 (s, 3H), 3.63-3.69 (m, 2H), 3.80-3.86 (m, 2H), 4.23 (q, J=7.2 Hz, 2H), 4.62 (bs, 1H), 6.23-6.63 (m, 2H), 7.16-7.18 (m, 1H), 7.39 (s, 2H), 7.59 (d, J=3.6 Hz, 1H), 7.74 (bs, 1H), 7.99 (d, J=8.8 Hz, 1H), 8.23 (s, 1H); MS: 463 (M+1).

Example-141

Ethyl(1-(5-((1-(3-isopropyl-1,2,4-oxadiazol-5-yl)piperidin-4-yl)oxy)pyridin-2-yl)-1H-indol-5-yl)carbamate

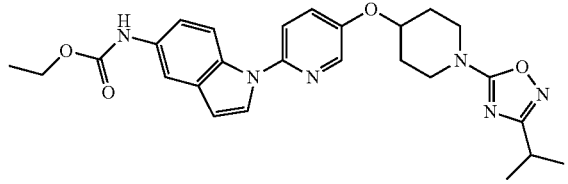 [SMILES: CCOC(=O)Nc1ccc2c(ccn2-c2ccc(OC3CCN(c4nc(C(C)C)no4)CC3)cn2)c1]

The title compound was prepared by following the similar procedure as described in Example-4 by using Example-8

$^1$H NMR (400 MHz, CDCl$_3$)δ; 1.30-1.36 (m, 9H), 1.97-2.03 (m, 2H), 2.06-2.13 (m, 2H), 2.90-2.93 (m, 1H), 3.64-3.70 (m, 2H), 3.84-3.90 (m, 2H), 4.26 (q, J=7.2 Hz, 2H), 4.62-4.64 (m, 1H), 6.62 (bs, 1H), 6.65 (d, J=3.6 Hz, 1H), 7.20 (d, J=7.6 Hz, 1H), 7.39-7.44 (m, 2H), 7.62 (d, J=3.6 Hz, 1H), 7.77 (bs, 1H), 8.02 (d, J=8.8 Hz, 1H), 8.26 (bs, 1H); MS: 491 (M+1).

Example-142

Ethyl(1-(5-((1-(3-ethyl-1,2,4-oxadiazol-5-yl)piperidin-4-yl)oxy)pyridin-2-yl)-1H-indol-5-yl)carbamate

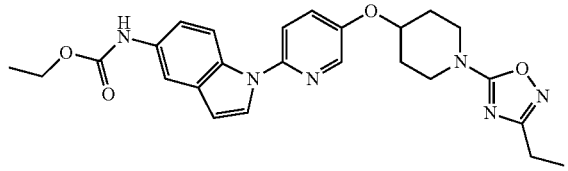 [SMILES: CCOC(=O)Nc1ccc2c(ccn2-c2ccc(OC3CCN(c4nc(CC)no4)CC3)cn2)c1]

The title compound was prepared by following the similar procedure as described in Example-4 by using Example-8.

$^1$H NMR (400 MHz, CDCl$_3$) δ; 1.26-1.34 (m, 6H), 1.97-2.00 (m, 2H), 2.05-2.09 (m, 2H), 2.59 (q, J=7.6 Hz, 2H), 3.64-3.69 (m, 2H), 3.82-3.85 (m, 2H), 4.24 (q, J=7.2 Hz, 2H), 4.61-4.63 (m, 1H), 6.60 (bs, 1H), 6.63 (d, J=3.2 Hz, 1H), 7.18 (d, J=8.8 Hz, 1H), 7.39-7.40 (m, 2H), 7.60 (d, J=3.2 Hz, 1H), 7.75 (bs, 1H), 8.00 (d, J=8.8 Hz, 1H), 8.24-8.25 (m, 1H); MS: 477 (M+1).

Example-143

Isopropyl(1-(5-((1-(3-ethyl-1,2,4-oxadiazol-5-yl)piperidin-4-yl)oxy)pyridin-2-yl)-1H-indol-5-yl)carbamate

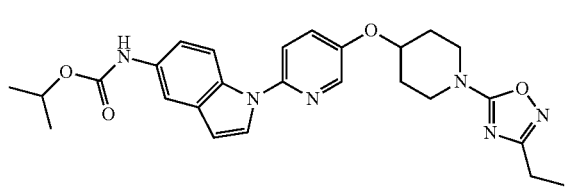 [SMILES: CCc1noc(N2CCC(Oc3ccc(-n4ccc5cc(NC(=O)OC(C)C)ccc54)nc3)CC2)n1]

The title compound was prepared by following the similar procedure as described in Example-4 by using Example-131.

$^1$H NMR (400 MHz, CDCl$_3$) δ; 1.23-1.31 (m, 9H), 1.95-1.96 (m, 2H), 1.97-2.01 (m, 2H), 2.03-2.10 (m, 2H), 2.30 (q, J=7.6 Hz, 2H), 3.62-3.68 (m, 2H), 3.81-3.87 (m, 2H), 4.60-4.63 (m, 1H), 4.99-5.04 (m, 1H), 6.55 (bs, 1H), 6.62 (d, J=3.2 Hz, 1H), 7.17 (d, J=8.8 Hz, 1H), 7.39-7.39 (m, 2H), 7.59 (d, J=3.6 Hz, 1H), 7.74 (bs, 1H), 7.99 (d, J=8.8 Hz, 1H); MS: 491 (M+1).

Example-144

3-Ethyl-5-(4-((6-(5-(methylsulfonyl)-1H-indol-1-yl)pyridin-3-yl)oxy) piperidin-1-yl)-1,2,4-oxadiazole

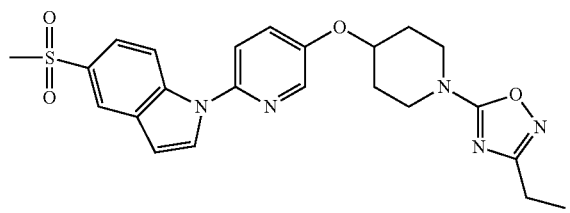 [SMILES: CCc1noc(N2CCC(Oc3ccc(-n4ccc5cc(S(C)(=O)=O)ccc54)nc3)CC2)n1]

The title compound was prepared by following the similar procedure as described in Example-4 using Example-1.

$^1$H NMR (400 MHz, CDCl$_3$) δ; 1.32 (t, J=7.6 Hz, 3H), 1.99-2.05 (m, 2H), 2.08-2.16 (m, 2H), 2.61 (q, J=7.6 Hz, 2H), 3.10 (s, 3H), 3.67-3.73 (m, 2H), 3.84-3.91 (m, 2H), 4.68-4.71 (m, 1H), 6.85 (d, J=3.2 Hz, 1H), 7.46-7.46 (m, 2H), 7.74 (d, J=3.6 Hz, 1H), 7.82 (dd, 8.8, 1.6 Hz, 1H), 8.22 (d, J=8.8 Hz, 1H), 8.31-8.31 (m, 2H); MS: 468 (M+1).

Example-145

5-(4-((6-(5-(Ethylsulfonyl)-1H-indol-1-yl)pyridin-3-yl)oxy)piperidin-1-yl)-3-methyl-1,2,4-oxadiazole

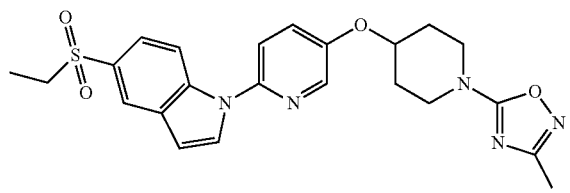 [SMILES: CCS(=O)(=O)c1ccc2c(ccn2-c2ccc(OC3CCN(c4nc(C)no4)CC3)cn2)c1]

The title compound was prepared by following the similar procedure as described in Example-4 by using Example-10.

$^1$H NMR (400 MHz, CDCl$_3$) δ; 1.26 (t, J=7.6 Hz, 3H), 1.96-2.02 (m, 2H), 2.06-2.11 (m, 2H), 2.22 (s, 3H), 3.13 (q, J=7.6 Hz, 2H), 3.64-3.70 (m, 2H), 3.81-3.87 (m, 2H), 4.64-4.67 (m, 1H), 6.81 (d, J=3.2 Hz, 1H), 7.40-7.45 (m, 2H), 7.70 (d, J=3.2 Hz, 1H), 7.74 (dd, J=8.4, 1.2 Hz, 1H), 8.18 (d, J=8.8 Hz, 1H), 8.24 (d, J=1.2 Hz, 1H), 8.28 (d, J=1.2 Hz, 1H).

Example-146

3-Ethyl-5-(4-((6-(5-(ethylsulfonyl)-1H-indol-1-yl)pyridin-3-yl)oxy) piperidin-1-yl)-1,2,4-oxadiazole

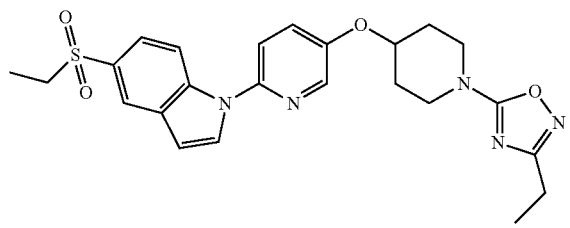 [SMILES: CCc1noc(N2CCC(Oc3ccc(-n4ccc5cc(S(=O)(=O)CC)ccc54)nc3)CC2)n1]

The title compound was prepared by following the similar procedure as described in Example-18 by using Example-10.

$^1$H NMR (400 MHz, CDCl$_3$) δ; 1.23-1.29 (m, 6H), 1.99-2.01 (m, 2H), 2.06-2.10 (m, 2H), 2.58 (q, J=7.6 Hz, 2H), 3.14 (q, J=7.2 Hz, 2H), 3.64-3.70 (m, 2H), 3.82-3.88 (m, 2H), 4.66-4.67 (m, 1H), 6.82 (d, J=3.6 Hz, 1H), 7.41-7.46 (m, 2H), 7.70 (d, J=3.6 Hz, 1H), 7.75 (dd, J=8.8, 2.0 Hz, 1H), 8.19 (d, J=8.8 Hz, 1H), 8.24 (d, J=1.6 Hz, 1H), 8.29 (m, 1H); MS: 467.1 (M+1).

Example-147

1-(5-((1-(3-Ethyl-1,2,4-oxadiazol-5-yl)piperidin-4-yl)oxy)pyridin-2-yl)-N,N-dimethyl-1H-indole-5-carboxamide

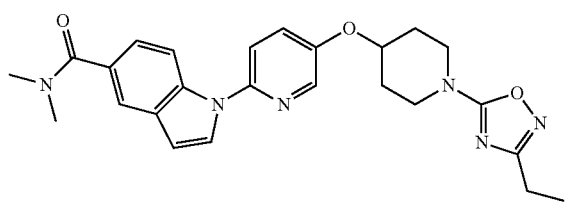 [SMILES: CCc1noc(N2CCC(Oc3ccc(-n4ccc5cc(C(=O)N(C)C)ccc54)nc3)CC2)n1]

The title compound was prepared by following the similar procedure as described in Example-4 by using Example-39.

$^1$H NMR (400 MHz, CDCl$_3$) δ; 1.28 (t, J=7.6 Hz, 3H), 2.00-2.02 (m, 2H), 2.05-2.12 (m, 2H), 2.59 (q, J=7.6 Hz, 2H), 3.09 (bs, 6H), 3.64-3.70 (m, 2H), 3.82-3.89 (m, 2H), 4.63-4.65 (m, 1H), 6.72 (d, J=3.2 Hz, 1H), 7.35 (dd, J=8.4, 1.2 Hz, 1H), 7.42-7.43 (m, 2H), 7.65 (d, J=3.2 Hz, 1H), 7.75 (d, J=1.2 Hz, 1H), 8.06 (d, J=8.8 Hz, 1H), 8.27-8.28 (m, 1H); MS: 461 (M+1).

Example-148

1-(5-((1-(3-Isopropyl-1,2,4-oxadiazol-5-yl)piperidin-4-yl)oxy)-pyridin-2-yl)-N,N-dimethyl-1H-indole-5-carboxamide

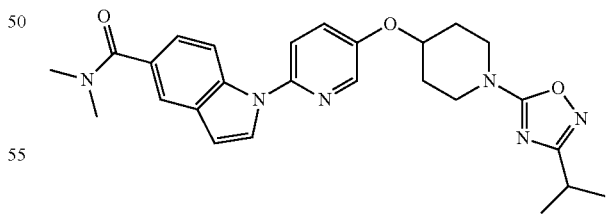

The title compound was prepared by following the similar procedure as described in Example-4 by using Example-39.

$^1$H NMR (400 MHz, DMSO-d$_6$) δ; 1.19 (d, J=6.8 Hz, 6H), 1.73-1.80 (m, 2H), 2.06-2.11 (m, 2H), 2.08-2.84 (m, 1H), 2.99 (s, 6H), 3.47-3.54 (m, 2H), 3.79-3.85 (m, 2H), 4.78-4.80 (m, 1H), 6.78 (d, J=3.2 Hz, 1H), 7.29 (dd, J=8.8, 1.6 Hz, 1H), 7.70-7.73 (m, 3H), 8.00 (d, J=3.6 Hz, 1H), 8.23 (d, J=8.4 Hz, 1H), 8.36-8.36 (m, 1H); MS: 475 (M+1).

Example-149

Ethyl(1-(5-((1-(3-cyclopropyl-1,2,4-oxadiazol-5-yl)piperidin-4-yl)oxy) pyridin-2-yl)-1H-indol-5-yl)carbamate

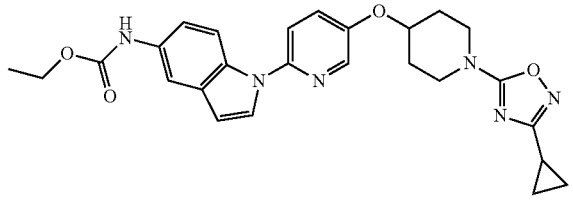 [SMILES: CCOC(=O)Nc1ccc2c(ccn2-c2ccc(OC3CCN(c4nc(C5CC5)no4)CC3)cn2)c1]

The title compound was prepared by following the similar procedure as described in Example-4 by using Example-8.

$^1$H NMR (400 MHz, CDCl$_3$) δ; 0.93-0.97 (m, 4H), 1.32 (t, J=7.2 Hz, 3H), 1.86-1.89 (m, 1H), 1.95-1.97 (m, 2H), 2.02-2.06 (m, 2H), 3.59-3.65 (m, 2H), 3.79-3.84 (m, 2H), 4.24 (q, J=7.2 Hz, 2H), 4.60-4.61 (m, 1H), 6.59 (bs, 1H), 6.63 (d, J=3.6 Hz, 1H), 7.17-7.20 (m, 1H), 7.37-7.42 (m, 2H), 7.60 (d, J=3.6 Hz, 1H), 7.74 (bs, 1H), 8.00 (d, J=8.8 Hz, 1H), 8.24 (m, 1H); MS: 489 (M+1).

Example-150

N-(2-Hydroxyethyl)-1-(5-((1-(3-isopropyl-1,2,4-oxadiazol-5-yl)piperidin-4-yl)oxy)pyridin-2-yl)-1H-indole-5-carboxamide

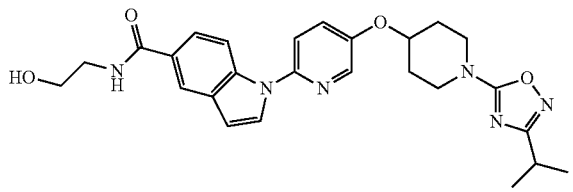 [SMILES: CC(C)c1noc(N2CCC(Oc3ccc(-n4ccc5cc(C(=O)NCCO)ccc54)nc3)CC2)n1]

The title compound was prepared by following the similar procedure as described in Example-4 by using Example-76.

$^1$H NMR (400 MHz, CDCl$_3$) δ; 1.31 (d, J=6.8 Hz, 6H), 1.98-2.04 (m, 2H), 2.07-2.14 (m, 2H), 2.88-2.93 (m, 1H), 3.65-3.71 (m, 4H), 3.84-3.90 (m, 4H), 4.65-4.67 (m, 1H), 6.71-6.73 (m, 1H), 6.77 (d, J=3.2 Hz, 1H), 7.45 (s, 2H), 7.68 (d, J=3.6 Hz, 1H), 7.73 (dd, J=8.8, 1.6 Hz, 1H), 8.08 (d, J=8.8 Hz, 1H), 8.15 (d, J=1.6 Hz, 1H), 8.29-8.30 (m, 1H); MS: 491 (M+1).

Example-151

(±)-1-(5-((1-(5-Ethylpyrimidin-2-yl)pyrrolidin-3-yl)oxy)pyridin-2-yl)-N-(2-hydroxyethyl)-1H-indole-5-carboxamide

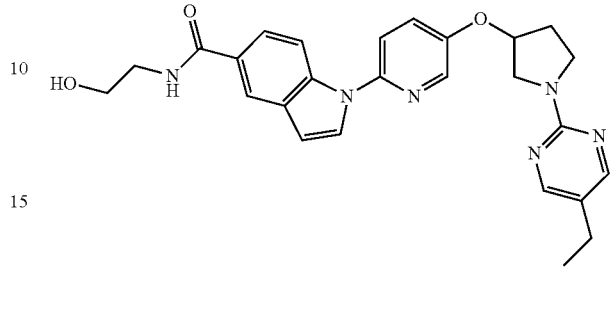

The title compound was prepared by following the similar procedure as described in Example-2 using (±)-tert-butyl 3-((6-(5-((2-hydroxyethyl)carbamoyl)-1H-indol-1-yl)pyridin-3-yl)oxy)pyrrolidine-1-carboxylate (intermediate-33).

$^1$H NMR (400 MHz, CDCl$_3$) δ; 1.20 (t, J=7.6 Hz, 3H), 2.32-2.38 (m, 2H), 2.49 (q, J=7.6 Hz, 2H), 2.96 (bs, 1H), 3.66-3.70 (m, 2H), 3.74-3.81 (m, 1H), 3.86-3.99 (m, 5H), 5.13-5.14 (m, 1H), 6.70-6.75 (m, 2H), 7.38-7.43 (m, 2H), 7.66 (d, J=3.2 Hz, 1H), 7.72 (dd, J=8.4, 1.6 Hz, 1H), 8.14 (d, J=1.2 Hz, 1H), 8.22-8.26 (m, 3H); MS: 473.1 (M+1).

Example-152

(±)-3-Ethyl-5-(3-((6-(5-(methyl sulfonyl)-1H-indol-1-yl)pyridin-3-yl)oxy) pyrrolidin-1-yl)-1,2,4-oxadiazole

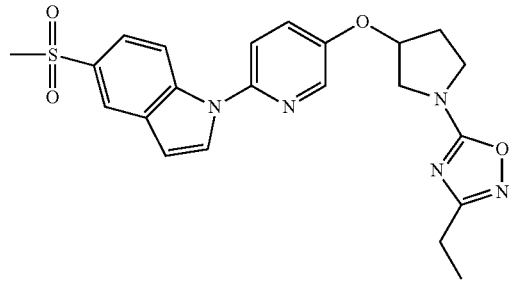 [SMILES: CCc1noc(N2CCC(Oc3ccc(-n4ccc5cc(S(C)(=O)=O)ccc54)nc3)C2)n1]

The title compound was prepared by following the similar procedure as described in Example-4 by using Example-24.

$^1$H NMR (400 MHz, CDCl$_3$) δ; 1.30 (t, J=7.6 Hz, 3H), 2.34-2.38 (m, 1H), 2.45-2.46 (m, 1H), 2.62 (q, J=7.6 Hz, 2H), 3.11 (s, 3H), 3.82-3.90 (m, 2H), 3.93-3.94 (m, 2H), 5.15-5.17 (m, 1H), 6.85-6.86 (m, 1H), 7.41-7.47 (m, 2H), 7.74 (d, J=3.6 Hz, 1H), 7.82 (dd, J=8.8, 1.6 Hz, 1H), 8.22 (d, J=8.8 Hz, 1H), 8.28 (dd, J=2.8, 0.8 Hz, 1H), 8.31 (d, J=1.6 Hz, 1H); MS: 454.23 (M+1).

(±)-3-ethyl-5-(3-((6-(5-(methylsulfonyl)-1H-indol-1-yl)pyridin-3-yl)oxy)pyrrolidin-1-yl)-1,2,4-oxadiazole was purified into its enantiomers via preparatory HPLC utilizing a CHIRAL CEL OJ-H 250×30 mm, with mobile phase (MeOH: 85% CH$_3$CN: 15%) at a Flow rate of 50 mL/min wavelength for monitoring the separation was 210 nm.

Isomer 1 RT=8.85 min. and isomer 2 RT=9.96 min.

Example-153

5-(Methylsulfonyl)-1-(5-((1-(4-(trifluoromethyl)benzyl)piperidin-4-yl) oxy)pyridin-2-yl)-1H-indole

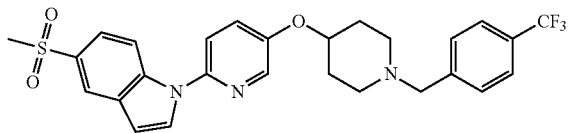 [SMILES: CS(=O)(=O)c1ccc2c(ccn2-c2ccc(OC3CCN(Cc4ccc(C(F)(F)F)cc4)CC3)cn2)c1]

The title compound was prepared by following the similar procedure as described in Example-82 by using Example-1 and 4-(trifluoromethyl)benzaldehyde.

¹H NMR (400 MHz, CDCl₃) δ; 1.93-1.94 (m, 2H), 2.03-2.08 (m, 2H), 2.33-2.38 (m, 2H), 2.76 (bs, 2H), 3.08 (s, 3H), 3.60 (s, 2H), 4.41-4.44 (m, 1H), 6.82 (d, J=3.6 Hz, 1H), 7.38-7.48 (m, 4H), 7.58 (d, J=8.0 Hz, 2H), 7.71 (d, J=3.2 Hz, 1H), 7.79 (dd, J=8.8, 1.6 Hz, 1H), 8.16-8.19 (m, 1H), 8.26-8.29 (m, 2H); MS: 529 (M+1).

Example-154 tert-Butyl-4-((6-(5-methoxy-1H-indol-1-yl)pyridin-3-yl)oxy)-piperidine-1-carboxylate

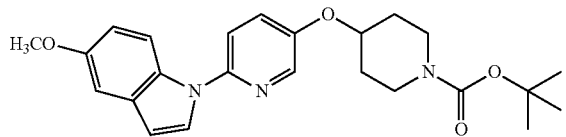 [SMILES: COc1ccc2c(ccn2-c2ccc(OC3CCN(C(=O)OC(C)(C)C)CC3)cn2)c1]

The title compound was prepared by following the similar procedure as described in Example-1 using tert-butyl 4-((6-chloropyridin-3-yl)oxy)piperidine-1-carboxylate (intermediate-06) and 5-methoxy-1H-indole (0.085 g, 20%).

¹H NMR (400 MHz, CDCl₃) δ; 1.49 (s, 9H), 1.79-1.84 (m, 2H), 1.96-2.02 (m, 2H), 3.35-3.41 (m, 2H), 3.71-3.78 (m, 2H), 3.89 (s, 3H), 4.51-4.53 (m, 1H), 6.63 (d, J=3.2 Hz, 1H), 6.93 (dd, J=8.8, 2.4 Hz, 1H), 7.13 (d J=2.4 Hz, 1H), 7.37-7.42 (m, 2H), 7.60-7.6 (d, J=3.2 Hz, 1H) 7.99 (d, J=9.2 Hz, 1H), 8.24-8.25 (m, 1H); MS: 424 (M+1).

Example-155

(±)-3-Isopropyl-5-(3-((6-(5-(methylsulfonyl)-1H-indol-1-yl)pyridin-3-yl) oxy)pyrrolidin-1-yl)-1,2,4-oxadiazole

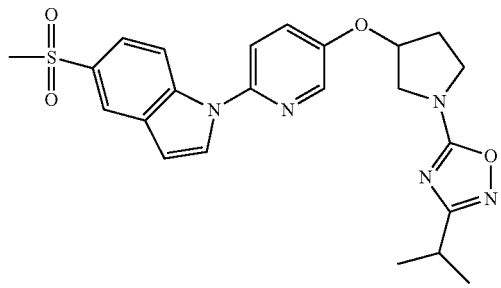 [SMILES: CC(C)c1noc(N2CCC(Oc3ccc(-n4ccc5cc(S(C)(=O)=O)ccc54)nc3)C2)n1]

The title compound was prepared by following the similar procedure as described in Example-4 by using Example-24.

¹H NMR (400 MHz, CDCl₃) δ; 1.31 (d, J=6.8 Hz, 6H), 2.34-2.38 (m, 1H), 2.44-2.45 (m, 1H), 2.90-2.97 (m, 1H), 3.11 (s, 3H), 3.81-3.90 (m, 2H), 3.91-3.94 (m, 2H), 5.15-5.16 (m, 1H), 6.85 (d, J=3.6 Hz, 1H), 7.41-7.47 (m, 2H), 7.74 (d, J=3.2 Hz, 1H), 7.83 (dd, J=8.8, 1.6 Hz, 1H), 8.22 (d, J=8.8 Hz, 1H), 8.28 (d, J=2.0 Hz, 1H), 8.31 (d, J=1.6 Hz, 1H); MS: 468.1 (M+1).

Example-155 was purified into its enantiomers via preparatory HPLC utilizing a CHIRAL IA 250×30 mm, with mobile phase (MeOH: 90% CH₃CN: 10%) at a Flow rate of 60 mL/min wavelength for monitoring the separation was 210 nm. isomer 1 RT=8.99 min. and isomer 2 RT=11.20 min.

Example-156

1-(5-((1-(5-Ethylpyrimidin-2-yl)piperidin-4-yl)oxy)pyridin-2-yl)-5-methoxy-1H-indole

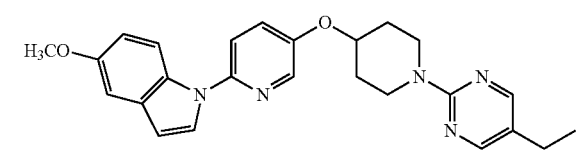 [SMILES: CCc1cnc(N2CCC(Oc3ccc(-n4ccc5cc(OC)cnc54)nc3)CC2)nc1]

The title compound was prepared by following the similar procedure as described in Example-2 by using Example-154 (0.031 g, 20%).

¹H NMR (400 MHz, CDCl₃) δ; 1.21 (t, J=7.6 Hz, 3H), 1.85-1.92 (m, 2H), 2.06-2.12 (m, 2H), 2.50 (q, J=7.6 Hz, 2H), 3.64-3.71 (m, 2H), 3.89 (s, 3H), 4.21-4.27 (m, 2H), 4.60-4.62 (m, 1H), 6.63 (d, J=3.2 Hz, 1H), 6.93 (dd, J=2.4, 9.2 Hz, 1H), 7.13 (d, J=2.4 Hz, 1H), 7.42 (bs, 2H), 7.61 (d, J=3.2 Hz, 1H), 8.0 (d, J=8.8 Hz, 1H), 8.21 (bs, 2H), 8.28 (d, J=2.0 Hz, 1H); MS: 430 (M+1).

Example-157

1-(5-((1-(5-Ethylpyrimidin-2-yl)piperidin-4-yl)oxy)pyridin-2-yl)-5-methoxy-1H-pyrrolo[2,3-b]pyridine

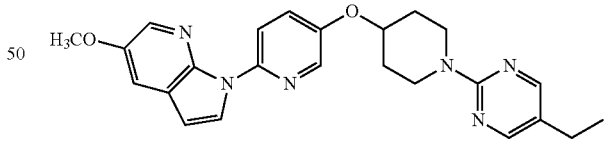

The title compound was prepared by following the similar procedure as described in Example-2 using tert-Butyl-4-((6-(5-methoxy-1H-pyrrolo[2,3-b]pyridin-1-yl)pyridin-3-yl)oxy)-piperidine-1-carboxylate (intermediate-76) (0.031 g, 20%).

¹H NMR (400 MHz, CDCl₃) δ; 1.21 (t, J=7.6 Hz, 3H), 1.86-1.92 (m, 2H), 2.05-2.11 (m, 2H), 2.50 (q, J=7.6 Hz, 2H), 3.71 (bs, 2H), 3.92 (s, 3H), 4.18-4.25 (m, 2H), 4.57-4.60 (m, 1H), 6.57 (d, J=4.0 Hz, 1H), 7.45 (d, J=2.8 Hz, 1H), 7.47 (d, J=2.8 Hz, 1H), 8.15 (d, J=2.8 Hz, 1H), 8.20 (d, J=3.2 Hz, 1H), 8.22 (d, J=3.2 Hz, 3H), 8.69 (d, J=8.8 Hz, 1H); MS: 431(M+1).

Example-158

(±)-3-Ethyl-5(3((6-(5-(methylsulfonyl)-1H-indol-1-yl)pyridin-3-yl) oxy)pyrrolidin-1-yl)methyl)-1,2,4-oxadiazole

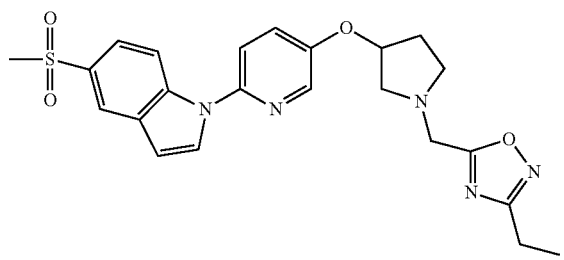 [SMILES: CCc1noc(CN2CCC(Oc3ccc(-n4ccc5cc(S(C)(=O)=O)ccc54)nc3)C2)n1]

The title compound was prepared according to procedure described in Example-79 by using Example-24.

¹H NMR (400 MHz, CDCl₃) δ; 1.37 (t, J=7.6 Hz, 3H), 2.12-2.15 (m, 1H), 2.39-2.48 (m, 1H), 2.80 (q, J=7.6 Hz, 2H), 2.84 (bs, 1H), 3.02-3.08 (m, 2H), 3.10 (s, 3H), 3.24-3.26 (m, 1H), 3.28 (s, 2H), 4.97 (m, 1H), 6.84 (d, J=3.6 Hz, 1H), 7.37-7.44 (m, 2H), 7.73 (d, J=3.6 Hz, 1H), 7.80-7.82 (m, 1H), 8.19-8.23 (m, 2H), 8.31 (s, 1H); MS: 468.1 (M+1).

Example-159

(±)-3-Isopropyl-5-((3-((6-(5-(methylsulfonyl)-1H-indol-1-yl) oxy)pyrrolidin-1-yl)methyl)-1,2,4-oxadiazole

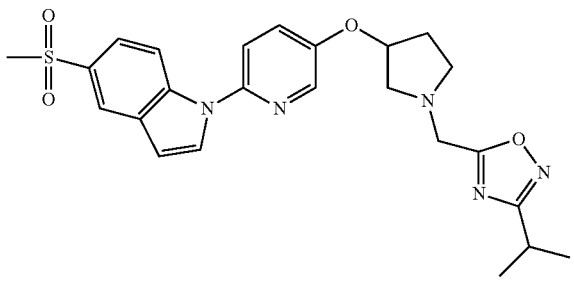 [SMILES: CC(C)c1noc(CN2CCC(Oc3ccc(-n4ccc5cc(S(C)(=O)=O)ccc54)nc3)C2)n1]

The title compound was prepared according to procedure described in Example-79 by using Example-24.

¹H NMR (400 MHz, CDCl₃) δ; 1.36 (d, J=6.8 Hz, 6H), 2.11-2.15 (m, 1H), 2.41-2.46 (m, 1H), 2.83-2.87 (m, 1H), 3.02-3.07 (m, 2H), 3.10-3.16 (m, 4H), 3.21-3.25 (m, 1H), 4.04 (s, 2H), 4.95-4.99 (m, 1H), 6.83-6.84 (m, 1H), 7.37-7.43 (m, 2H), 7.73 (d, J=3.6 Hz, 1H), 7.81 (dd, J=8.8, 2.0 Hz, 1H), 8.20 (d, J=8.8 Hz, 1H), 8.23 (d, J=2.4 Hz, 1H), 8.31 (d, J=1.6 Hz, 1H); MS: 481.9 (M+1).

Example-160

3-Isopropyl-5-((3-((6-(5-(methylsulfonyl)-1H-indol-1-yl)pyridin-3-yl) oxy)azetidin-1-yl)methyl)-1,2,4-oxadiazole

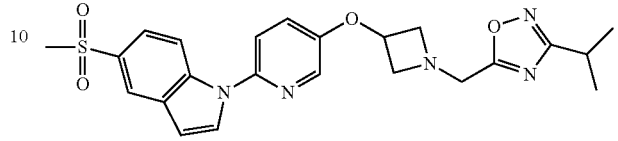

The title compound was prepared according to procedure described in Example-79 by using Example-27.

¹H NMR (400 MHz, CDCl₃) δ; 1.36 (d, J=6.8 Hz, 6H), 3.10 (s, 3H), 3.11-3.16 (m, 1H), 3.45-3.52 (m, 2H), 3.99 (s, 2H), 4.07-4.10 (m, 2H), 4.93-4.99 (m, 1H), 6.84-6.85 (m, 1H), 7.32 (dd, J=8.8, 2.8 Hz, 1H), 7.73 (d, J=3.6 Hz, 1H), 7.81 (dd, J=8.8, 1.6 Hz, 1H), 8.16(d, J=2.8 Hz, 1H), 8.11 (d, J=8.8 Hz, 1H), 8.12 (d, J=8.8 Hz, 1H), 8.31 (d, J=1.6 Hz, 1H); MS: 467.48 (M+1).

Example-161

3-Ethyl-5-((3-((6-(5-(methylsulfonyl)-1H-indol-1-yl) pyridin-3-yl)oxy) azetidin-1-yl)methyl)-1,2,4-oxadiazole

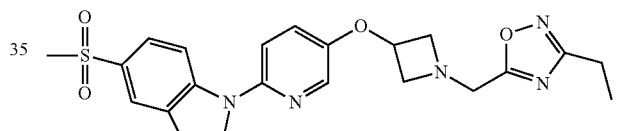

The title compound was prepared according to procedure described in Example-79 by using Example-27.

¹H NMR (400 MHz, CDCl₃) δ; 1.35 (t, J=7.6 Hz, 3H), 2.79 (q, J=7.6 Hz, 2H), 3.10 (s, 3H), 3.45-3.49 (m, 2H), 3.99 (s, 2H), 4.07-4.10 (m, 2H), 4.95-4.98 (m, 1H), 6.84 (d, J=3.2 Hz, 1H), 7.32 (dd, J=8.8, 3.2 Hz, 1H), 7.43 (d, J=8.8 Hz, 1H), 7.73 (d, J=3.6 Hz, 1H), 7.81 (dd, J=8.8, 2.0 Hz, 1H), 8.16 (d, J=2.8 Hz, 1H), 8.20 (d, J=8.8 Hz, 1H), 8.31 (d, 1.6 Hz, 1H); MS: 454.23 (M+1).

Example-162

1-(5-((1-(2-Fluoro-2-methylpropyl)piperidin-4-yl) oxy)pyridin-2-yl)-N-(2-hydroxyethyl)-1H-indole-5-carboxamide

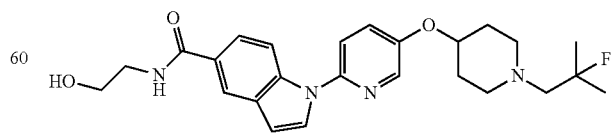

The title compound was prepared by following the similar procedure as described in Example-1 using N-(2-hydroxyethyl)-1H-indole-5-carboxamide (intermediate-19) and 2-Chloro-5-((1-(2-fluoro-2-methylpropyl)piperidin-4-yl) oxy)pyridine (intermediate-54).

¹H NMR (400 MHz, CDCl₃) δ; 1.40 (d, J=21.2 Hz, 6H), 1.90 (bs, 2H), 2.05 (bs, 2H), 2.47-2.53 (m, 3H), 2.90-2.97 (m, 3H), 3.66-3.70 (m, 2H), 3.87-3.88 (m, 2H), 4.38 (bs, 1H), 6.71-6.72 (m, 1H), 6.75 (d, J=3.2 Hz, 1H), 7.41-4.41 (m, 2H), 7.67 (d, J=3.2 Hz, 1H), 7.72 (dd, J=8.8, 1.6 Hz, 1H), 8.05 (d, J=8.4 Hz, 1H), 8.14 (d, J=1.6 Hz, 1H), 8.26-8.27 (m, 1H); MS: 454.5 (M+1).

Example-163 cis (±)-tert-Butyl-3-fluoro-4-((6-(5-(methylsulfonyl)- 1H-indol-1-yl)-pyridin-3-yl)oxy)piperidine-1-carboxylate

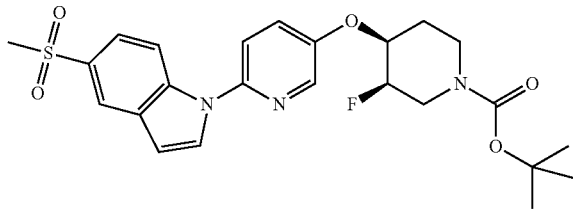 [SMILES: CC(C)(C)OC(=O)N1CC[C@H](Oc2ccc(-n3ccc4cc(S(C)(=O)=O)ccc43)nc2)[C@H](F)C1]

The title compound was prepared by following the similar procedure as described in Example-1 by using 5-(methylsulfonyl)-1H-indole (intermediate 21) and cis(±)-tert-butyl-4-((6-chloropyridin-3-yl)oxy)-3-fluoropiperidine-1-carboxylate (intermediate 7).

¹H NMR (400 MHz, CDCl₃) δ; 1.49 (s, 9H), 1.92 (bs, 1H), 2.11-2.17 (m, 1H), 3.09 (s, 3H), 3.41-3.50 (m, 2H), 3.73 (bs, 3H), 3.96-3.99 (m, 1H), 6.83 (d, J=3.6 Hz, 1H), 7.43 (d, J=8.8 Hz, 1H), 7.51 (dd, J=8.8, 2.8 Hz, 1H), 7.73 (d, J=3.2 Hz, 1H), 7.80 (dd, J=8.8, 1.6 Hz, 1H), 8.21 (d, J=8.8 Hz, 1H), 8.30 (d, J=1.2 Hz, 1H), 8.34 (d, J=2.8 Hz, 1H); MS: 490.2 (M+1).

Example-164 cis(±)(1-(5-(-1-(5-Ethylpyrimidin-2-yl)-3-fluoropiperidin-4-yl)oxy) pyridin-2-yl)-5-(methylsulfonyl)- 1H-indole

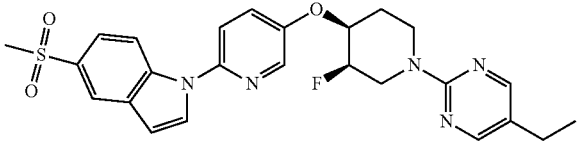 [SMILES: CCc1cnc(N2CC[C@H](Oc3ccc(-n4ccc5cc(S(C)(=O)=O)ccc54)nc3)[C@H](F)C2)nc1]

The title compound was prepared by following the similar procedure as described in Example-2 by using Example-163 (0.71 g, 46%);

¹H NMR (400 MHz, CDCl₃) δ; 1.20 (t, J=7.6 Hz, 3H), 1.97-2.01 (m, 1H), 2.18-2.23 (m, 1H), 2.49 (q, J=7.6 Hz, 2H), 3.09 (s, 3H), 3.82-3.85 (m, 1H), 4.03-4.14 (m, 2H), 4.36-4.41 (m, 1H), 4.69-4.75 (m, 1H), 4.83-4.84 (m, 0.5H), 4.94-4.96 (m, 0.5H), 6.83 (d, J=3.6 Hz, 1H), 7.44 (d, J=8.8 Hz, 1H), 7.55 (dd, J=8.8, 3.2 Hz, 1H), 7.73 (d, J=3.6 Hz, 1H), 7.81 (dd, J=8.8, 1.6 Hz, 1H), 8.21 (s, 2H), 8.23 (s, 1H), 8.30 (d, J=1.6 Hz, 1H), 8.37 (s, 1H); MS: 496.2 (M+1).

Cis(±)(1-(5-(-1-(5-ethylpyrimidin-2-yl)-3-fluoropiperidin-4-yl)oxy)pyridin-2-yl)-5-(methylsulfonyl)-1H-indole was purified into its enantiomers via preparatory HPLC utilizing a Cellulose-1 250 mm×21 mm, Column No-CRL-023 with mobile phase (MeOH:85% CH₃CN 15%) at a Flow rate of 21 mL/min wavelength for monitoring the separation was 210 nm. isomer 1 RT=8.75 min. and isomer 2 RT=9.89 min.

Example-165 tert-Butyl-4-((6-(5-(2-oxooxazolidin-3-yl)-1H-indol- 1-yl)pyridin-3-yl)oxy)piperidine-1-carboxylate

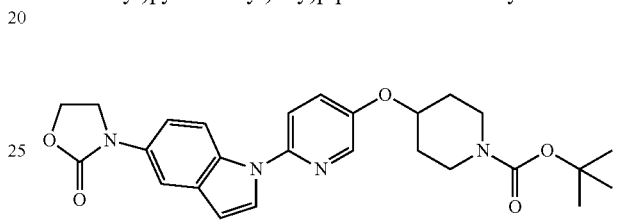

The title compound was prepared by following the similar procedure as described in Example-1 using tert-butyl 4-((6-chloropyridin-3-yl)oxy)piperidine-1-carboxylate (intermediate-06) and 3-(1H-indol-5-yl)oxazolidin-2-one (intermediate-59) (0.390 g, 63%).

¹H NMR (400 MHz, CDCl₃) δ; 1.49 (s, 9H), 1.83(bs, 2H), 1.99 (bs, 2H), 3.35-3.41 (m, 2H), 3.74-3.78 (m, 2H), 4.13-4.18 (m, 2H), 4.50-4.54 (m, 3H), 6.68-6.71 (m, 1H), 7.42 (bs, 2H), 7.52 (d, J=8.8 Hz, 1H), 7.65 (d, J=3.2 Hz, 1H), 7.73 (bs, 1H), 8.07 (d, J=9.2 Hz, 1H), 8.26 (bs, 1H); MS: 423 (M−56).

Example-166

Isopropyl 4-((6-(5-(2-oxooxazolidin-3-yl)-1H-indol- 1-yl)pyridin-3-yl)oxy)piperidine-1-carboxylate

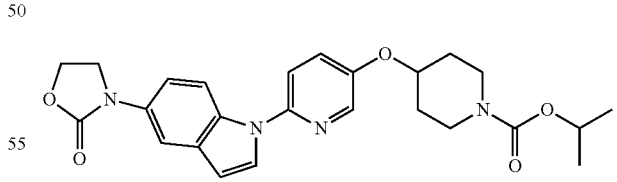

The title compound was prepared by following the similar procedure as described in Example-70 by using Example-165 (0.011 g, 08%).

¹H NMR (400 MHz, CDCl₃) δ; 1.28 (d, J=3.6 Hz, 6H), 1.84-1.86 (m, 2H), 2.00-2.02 (m, 2H), 3.41-3.47 (m, 2H), 3.77-3.81 (m, 2H), 4.14-4.18 (m, 2H), 4.51-4.57 (m, 3H), 4.94-4.97 (m, 1H), 6.68 (d, J=3.6 Hz, 1H), 7.42 (bs, 2H), 7.52-7.55 (m, 1H), 7.66 (d, J=3.6 Hz, 1H), 7.73 (d, J=2.0 Hz, 1H), 8.08 (d, J=8.8 Hz, 1H), 8.26 (bs, 1H); MS: 465 (M+1).

Example-167 tert-Butyl-4-((6-(3-methyl-5-(methylsulfonyl)-1H-indol-1-yl)pyridin-3-yl)oxy)piperidine-1-carboxylate

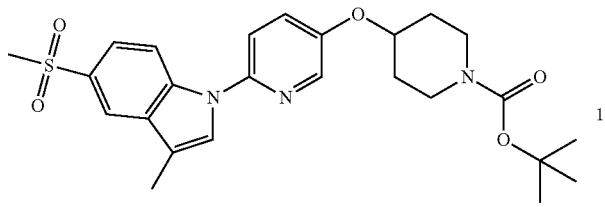

The title compound was prepared by following the similar procedure as described in Example-1 by using tert-butyl 4-((6-chloropyridin-3-yl)oxy)piperidine-1-carboxylate (intermediate-6) and 3-methyl-5-(methylsulfonyl)-1H-indole (intermediate-23).

$^1$H NMR (400 MHz, CDCl$_3$) δ; 1.47 (s, 9H), 1.77-1.85 (m, 2H), 1.96-2.01 (m, 2H), 2.41 (s, 3H), 3.09 (s, 3H), 3.34-3.40 (m, 2H), 3.71-3.77 (m, 2H), 4.51-4.55 (m, 1H), 7.35-7.43 (m, 2H), 7.50 (d, J=0.8 Hz, 1H), 7.79 (dd, J=8.8, 1.6 Hz, 1H), 8.18-8.25 (m, 31-1); MS: 508.2 (M+23).

Example-168

1-(5-((1-(5-Ethylpyrimidin-2-yl)piperidin-4-yl)oxy) pyridin-2-yl)-3-methyl-5-(methylsulfonyl)-1H-indole

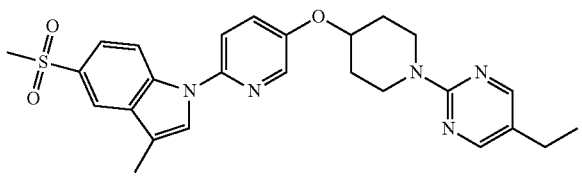 [SMILES: CCc1cnc(N2CCC(Oc3ccc(-n4cc(C)c5cc(S(C)(=O)=O)ccc54)nc3)CC2)nc1]

The title compound was prepared by following the similar procedure as described in Example-2 by using Example-167.

$^1$H NMR (400 MHz, CDCl$_3$) δ; 1.20 (t, J=7.6 Hz, 3H), 1.85-1.91 (m, 2H), 2.06-2.11 (m, 2H), 2.41 (s, 3H), 2.48 (q, J=7.6 Hz, 2H), 3.10 (s, 3H), 3.63-3.70 (m, 2H), 4.19-4.25 (m, 2H), 4.61-4.63 (m, 1H), 7.38 (d, J=8.8 Hz, 1H), 7.44 (dd, J=8.8, 2.8 Hz, 1H), 7.51 (d, J=0.8 Hz, 1H), 7.79 (dd, J=8.8, 2.0 Hz, 1H), 8.20 (d, J=8.0 Hz, 1H), 8.23 (d, J=1.6 Hz, 1H), 8.28 (s, 1H); MS: 492.2 (M+1).

Example-169

Isopropyl 4-((6-(5-(methylsulfonyl)-1H-indol-1-yl) pyridin-3-yl)oxy) piperidine-1-carboxylate

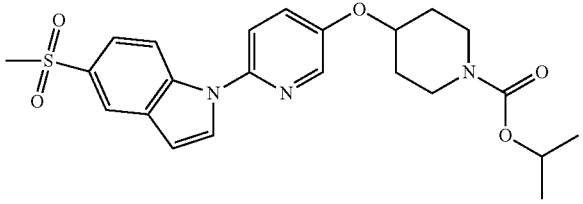 [SMILES: CC(C)OC(=O)N1CCC(Oc2ccc(-n3ccc4cc(S(C)(=O)=O)ccc43)nc2)CC1]

The title compound was prepared by following the similar procedure as described in Example-70 by using Example-1 (0.011 g, 9%).

$^1$H NMR (400 MHz, CDCl$_3$) δ; 1.26 (d, J=6.0 Hz, 6H), 1.80-1.84 (m, 2H), 1.98-2.02 (m, 2H), 3.09 (s, 3H), 3.40-3.48 (m, 2H), 3.74-3.80 (m, 2H), 4.54-4.60 (m, 1H), 4.91-4.97 (m, 1H), 6.68 (d, J=3.2 Hz, 1H), 7.43 (dd, J=8.8, 2.4 Hz, 2H), 7.72 (d, J=3.6 Hz, 1H), 7.80 (dd, J=8.8, 1.6 Hz, 1H), 8.19 (d, J=8.8 Hz, 1H), 8.28 (dd, J=3.6, 2.8 Hz, 2H); MS: 458 (M+1).

Example-170

Isopropyl 4-((6-(7-fluoro-5-(methylsulfonyl)-1H-indol-1-yl)pyridin-3-yl)oxy)piperidine-1-carboxylate

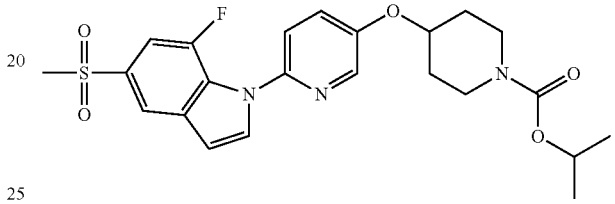

The title compound was prepared by following the similar procedure as described in Example-70 by using Example-91.

$^1$H NMR (400 MHz, CDCl$_3$) δ; 1.28 (d, J=6.4 Hz, 6H), 1.82-1.88 (m, 2H), 2.00-2.03 (m, 2H), 3.11 (s, 3H), 3.42-3.50 (m, 2H), 3.75-3.81 (m, 2H), 4.58-4.62 (m, 1H), 4.92-4.98 (m, 1H), 6.86-6.88 (m, 1H), 7.39-7.41 (m. 2H), 7.51 (dd, J=11.6, 1.6 Hz, 1H), 7.68 (d, J=3.2 Hz, 1H), 8.12 (d, J=1.6 Hz, 1H), 8.25 (s, 1H); MS: 476.1 (M+1).

Example-171

1-(5-((1-(5-Ethylpyrimidin-2-yl)piperidin-4-yl)oxy) pyridin-2-yl)-7-fluoro-5-(methylsulfonyl)-1H-indole

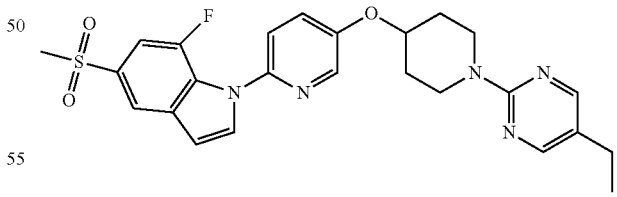

The title compound was prepared by following the similar procedure as described in Example-2 by using Example-91 (0.011 g, 22%).

$^1$H NMR (400 MHz, CDCl$_3$) δ; 1.22 (t, J=7.6 Hz, 3H), 1.93 (bs, 2H), 2.10-2.14 (m, 2H), 2.51 (q, J=8.0 Hz, 2H), 3.11 (s, 3H), 3.74 (bs, 2H), 4.22-4.25 (m, 2H), 4.68 (bs, 1H), 6.87 (d, J=3.2 Hz, 1H), 7.39-7.45 (m, 2H), 7.52 (dd, J=11.6, 1.2 Hz, 1H), 7.69 (d, J=3.6 Hz, 1H), 8.13 (d, J=1.2 Hz, 1H), 8.23 (bs, 2H), 8.27 (d, J=2.8 Hz, 1H); MS: 496 (M+1).

Example-172

2,2,2-Trifluoro-1-(4-((6-(5-(methylsulfonyl)-1H-indol-1-yl)pyridin-3-yl) oxy)piperidin-1-yl)ethanone

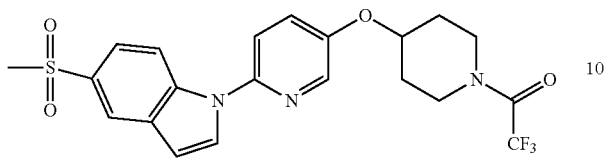

The title compound was prepared by following the similar procedure as described in Example-129 by using Example-1.

$^1$H NMR (400 MHz, CDCl$_3$) δ; 2.01-2.11 (m, 4H), 3.11 (s, 3H), 3.70-3.79 (m, 2H), 3.81-3.93 (m, 1H), 3.94-3.99 (m, 1H), 4.72-4.77 (m, 1H), 6.86 (dd, J=3.2, 0.4 Hz, 1H), 7.46-7.47 (m, 2H), 7.74 (d, J=3.6 Hz, 1H), 7.83 (dd, J=8.8, 2.0 Hz, 1H), 8.23 (d, J=8.8 Hz, 1H), 8.32 (d, J=1.6 Hz, 2H); MS: 467 (M$^+$)

Example-173 tert-Butyl-4-((5-(5-(methylsulfonyl)-1H-indol-1-yl)pyridin-2-yl)oxy)-piperidine-1-carboxylate

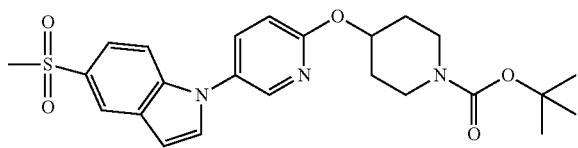 [SMILES: CC(C)(C)OC(=O)N1CCC(Oc2ccc(-n3ccc4cc(S(C)(=O)=O)ccc43)cn2)CC1]

The title compound was prepared by following the similar procedure as described in Example-1 by using 5-(methylsulfonyl)-1H-indole (intermediate 21) and tert-butyl-4-((5-bromopyridin-2-yl)oxy)piperidine-1-carboxylate (intermediate 65) (0.610 g, 46%).

$^1$H NMR (400 MHz, CDCl$_3$) δ; 1.51 (s, 9H), 1.78-1.85 (m, 2H), 1.98-2.07 (m, 2H), 3.12 (s, 3H), 3.27-3.38 (m, 2H), 3.71-3.84 (m, 2H), 5.29-5.33 (m, 1H), 6.87 (d, J=3.2 Hz, 1H), 6.93 (d, J=8.4 Hz, 1H), 7.41 (d, J=3.2 Hz, 1H), 7.50 (d, J=8.8 Hz, 1H), 7.70 (dd, J=8.8, 2.8 Hz, 1H), 7.78 (dd, J=8.8, 1.6 Hz, 1H), 8.29 (d, J=2.4 Hz, 1H), 8.36 (d, J=1.6 Hz, 1H); MS: 416 (M−56).

Example-174

1-(6-((1-(5-Ethylpyrimidin-2-yl)piperidin-4-yl)oxy)pyridin-3-yl)-5-(methylsulfonyl)-1H-indole

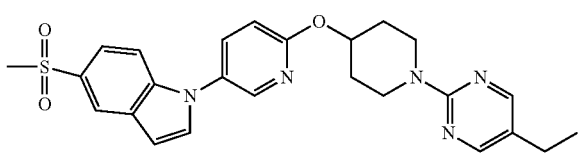 [SMILES: CCc1cnc(N2CCC(Oc3ccc(-n4ccc5cc(S(C)(=O)=O)ccc54)cn3)CC2)nc1]

The title compound was prepared by following the similar procedure as described in Example-2 by using Example-173 (0.011 g, 21%).

$^1$H NMR (400 MHz, CDCl$_3$) δ; 1.19 (d, J=7.6 Hz, 3H), 1.82-1.89 (m, 2H), 2.11-2.17 (m, 2H), 2.47 (q, J=7.6 Hz, 2H), 3.09 (s, 3H), 3.58-3.64 (m, 2H), 4.27-4.33 (m, 2H), 5.37-5.38 (m, 1H), 6.84 (d, J=3.2 Hz, 1H), 6.91 (d, J=8.8 Hz, 1H), 7.39 (d, J=3.2 Hz, 1H), 7.45 (d, J=8.4 Hz, 1H), 7.68 (dd, J=8.8, 2.8 Hz, 1H), 7.76 (dd, J=8.8, 2.0 Hz, 1H), 8.19 (s, 2H), 8.28 (d, J=2.8 Hz, 1H), 8.34 (s, 1H); MS: 478 (M+1).

Example-175

(4-((6-(5-(Methylsulfonyl)-1H-indol-1-yl)pyridin-3-yl)oxy)piperidin-1-yl)(1-(trifluoromethyl)cyclopropyl)methanone

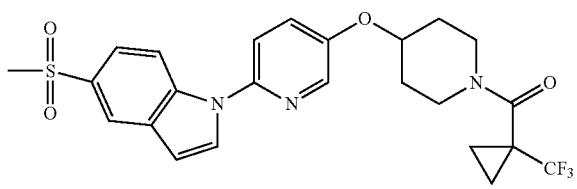 [SMILES: CS(=O)(=O)c1ccc2c(ccn2-c2ccc(OC3CCN(C(=O)C4(C(F)(F)F)CC4)CC3)cn2)c1]

The title compound was prepared by following the similar procedure as described in Example-23 by using Example-1 and 1-(trifluoromethyl)cyclopropanecarboxylic acid $^1$H NMR (400 MHz, CDCl$_3$) δ: 1.20-1.28 (m, 2H), 1.36-1.39 (m, 2H), 1.93-2.05 (m, 4H), 3.11 (s, 3H), 3.80-3.81 (m, 4H), 4.68-4.71 (m, 1H), 6.85 (d, J=3.6 Hz, 1H), 7.46 (d, J=2.4 Hz, 2H), 7.74 (d, J=3.6 Hz, 1H), 7.82 (dd, J=8.8, 2.0 Hz, 1H), 8.21 (d, J=8.8 Hz, 1H), 8.30-8.32 (m, 2H); MS: 507.5 (M+1).

Example-176

3-Isopropyl-5-(4-((5-(5-(methylsulfonyl)-1H-indol-1-yl)pyridin-2-yl)oxy) piperidin-1-yl)-1,2,4-oxadiazole

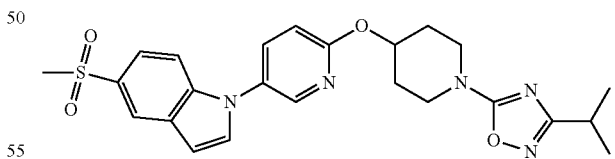

The title compound was prepared by following the similar procedure as described in Example-4 by using Example-173 (0.017 g, 9%).

$^1$H NMR (400 MHz, CDCl$_3$) δ; 1.29 (d, J=6.8 Hz, 6H), 2.10-2.16 (m, 2H), 2.86-2.93 (m, 2H), 3.08 (s, 3H), 3.58-3.64 (m, 2H), 3.87-3.94 (m, 2H), 4.66 (bs, 1H), 5.37-5.39 (m, 1H), 6.84 (d, J=0.8 Hz, 1H), 6.92 (dd, J=8.8, 0.4 Hz, 1H), 7.38 (d, J=3.6 Hz, 1H), 7.48 (d, J=8.8 Hz, 1H), 7.69 (dd, J=8.8, 2.8 Hz, 1H), 7.75 (dd, J=8.0, 2.8 Hz, 1H), 8.27 (d, J=2.0 Hz, 1H), 8.33 (s, 1H); MS: 482 (M+1).

Example-177

5-(4-((6-(7-Fluoro-5-(methyl sulfonyl)-1H-indol-1-yl)pyridin-3-yl)oxy) piperidin-1-yl)-3-isopropyl-1,2,4-oxadiazole

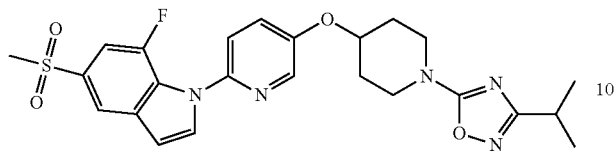

The title compound was prepared by following the similar procedure as described in Example-4 by using Example-90 (0.018 g, 11%).

$^1$H NMR (400 MHz, CDCl$_3$) δ; 1.28 (d, J=7.2 Hz, 6H), 1.96-2.02 (m, 2H), 2.05-2.12 (m, 2H), 2.87-2.90 (m, 1H), 3.08 (s, 3H), 3.63-3.69 (m, 2H), 3.81-3.88 (m, 2H), 4.66-4.67 (m, 1H), 6.84 (dd, J=3.2, 2.4 Hz, 1H), 7.39 (bs, 2H), 7.49 (dd, J=11.6, 1.6 Hz, 1H), 7.66 (d, J=3.6 Hz, 1H), 8.09 (bs, 1H), 8.23 (d, J=1.2 Hz, 1H); MS: 500 (M+1).

Example-178 tert-Butyl-4-((6-(5-(2-oxopyrrolidin-1-yl)-1H-indol-1-yl)pyridin-3-yl) oxy)piperidine-1-carboxylate

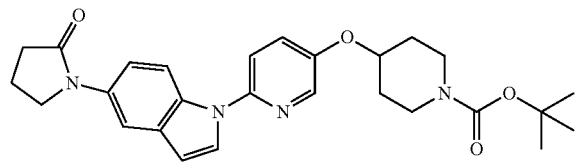 [SMILES: CC(C)(C)OC(=O)N1CCC(Oc2ccc(-n3ccc4cc(N5CCCC5=O)ccc43)nc2)CC1]

The title compound was prepared by following the similar procedure as described in Example-1 using tert-butyl 4-((6-chloropyridin-3-yl)oxy)piperidine-1-carboxylate (intermediate-6) and tert-butyl 5-(2-oxopyrrolidin-1-yl)-1H-indole-1-carboxylate (intermediate-27) (0.011 g, 6%).

$^1$H NMR (400 MHz, CDCl$_3$) δ; 1.48 (s, 9H), 1.78-1.83 (m, 2H), 1.95-2.00 (m, 2H), 2.17-2.23 (m, 2H), 2.64 (t, J=7.6 Hz, 2H), 3.34-3.40 (m, 2H), 3.71-3.76 (m, 2H), 3.94 (t, J=6.8 Hz, 2H), 4.51-4.53 (m, 1H), 6.67 (d, J=2.8 Hz, 1H), 7.40 (dd, J=2.8, 0.8 Hz, 2H), 7.52 (dd, J=9.2, 2.4 Hz, 1H), 7.63 (d, J=3.2 Hz, 1H), 7.77 (d, J=2.0 Hz, 1H), 8.03 (d, J=8.8 Hz, 1H), 8.24 (d, J=1.6 Hz, 1H); MS: 477 (M+1).

Example-179

1-(1-(5-((1-(5-Ethylpyrimidin-2-yl)piperidin-4-yl)oxy)pyridin-2-yl)-1H-indol-5-yl)pyrrolidin-2-one

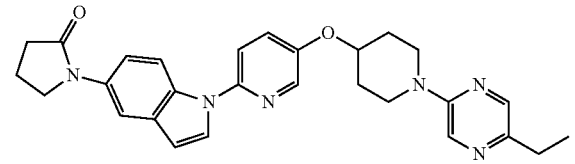 [SMILES: CCc1cnc(N2CCC(Oc3ccc(-n4ccc5cc(N6CCCC6=O)ccc54)nc3)CC2)cn1]

The title compound was prepared by following the similar procedure as described in Example-2 by using Example-178 (0.022 g, 29%).

$^1$H NMR (400 MHz, CDCl$_3$) δ; 1.20 (t, J=7.6 Hz, 3H), 1.85-1.89 (m, 2H), 2.06-2.08 (m, 2H), 2.17-2.21 (m, 2H), 2.44-2.51 (m, 2H), 2.64 (t, J=8.0 Hz, 2H), 3.63-3.69 (m, 2H), 3.94 (t, J=6.8 Hz, 2H), 4.20-4.22 (m, 2H), 4.60 (bs, 1H), 6.66 (d, J=3.6 Hz, 1H), 7.42 (d, J=2.0 Hz, 2H), 7.52 (dd, J=8.8, 2.0 Hz, 1H), 7.64 (d, J=3.6 Hz, 1H), 7.77 (d, J=2.0 Hz, 1H), 8.04 (d, J=9.2 Hz, 1H), 8.19 (bs, 2H), 8.26 (d, J=2.0 Hz, 1H); MS: 483(M+1).

Example-180 tert-Butyl-4-((6-(5-cyano-7-fluoro-1H-indol-1-yl)pyridin-3-yl)oxy)-piperidine-1-carboxylate

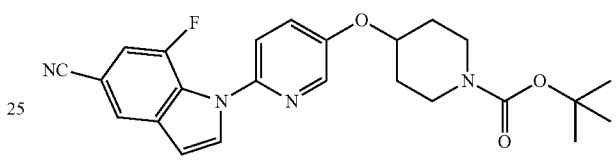

The title compound was prepared by following the similar procedure as described in Example-1 using tert-butyl 4-((6-chloropyridin-3-yl)oxy)piperidine-1-carboxylate (intermediate-6) and 7-fluoro-1H-indole-5-carbonitrile (0.085 g, 44%), $^1$H NMR (400 MHz, CDCl$_3$) δ; 1.48 (s, 9H), 1.78-1.81 (m, 2H), 1.97-2.05 (m, 2H), 3.35-3.42 (m, 2H), 3.71-3.77 (m, 2H), 4.54-4.58 (m, 1H), 6.78-6.80 (m, 1H), 7.17-7.20 (m, 1H), 7.36-7.38 (m, 2H), 7.64 (d, J=3.2 Hz, 1H), 7.82 (d, J=1.2 Hz, 1H), 8.22 (bs, 1H); MS: 459 (M+23).

Example-181

1-(5-((1-(5-Ethylpyrimidin-2-yl)piperidin-4-yl)oxy)pyridin-2-yl)-7-fluoro-1H-indole-5-carbonitrile

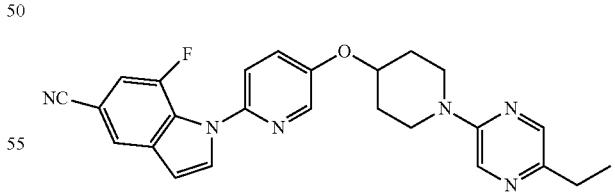

The title compound was prepared by following the similar procedure as described in Example-2 by using Example-180 (0.022 g, 29%).

$^1$H NMR (400 MHz, CDCl$_3$) δ; 1.20 (t, J=7.6 Hz, 3H), 1.85-1.89 (m, 2H), 2.06-2.09 (m, 2H), 2.47 (q, J=7.6 Hz, 2H), 3.64-3.71 (m, 2H), 4.18-4.23 (m, 2H), 4.63-4.64 (m, 1H) 6.78 (dd, J=3.2, 2.4 Hz, 1H), 7.19 (dd, J=11.6, 1.2 Hz, 1H), 7.35-7.42 (m, 2H), 7.64 (d, J=3.2 Hz, 1H), 7.82 (d, J=1.6 Hz, 1H), 8.19 (s, 2H), 8.24 (bs, 1H); MS: 443 (M+1).

Example-182

Ethyl 4-((6-(5-(2-oxopyrrolidin-1-yl)-1H-indol-1-yl)pyridin-3-yl)oxy) piperidine-1-carboxylate

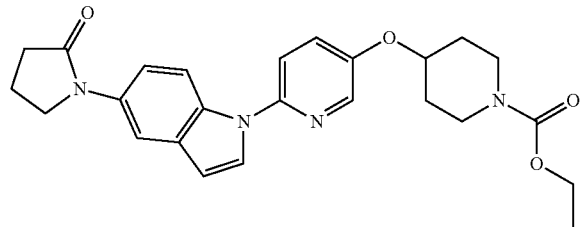 [SMILES: CCOC(=O)N1CCC(Oc2ccc(-n3ccc4cc(N5CCCC5=O)ccc43)nc2)CC1]

The title compound was prepared by following the similar procedure as described in Example-70 by using Example-181 (0.031 g, 27%).

$^1$H NMR (400 MHz, CDCl$_3$) δ; 1.27 (t, J=7.2 Hz, 3H), 1.81-1.84 (m, 2H), 1.95-1.98 (m, 2H), 2.16-2.20 (m, 2H), 2.63 (t, J=8.0 Hz, 2H), 3.41-3.46 (m, 2H), 3.74-3.76 (m, 2H), 3.93 (t, J=7.2 Hz, 2H) 4.15 (q, J=7.2 Hz, 2H), 4.52-4.54 (m, 1H), 6.66 (d, J=3.2 Hz, 1H), 7.36-7.42 (m, 2H), 7.51 (dd, J=9.2, 2.4 Hz, 1H), 7.62 (d, J=3.6 Hz, 1H), 7.76 (d, J=2.0 Hz, 1H), 8.02 (d, J=8.8 Hz, 1H), 8.23 (d, J=2.8 Hz, 1H); MS: 449 (M+1).

Example-183 tert-Butyl-4-((6-(5-(cyclopropylsulfonyl)-1H-indol-1-yl)pyridin-3-yl)oxy)piperidine-1-carboxylate

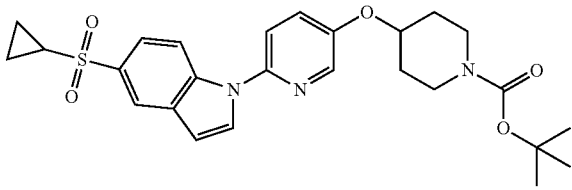 [SMILES: CC(C)(C)OC(=O)N1CCC(Oc2ccc(-n3ccc4cc(S(=O)(=O)C5CC5)ccc43)nc2)CC1]

The title compound was prepared by following the similar procedure as described in Example-1 by using tert-butyl 4-((6-chloropyridin-3-yl)oxy)piperidine-1-carboxylate (intermediate-6) and 5-(Cyclopropylsulfonyl)-1H-indole (intermediate 24).

$^1$H NMR (400 MHz, CDCl$_3$) δ; 0.98-1.01 (m, 2H), 1.36-1.37 (m, 2H), 1.48 (s, 9H), 1.80-1.84 (m, 2H), 1.97-2.04 (m, 2H), 2.48-2.52 (m, 1H), 3.35-3.41 (m, 2H), 3.71-3.74 (m, 2H), 4.55-4.57 (m, 1H), 6.82 (dd, J=3.6, 0.4 Hz, 1H), 7.42-7.43 (m, 2H), 7.71 (d, J=3.6 Hz, 1H), 7.76 (dd, J=8.8, 2.0 Hz, 1H), 8.17 (d, J=8.8 Hz, 1H), 8.24 (d, J=1.6 Hz, 1H), 8.27-8.28 (m, 1H); MS: 498.09 (M+1).

Example-184

5-(Cyclopropylsulfonyl)-1-(5-((1-(5-ethylpyrimidin-2-yl)piperidin-4-yl) oxy)pyridin-2-yl)-1H-indole

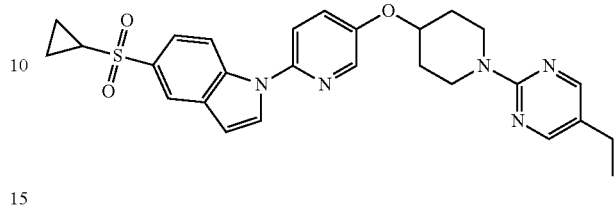

The title compound was prepared by following the similar procedure as described in Example-2 by using Example-183.

$^1$H NMR (400 MHz, CDCl$_3$) δ; 0.99-1.00 (m, 2H), 1.20 (t, J=7.2 Hz, 3H), 1.37 (bs, 2H), 1.89 (bs, 2H), 2.09 (bs, 2H), 2.47-2.49 (m, 3H), 3.68 (bs, 2H), 4.23 (bs, 2H), 4.64 (bs, 1H), 6.83 (bs, 1H), 7.44 (bs, 2H), 7.72-7.78 (m, 2H), 8.20-8.31 (m, 5H); MS: 504.2 (M+1).

Example-185

Ethyl-4-((6-(5-(methylsulfonyl)-1H-indol-1-yl)pyridin-3-yl)oxy)-piperidine-1-carboxylate

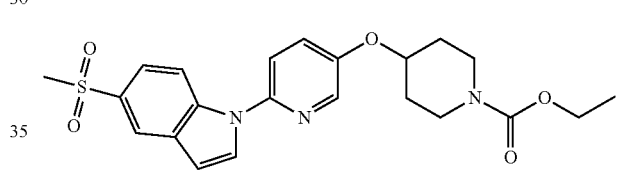

The title compound was prepared by following the similar procedure as described in Example-70 by using Example-1 (0.031 g, 22%).

$^1$H NMR (400 MHz, CDCl$_3$) δ; 1.27 (t, J=7.2 Hz, 3H), 1.82-1.85 (m, 2H), 1.97-2.01 (m, 2H), 3.08 (s, 3H), 3.41-3.48 (m, 2H), 3.73-3.80 m, 2H), 4.15 (q, J=6.8 Hz, 2H), 4.56-4.58 (m, 2H), 6.82 (d, J=3.2 Hz, 1H), 7.41 (d, J=2.4 Hz, 1H), 7.71 (d, J=3.2 Hz, 1H), 7.79 (dd, J=8.8, 2.0 Hz, 1H), 8.18 (d, J=8.8 Hz, 1H), 8.27 (bs, 1H), 8.28 (d, J=1.6 Hz, 1H); MS: 444 (M+1).

Example-186 tert-Butyl-4-((6-(5-(1H-tetrazol-1-yl)-1H-indol-1-yl)pyridin-3-yl)oxy) piperidine-1-carboxylate

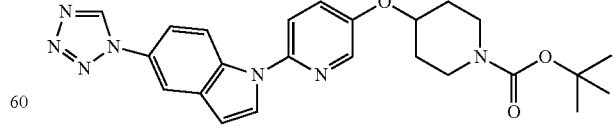

The title compound was prepared by following the similar procedure as described in Example-1 using tert-butyl 4-((6-chloropyridin-3-yl)oxy)piperidine-1-carboxylate (intermediate 06) and 5-(1H-tetrazol-1-yl)-1H-indole (intermediate 57) (0.110 g, 24%).

¹H NMR (400 MHz, CDCl₃) δ; 1.49 (s, 9H), 1.80-1.86 (m, 2H), 1.98-2.03 (m, 2H), 3.36-3.49 (m, 2H), 3.71-3.78 (m, 2H), 4.54-4.58 (m, 1H), 6.81 (dd, J=3.4, 0.4 Hz, 1H), 7.44 (bs, 2H), 7.55 (dd, J=8.8, 2.4 Hz, 1H), 7.73 (d, J=3.6 Hz, 1H), 7.95 (d, J=2.0 Hz, 1H), 8.27 (s, 1H), 8.29 (d, J=2.0 Hz, 1H), 9.03 (s, 1H); MS: 462 (M+1).

Example-187

Ethyl-4-((6-(5-(1H-tetrazol-1-yl)-1H-indol-1-yl)pyridin-3-yl)oxy)-piperidine-1-carboxylate

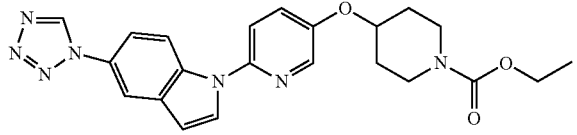 [SMILES: CCOC(=O)N1CCC(Oc2ccc(-n3ccc4cc(-n5cnnn5)ccc43)nc2)CC1]

The title compound was prepared by following the similar procedure as described in Example-70 by using Example-186 (0.018 g, 19%).

¹H NMR (400 MHz, CDCl₃) δ; 1.30 (t, J=7.2 Hz, 3H), 1.82-1.89 (m, 2H), 1.99-2.05 (m, 2H), 3.44-3.50 (m, 2H), 3.76-3.82 (m, 2H), 4.13 (q, J=7.2 Hz, 2H), 4.57-4.62 (m, 1H), 6.82 (dd, J=3.6, 0.4 Hz, 1H), 7.45 (dd, J=2.0, 0.8 Hz, 2H), 7.55 (dd, J=9.2, 2.4 Hz, 1H), 7.74 (d, J=3.2 Hz, 1H), 7.94 (d, J=1.6 Hz, 1H), 8.28 (s, 1H), 8.30 (d, J=2.0 Hz, 1H), 9.03 (s, 1H); MS: 434 (M+1).

Example-188

Ethyl(1-(5-((1-(5-ethylpyrimidin-2-yl)piperidin-4-yl)oxy)pyridin-2-yl)-1H-indol-5-yl)(methyl)carbamate

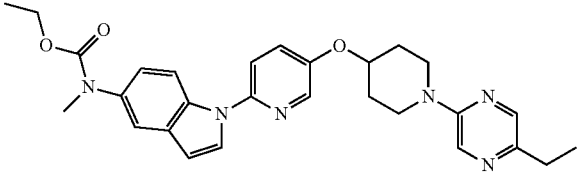 [SMILES: CCOC(=O)N(C)c1ccc2c(ccn2-c2ccc(OC3CCN(c4cnc(CC)cn4)CC3)cn2)c1]

To a stirred solution of Example-9 (0.10 g, 0.20 mmol) in anhydrous DMF (10 mL), NaH (0.012 g, 0.514 mmol) and methyl iodide (0.035 g, 0.0.246 mmol) were added at 0° C. and stirred at 60° C. for 4-5 h. The reaction was quenched with water. The organic layer was extracted with ethyl acetate. The organic layer was separated, concentrated in vacuo and the resultant crude was purified by flash column chromatography to give ethyl (1-(5-((1-(5-ethylpyrimidin-2-yl)piperidin-4-yl)oxy)pyridin-2-yl)-1H-indol-5-yl)(methyl)carbamate (0.020 g, 19%).

¹H NMR (400 MHz, CDCl₃) δ; 1.21 (t, J=7.6 Hz, 6H), 1.90-1.93 (m, 2H), 2.05-2.11 (m, 2H), 2.48 (q, J=7.6 Hz, 2H), 3.34 (s, 3H), 3.63-3.70 (m, 2H), 4.14-4.25 (m, 4H), 4.59-4.62 (m, 1H), 6.66 (d, J=3.6 Hz, 1H), 7.13 (d, J=8.0 Hz, 1H), 7.42 (d, J=1.6 Hz, 2H), 7.48 (bs, 1H), 7.64 (d, J=3.6 Hz, 1H), 8.01 (d, J=8.8 Hz, 1H), 8.20 (bs, 2H), 8.27 (d, J=2.0 Hz, 1H); MS: 501(M+1).

Example-189 tert-Butyl 4-((6-(5-(1H-1,2,4-triazol-1-yl)-1H-indol-1-yl)pyridin-3-yl) oxy)piperidine-1-carboxylate

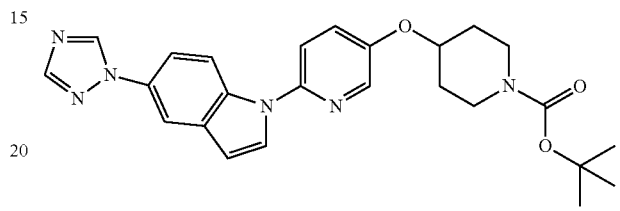

The title compound was prepared by following the similar procedure as described in Example-1 using tert-butyl 4-((6-chloropyridin-3-yl)oxy)piperidine-1-carboxylate (intermediate-6) and 5-(1H-1,2,4-triazol-1-yl)-1H-indole (intermediate 58) (0.440 g, 29%).

¹H NMR (400 MHz, CDCl₃) δ; 1.48 (s, 9H), 1.78-1.85 (m, 2H), 1.97-2.02 (m, 2H), 3.34-3.41 (m, 2H), 3.72-3.78 (m, 2H), 4.53-4.56 (m, 1H), 6.76 (d, J=3.6 Hz, 1H), 7.43 (d, J=1.6 Hz, 2H), 7.55 (dd, J=8.8, 2.0 Hz, 1H), 7.70 (d, J=3.2 Hz, 1H), 7.91 (d, J=2.0 Hz, 1H), 8.13 (s, 1H), 8.20 (d, J=9.2 Hz, 1H), 8.28 (t, J=1.6 Hz, 1H), 8.58 (s, 1H); MS: 461(M+1).

Example-190

1-(5-((1-(5-Ethylpyrimidin-2-yl)piperidin-4-yl)oxy)pyridin-2-yl)-5-(1H-1,2,4-triazol-1-yl)-1H-indole

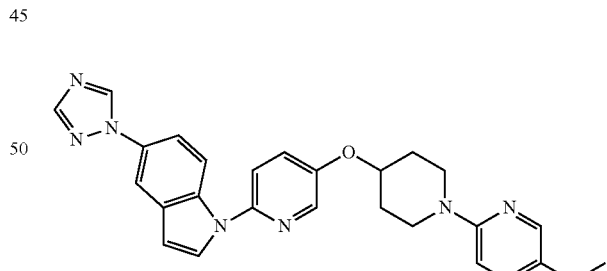

The title compound was prepared by following the similar procedure as described in Example-2 by using Example-189 (0.022 g, 14%).

¹H NMR (400 MHz, CDCl₃) δ; 1.22 (t, J=7.6 Hz, 3H), 1.86-1.94 (m, 2H), 2.09-2.14 (m, 2H), 2.51 (q, J=7.6 Hz, 2H), 3.67-3.73 (m, 2H), 4.21-4.27 (m, 2H), 4.63-4.68 (m, 1H), 6.78 (d, J=3.6 Hz, 1H), 7.41 (m, 2H), 7.57 (dd, J=8.8, 2.4 Hz, 1H), 7.72 (d, J=3.2 Hz, 1H), 7.93 (d, J=2.0 Hz, 1H), 8.14 (s, 1H), 8.22 (bs, 2H), 8.23 (s, 1H), 8.32 (d, J=2.0 Hz, 1H), 8.58 (bs, 1H); MS: 466 (M⁺).

Example-191

Isopropyl 4-((6-(5-(1H-1,2,4-triazol-1-yl)-1H-indol-1-yl)pyridin-3-yl)oxy)piperidine-1-carboxylate

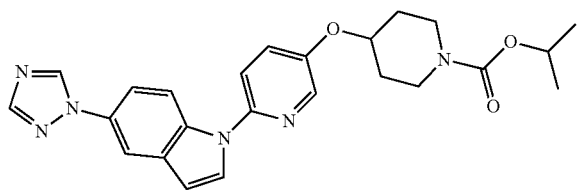 [SMILES: CC(C)OC(=O)N1CCC(Oc2ccc(-n3ccc4cc(-n5cncn5)ccc43)nc2)CC1]

The title compound was prepared by following the similar procedure as described in Example-70 by using Example-189 (0.051 g, 26%).

¹H NMR (400 MHz, CDCl₃) δ; 1.26 (d, J=6.4 Hz, 6H), 1.79-1.87 (m, 2H), 1.97-2.03 (m, 2H), 3.40-3.46 (m, 2H), 3.71-3.81 (m, 2H), 4.54-4.58 (m, 1H), 4.91-4.94 (m, 1H), 6.77 (d, J=3.2 Hz, 1H), 7.43 (d, J=1.6 Hz, 1H), 7.55 (dd, J=8.8, 2.0 Hz, 2H), 7.70 (d, J=3.2 Hz, 1H), 7.91 (d, J=2.4 Hz, 1H), 8.13 (s, 1H), 8.20 (d, J=8.8 Hz, 1H), 8.27 (t, J=3.6, 1.6 Hz, 1H), 8.56 (s, 1H); MS: 447 (M+1).

Example-192

Ethyl-4-((6-(5-(1H-1,2,4-triazol-1-yl)-1H-indol-1-yl)pyridin-3-yl)oxy) piperidine-1-carboxylate

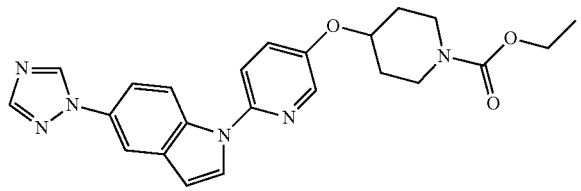 [SMILES: CCOC(=O)N1CCC(Oc2ccc(-n3ccc4cc(-n5cncn5)ccc43)nc2)CC1]

The title compound was prepared by following the similar procedure as described in Example-70 by using Example-189 (0.041 g, 22%).

¹H NMR (400 MHz, CDCl₃) δ; 1.30 (t, J=7.2 Hz, 3H), 1.84-1.90 (m, 2H), 1.99-2.05 (m, 2H), 3.44-3.52 (m, 2H), 3.77-3.83 (m, 2H), 4.18 (q, J=7.2 Hz, 2H), 4.56-4.58 (m, 1H), 6.78 (d, J=3.6 Hz, 1H), 7.44 (d, J=1.6 Hz, 2H), 7.56 (dd, J=9.2, 2.0 Hz, 1H), 7.72 (d, J=3.6 Hz, 1H), 7.93 (d, J=1.6 Hz, 1H), 8.14 (s, 1H), 8.22 (d, J=8.8 Hz, 1H), 8.29 (t, J=3.2 Hz, 1H), 8.66 (s, 1H); MS: 433(M+1).

Example-193

5-(Methylsulfonyl)-1-(5-((1-((1-(trifluoromethyl)cyclopropyl)methyl)-piperidin-4-yl)oxy)pyridin-2-yl)-1H-indole

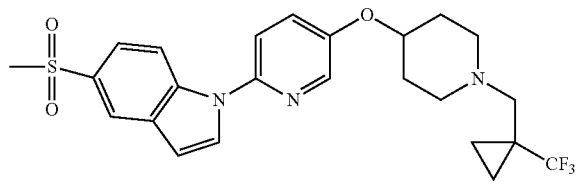 [SMILES: CS(=O)(=O)c1ccc2c(ccn2-c2ccc(OC3CCN(CC4(C(F)(F)F)CC4)CC3)cn2)c1]

The title compound was prepared by following the similar procedure as described in Example-30 by using Example-175.

¹H NMR (400 MHz, CDCl₃) δ; 0.67 (m, 2H), 1.01-1.04 (m, 2H), 1.85-1.93 (m, 2H), 2.03-2.08 (m, 2H), 2.37-2.41 (m, 2H), 2.59 (s, 2H), 2.79 (bs, 2H), 3.10 (s, 3H), 4.40-4.44 (m, 1H), 6.83-6.84 (m, 1H), 7.40-7.45 (m, 2H), 7.73 (d, J=3.6 Hz, 1H), 7.81 (dd, J=8.8, 2.0 Hz, 1H). 8.19 (d, J=8.8 Hz, 1H), 8.27-8.31 (m, 2H); MS: 494.2 (M+1).

Example-194

3-(1-(5-((1-(4-Ethylphenyl)piperidin-4-yl)oxy)pyridin-2-yl)-1H-indol-5-yl)oxazolidin-2-one

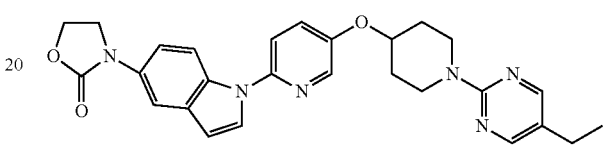

The title compound was prepared by following the similar procedure as described in Example-2 by using Example-165 (0.031 g, 20%).

¹H NMR (400 MHz, CDCl₃) δ; 1.19 (t, J=7.2 Hz, 3H), 1.85-1.88 (m, 2H), 2.05-2.09 (m, 2H), 2.47 (q, J=7.6 Hz, 2H), 3.64-3.69 (m, 2H), 4.14 (q, J=8.0 Hz, 2H), 4.18-4.24 (m, 2H), 4.50 (q, J=7.6 Hz, 2H), 4.60-4.66 (m, 1H), 6.66 (d, J=3.2 Hz, 1H), 7.41 (bs, 2H), 7.51 (dd, J=8.8, 2.0 Hz, 1H), 7.64 (d, J=3.6 Hz, 1H), 7.71 (d, J=2.4 Hz, 1H), 8.06 (d, J=9.2 Hz, 1H), 8.19 (bs, 2H), 8.26 (d, J=1.6 Hz, 1H); MS: 485 (M+1).

Example-195

5-(Methylsulfonyl)-1-(5-((1-(4-(trifluoromethyl)phenyl)piperidin-4-yl) oxy)pyridin-2-yl)-1H-indole

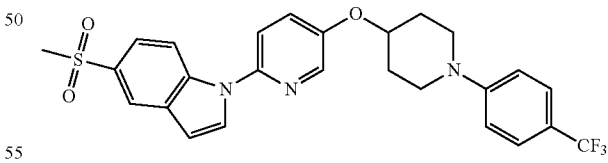

The title compound was prepared by following the similar procedure as described in Example-81 using Example-1 and 1-bromo-4-(trifluoromethyl)benzene (0.074 g, 0.424 mmol) (0.041 g, 23%).

¹H NMR (400 MHz, CDCl₃) δ; 2.00-2.03 (m, 2H), 2.12-2.19 (m, 2H), 3.08 (s, 3H), 3.24-3.30 (m, 2H), 3.59-3.65 (m, 2H), 4.58-4.61 (m, 1H), 6.82 (d, J=3.2 Hz, 1H), 6.96 (d, J=8.8 Hz, 2H), 7.40-7.50 (m, 4H), 7.72 (d, J=3.2 Hz, 1H), 7.80 (d, J=2.0 Hz, 1H), 8.19 (d, J=8.8 Hz, 1H), 8.29 (d, J=1.6 Hz, 2H); MS: 516 (M+1).

Example-196

1-(4-((6-(5-(Methylsulfonyl)-1H-indol-1-yl)pyridin-3-yl)oxy)-piperidin-1-yl)-2-(pyrrolidin-1-yl)ethanone

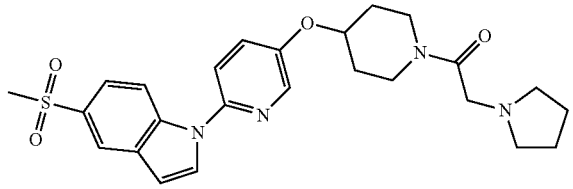 [SMILES: CS(=O)(=O)c1ccc2c(ccn2-c2ccc(OC3CCN(C(=O)CN4CCCC4)CC3)cn2)c1]

To a solution of 2-chloro-1-(4-((6-(5-(methylsulfonyl)-1H-indol-1-yl)pyridin-3-yl)oxy)piperidin-1-yl)ethanone (0.080 g, 0.179 mmol) in DMF (2 mL), potassium iodide (0.009 g, 0.054 mmol), pyrrolidine (0.044 mL, 0.536 mmol), potassium carbonate (0.025 g, 0.179 mmol) were added and stirred at 80° C. for 45 minutes. The reaction was quenched by adding water (20 mL), the mixture was extracted with ethyl acetate, organic layer was concentrated under reduced pressure. The resulting crude was purified by flash column chromatography to give 1-(4-((6-(5-(methylsulfonyl)-1H-indol-1-yl)pyridin-3-yl)oxy)piperidin-1-yl)-2-(pyrrolidin-1-yl)ethanon (0.045 g, 52.32%).

$^1$H NMR (400 MHz, CDCl$_3$) δ; 1.77-1.91 (m, 6H), 2.00-2.05 (m, 2H), 2.64 (s, 4H), 3.11 (s, 3H), 3.39 (s, 2H), 3.56-3.68 (m, 2H), 3.86-3.90 (m, 2H), 4.63-4.67 (m, 1H), 6.85 (d, J=3.2 Hz, 1H), 7.43-7.48 (m, 2H), 7.74 (d, J=3.2 Hz, 1H), 7.82 (dd, J=8.8, 1.6 Hz, 1H), 8.21 (d, J=8.8 Hz, 1H), 8.30-8.32 (m, 2H); MS: 483 (M+1).

Example-197

1-(4-((6-(5-(Methylsulfonyl)-1H-indol-1-yl)pyridin-3-yl)oxy)-piperidin-1-yl)-2-(piperidin-1-yl)ethanone

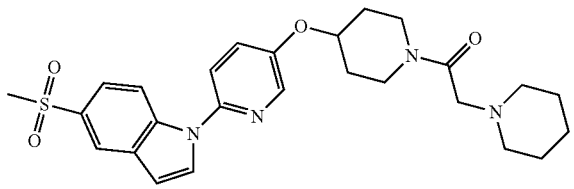 [SMILES: CS(=O)(=O)c1ccc2c(ccn2-c2ccc(OC3CCN(C(=O)CN4CCCCC4)CC3)cn2)c1]

The title compound was prepared by following the similar procedure as described in Example-196 using 2-chloro-1-(4-((6-(5-(methylsulfonyl)-1H-indol-1-yl)pyridin-3-yl)oxy)piperidin-1-yl)ethanone and piperidine (0.045 g, 50.56%).

$^1$H NMR (400 MHz, CDCl$_3$) δ; 1.46-1.47 (m, 2H), 1.58-1.64 (m, 4H), 1.85-2.07 (m, 4H), 2.47(bs, 4H), 3.11 (s, 3H), 3.20 (s, 2H), 3.60-3.67 (m, 2H), 3.85-3.93 (m, 2H), 4.64-4.67 (m, 1H), 6.85 (d, J=3.6 Hz, 1H), 7.43-7.48 (m, 2H), 7.74 (d, J=3.6 Hz, 1H), 7.82 (dd, J=8.8, 1.6 Hz, 1H), 8.21(d, J=8.8 Hz 1H), 8.31-8.32 (m, 2H); MS: 497(M+1).

Example-198

1-(4-((6-(5-(Methylsulfonyl)-1H-indol-1-yl)pyridin-3-yl)oxy)-piperidin-1-yl)-2-morpholinoethanone

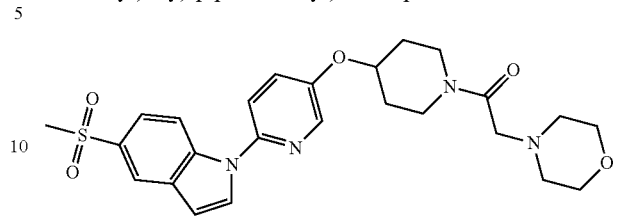

The title compound was prepared by following the similar procedure as described in Example-196 using 2-chloro-1-(4-((6-(5-(methylsulfonyl)-1H-indol-1-yl)pyridin-3-yl)oxy)piperidin-1-yl)ethanone and morpholine. (0.050 g, 56.18%).

$^1$H NMR (400 MHz, CDCl$_3$) δ; 1.87-2.07 (m, 4H), 2.56 (bs, 4H), 3.11 (s, 3H), 3.25 (s, 2H), 3.58-3.71 (m, 2H), 3.75-3.77 (m, 4H), 3.83-3.91 (m, 2H), 4.65-4.68 (m, 1H), 6.85 (d, J=3.2 Hz, 1H), 7.43-7.48 (m, 2H), 7.74 (d, J=3.2 Hz, 1H), 7.82 (dd, J=8.8, 2.0 Hz, 1H), 8.21 (d, J=8.8 Hz, 1H), 8.31-8.32 (m, 2H); MS: 499 (M+1).

Example-199

1-(4-((1-(5-Ethylpyrimidin-2-yl)piperidin-4-yl)oxy)phenyl)-5-(methylsulfonyl)-1H-indole

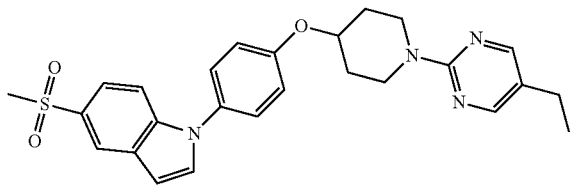 [SMILES: CCc1cnc(N2CCC(Oc3ccc(-n4ccc5cc(S(C)(=O)=O)ccc54)cc3)CC2)nc1]

The title compound was prepared by following the similar procedure as described in Example-2 by using Example-3 (0.049 g, 48%).

$^1$H NMR (400 MHz, CDCl$_3$) δ; 1.20 (t, J=7.6 Hz, 3H), 1.87-1.89 (m, 2H), 2.06-2.10 (m, 2H), 2.47 (q, J=7.6 Hz, 2H), 3.09 (s, 3H), 3.65-3.72 (m, 2H), 4.18-4.24 (m, 2H), 4.62-4.63 (m, 1H), 6.80 (dd, J=3.2, 0.8 Hz, 1H), 7.10 (dd, J=6.8, 2.4 Hz, 2H), 7.38 (dd, J=6.8, 2.4 Hz, 2H), 7.42 (d, J=3.2 Hz, 1H), 7.54 (d, J=8.8 Hz, 1H), 7.73(dd, J=8.8, 2.0 Hz, 1H), 8.20 (s, 2H), 8.32 (d, J=1.6 Hz, 1H); MS: 477 (M+1).

Example-200

1-(4-((1-(5-Ethylpyrimidin-2-yl)piperidin-4-yl)oxy)phenyl)-5-(methylsulfonyl)indoline

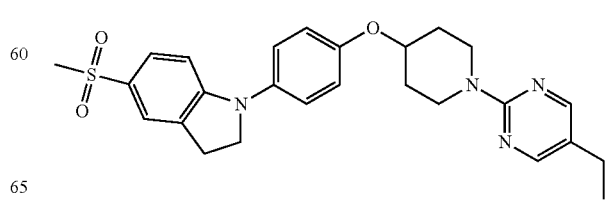

The title compound was prepared by following the similar procedure as described in Example-2 using tert-Butyl-4-(4-(5-(methylsulfonyl)indolin-1-yl)phenoxy)piperidine-1-carboxylate (intermediate 80) (0.035 g, 34%).

$^1$H NMR (400 MHz, CDCl$_3$) δ; 1.19 (t, J=7.6 Hz, 3H), 1.80-1.86 (m, 2H), 2.00-2.06 (m, 2H), 2.47 (q, J=7.6 Hz, 2H), 3.10 (s, 3H), 3.19 (t, J=8.4 Hz, 2H), 3.60-3.67 (m, 2H), 4.03 (t, J=8.4 Hz, 2H), 4.16-4.22 (m, 2H), 4.50-4.53 (m, 1H), 6.81 (d, J=7.6 Hz, 1H), 6.97 (dd, J=6.4, 2.0 Hz, 2H), 7.19 (dd, J=6.8, 2.4 Hz, 2H), 7.57 (s, 1H), 7.59 (d, J=7.2 Hz, 1H), 8.18 (s, 1H); MS: 479 (M+1).

Example-201 tert-Butyl 4-((2-(5-(methylsulfonyl)-1H-indol-1-yl) pyridin-4-yl)methoxy) piperidine-1-carboxylate

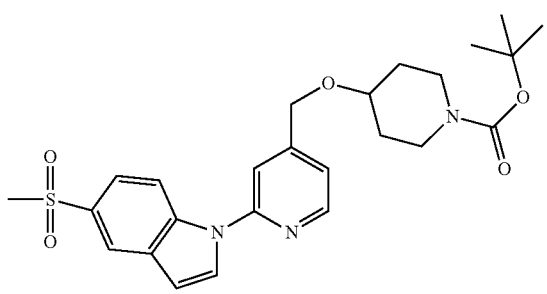 [SMILES: CC(C)(C)OC(=O)N1CCC(OCc2ccnc(-n3ccc4cc(S(C)(=O)=O)ccc43)c2)CC1]

The title compound was prepared by following the similar procedure as described in Example-1 by using 5-(methylsulfonyl)-1H-indole (intermediate 21) and tert-Butyl 4-((2-chloropyridin-4-yl)methoxy)piperidine-1-carboxylate (intermediate 44).

$^1$H NMR (400 MHz, CDCl$_3$) δ; 1.46 (s, 9H), 1.62-1.66 (m, 2H), 1.91 (m, 2H), 3.08 (s, 3H), 3.12-3.18 (m, 2H), 3.62-3.66 (m, 1H), 3.79-3.82 (m, 2H), 4.68 (s, 2H), 6.85-6.86 (m, 1H), 7.21 (d, J=5.2, 1H), 7.49 (s, 1H), 7.81-7.84 (m, 2H), 8.29 (d, J=1.6, 1H), 8.39 (d, J=9.2, 1H), 8.54-8.55 (m, 1H); MS: 484.3 (M+1).

Example-202

1-(4-(((1-(5-Ethylpyrimidin-2-yl)piperidin-4yl)oxy) methyl)pyridin-2-yl)-5-(methylsulfonyl)-1H-indole

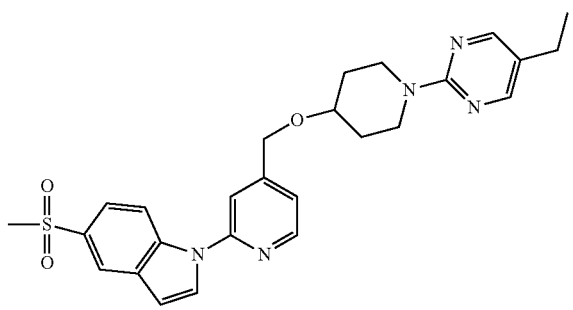 [SMILES: CCc1cnc(N2CCC(OCc3ccnc(-n4ccc5cc(S(C)(=O)=O)ccc54)c3)CC2)nc1]

The title compound was prepared by following the similar procedure as described in Example-2 by using Example-201.

$^1$H NMR (400 MHz, CDCl$_3$) δ; 1.20 (t, J=7.6 Hz, 3H), 1.66-1.74 (m, 2H), 1.99-2.04 (m, 2H), 2.46 (q, J=7.6 Hz, 2H), 3.08 (s, 3H), 3.37-3.43 (m, 2H), 3.71-3.76 (m, 1H), 4.29-4.39 (m, 2H), 4.71 (s, 2H), 6.84 (d, J=3.2 Hz, 1H), 7.22 (d, J=5.6 Hz, 1H), 7.51 (s, 1H), 7.80-7.82 (m, 2H), 8.17 (s, 2H), 8.28 (d, J=1.6 Hz, 1H), 8.39 (d, J=8.8 Hz, 1H), 8.54 (d, J=4.8 Hz, 1H); MS: 492.2 (M+1).

Example-203

5-(Methylsulfonyl)-1-(5-((1-(2,2,2-trifluoroethyl) piperidin-4-yl)oxy)pyridin-2-yl)-1H-indole

To a stirred solution of example 172 (0.10 g, 0.214 mmol) in dry THF (10 mL) borane methyl sulfide complex (0.041 mL, 0.428 mmol) was added at 0° C. and heated at 65° C. for 3 h. Reaction was quenched with 10% HCl at 0° C. and extracted with ethyl acetate. Organic layer was concentrated in vacuo and residue was purified by flash column chromatography to give 5-(methyl sulfonyl)-1-(5-((1-(2,2,2-trifluoroethyl)piperidin-4-yl)oxy)pyridin-2-yl)-1H-indole (0.014 g, 14%)

$^1$H NMR (400 MHz, CDCl$_3$) δ; 1.95 (bs, 2H), 2.08 (bs, 2H), 2.67-2.69 (m, 2H), 2.97-3.11 (m, 7H), 4.46 (bs, 1H), 6.84 (d, J=2.4 Hz, 1H), 7.43 (bs, 2H), 7.74 (d, J=1.2 Hz, 1H), 7.81 (d, J=8.4 Hz, 1H), 8.20 (d, J=8.4 Hz, 1H), 8.30 (d, J=9.6 Hz, 2H) MS: 453.48 (M$^+$).

Example-204

2-(4-((6-(5-(Methylsulfonyl)-1H-indol-1-yl)pyridin-3yl)oxy)piperidin-1-yl)-1-(pyrrolidin-1-yl)ethanone

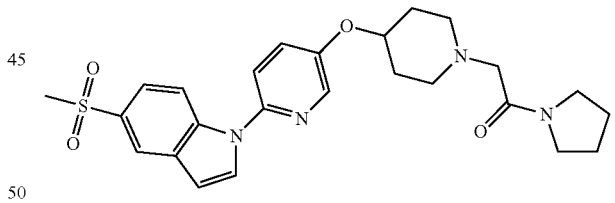

To a stirred solution of 2-chloro-1-(pyrrolidin-1-yl)ethanone (Intermediate 71) (0.055 g, 0.366 mmol) in DMF (2 mL), potassium iodide (0.023 g, 0.137 mmol), 5-(methylsulfonyl)-1-(5-(piperidin-4-yloxy)pyridin-2-yl)-1H-indole (0.170 g, 0.458 mmol) and potassium carbonate (0.064 g, 0.458 mmol) were added. The resulting mixture was heated at 80° C. for 45 minutes. Reaction was quenched with water and extracted with ethyl acetate. The organic extract was concentrated in vacuo and resultant residue was purified by column chromatography to yield title compound (0.075 g, 33.3%).

$^1$H NMR (400 MHz, CDCl$_3$) δ; 1.85-1.91 (m, 6H), 1.95-2.11 (m, 2H), 2.55 (bs, 2H), 2.89 (bs, 2H), 3.00 (s, 3H), 3.10 (s, 2H), 3.51(t, J=6.4 Hz, 4H), 4.44 (bs, 1H), 6.83 (d, J=2.4 Hz, 1H), 7.42 (bs, 2H), 7.73 (d, J=3.2 Hz, 1H), 7.81 (d, J=8.0 Hz, 1H), 8.19 (d, J=8.8 Hz, 1H), 8.30 (d, J=9.6 Hz, 2H); MS: 482.98 (M$^+$).

Example-205

2-Cyclopentyl-1-(4-((6-(5-(methylsulfonyl)-1H-indol-1-yl)pyridin-3-yl)oxy)piperidin-1-yl)ethanone

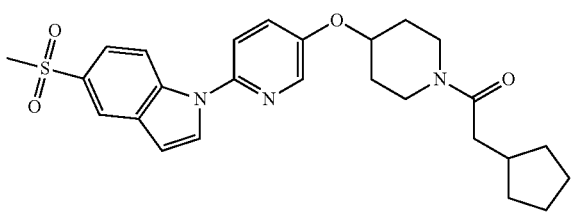 [SMILES: CS(=O)(=O)c1ccc2c(ccn2-c2ccc(OC3CCN(C(=O)CC4CCCC4)CC3)cn2)c1]

The title compound was prepared by following the similar procedure as described in Example-127 by using Example-1 and 2-cyclopentylacetic acid.

$^1$H NMR (400 MHz, CDCl$_3$) δ; 1.20-1.28 (m, 4H), 1.58-1.66 (m, 4H), 1.88-1.89 (m, 2H), 2.02-2.04 (m, 2H), 2.23-2.31 (m, 1H), 2.40-2.42 (m, 2H), 3.11 (s, 3H), 3.48-3.50 (m, 1H), 3.67-3.68 (m, 1H), 3.78-3.80 (m, 1H), 3.85-3.87 (m, 1H), 4.65 (m, 1H), 6.85 (d, J=2.8 Hz, 1H), 7.45 (s, 2H), 7.74 (d, J=3.2 Hz, 1H), 7.81-7.83 (m, 1H), 8.21 (d, J=8.8 Hz, 1H), 8.31 (d, J=2.4 Hz, 2H); MS: 481.9 (M$^+$).

Example-206 tert-Butyl-4-((4-(5-(methylsulfonyl)-1H-indol-1-yl)thiazol-2-yl)oxy)-piperidine-1-carboxylate

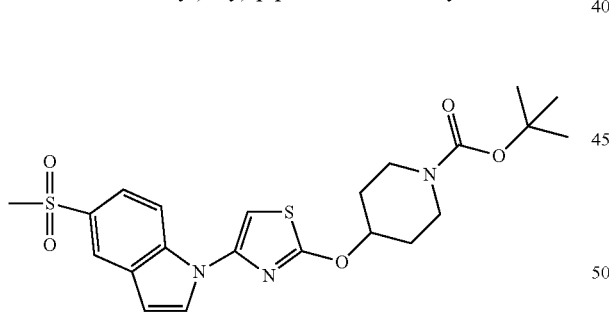

The title compound was prepared by following the similar procedure as described in Example-1 by using 5-(methylsulfonyl)-1H-indole (intermediate 21) and tert-butyl 4-((4-bromothiazol-2-yl)oxy)piperidine-1-carboxylate (intermediate 46) (0.007 g, 5%).

$^1$H NMR (400 MHz, CDCl$_3$) δ; 1.47 (s, 9H), 1.87-1.91 (m, 2H), 2.04-2.09(m, 2H), 3.08 (s, 3H), 3.35-3.42 (m, 2H), 3.70-3.74 (m, 2H), 5.21-5.23 (m, 1H), 6.49 (s, 1H), 6.77 (d, J=3.2 Hz, 1H), 7.64 (d, J=3.6 Hz, 1H), 7.80 (dd, J=8.8, 1.8 Hz, 1H), 7.98 (d, J=8.8 Hz, 1H), 8.27 (d, J=1.6 Hz, 1H); MS: 477 (M+1).

Example-207 tert-Butyl-4-(((4-(5-(methylsulfonyl)-1H-indol-1-yl)thiazol-2-yl)oxy) methyl)piperidine-1-carboxylate

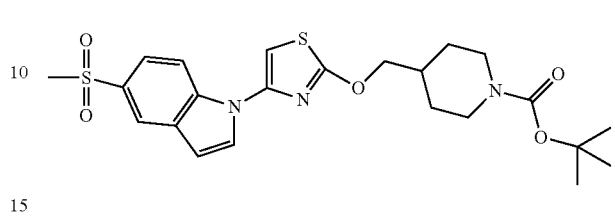

The title compound was prepared by following the similar procedure as described in Example-1 by using 5-(methylsulfonyl)-1H-indole (intermediate-21) and tert-Butyl 4-(((4-bromothiazol-2-yl)oxy)methyl)piperidine-1-carboxylate (intermediate 47) (0.013 g, 10%).

$^1$H NMR (400 MHz, CDCl$_3$) δ; 1.29-1.33 (m, 2H), 1.47 (s, 9H), 1.81-1.83 (m, 2H), 2.02-2.05 (m, 1H), 2.75 (bs, 2H), 3.10 (s, 3H), 4.18 (bs, 2H), 4.36 (d, J=6.4 Hz, 2H), 6.51 (s, 1H), 6.77 (d, J=3.2 Hz, 1H), 7.65 (d, J=3.2 Hz, 1H), 7.79-7.82 (m, 1H), 8.02 (d, J=8.8 Hz, 1H), 8.28 (bs, 1H); MS: 491.6 (M+1).

Example-208

2-((1-(5-Ethylpyrimidin-2-yl)piperidin-4-yl)oxy)-4-(5-(methyl-sulfonyl)-1H-indol-1-yl)thiazole

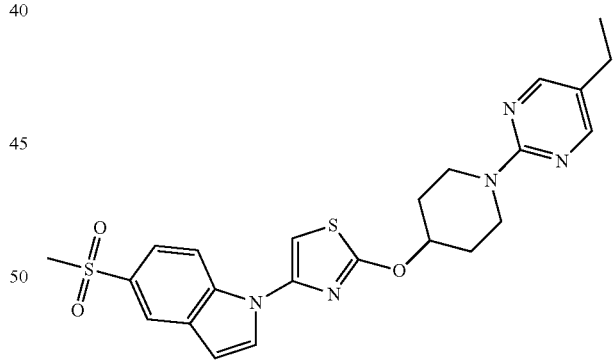

The title compound was prepared by following the similar procedure as described in Example-2 by using Example-206 (0.015 g, 29%).

$^1$H NMR (400 MHz, CDCl$_3$) δ; 1.90 (d, J=7.6 Hz, 3H), 1.92-1.98 (m, 2H), 2.13-2.18 (m, 2H), 2.47 (q, J=7.6 Hz, 2H), 3.08 (s, 3H), 3.67-3.73 (m, 2H), 4.15-4.21 (m, 2H), 5.28-5.32 (m, 1H), 6.50 (s, 1H), 6.77 (d, J=3.6 Hz, 1H), 7.65 (d, J=3.6 Hz, 1H), 7.78-7.81 (m, 1H), 8.0 (d, J=8.8 Hz, 1H), 8.18 (bs, 2H), 8.28 (s, 1H); MS: 484 (M+1).

Example-209

4-(5-(1H-Tetrazol-1-yl)-1H-indol-1-yl)-2-((1-(5-ethylpyrimidin-2-yl) piperidin-4-yl)oxy)thiazole

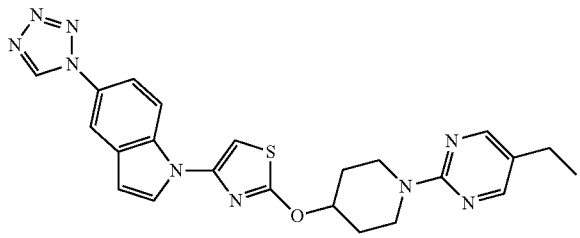 [SMILES: CCc1cnc(N2CCC(Oc3nc(-n4ccc5cc(-n6cnnn6)ccc54)cs3)CC2)nc1]

To a stirred solution of 1-(2-((1-(5-ethylpyrimidin-2-yl) piperidin-4-yl)oxy)thiazol-4-yl)-1H-indol-5-amine (0.090 g, 0.214 mmol) in acetic acid (3 mL), triethylorthoformate (0.047 g, 0.324 mmol) and NaN$_3$ (0.020 g. 324 mmol) were added and stirred at 100° C. for 1 h. The reaction was quenched with water and the mixture was extracted with ethyl acetate. The organic layer was concentrated in vacuo and the residue was purified by flash column chromatography to give 4-(5-(1H-tetrazol-1-yl)-1H-indol-1-yl)-2-((4-(5-ethylpyrazin-2-yl)cyclohexyl)oxy)thiazole (0.012 g, 11%)

$^1$H NMR (400 MHz, CDCl$_3$) δ; 1.20 (t, J=7.6 Hz, 3H), 1.94-2.01 (m, 2H), 2.16-2.21 (m, 2H), 2.48 (q, J=7.6 Hz, 2H), 3.69-3.76 (m, 2H), 4.22-4.16 (m, 2H), 5.32-5.35 (m, 1H), 6.50 (s, 1H), 6.76 (m, 1H), 7.54 (dd, J=8.8, 2.0 Hz, 1H), 7.68 (d, J=3.6 Hz, 1H), 7.94 (d, J=2.0 Hz, 1H), 8.06 (d, J=3.6 Hz, 1H), 8.20 (s, 2H), 9.01 (s, 1H); MS: 474.1 (M+1).

Example-210 tert-Butyl-4-((4-(5-(1H-tetrazol-1-yl)-1H-indol-1-yl) thiazol-2-yl)oxy) piperidine-1-carboxylate

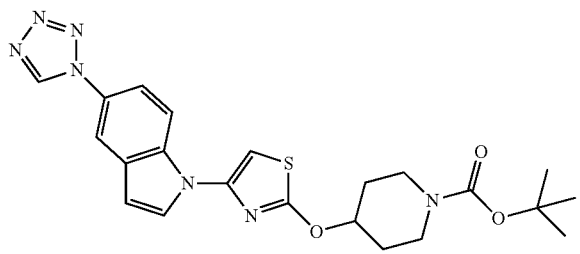 [SMILES: CC(C)(C)OC(=O)N1CCC(Oc2nc(-n3ccc4cc(-n5cnnn5)ccc43)cs2)CC1]

The title compound was prepared by following the similar procedure as described in Example-209 using tert-butyl 4-((4-(5-amino-1H-indol-1-yl)thiazol-2-yl)oxy)-piperidine-1-carboxylate (intermediate-35).

$^1$H NMR (400 MHz, CDCl$_3$) δ; 1.47 (s, 9H), 1.90-1.95 (m, 2H), 2.07-2.12 (m, 2H), 3.39-3.46 (m, 2H), 3.71-3.77 (m, 2H), 5.24-5.28 (m, 1H), 6.51 (s, 1H), 6.76-6.77 (m, 1H), 7.56 (dd, J=8.8, 2.0 Hz, 1H), 7.67 (d, J=3.6 Hz, 1H), 7.94 (d, J=2 Hz, 1H), 8.04 (d, J=8.8 Hz, 1H), 9.01 (s, 1H); MS: 468.1 (M+1).

Example-211 tert-Butyl-4-((4-(5-((ethoxycarbonyl)amino)-1H-indol-1-yl)thiazol-2-yl) oxy)piperidine-1-carboxylate

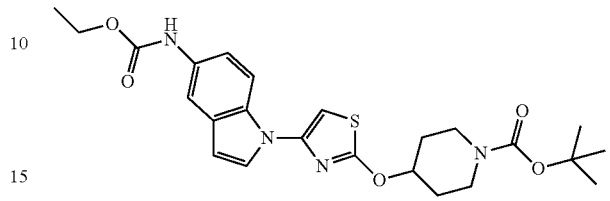

To a stirred solution of tert-butyl 4-((4-(5-amino-1H-indol-1-yl)thiazol-2-yl)oxy)piperidine-1-carboxylate (intermediate-35) (0.100 g, 0.214 mmol) in dichloromethane (4 mL), triethylamine (0.036 g, 0.362 mmol), and chloroethylformate (0.026 g, 0.214 mmol) were added at 0° C. and stirred at room temperature for 10 minutes. The reaction was quenched with water and the mixture was extracted with dichloromethane. The organic layer was concentrated in vacuo and the residue was purified by flash column chromatography to give tert-butyl 4-((4-(5-((ethoxycarbonyl)amino)-1H-indol-1-yl)thiazol-2-yl)oxy)piperidine-1-carboxylate (0.010 g, 8.5%)

$^1$H NMR (400 MHz, CDCl$_3$) δ; 1.32 (t, J=6.8 Hz, 3H), 1.47 (s, 9H), 1.86-1.90 (m, 2H), 2.03-2.09 (m, 2H), 3.34-3.41 (m, 2H), 3.69-3.74 (m, 2H), 4.23 (q, J=7.2 Hz, 2H), 5.21-5.23 (m, 1H), 6.36 (s, 1H), 6.56 (d, J=3.2 Hz, 2H), 7.19 (d, J=9.2 Hz, 1H), 7.52 (d, J=3.6 Hz, 1H), 7.70 (bs, 1H), 7.76 (d, J=8.8 Hz, 1H); MS: 487.1 (M+1).

Example-212 tert-Butyl-4-((4-(5-((isopropoxycarbonyl)amino)-1H-indol-1-yl)thiazol-2-yl)oxy)piperidine-1-carboxylate

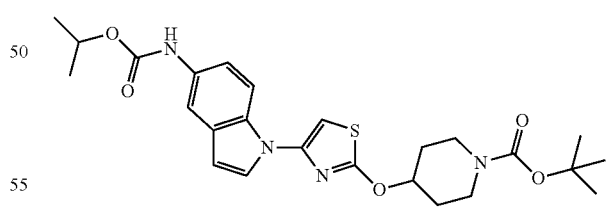

The title compound was prepared by following the similar procedure as described in Example-211 using tert-butyl 4-((4-(5-amino-1H-indol-1-yl)thiazol-2-yl)oxy)-piperidine-1-carboxylate (intermediate-35).

$^1$H NMR (400 MHz, CDCl$_3$) δ; 1.33 (d, J=6.4 Hz, 6H), 1.49 (s, 9H), 1.89-1.92 (m, 2H), 2.06-2.11 (m, 2H), 3.36-3.43 (m, 2H), 3.72-3.76 (m, 2H), 5.02-5.08 (m, 1H), 5.22-5.26 (m, 1H), 6.38 (s, 1H), 6.57 (m, 2H), 7.21 (d, J=8.8 Hz, 1H), 7.54 (d, J=3.2 Hz, 1H), 7.77 (m, 2H); MS: 400.1 (M−100).

Example-213

Ethyl(1-(2-((1-(5-ethylpyrimidin-2-yl)piperidin-4-yl)oxy)thiazol-4-yl)-1H-indol-5-yl)carbamate

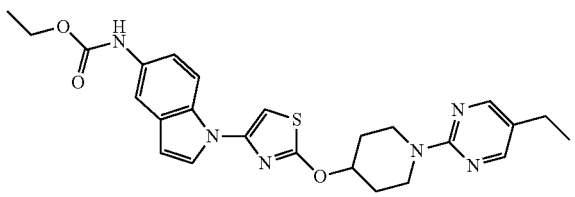 [SMILES: CCOC(=O)Nc1ccc2c(ccn2-c2csc(OC3CCN(c4ncc(CC)cn4)CC3)n2)c1]

The title compound was prepared by following the similar procedure as described in Example-211 using 1-(2-((1-(5-ethylpyrazin-2-yl)piperidin-4-yl)oxy)thiazol-4-yl)-1H-indol-5-amine (intermediate-34) (0.010 g, 22%).

$^1$H NMR (400 MHz, CDCl$_3$) δ; 1.19 (t, J=7.6 Hz, 3H), 1.32 (t, J=7.2 Hz, 3H), 1.92-1.97 (m, 2H), 2.13-2.17 (m, 2H), 2.47 (q, J=7.2 Hz, 2H), 3.70-3.72 (m, 2H), 4.16-4.26 (m, 4H), 5.29-5.32 (m, 2H), 6.37 (s, 1H), 6.57 (d, J=3.2 Hz, 2H), 7.18 (d, J=9.6 Hz, 1H), 7.51-7.55 (m, 1H), 7.72 (s, 1H), 7.79 (d, J=8.8 Hz, 1H), 8.20 (s, 1H); MS: 493.1 (M+1).

Example-214

Isopropyl(1-(2-((1-(5-ethylpyrimidin-2-yl)piperidin-4-yl)oxy)thiazol-4-yl)-1H-indol-5-yl)carbamate

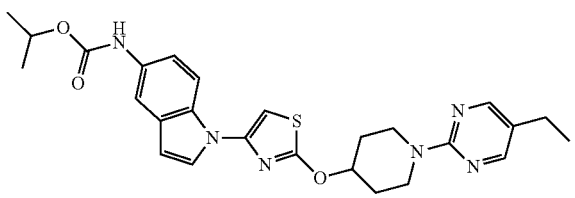 [SMILES: CCc1cnc(N2CCC(Oc3nc(-n4ccc5cc(NC(=O)OC(C)C)ccc54)cs3)CC2)nc1]

The title compound was prepared by following the similar procedure as described in Example-212 using 1-(2-((1-(5-ethylpyrazin-2-yl)piperidin-4-yl)oxy)thiazol-4-yl)-1H-indol-5-amine (intermediate 34).

$^1$H NMR (400 MHz, CDCl$_3$) δ; 1.20 (t, J=7.6 Hz, 3H), 1.32 (d, J=2.8 Hz, 6H), 1.93-1.98 (m, 2H), 2.14-2.19 (m, 2H), 2.48 (q, J=7.6 Hz, 2H), 3.68-3.73 (m, 2H), 4.15-4.21 (m, 2H), 5.02-5.05 (m, 2H), 5.31-5.32 (m, 1H), 6.37 (s, 1H), 6.57 (d, J=3.6 Hz, 2H), 7.13-7.21 (m, 1H), 7.52-7.55 (m, 1H), 7.69-7.73 (m, 1H), 7.79 (d, J=8.8 Hz, 1H), 8.04 (s, 1H); MS: 507.1 (M+1).

Example-215

5-(4-((4-(5-(1H-Tetrazol-1-yl)-1H-indol-1-yl)thiazol-2-yl)oxy)-piperidin-1-yl)-3-isopropyl-1,2,4-oxadiazole

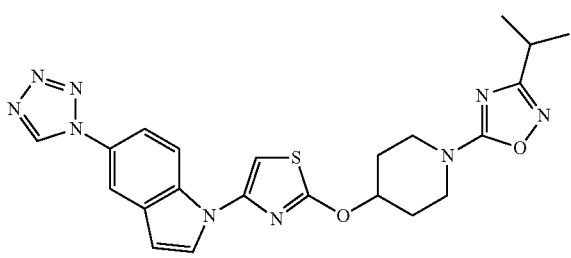 [SMILES: CC(C)c1noc(N2CCC(Oc3nc(-n4ccc5cc(-n6cnnn6)ccc54)cs3)CC2)n1]

The title compound was prepared by following the similar procedure as described in Example-209 using 1-(2-((1-(3-isopropyl-1,2,4-oxadiazol-5-yl)piperidin-4-yl)oxy)thiazol-4-yl)-1H-indol-5-amine (intermediate 70).

$^1$H NMR (400 MHz, CDCl$_3$) δ; 1.30 (d, J=7.2 Hz, 6H), 2.09-2.23 (m, 4H), 2.88-2.95 (m, 1H), 3.68-3.74 (m, 2H), 3.83-3.89 (m, 2H). 5.35-3.39 (m, 1H), 6.54 (s, 1H), 6.77 (d, J=3.2 Hz, 1H), 7.57 (dd, J=8.8 Hz, J=2.4 Hz, 1H), 7.67 (d, J=3.2 Hz, 1H), 7.95 (d, J=2.0 Hz, 1H), 8.03 (d, J=8.8 Hz, 1H). 9.02 (s, 1H); MS: 478.1 (M+1).

Example-216 tert-Butyl 4-((4-(7-fluoro-5-(methylsulfonyl)-1H-indol-1-yl)thiazol-2-yl) oxy)piperidine-1-carboxylate

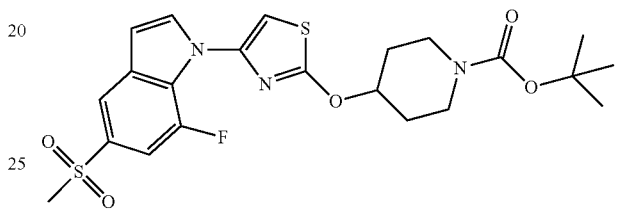

The title compound was prepared by following the similar procedure as described in Example-1 using 7-Fluoro-5-(methylsulfonyl)-1H-indole (intermediate 22) and tert-butyl 4-((4-bromothiazol-2-yl)oxy)piperidine-1-carboxylate (intermediate 46).

$^1$H NMR (400 MHz, CDCl$_3$) δ; 1.46 (s, 9H), 1.82-1.87 (m, 2H), 2.00-2.06 (m, 2H), 3.09 (s, 3H), 3.30-3.37 (m, 2H), 3.70-3.73 (m, 2H), 5.14-5.19 (m, 1H), 6.61 (d, J=2.8 Hz, 1H), 6.78-6.80 (m, 1H), 7.47-7.51 (m, 1H), 7.55 (d, J=3.2 Hz, 1H), 8.07 (d, J=1.6 Hz, 1H); MS: 518.1 (M+23).

Example-217 tert-Butyl-4-((4-(5-(methylsulfonyl)indolin-1-yl)thiazol-2-yl)oxy)-piperidine-1-carboxylate

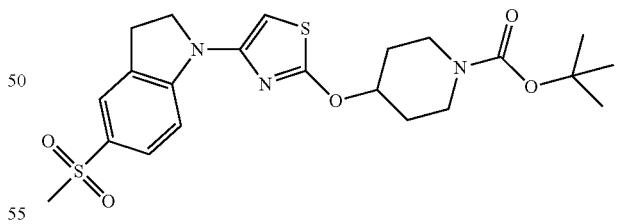

The title compound was prepared by following the similar procedure as described in Example-1 using 5-(methylsulfonyl)indoline (intermediate 26) and tert-Butyl 4-((4-bromothiazol-2-yl)oxy)piperidine-1-carboxylate (intermediate 46).

$^1$H NMR (400 MHz, CDCl$_3$) δ; 1.47 (s, 9H), 1.88-1.92 (m, 2H), 2.04-2.10 (m, 2H), 3.03 (s, 3H), 3.25 (t, J=8.8 Hz, 2H), 3.39-3.45 (m, 2H), 3.69-3.75 (m, 2H), 4.00 (t, J=8.8 Hz, 2H), 5.15.518 (m, 1H), 5.58 (s, 1H), 7.63 (s, 1H), 7.70-7.74 (m, 2H); MS: 480.0 (M+1).

Example-218

2-((1-(5-Ethylpyrimidin-2-yl)piperidin-4-yl)oxy)-4-(5-(methylsulfonyl) indolin-1-yl)thiazole

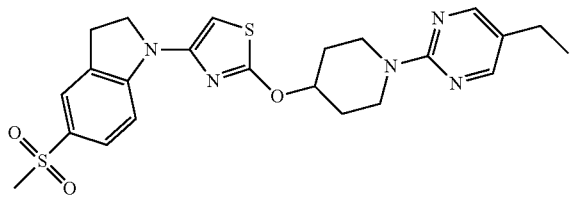 [SMILES: CCc1cnc(N2CCC(Oc3nc(N4CCc5cc(S(C)(=O)=O)ccc54)cs3)CC2)nc1]

The title compound was prepared by following the similar procedure as described in Example-2 by using Example-217.
$^1$H NMR (400 MHz, CDCl$_3$) δ; 1.21 (t, J=7.6 Hz, 3H), 1.95-1.98 (m, 2H), 2.12-2.18 (m, 2H), 2.48 (q, J=7.6 Hz, 2H), 3.03 (s, 3H), 3.24 (t, J=8.8 Hz, 2H), 3.74 (m, 2H), 4.00 (t, J=8.4 Hz, 2H), 4.09-4.19 (m, 2H), 5.22-5.25 (m, 1H), 5.28 (s, 1H), 7.62 (bs, 1H), 7.65-8.20 (m, 2H), 8.70 (s, 2H); MS: 486.0 (M+1).

Example-219

Isopropyl 4-((4-(5-(methylsulfonyl)indolin-1-yl)thiazol-2-yl)oxy)piperidine-1-carboxylate

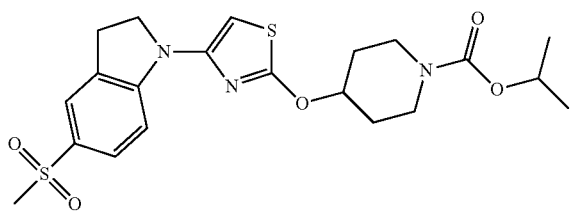 [SMILES: CC(C)OC(=O)N1CCC(Oc2nc(N3CCc4cc(S(C)(=O)=O)ccc43)cs2)CC1]

The title compound was prepared by following the similar procedure as described in Example-70 by using Example-217.
$^1$H NMR (400 MHz, CDCl$_3$) δ; 1.26 (d, J=6.4 Hz, 6H), 1.89-1.93 (m, 2H), 2.03-2.09 (m, 2H), 3.02 (s, 3H), 3.23 (t, J=8.8 Hz, 2H), 3.43-3.48 (m, 2H), 3.70-3.75 (m, 2H), 3.99 (t, J=8.8 Hz, 2H), 4.90-4.97 (m, 1H), 5.15-5.19 (m, 1H), 5.58 (s, 1H), 7.61 (s, 1H), 7.61-7.72 (m, 2H); MS: 466.0 (M+1).

Example-220 tert-Butyl-4-((4-(5-(1H-1,2,4-triazol-1-yl)-1H-indol-1-yl)thiazol-2-yl) oxy)piperidine-1-carboxylate

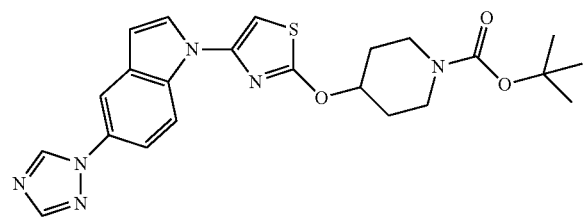 [SMILES: CC(C)(C)OC(=O)N1CCC(Oc2nc(-n3ccc4cc(-n5cncn5)ccc43)cs2)CC1]

The title compound was prepared by following the similar procedure as described in Example-1 using tert-Butyl 4-((4-bromothiazol-2-yl)oxy)piperidine-1-carboxylate (intermediate 46) and 5-(1H-1,2,4-triazol-1-yl)-1H-indole (intermediate 58).

$^1$H NMR (400 MHz, CDCl$_3$) δ; 1.48 (s, 9H), 1.89-1.93 (m, 2H), 2.06-2.11 (m, 2H), 3.37-3.43 (m, 2H), 3.70-3.76 (m, 2H), 5.25-5.30 (m, 1H), 6.47 (s, 1H), 6.71 (d, J=3.2 Hz, 1H), 7.56 (dd, J=8.8, 2.0 Hz, 1H), 7.63 (d, J=3.6 Hz, 1H), 7.90 (d, J=2.0 Hz, 1H), 7.97 (d, J=8.8 Hz, 1H), 8.13 (s, 1H), 8.56 (s, 1H); MS: 367.0 (M−100).

Example-221

Cyclobutyl(4-((6-(5-(methylsulfonyl)-1H-indol-1-yl)pyridin-3-yl)oxy)piperidin-1-yl)methanone

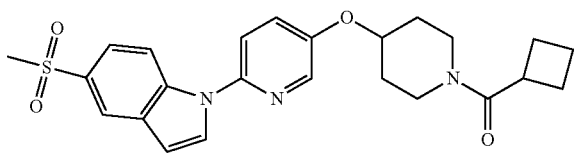 [SMILES: CS(=O)(=O)c1ccc2c(ccn2-c2ccc(OC3CCN(C(=O)C4CCC4)CC3)cn2)c1]

The title compound was prepared by following the similar procedure as described in Example-127 by using Example-1 and cyclobutanecarboxylic acid (0.035 g, 18%); MS: 453.98 (M$^+$).

Example-222

Cyclopentyl(4-((6-(5-(methylsulfonyl)-1H-indol-1-yl)pyridin-3-yl)oxy)piperidin-1-yl)methanone

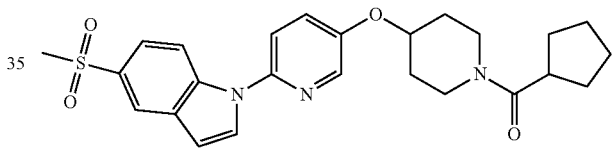

The title compound was prepared by following the similar procedure as described in Example-127 by using Example-1 and cyclopentanecarboxylic acid (0.020 g, 10%)); MS: 468.1 (M+1).

Example-223

Cyclohexyl(4-((6-(5-(methylsulfonyl)-1H-indol-1-yl)pyridin-3-yl)oxy)piperidin-1-yl)methanone

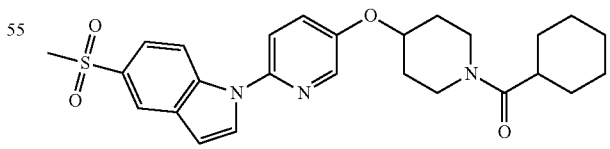

The title compound was prepared by following the similar procedure as described in Example-127 by using Example-1 and cyclohexanecarboxylic acid (0.068 g, 33%)); MS: 481.9 (M$^+$).

Following examples given Table-1 may be prepared by following one or more procedure as described herein above

TABLE-1

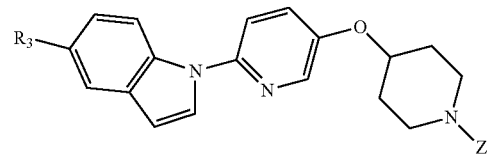

(VI)

| Example | R₃ | Z | Example | R₃ | Z |
|---|---|---|---|---|---|
| 224 | H₃CO₂S— | cyclobutylmethyl | 329 | N,N-dimethyl carbamoyl-C(CH₃)₂— | isobutyl |
| 225 | H₃CO₂S— | —CH₂C(O)CF₃ | 330 | azetidin-1-yl-C(O)-C(CH₃)₂— | cyclobutylmethyl |
| 226 | H₃CO₂S— | —CH₂CH(CH₂F)₂ | 331 | azetidin-1-yl-C(O)-C(CH₃)₂— | —C(CH₃)(F)CH₂F |
| 227 | H₃CO₂S— | (1-fluorocyclopentyl)methyl | 332 | azetidin-1-yl-C(O)-C(CH₃)₂— | (1-fluorocyclopentyl)methyl |
| 228 | H₃CO₂S— | (1-fluorocyclobutyl)methyl | 333 | azetidin-1-yl-C(O)-C(CH₃)₂— | (1-fluorocyclobutyl)methyl |
| 229 | H₃CO₂S— | —CH₂C(CH₃)₂F | 334 | azetidin-1-yl-C(O)-C(CH₃)₂— | —CH₂C(CH₃)₂F |
| 230 | H₃CO₂S— | (5-fluoropyrimidin-2-yl)methyl | 335 | azetidin-1-yl-C(O)-C(CH₃)₂— | (5-fluoropyridin-2-yl)methyl |
| 231 | H₃CO₂S— | 1-(5-fluoropyrimidin-2-yl)-1-methylethyl | 336 | azetidin-1-yl-C(O)-C(CH₃)₂— | 1-(furan-2-yl)-2-oxopropyl |
| 232 | H₃CO₂S— | 1-(furan-2-yl)-2-oxopropyl | 337 | azetidin-1-yl-C(O)-C(CH₃)₂— | 1,3-difluoropropan-2-yl 2-methylpropanoate |

TABLE-1-continued
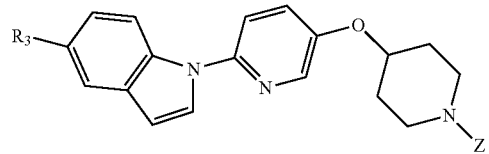
(VI)
| Example | R₃ | Z | Example | R₃ | Z |
|---|---|---|---|---|---|
| 233 | H₃CO₂S— | | 338 | | |
| 234 | H₃CO₂S— | | 339 | | |
| 235 | H₃CO₂S— | | 340 | | |
| 236 | H₃CO₂S— | | 341 | | |
| 237 | H₃CO₂S— | | 342 | | |
| 238 | H₃CO₂S— | | 343 | | |
| 239 | H₃CO₂S— | | 344 | | |
| 240 | H₃CO₂S— | | 345 | | |
| 241 | H₃CO₂S— | | 346 | | |

TABLE-1-continued

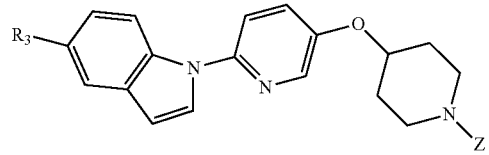

(VI)

| Example | R₃ | Z | Example | R₃ | Z |
|---|---|---|---|---|---|
| 242 | H₃CO₂S— | cyclopropyl | 347 | azetidinyl-C(O)-C(CH₃)₂- | cyclopropyl |
| 423 | H₃CO₂S— | cyclobutyl | 348 | azetidinyl-C(O)-C(CH₃)₂- | cyclobutyl |
| 244 | H₃CO₂S— | cyclopentyl | 349 | azetidinyl-C(O)-C(CH₃)₂- | cyclopentyl |
| 245 | H₃CO₂S— | cyclohexyl | 350 | azetidinyl-C(O)-C(CH₃)₂- | cyclohexyl |
| 246 | H₃CO₂S— | -CH₂-cyclohexyl | 351 | azetidinyl-C(O)-C(CH₃)₂- | -CH₂-cyclohexyl |
| 247 | H₃CO₂S— | -CH₂CH₂OCH₃ | 352 | azetidinyl-C(O)-C(CH₃)₂- | -CH₂CH₂OCH₃ |
| 248 | H₃CO₂S— | -C(O)OCH₂CH₂OCH₃ | 353 | azetidinyl-C(O)-C(CH₃)₂- | -C(O)OCH₂CH₂OCH₃ |
| 249 | H₃CO₂S— | -CH₂C(O)CF₃ | 354 | azetidinyl-C(O)-C(CH₃)₂- | -CH(CH₃)C(O)CH₃ |
| 250 | H₃CO₂S— | -CH₂-cyclopropyl | 355 | azetidinyl-C(O)-C(CH₃)₂- | -CH₂C(O)CF₃ |
| 251 | H₃CO₂S— | -CH₂-cyclobutyl | 356 | azetidinyl-C(O)-C(CH₃)₂- | -CH₂-cyclopropyl |

TABLE-1-continued

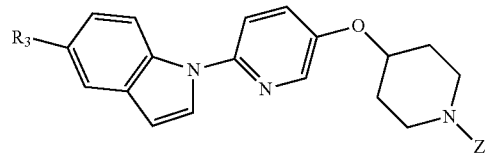

(VI)

| Example | R₃ | Z | Example | R₃ | Z |
|---|---|---|---|---|---|
| 252 | H₃CO₂S— | cyclohexylmethyl | 357 | azetidinyl-C(O)-C(CH₃)₂- | cyclobutylmethyl |
| 253 | H₃CO₂S— | 3-pentyl | 358 | azetidinyl-C(O)-C(CH₃)₂- | cyclohexylmethyl |
| 254 | H₃CO₂S— | neopentyl ester | 359 | azetidinyl-C(O)-C(CH₃)₂- | 3-pentyl |
| 255 | H₃CO₂S— | cyclohexyl ester | 360 | azetidinyl-C(O)-C(CH₃)₂- | neopentyl ester |
| 256 | H₃CO₂S— | cyclopropyl ester | 361 | azetidinyl-C(O)-C(CH₃)₂- | cyclohexyl ester |
| 257 | H₃CO₂S— | 2-fluoroethyl ester | 362 | azetidinyl-C(O)-C(CH₃)₂- | cyclopropyl ester |
| 258 | H₃CO₂S— | cyclopropyl ketone | 363 | azetidinyl-C(O)-C(CH₃)₂- | 2-fluoroethyl ester |
| 259 | H₃CO₂S— | cyclobutyl ketone | 364 | azetidinyl-C(O)-C(CH₃)₂- | cyclopropyl ketone |
| 260 | H₃CO₂S— | cyclopentyl ketone | 365 | azetidinyl-C(O)-C(CH₃)₂- | cyclobutyl ketone |

TABLE-1-continued

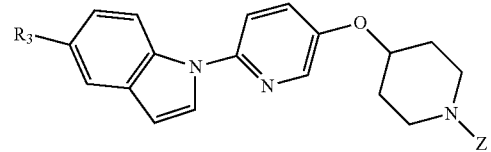

(VI)

| Example | R₃ | Z | Example | R₃ | Z |
|---|---|---|---|---|---|
| 261 | H₃CO₂S— | pyrazine-ethyl | 366 | azetidine-C(O)-C(CH₃)₂- | cyclopentyl-C(O)- |
| 262 | H₃CO₂S— | pyrazine-F | 367 | azetidine-C(O)-C(CH₃)₂- | pyrazine-ethyl |
| 263 | H₃CO₂S— | CH₂CH₂-morpholine | 368 | azetidine-C(O)-C(CH₃)₂- | CH₂CH₂-morpholine |
| 264 | H₃CO₂S— | CH₂C(O)N(CH₃)₂ | 369 | azetidine-C(O)-C(CH₃)₂- | CH₂C(O)N(CH₃)₂ |
| 265 | H₃CO₂S— | CH₂-morpholine | 370 | azetidine-C(O)-C(CH₃)₂- | CH₂-morpholine |
| 266 | H₃CO₂S— | CH(CH₃)-oxabicycle | 371 | azetidine-C(O)-C(CH₃)₂- | CH(CH₃)-oxabicycle |
| 267 | H₃CO₂S— | CH(CH₃)-oxa-azaspiro | 372 | azetidine-C(O)-C(CH₃)₂- | CH(CH₃)-oxa-azaspiro |
| 268 | H₃CO₂S— | bicyclic | 373 | azetidine-C(O)-C(CH₃)₂- | bicyclic |
| 269 | H₃CO₂S— | SO₂-iPr | 374 | azetidine-C(O)-C(CH₃)₂- | SO₂-iPr |

TABLE-1-continued

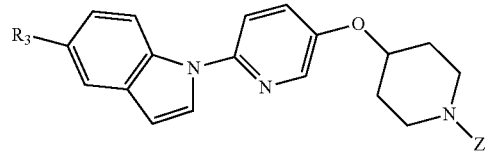

(VI)

| Example | R₃ | Z | Example | R₃ | Z |
|---|---|---|---|---|---|
| 270 | H₃CO₂S– | cyclopropyl-SO₂– | 375 | azetidinyl-C(O)-C(CH₃)₂– | cyclopropyl-SO₂– |
| 271 | H₃CO₂S– | CH₃-SO₂– | 376 | azetidinyl-C(O)-C(CH₃)₂– | CH₃-SO₂– |
| 272 | H₃CO₂S– | Et-SO₂– | 377 | azetidinyl-C(O)-C(CH₃)₂– | Et-SO₂– |
| 273 | H₃CO₂S– | –CH₂C(CH₃)₂CF₃ | 378 | azetidinyl-C(O)-C(CH₃)₂– | –CH₂C(CH₃)₂CF₃ |
| 274 | H₃CO₂S– | –CH₂-(1-CF₃-cyclobutyl) | 379 | azetidinyl-C(O)-C(CH₃)₂– | –CH₂-(1-CF₃-cyclopropyl) |
| 275 | H₃CO₂S– | –CH₂CH(CH₃)₂ | 380 | azetidinyl-C(O)-C(CH₃)₂– | –CH₂-(1-CF₃-cyclobutyl) |
| 276 | (CH₃)₂N-C(O)-C(CH₃)₂– | –CH₂-cyclobutyl | 381 | azetidinyl-C(O)-C(CH₃)₂– | –CH₂CH(CH₃)₂ |
| 277 | (CH₃)₂N-C(O)-C(CH₃)₂– | –C(O)CH₂CF₃ | 382 | pyrrolidinyl-C(O)-C(CH₃)₂– | –CH₂-cyclobutyl |
| 278 | (CH₃)₂N-C(O)-C(CH₃)₂– | –CH₂CH(CH₂F)₂ | 383 | pyrrolidinyl-C(O)-C(CH₃)₂– | –C(CH₃)F₂ |
| 279 | (CH₃)₂N-C(O)-C(CH₃)₂– | –C(CH₃)F₂ | 384 | pyrrolidinyl-C(O)-C(CH₃)₂– | –CH₂-(1-F-cyclopentyl) |

TABLE-1-continued (VI)

| Example | R₃ | Z | Example | R₃ | Z |
|---|---|---|---|---|---|
| 280 | N,N-dimethylamide gem-dimethyl | 1-fluorocyclopentylmethyl | 385 | pyrrolidinyl carbonyl gem-dimethyl | 1-fluorocyclobutylmethyl |
| 280 | N,N-dimethylamide gem-dimethyl | 1-fluorocyclobutylmethyl | 386 | pyrrolidinyl carbonyl gem-dimethyl | 3-fluoro-2,2-dimethylpropyl |
| 282 | N,N-dimethylamide gem-dimethyl | 3-fluoro-2,2-dimethylpropyl | 387 | pyrrolidinyl carbonyl gem-dimethyl | (5-fluoropyrimidin-2-yl)methyl |
| 283 | N,N-dimethylamide gem-dimethyl | (5-fluoropyrimidin-2-yl)methyl | 388 | pyrrolidinyl carbonyl gem-dimethyl | 2-(furan-2-yl)-2-oxoethyl |
| 284 | N,N-dimethylamide gem-dimethyl | 2-(furan-2-yl)-2-oxoethyl | 389 | pyrrolidinyl carbonyl gem-dimethyl | 1,3-difluoropropan-2-yl ester |
| 285 | N,N-dimethylamide gem-dimethyl | 1,3-difluoropropan-2-yl ester | 390 | pyrrolidinyl carbonyl gem-dimethyl | pyrrolidinyl carbonyl |
| 286 | N,N-dimethylamide gem-dimethyl | pyrrolidinyl carbonyl | 391 | pyrrolidinyl carbonyl gem-dimethyl | N,N-diethylamide |
| 287 | N,N-dimethylamide gem-dimethyl | N,N-diethylamide | 392 | pyrrolidinyl carbonyl gem-dimethyl | 3,3,3-trifluoro-2,2-dimethylpropyl |
| 288 | N,N-dimethylamide gem-dimethyl | 3,3,3-trifluoro-2,2-dimethylpropyl | 393 | pyrrolidinyl carbonyl gem-dimethyl | 2,2-difluoro-3-methylbutyl |

TABLE-1-continued

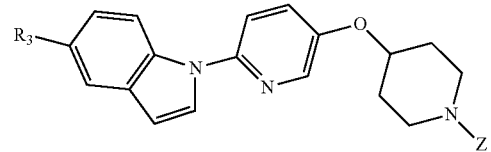

(VI)

| Example | R₃ | Z | Example | R₃ | Z |
|---|---|---|---|---|---|
| 289 | N,N-dimethylamide gem-dimethyl | CH(iPr) with CF₂ | 394 | pyrrolidinyl amide gem-dimethyl | CH-C(=O)-CF₂-CH₃ |
| 290 | N,N-dimethylamide gem-dimethyl | CH-C(=O)-CF₂-CH₃ | 395 | pyrrolidinyl amide gem-dimethyl | isobutyl |
| 291 | N,N-dimethylamide gem-dimethyl | isobutyl | 396 | pyrrolidinyl amide gem-dimethyl | -CH₂CH₂-N(pyrrolidine) |
| 292 | N,N-dimethylamide gem-dimethyl | -CH₂CH₂-N(pyrrolidine) | 397 | pyrrolidinyl amide gem-dimethyl | isopropyl |
| 293 | N,N-dimethylamide gem-dimethyl | isopropyl | 398 | pyrrolidinyl amide gem-dimethyl | cyclopropyl |
| 294 | N,N-dimethylamide gem-dimethyl | n-propyl | 399 | pyrrolidinyl amide gem-dimethyl | cyclobutyl |
| 295 | N,N-dimethylamide gem-dimethyl | cyclopropyl | 400 | pyrrolidinyl amide gem-dimethyl | cyclopentyl |
| 296 | N,N-dimethylamide gem-dimethyl | cyclobutyl | 401 | pyrrolidinyl amide gem-dimethyl | cyclohexyl |
| 297 | N,N-dimethylamide gem-dimethyl | cyclopentyl | 402 | pyrrolidinyl amide gem-dimethyl | CH₂-cyclohexyl |
| 298 | N,N-dimethylamide gem-dimethyl | cyclohexyl | 403 | pyrrolidinyl amide gem-dimethyl | -CH₂CH₂-OCH₃ |

TABLE-1-continued
(VI)
| Example | R₃ | Z | Example | R₃ | Z |
|---|---|---|---|---|---|
| 299 |  | 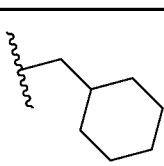 | 404 | 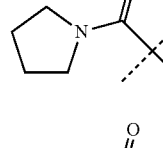 | 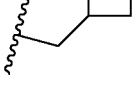 |
| 300 | 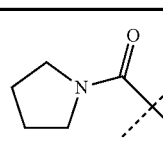 | 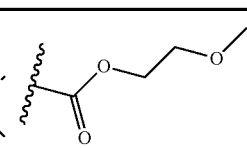 | 405 | 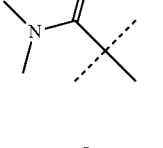 | 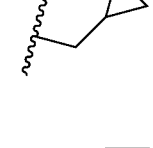 |
| 301 | 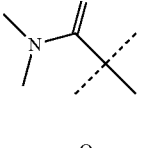 | 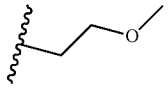 [SMILES: *CCOC] | 406 | 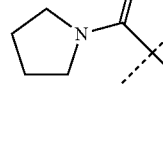 | 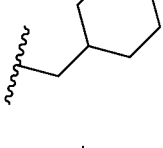 |
| 302 | 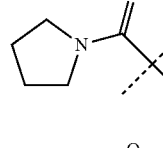 | 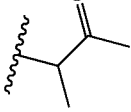 | 407 | 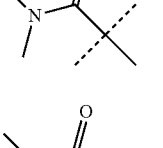 | 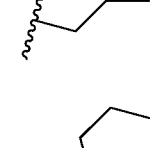 |
| 303 | 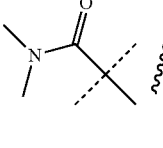 | 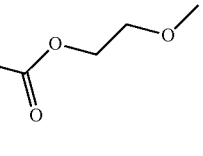 | 408 | 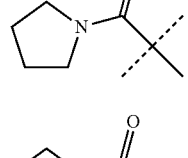 | 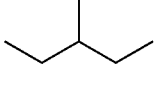 |
| 304 | 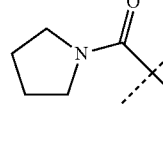 | 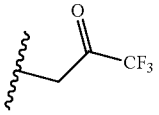 | 409 | 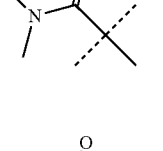 | 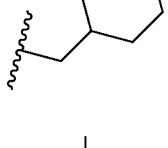 |
| 305 | 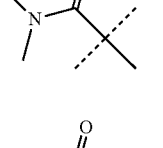 | 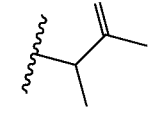 | 410 | 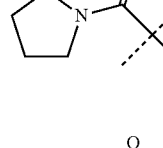 | 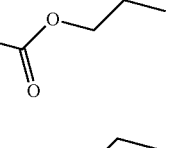 |
| 306 | 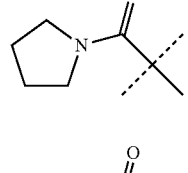 |  | 411 | 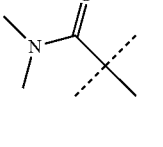 | 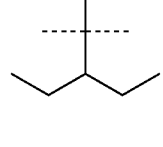 |
| 307 | 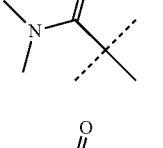 | 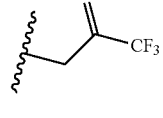 | 412 | 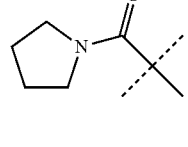 | 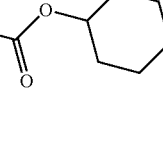 |

TABLE-1-continued

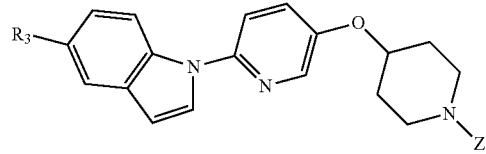

(VI)

| Example | R₃ | Z | Example | R₃ | Z |
|---|---|---|---|---|---|
| 308 | N,N-dimethylamide | neopentyl ester | 413 | pyrrolidine amide | cyclopropyl ester |
| 309 | N,N-dimethylamide | cyclohexyl ester | 414 | pyrrolidine amide | 2-fluoroethyl ester |
| 310 | N,N-dimethylamide | cyclopropyl ester | 415 | pyrrolidine amide | cyclopropyl ketone |
| 311 | N,N-dimethylamide | 2-fluoroethyl ester | 416 | pyrrolidine amide | cyclobutyl ketone |
| 312 | N,N-dimethylamide | cyclopropyl ketone | 417 | pyrrolidine amide | cyclopentyl ketone |
| 313 | N,N-dimethylamide | cyclobutyl ketone | 418 | pyrrolidine amide | 5-ethylpyrazin-2-yl |
| 314 | N,N-dimethylamide | cyclopentyl ketone | 419 | pyrrolidine amide | 3-morpholinopropyl |
| 315 | N,N-dimethylamide | 5-ethylpyrazin-2-yl | 420 | pyrrolidine amide | N,N-dimethylpropanamide |
| 316 | N,N-dimethylamide | 3-morpholinopropyl | 421 | pyrrolidine amide | 2-morpholinoethyl |

TABLE-1-continued

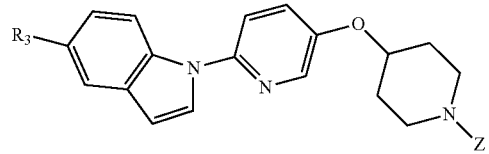

(VI)

| Example | R₃ | Z | Example | R₃ | Z |
|---|---|---|---|---|---|
| 317 | N,N-dimethylamide | N,N-dimethylamide acetyl | 422 | pyrrolidinyl carbonyl | 2-oxa-5-azabicyclo[2.2.1] with methyl |
| 318 | N,N-dimethylamide | morpholinyl ethyl | 423 | pyrrolidinyl carbonyl | 2-oxa-6-azaspiro[3.3]heptyl with methyl |
| 319 | N,N-dimethylamide | 2-oxa-5-azabicyclo[2.2.1] carbonyl | 424 | pyrrolidinyl carbonyl | bicyclo[2.2.1]heptyl |
| 320 | N,N-dimethylamide | 2-oxa-6-azaspiro[3.3]heptyl with methyl | 425 | pyrrolidinyl carbonyl | isopropyl sulfonyl |
| 321 | N,N-dimethylamide | bicyclo[2.2.1]heptyl | 426 | pyrrolidinyl carbonyl | cyclopropyl sulfonyl |
| 322 | N,N-dimethylamide | isopropyl sulfonyl | 427 | pyrrolidinyl carbonyl | methyl sulfonyl |
| 323 | N,N-dimethylamide | cyclopropyl sulfonyl | 428 | pyrrolidinyl carbonyl | ethyl sulfonyl |
| 324 | N,N-dimethylamide | methyl sulfonyl | 429 | pyrrolidinyl carbonyl | 3,3,3-trifluoro-2,2-dimethylpropyl |
| 325 | N,N-dimethylamide | ethyl sulfonyl | 430 | pyrrolidinyl carbonyl | (1-(trifluoromethyl)cyclopropyl)methyl |

TABLE-1-continued (VI)

| Example | R₃ | Z | Example | R₃ | Z |
|---|---|---|---|---|---|
| 326 | N,N-dimethylamide | C(CH₃)₂CF₃ | 431 | pyrrolidinyl carbonyl | 1-(CF₃)cyclobutylmethyl |
| 327 | N,N-dimethylamide | 1-(CF₃)cyclopropylmethyl | 432 | pyrrolidinyl carbonyl | isobutyl |
| 328 | N,N-dimethylamide | 1-(CF₃)cyclobutylmethyl | | | |

Following examples in Table-2 may be prepared by following one or more procedure as described herein above

TABLE-2

(VII)

| Example | R₃ | Z | Example | R₃ | Z |
|---|---|---|---|---|---|
| 433 | N,N-dimethylamide | cyclobutylmethyl | 459 | N,N-dimethylamide | cyclopropylmethyl |
| 434 | N,N-dimethylamide | CF₂-type (CHF₂) | 460 | N,N-dimethylamide | cyclobutylmethyl |
| 435 | N,N-dimethylamide | 1-F-cyclopentylmethyl | 461 | N,N-dimethylamide | cyclohexylmethyl |
| 436 | N,N-dimethylamide | 1-F-cyclobutylmethyl | 462 | N,N-dimethylamide | 3-pentyl |

TABLE-2-continued

TABLE-2-continued (VII)

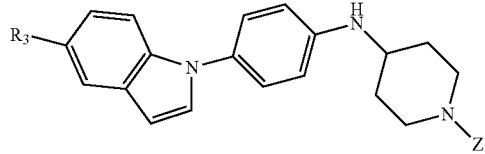

| Example | R₃ | Z | Example | R₃ | Z |
|---------|----|----|---------|----|----|
| 446 | N,N-dimethylamide | isobutyl | 472 | N,N-dimethylamide | CH₂C(O)N(CH₃)₂ |
| 447 | N,N-dimethylamide | propyl-pyrrolidinyl | 473 | N,N-dimethylamide | CH₂-morpholinyl |
| 448 | N,N-dimethylamide | isopropyl | 474 | N,N-dimethylamide | CH(CH₃)-(oxa-azabicyclic) |
| 449 | N,N-dimethylamide | sec-butyl | 475 | N,N-dimethylamide | CH(CH₃)-(oxa-azaspiro) |
| 450 | N,N-dimethylamide | cyclopropyl | 476 | N,N-dimethylamide | bicycloheptyl |
| 451 | N,N-dimethylamide | cyclobutyl | 477 | N,N-dimethylamide | SO₂-isopropyl |
| 452 | N,N-dimethylamide | cyclopentyl | 478 | N,N-dimethylamide | SO₂-cyclopropyl |
| 453 | N,N-dimethylamide | cyclohexyl | 479 | N,N-dimethylamide | SO₂CH₃ |
| 454 | N,N-dimethylamide | CH₂-cyclohexyl | 480 | N,N-dimethylamide | SO₂-ethyl |

TABLE-2-continued

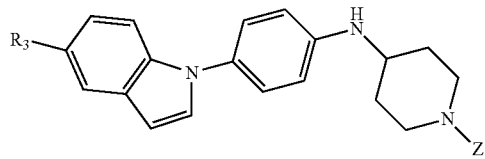

(VII)

| Example | R₃ | Z | Example | R₃ | Z |
|---|---|---|---|---|---|
| 455 | —N(CH₃)C(O)CH< | —CH₂CH₂—O—CH₃ | 481 | —N(CH₃)C(O)CH< | —CH₂C(CH₃)₂CF₃ |
| 456 | —N(CH₃)C(O)CH< | —CH₂C(O)OCH₂CH₂OCH₃ | 482 | —N(CH₃)C(O)CH< | —CH₂-(cyclopropyl)-CF₃ |
| 457 | —N(CH₃)C(O)CH< | —CH₂C(O)CH(CH₃)— | 483 | —N(CH₃)C(O)CH< | —CH₂-(cyclobutyl)-CF₃ |
| 458 | —N(CH₃)C(O)CH< | —CH₂C(O)CH₂CF₃ | 484 | —N(CH₃)C(O)CH< | —CH₂CH(CH₃)₂ |

Biological Example-1

Cyclic AMP Assay in Stable Cell Line:

Chinese Hamster Ovary (CHO-K1) cells were stably transfected with human GPR119 and were maintained in Ham's F-12 complete medium containing 10% heat inactivated FBS (Sigma, UK). The cells were maintained under a selection pressure with 500 μg/ml G418 (GENETICIN). Stable clones were analyzed for functional cAMP response to OEA (oleoylethanolamide).

To estimate activation of GPR119 and induction of cAMP levels by GPR119 agonists, cells were serum starvation for 18-24 h, trypsinized and seeded in 96 well plates at a, density of 7500 cells/well. The cells were then treated with test compounds diluted in serum free Ham's F12 for 1 h at 37° C. The cAMP levels were measured by using the cAMP femto kit (CisBio) by following the manufacturer's instructions. Following treatment with a test compound, the cells were lysed and cAMP levels were estimated by adding D2-labelled cAMP and europium-cryptate conjugated anti-cAMP antibody. Close proximity of D2 and cryptate results in FRET and the subsequent fluorescence that is measured at 665 and 620 nm. The FRET response is calculated as the ratio of fluorescence at 665 to fluorescence at 620 nm. The unlabelled cAMP produced as a result of GPR119 activation/agonism competes with the D2-cAMP leading to a decrease in the FRET signal. Thus the FRET signal is inversely proportional to the amount of cAMP produced by the treated cells. In a separate set of wells, known concentrations of cAMP were added in order to get a standard linear curve for extrapolation of the cAMP values in the unknown/test samples. Fluorescence was measured on BMG Labtech PHERAstar machine.

The concentration of compound required to stimulate a half-maximal response ($EC_{50}$) was determined using the GraphPad Prism software.

The compounds prepared were tested using the above assay procedure and the results obtained are given below. The $EC_{50}$ (nM) values of the compounds are set forth in Table-3 wherein "A" refers to an $EC_{50}$ value of less than 50 nM, "B" refers to an $EC_{50}$ value in range of 50.01 to 250 nM and "C" refers to an $EC_{50}$ value in range of 250.01 to 1000 nM.

Activity data has been given in Table-3 for representative compounds.

TABLE 3

| Compound (Example number) | $EC_{50}$ Range |
|---|---|
| 1, 2, 4, 5, 6, 8, 9, 11, 14, 22, 30, 35, 39, 40, 45, 46, 49, 51, 54, 56, 57, 63, 71, 74, 77, 80, 91, 98, 118, 120, 123, 126, 127, 132, 136, 141, 143, 168, 169, 171, 187, 190, 193 | A |
| 13, 18, 30, 42, 45, 48, 62, 66, 67, 70, 72, 76, 82, 92, 103, 108, 119, 126, 147, 153, 157, 182, 185 | B |
| 58, 72, 84, 88, 94, 99, 100, 107, 112, 113, 166, 192 | C |

Thus, certain compounds of the present invention are shown to have functional activity as agonists of GPR 119.

Biological Example-2

Oral Glucose Tolerance Test:

9-10 weeks old male C57 BL/6J mice were maintained on a regular chow diet. The day of the experiment mice were fasted for 16 h and then randomized in to groups (n=7-8) based on blood glucose and bodyweight to receive vehicle (80% PEG400, 10% Tween80, 10% Ethanol) or test compounds (at 10 mg/kg). Vehicle or test compounds were delivered via oral gavage at 10 ml/kg volume. Thirty minutes later, the mice were dosed orally with a glucose bolus (3 g/kg) at 10 ml/kg volume. Blood glucose measurements were taken at 20, 40, 60 and 120 minutes after glucose administration by glucometer (CONTOUR TS, Bayer). Total AUC and Delta AUC were calculated by using graph pad prism (5.0).

TABLE 4

| Compound | % reduction in delta AUC at 10 mg/kg | % reduction in total AUC at 10 mg/kg |
| --- | --- | --- |
| Example-63 | 28% | 19% |
| Example-142 | 35% | 20% |

Thus, the compound of the present invention has been shown to decrease plasma glucose levels in vivo, indicating potential for use of the compounds of the present invention in the treatment of diabetes.

All patents, patent applications and publications cited in this application are hereby incorporated by reference in their entirety for all purposes to the same extent as if each individual patent, patent application or publication were so individually denoted.

Although certain embodiments and examples have been described in detail above, those having ordinary skill in the art will clearly understand that many modifications are possible in the embodiments and examples without departing from the teachings thereof. All such modifications are intended to be encompassed within the below claims of the invention.

The invention claimed is:

1. A compound of Formula (II):

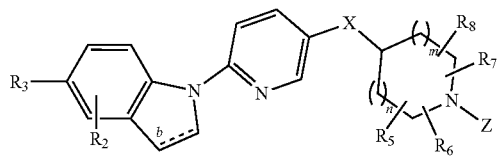

(II)

or pharmaceutically acceptable salt thereof;
wherein, $\underset{===}{b}$ is a double bond;

$R_2$ is selected from the group consisting of hydrogen, alkyl, and halo;

$R_3$ is selected from the group consisting of —S(O)$_p$R$_a$, —C(O)OR$_a$, —(CH$_2$)$_q$C(O)NR$_a$R$_b$, —(CH$_2$)$_q$N(R$_a$)C(O)R$_b$, —N(R$_a$)C(O)OR$_b$, —N(R$_a$)C(O)NR$_a$R$_b$, —S(O)$_2$NR$_a$R$_b$, —N(R$_a$)S(O)$_2$R$_b$, —CN, alkoxy, hydroxyalkyl, heterocyclyl and heteroaryl;

$R_a$ and $R_b$ are each independently selected from the group consisting of hydrogen, alkyl, haloalkyl, hydroxy, alkenyl, alkynyl, cycloalkyl, hydroxyalkyl, alkoxyalkyl, aryl, heteroaryl, arylalkyl, and heterocyclyl; or $R_a$ and $R_b$ may join together with the nitrogen atom to which they are attached to form a heterocyclic ring;

Z is selected from the group consisting of alkyl, cycloalkyl, heterocyclyl, aryl, heteroaryl, cycloalkylalkyl, heterocyclylalkyl, heteroarylalkyl, arylalkyl, haloalkyl, hydroxyalkyl, —(CH$_2$)$_q$C(O)OR$_a$, —(CH$_2$)$_q$C(O)R$_a$, —C(O)(CH$_2$)$_q$NR$_a$R$_b$, —(CH$_2$)$_q$C(O)NR$_a$R$_b$, —S(O)$_2$R$_a$, —S(O)$_2$NR$_a$R$_b$, —C(O)CR$_c$R$_d$R$_e$ and —(CH$_2$)$_q$CR$_c$R$_d$R$_e$;

$R_c$R$_d$ and R$_e$ are each independently selected from the group consisting of hydrogen, halogen, hydroxyl, alkyl, haloalkyl, alkenyl, alkynyl, cycloalkyl, aryl, heteroaryl, arylalkyl, and heterocyclyl; or R$_c$ and R$_d$ may join together with the carbon atom to which they are attached to form a 3 to 7 membered carbocyclic or heterocyclic ring;

$R_5$, $R_6$, $R_7$, $R_8$ are hydrogen; or any two of $R_5$, $R_6$, $R_7$, $R_8$ and Z may join together to form a cycloalkyl or heterocyclyl ring;

X is selected from the group consisting of —(CR$_{10}$R$_{11}$)$_q$O(CR$_{10}$R$_{11}$)$_t$—, —(CR$_{10}$R$_{11}$)$_q$S(O)$_p$(CR$_{10}$R$_{11}$)$_t$— and —(CR$_{10}$R$_{11}$)$_q$NR$_9$(CR$_{10}$R$_{11}$)$_t$—;

$R_9$ is hydrogen or alkyl;

$R_{10}$ and $R_{11}$ are hydrogen;

'm', 'n' and 'p' are each independently selected from 0, 1 or 2;

'q' is an integer ranging from 0 to 4, both inclusive;

't' is an integer ranging from 0 to 4, both inclusive; and wherein, alkyl, alkenyl, alkynyl, cycloalkyl, aryl, heteroaryl, heterocyclyl, heterocyclic ring, alkoxy, hydroxyalkyl, haloalkyl, arylalkyl, heterocyclylalkyl, heteroarylalkyl and carbocyclic ring wherever they occur may optionally be substituted with one or more substituents independently selected from hydroxy, halo, cyano, nitro, oxo (═O), thio (═S), alkyl, haloalkyl, alkenyl, alkynyl, aryl, arylalkyl, cycloalkyl, cycloalkylalkyl, cycloalkenyl, heteroaryl, heterocyclic ring, heterocyclylalkyl, heteroarylalkyl, —C(O)OR$^x$, —C(O)R$^x$, —C(S)R$^x$, —C(O)NR$^x$R$^y$, —NR$^x$C(O)NR$^y$R$^z$, —N(R$^x$)S(O)R$^y$, —N(R$^x$)S(O)$_2$R$^y$, —NR$^x$R$^y$, —NR$^x$C(O)R$^y$, —NR$^x$C(S)R$^y$, —NR$^x$C(S)NR$^y$R$^z$, —S(O)NR$^x$R$^y$, —S(O)$_2$NR$^x$R$^y$, —OR$^x$, —OC(O)R$^x$, —OC(O)NR$^x$R$^y$, —R$^x$C(O)OR$^y$, —R$^x$C(O)NR$^y$R$^z$, —R$^x$C(O)R$^y$, —SR$^x$, —S(O)R$^x$, and —S(O)$_2$R$^x$; wherein each occurrence of R$^x$, R$^y$ and R$^z$ are independently selected from hydrogen, alkyl, haloalkyl, alkenyl, alkynyl, aryl, arylalkyl, cycloalkyl, cycloalkenyl, heteroaryl, heterocyclic ring, heterocyclylalkyl ring and heteroarylalkyl.

2. The compound of claim 1, having the Formula (V):

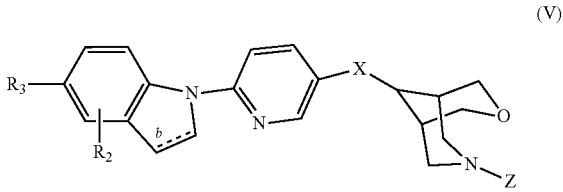

(V)

or pharmaceutically acceptable salt thereof;
wherein, $\underset{===}{b}$ is a double bond;

X is selected from the group consisting of —(CR$_{10}$R$_{11}$)$_q$O(CR$_{10}$R$_{11}$)$_t$—, —(CR$_{10}$R$_{11}$)$_q$S(O)$_p$(CR$_{10}$R$_{11}$)$_t$— and —(CR$_{10}$R$_{11}$)$_q$NR$_9$(CR$_{10}$R$_{11}$)$_t$—;

Z is selected from the group consisting of alkyl, cycloalkyl, heterocyclyl, aryl, heteroaryl, cycloalkylalkyl, heterocyclylalkyl, heteroarylalkyl, arylalkyl, haloalkyl, hydroxyalkyl, —(CH$_2$)$_q$C(O)OR$_a$, —(CH$_2$)$_q$C(O)R$_a$, —C(O)(CH$_2$)$_q$NR$_a$R$_b$, —(CH$_2$)$_q$C(O)NR$_a$R$_b$, —S(O)$_2$R$_a$, —S(O)$_2$NR$_a$R$_b$, —C(O)CR$_c$R$_d$R$_e$ and —(CH$_2$)$_q$CR$_c$R$_d$R$_e$;

$R_2$ is selected from the group consisting of hydrogen, alkyl, and halo;

R₃ is selected from the group consisting of —S(O)$_p$R$_a$, —C(O)OR$_a$, —(CH$_2$)$_q$C(O)NR$_a$R$_b$, —(CH$_2$)$_q$N(R$_a$)C(O)R$_b$, —N(R$_a$)C(O)OR$_b$, —N(R$_a$)C(O)NR$_a$R$_b$, —S(O)$_2$NR$_a$R$_b$, —N(R$_a$)S(O)$_2$R$_b$, —CN, alkoxy, hydroxyalkyl, heterocyclyl and heteroaryl;

R$_a$ and R$_b$ are each independently selected from the group consisting of hydrogen, alkyl, haloalkyl, hydroxy, alkenyl, alkynyl, cycloalkyl, hydroxyalkyl, alkoxyalkyl, aryl, heteroaryl, arylalkyl, and heterocyclyl; or R$_a$ and R$_b$ may join together with the nitrogen atom to which they are attached to form a heterocyclic ring;

R$_c$, R$_d$ and R$_e$ are each independently selected from the group consisting of hydrogen, halogen, hydroxyl, alkyl, haloalkyl, alkenyl, alkynyl, cycloalkyl, aryl, heteroaryl, arylalkyl, and heterocyclyl; or R$_c$ and R$_d$ may join together with the carbon atom to which they are attached to form a 3 to 7 membered carbocyclic or heterocyclic ring;

R$_9$ is hydrogen or alkyl;

R$_{10}$ and R$_{11}$ are hydrogen;

'p' is each independently selected from 0, 1 or 2;

'q' is each an integer ranging from 0 to 4, both inclusive; and

't' is each an integer ranging from 0 to 4, both inclusive.

3. The compound of claim 1, wherein:
R$_3$ is hydroxyalkyl, —C(O)OR$_a$, —S(O)$_2$R$_a$, —C(O)NR$_a$R$_b$, —N(R$_a$)C(O)R$_b$, —CH$_2$N(R$_a$)C(O)R$_b$, —N(R$_a$)C(O)OR$_b$, —N(R$_a$)C(O)NR$_a$R$_b$, —S(O)$_2$NR$_a$R$_b$, —N(R$_a$)S(O)$_2$R$_b$, heterocyclyl; and R$_a$ and R$_b$ are each independently a hydrogen, alkyl, haloalkyl, cycloalkyl, hydroxyalkyl, aryl, heteroaryl or heterocyclyl; or R$_a$ and R$_b$ may join together with the nitrogen atom to which they are attached to form a heterocyclic ring.

4. The compound of claim 1, wherein R$_3$ is substituted or unsubstituted heteroaryl or heterocyclyl.

5. The compound of claim 4, wherein heteroaryl is oxazole, oxadiazole, triazole or tetrazole.

6. The compound of claim 4, wherein heterocyclyl is pyrrolidine, pyrrolidine-2-one or oxazolidin-2-one.

7. The compound of claim 3, wherein X is —(CR$_{10}$R$_{11}$)$_q$O (CR$_{10}$R$_{11}$)$_t$— or —CR$_{10}$R$_{11}$)$_q$NR$_9$(CR$_{10}$R$_{11}$)$_t$—; 'q' is 0 or 1; 't' is 0 or 1; and each of R$_{10}$ and R$_{11}$ are hydrogen.

8. The compound of claim 1, wherein Z is alkyl, haloalkyl, cycloalkyl, heterocyclyl, aryl, heteroaryl, heterocyclylalkyl, heteroarylalkyl, arylalkyl, hydroxyalkyl, —C(O)OR$_a$, —C(O)R$_a$, —C(O)CR$_c$R$_d$R$_e$, —(CH$_2$)$_{0-2}$CR$_c$R$_d$R$_e$, —S(O)$_2$R$_a$ or —S(O)$_2$NR$_a$R$_b$ wherein R$_a$, R$_b$, R$_c$, R$_d$ and R$_e$ are each independently a hydrogen, alkyl, haloalkyl, cycloalkyl, aryl, heteroaryl, arylalkyl, and heterocyclyl; or R$_a$ and R$_b$ may join together with the nitrogen atom to which they are attached to form a heterocyclic ring; or R$_c$ and R$_d$ may join together with the carbon atom to which they are attached to form a 3 to 7 membered carbocyclic or heterocyclic ring; 'm' is 0 or 1; and 'n' is 0 or 1.

9. The compound of claim 1, wherein:
R$_2$ is hydrogen or halogen;
R$_3$ is —S(O)$_2$R$_a$, —C(O)NR$_a$R$_b$, —N(R$_a$)C(O)R$_b$, —N(R$_a$)C(O)OR$_b$, heterocyclyl, or heteroaryl, wherein R$_a$ and R$_b$ are each independently a hydrogen or alkyl;
X is —O, or —NH—;
Z is alkyl, haloalkyl, heteroaryl, heterocyclyl, —C(O)Oalkyl, —C(O)CR$_c$R$_d$R$_e$, or —(CH$_2$)$_{0-2}$CR$_c$R$_d$R$_e$; R$_5$, R$_6$, R$_7$ and R$_8$ are hydrogen; 'm' is 1; and 'n' is 0 or 1.

10. The compound of claim 1, which is selected from:
tert-Butyl-4-((6-(5-(methylsulfonyl)-1H-indol-1-yl)pyridin-3-yl)oxy)piperidine-1-carboxylate;
1-(5-((1-(5-Ethylpyrimidin-2-yl)piperidin-4-yl)oxy)pyridin-2-yl)-5-(methylsulfonyl)-1H-indole;
3-Isopropyl-5-(4-((6-(5-(methylsulfonyl)-1H-indol-1-yl)pyridin-3-yl)oxy)piperidin-1-yl)-1,2,4-oxadiazole;
tert-Butyl-4-(((((6-(5-(methylsulfonyl)-1H-indol-1-yl)pyridin-3-yl)oxy)methyl)piperidine-1-carboxylate;
1-(5-((1-(5-ethylpyrimidin-2-yl)piperidin-4-yl)methoxy)pyridin-2-yl)-5-(methylsulfonyl)-1H-indole;
3-Isopropyl-5-(4-(((6-(5-(methylsulfonyl)-1H-indol-1-yl)pyridin-3-yl)oxy)methyl)piperidin-1-yl)-1,2,4-oxadiazole;
tert-Butyl-4-((6-(5-((ethoxycarbonyl)amino)-1H-indol-1-yl)pyridin-3-yl)oxy)piperidine-1-carboxylate;
Ethyl (1-(5-((1-(5-ethylpyrimidin-2-yl)piperidin-4-yl)oxy)pyridin-2-yl)-1H-indol-5-yl)carbamate;
tert-Butyl-4-((6-(5-((ethylsulfonyl)-1H-indol-1-yl)pyridin-3-yl)oxy)piperidine-1-carboxylate;
1-(5-((1-(5-Ethylpyrimidin-2-yl)piperidin-4-yl)oxy)pyridin-2-yl)-5-(ethylsulfonyl)-1H-indole;
2-Methyl-1-(4-((6-(5-(methylsulfonyl)-1H-indol-1-yl)pyridin-3-yl) oxy)piperidin-1-yl)propan-2-ol;
1-(4-((6-(5-(Ethysulfonyl)-1H-indol-1-yl)pyridin-3-yl)oxy)piperidin-1-yl)-2-methylpropan-2-ol;
1-(5-((1-(2-Fluoro-2-methylpropyl)piperidin-4-yl)oxy)pyridin-2-(methylsulfonyl)-1H-indole;
5-(Ethylsulfonyl)-1-(5-((1-(2-fluoro-2-methylpropyl)piperidin-4-yl)oxy)pyridin-2-yl)-1H-indole;
tert-Butyl 4-((6-(5-(isopropylsulfonyl)-1H-indol-1-yl)pyridin-3-yl)oxy)piperidine-1-carboxylate;
1-(5-((1-((5-Ethylpyrimidin-2-yl)piperidin-4-yl)oxy)pyridin-2-yl)-5-isopropylsulfonyl)-1H-indole;
5-(4-((6-(5-(Isopropylsulfonyl)-1H-indol-1-yl)pyridin-3-yl)oxy)piperidin-1-yl)-3-methyl-1,2,4-oxadiazole;
tert-Butyl-4-((6-(5-((2-hydroxyethyl)carbamoyl)-1H-indol-1-yl)pyridin-3-yl)amino)piperidine-1-carboxylate;
1-(5-((1-(5-Ethylpyrimidin-2-yl)piperidin-4-yl)amino)pyridin-2-yl)-N-(2-hydroxyethyl)-1H-indole-5-carboxamide;
tert-Butyl 4-((6-(5-(dimethylcarbamoyl)-1H-indol-1-yl)pyridin-3-yl)amino)piperidine-1-carboxylate;
1-(5-((1-(5-Ethylpyrimidin-2-yl)piperidin-4-yl)amino)pyridin-2-yl)-N,N-dimethyl-1H-indole-5-carboxamide;
2-Methyl-1-(4-((6-(5-(methylsulfonyl)-1H-indol-1-yl)pyridin-3-yl)oxy)piperidin-1-yl)propan-1-one;
(±)-tert-Butyl-3-((6-(5-(methylsulfonyl)-1H-indol-1-yl)pyridin-3-yl)oxy)pyrrolidine-1-carboxylate;
(±)-1-(5-((1-(5-Ethylpyrimidin-2-yl)pyrrolidin-3-yl)oxy)pyridin-2-yl)-5-(methylsulfonyl)-1H-indole;
(±)-5-(methylsulfonyl)-1-(5-((1-(4-(trifluorometh)benzyl)pyrrolidin-3-yl)oxy)pyridin-2-yl)-1H-indole;
tert-Butyl-3-((6-(5-(methylsulfonyl)-1H-indol-1-yl)pyridin-3-yl)oxy)-azetidine-1-carboxylate;
1-(5-((1-(5-Ethylpyrimidin-2-yl)azetidin-3-yl)oxy)pyridin-2-yl)-5-(methylsulfonyl)-1H-indole;
5-(Methylsulfonyl)-1-(5-((1-(4-(trifluoromethyl)benzyl)azetidin-3-yl)oxy)pyridin-2-yl)-1H-indole;
1-(5-((1-Isobutylpiperidin-4-yl)oxy)pyridin-2-yl)-5-(methylsulfonyl)-1H-indole;
2,2-Dimethyl-1-(4-((6-(5-(methylsulfonyl)-1H-indol-1-yl)pyridin-3-yl)oxy)piperidin-1-yl)propan-1-one;
5-(Methylsulfonyl)-1-(5-((1-neopentylpiperidin-4-yl)oxy)pyridin-2-yl)-1H-indole;
tert-Butyl-4-((6-(5-(dimethylcarbamoyl)-1H-indol-1-yl)pyridin-3-yl)oxy)piperidine-1-carboxylate;
1-(5-((1-(5-Ethylpyrimidin-2-yl)piperidin-4-yl)oxy)pyridin-2-yl)-N,N-dimethyl-1H-indole-5-carboxamide;

tert-Butyl-4-((6-(5-(methylsulfonyl)-1H-indol-1-yl)pyridin-3-yl)-methoxy)piperidine-1-carboxylate;
1-(5-(((1-(5-Ethylpyrimidin-2-yl)piperidin-4-yl)oxy)methyl)pyridin-2-yl)-5-(methylsulfonyl)-1H-indole;
tert-butyl 4-(((6-(5-(dimethylcarbamoyl)-1H-indol-1-yl)pyridin-3-yl)oxy)methyl)piperidine-1-carboxylate;
1-(5-(((1-(5-Ethylpyrimidin-2-yl)piperidin-4-yl)oxy)methyl)pyridin-2-yl)-N,N-dimethyl-1H-indole-5-carboxamide;
(syn)-tert-Butyl-9-((6-(5-(methylsulfonyl)-1H-indol-1-yl)pyridin-3-yl)oxy)-3-oxa-7-azabicyclo[3.3.1]nonane-7-carboxylate;
(anti) tert-Butyl-9-((6-(5-(methylsulfonyl)-1H-indol-1-yl)pyridin-3-yl)oxy)-3-oxa-7-azabicyclo[3.3.1]nonane-7-carboxylate;
syn 7-(5-Ethylpyrimidin-2-yl)-9-((6-(5-(methylsulfonyl)-1H-indol-1-yl)pyridin-3-yl)oxy)-3-oxa-7-azabicyclo[3.3.1]nonane;
anti 7-(5-Ethylpyrimidin-2-yl)-9-((6-(5-(methylsulfonyl)-1H-indol-1-yl)pyridin-3-yl)oxy)-3-oxa-7-azabicyclo[3.3.1]nonane;
tert-Butyl-4-((6-(5-cyano-1H-indol-1-yl)pyridin-3-yl)oxy)piperidine-1-carboxylate;
tert-Butyl-4-((6-(5-(cyclopropylcarbamoyl)-1H-indol-1-yl)pyridin-3-yl)oxy)piperidine-1-carboxylate;
N-cyclopropyl-1-(5-((1-(5-ethylpyrimidin-2-yl)piperidin-4-yl)oxy)pyridin-2-yl)-1H-indole-5-carboxamide;
tert-Butyl-4-((6-(5-(oxazol-2-yl)-1H-indol-1-yl)pyridin-3-yl)oxy)-piperidine-1-carboxylate;
tert-Butyl-4-((6-(5-isobutyramido-1H-indol-1-yl)pyridin-3-yl)oxy)-piperidine-1-carboxylate;
N-(1-(5-((1-(3-isopropyl-1,2,4-oxadiazol-5-yl)piperidin-4-yl)oxy)pyridin-2-yl)-1H-indol-5-yl)isobutyramide;
1-(5-((1-(5-Ethylpyrimidin-2-yl)piperidin-4-yl)oxy)pyridin-2-yl)-1H-indole-5-carbonitrile;
2-(1-(5-((1-(5-Ethylpyrimidin-2-yl)piperidin-4-yl)oxy)pyridin-2-yl)-1H-indol-5-yl)oxazole;
tert-Butyl-4-((6-(5-(methylcarbamoyl)-1H-indol-1-yl)pyridin-3-yl)-oxy)piperidine-1-carboxylate;
tert-Butyl-4-((6-(5-(ethylcarbamoyl)-1H-indol-1-yl)pyridin-3-yl)oxy)-piperidine-1-carboxylate;
tert-Butyl-4-((6-(5-(isopropylcarbamoyl)-1H-indol-1-yl)pyridin-3-yl)oxy)piperidine-1-carboxylate;
1-(5-((1-(5-Ethylpyrimidin-2-yl)piperidin-4-yl)oxy)pyridin-2-yl)-N-methyl-1H-indole-5-carboxamide;
N-ethyl-1-(5-((1-(5-ethylpyrimidin-2-yl)piperidin-4-yl)oxy)pyridin-2-yl)-1H-indole-5-carboxamide;
1-(5-((1-(5-Ethylpyrimidin-2-yl)piperidin-4-yl)oxy)pyridin-2-yl)-N-isopropyl-1H-indole-5-carboxamide;
tert-Butyl-4-4(((6-(5-(methylcarbamoyl)-1H-indol-1-yl)pyridin-3-yl)-oxy)methyl)piperidine-1-carboxylate;
1-(5-((1-(5-Ethylpyrimidin-2-yl)piperidin-4-yl)methoxy)pyridin-2-yl)-N-methyl-1H-indole-5-carboxamide;
1-(5-((1-(3-Isopropyl-1,2,4-oxadiazol-5-yl)piperidin-4-yl)oxy)pyridin-2-yl)-N-methyl-1H-indole-5-carboxamide;
tert-Butyl-4-((6-(5-(pyrrolidine-1-carbonyl)-1H-indol-1-yl)pyridin-3-yl)oxy)piperidine-1-carboxylate;
Isopropyl 4-((6-(5-(pyrrolidine-1-carbonyl)-1H-indol-1-yl)pyridin-3-yl)oxy)piperidine-1-carboxylate;
(1-(5-((1-(5-Ethylpyrimidin-2-yl)piperidin-4-yl)oxy)pyridin-2-yl)-1H-indol-5-yl)(pyrrolidin-1-yl)methanone;
Isopropyl 4-((6-(5-(isopropylcarbamoyl)-1H-indol-1-yl)pyridin-3-yl)oxy)piperidine-1-carboxylate;
Ethyl-4-((6-(5-(isopropylcarbamoyl)-1H-indol-1-yl)pyridin-3-yl)oxy)-piperidine-1-carboxylate;
Isopropyl 4-((6-(5-(dimethylcarbamoyl)-1H-indol-1-yl)pyridin-3-yl)oxy)piperidine-1-carboxylate;
Ethyl-4-((6-(5-(dimethylcarbamoyl)-1H-indol-1-yl)pyridin-3-yl)oxy)-piperidine-1-carboxylate;
tert-Butyl-4-((6-(5-((2-hydroxyethyl)carbamoyl)-1H-indol-1-yl)-pyridin-3-yl)oxy)piperidine-1-carboxylate;
1-(5-((1-(5-Ethylpyrimidin-2-yl)piperidin-4-yl)oxy)pyridin-2-yl)-N-(2-hydroxyethyl)-1H-indole-5-carboxamide;
3-Ethyl-5-((4-((6-(5-(methylsulfonyl)-1H-indol-1-yl)pyridin-3-yl)oxy)-piperidin-1-yl)methyl)-1,2,4-oxadiazole;
3-Isopropyl-5-((4-((6-(5-(methylsulfonyl)-1H-indol-1-yl)pyridin-3-yl)oxy)piperidin-1-yl)methyl)-1,2,4-oxadiazole;
1-(5-((1-(4-Fluorophenyl)piperidin-4-yl)oxy)pyridin-2-yl)-5-(methylsulfonyl)-1H-indole;
1-(5-((1-(4-Fluorobenzyl)piperidin-4-yl)oxy)pyridin-2-yl)-5-(methylsulfonyl)-1H-indole;
1-(5-((1-((4-Ethyloxazol-2-yl)methyl)piperidin-4-yl)oxy)pyridin-2-yl)-N,N-dimethyl-1H-indole-5-carboxamide;
1-(5-((1-((4-Isopropyloxazol-2-yl)methyl)piperidin-4-yl)oxy)pyridin-2-yl)-N,N-dimethyl-1H-indole-5-carboxamide;
3-Cyclopropyl-5-(4-((6-(5-(methylsulfonyl)-1H-indol-1-yl)pyridin-3-yl)oxy)piperidin-1-yl)-1,2,4-oxadiazole;
4-Cyclopropyl-2-((4-((6-(5-(methylsulfonyl)-1H-indol-1-yl)pyridin-3-yl)oxy)piperidin-1-yl)methyl)oxazole;
tert-Butyl-4-((6-(5-((2,2,2-trifluoroethyl)carbamoyl)-1H-indol-1-yl)-pyridin-3-yl)oxy)piperidine-1-carboxylate;
1-(5-((1-(5-Ethylpyrimidin-2-yl)piperidin-4-yl)oxy)pyridin-2-yl)-N-(2,2,2-trifluoroethyl)-1H-indole-5-carboxamide;
Isopropyl 4-((6-(5-((2-hydroxyethyl)carbamoyl)-1H-indol-1-yl)pyridin-3-yl)oxy)piperidine-1-carboxylate;
Ethyl 4-((6-(5-((2-hydroxyethyl)carbamoyl)-1H-indol-1-yl)pyridin-3-yl)oxy)piperidine-1-carboxylate;
tert-Butyl-4-((6-(7-fluoro-5-(methysulfonyl)-1H-indol-1-yl)pyridin-3-yl)oxypiperidine-1-carboxylate;
3-Methyl-5-(4-((6-(5-(methylsulfonyl)-1H-indol-1-yl)pyridin-3-yl)oxy)piperidin-1-yl)-1,2,4-oxadiazole;
Methyl-1-(5-((1-(tert-butoxycarbonyl)piperidin-4-yl)oxy)pyridin-2-yl)-1H-indole-5-carboxylate;
tert-Butyl-4-((6-(5-(hydroxymethyl)-1H-indol-1-yl)pyridin-3-yl) oxy)piperidine-1-carboxylate;
Methyl-1-(5-((1-(5-ethylpyrimidin-2-yl)piperidin-4-yl)oxy)pyridin-2-yl)-1H-indole-5-carboxylate;
(1-(5-((1-(5-Ethylpyrimidin-2-yl)piperidin-4-yl)oxy)pyridin-2-yl)-1H-indol-5-yl)methanol;
tert-Butyl-4-((6-(5-(isobutyramido methyl)-1H-indol-1-yl)pyridin-3-yl)oxy)piperidine-1-carboxylate;
N-((1-(5-((1-(5-ethylpyrimidin-2-yl)piperidin-4-yl)oxy)pyridin-2-yl)-1H-indol-5-yl)methyl)isobutyramide;
tert-Butyl-4-((6-(5-(3-isopropyl-1,2,4-oxadiazol-5-yl)-1H-indol-1-yl)pyridin-3-yl)oxy)piperidine-1-carboxylate;
5-(1-(5-((1-(5-Ethylpyrimidin-2-yl)piperidin-4-yl)oxy)pyridin-2-yl)-1H-indol-5-yl)-3-isopropyl-1,2,4-oxadiazole;
Isopropyl 4-((6-(5-(3-isopropyl-1,2,4-oxadiazol-5-yl)-1H-indol-1-yl)pyridin-3-yl)oxy)piperidine-1-carboxylate;
tert-Butyl-4-((6-(5-(3-methyl-1,2,4-oxadiazol-5-yl)-1H-indol-1-yl)pyridin-3-yl)oxy)piperidine-1-carboxylate;

5-(1-(5-((1-(5-Ethylpyrimidin-2-yl)piperidin-4-yl)oxy) pyridin-2-yl)-1H-indol-5-yl)-3-methyl-1,2,4-oxadiazole;
tert-Butyl-4-((6-(5-(pyrrolidin-1-yl)-1H-indol-1-yl)pyridin-3-yl) oxy)piperidine-1-carboxylate;
1-(5-((1-(5-Ethylpyrimidin-2-yl)piperidin-4-yl)oxy)pyridin-2-yl)-5-(pyrrolidin-1-yl)-1H-indole;
1-(5-(((1-(5-Ethylpyrimidin-2-yl)piperidin-4-yl)oxy)methyl)pyridine--2-yl)-5-(methylsulfonyl)-1H-indole;
Ethyl 4-((6-(5-(methylsulfonyl)-1H-indol-1-yl)pyridin-3-yl)methoxy)piperidine-1-carboxylate;
Isopropyl 4-((6-(5-methylsulfonyl)-1H-indol-1-yl)pyridin-3-yl)methoxy) piperidine-1-carboxylate;
2-Methyl-1-(4-((6-(5-(methylsulfonyl)-1H-indol-1-yl)pyridin-3-yl)methoxy)piperidin-1-yl)propan-2-ol;
1-(5-(((1-(2-Fluoro-2-methylpropyl)piperidin-4-yl)oxy) methyl)pyridin-2-yl)-5-(methylsulfonyl)-1H-indole;
3-Isopropyl-5-(4-((6-(5-(methylsulfonyl)-1H-indol-1-yl) pyridin-3-yl)methoxy)piperidin-1-yl)-1,2,4-oxadiazole;
3-Methyl-5-(4-((6-(5-(methylsulfonyl)-1H-indol-1-yl)pyridin-3-yl)methoxy)piperidin-1-yl)-1,2,4-oxadiazole;
tert-Butyl-4-((6-(5-isobutyramido-1H-indol-1-yl)pyridin-3-yl)oxy)-piperidine-1-carboxylate;
N-(1-(5-((1-(5-ethylpyrimidin-2-yl)piperidin-4-yl)oxy) pyridin-2-yl)-1H-indol-5-yl)pivalamide;
N-(1-(5-ethylpyrimidin-2-yl)piperidin-4-yl)-6-(5-(methylsulfonyl)-1H-indol-1-yl)pyridin-3-amine;
N-(1-(3-isopropyl-1,2,4-oxadiazol-5-yl)piperidin-4-yl)-6-(5-(methylsulfonyl)-1H-indol-1-yl)pyridin-3-amine;
tert-Butyl-4-(((6-(5-isobutyramido-1H-indol-1-yl)pyridin-3-yl)oxy)-methyl)piperidine-1-carboxylate;
N-(1-(5-((1-(5-ethylpyrimidin-2-yl)piperidin-4-yl)oxy) pyridin-2-yl)-1H-indol-5-yl)isobutyramide;
N-(1-(5-((1-(5-ethylpyrimidin-2-yl)piperidin-4-yl)methoxy)pyridin-2-yl)-1H-indol-5-yl)isobutyramide;
Isopropyl 4-(((6-(5-isobutyramido-1H-indol-1-yl)pyridin-3-yl)oxy)methyl)piperidine-1-carboxylate;
N-(1-(5-((1-isobutyrylpiperidin-4-yl)oxy)pyridin-2-yl)-1H-indol-5-yl)isobutyramide;
2-Chloro-1-(4-((6-(5-(methylsulfonyl)-1H-indol-1-yl)pyridin-3-yl)oxy)piperidin-1-yl)ethanone;
N-(1-(5-((1-(2,2,2-trifluoro acetyl)piperidin-4-yl)oxy)pyridin-2-yl)-1H-indol-5-yl)isobutyramide;
tert-Butyl-4-((6-(5-(cyclopropanecarboxamido)-1H-indol-1-yl)pyridine-3-yl)oxy)piperidine-1-carboxylate;
tert-Butyl-4-((6-(5-((isopropoxycarbonyl)amino)-1H-indol-1-yl)- pyridin-3-yl)oxy)piperidine-1-carboxylate;
Isopropyl(1-(5-((1-(5-ethylpyrimidin-2-yl)piperidin-4-yl) oxy)pyridin-2-yl)-1H-indol-5-yl)carbamate;
tert-Butyl-4-((6-(5-(N-methylisobutyramido)-1H-indol-1-yl)pyridin-3-yl)oxy)piperidine-1-carboxylate;
Isopropyl(1-(5-((1-(3-isopropyl-1,2,4-oxadiazol-5-yl)piperidin-4-yl)oxy)pyridin-2-yl)-1H-indol-5-yl)carbamate;
N-(1-(5-((1-(5-ethylpyrimidin-2-yl)piperidin-4-yl)oxy) pyridin-2-yl)-1H-indol-5-yl)-N-methylisobutyramide;
Isopropyl(1-(5-((1-(3-methyl-1,2,4-oxadiazol-5-yl)piperidin-4-yl)oxy)pyridin-2-yl)-1H-indol-5-yl)carbamate;
tert-Butyl-4-4(6-(5-(methylsulfonyl)-1H-indol-1-yl)pyridin-3-yl)methyl)amino)piperidine-1-carboxylate;
1-(5-Ethylpyrimidin-2-yl)-N-((6-(5-(methylsulfonyl)-1H-indol-1-yl)pyridin-3-yl)methyl)piperidin-4-amine;
Ethyl (1-(5-((1-(3-methyl-1,2,4-oxadiazol-5-yl)piperidin-4-yl)oxy)pyridin-2-yl)-1H-indol-5-yl)carbamate;
Ethyl (1-(5-((1-(3-isopropyl-1,2,4-oxadiazol-5-yl)piperidin-4-yl)oxy)pyridin-2-yl)-1H-indol-5-yl)carbamate;
Ethyl (1-(5-((1-(3-ethyl-1,2,4-oxadiazol-5-yl)piperidin-4-yl)oxy)pyridin-2-yl)-1H-indol-5-yl)carbamate;
Isopropyl(1-(5-((1-(3-ethyl-1,2,4-oxadiazol-5-yl)piperidin-4-yl)oxy)pyridin-2-yl)-1H-indol-5-yl)carbamate;
3-Ethyl-5-(4-((6-(5-(methylsulfonyl)-1H-indol-1-yl)pyridin-3-yl)oxy)piperidin-1-yl)-1,2,4-oxadiazole;
5-(4-((6-(5-(ethylsulfonyl)-1H-indol-1-yl)pyridin-3-yl) oxy)piperidin-1-yl)-3-methyl-1,2,4-oxadiazole;
3-ethyl-5-(4-((6-(5-(ethylsulfonyl)-1H-indol-1-yl)pyridin-3-yl)oxy)piperidin-1-yl)-1,2,4-oxadiazole;
1-(5-((1-(3-Ethyl-1,2,4-oxadiazol-5-yl)piperidin-4-yl) oxy)pyridin-2-yl)-N,N-dimethyl-1H-indole-5-carboxamide;
1-(5-((1-(3-Isopropyl-1,2,4-oxadiazol-5-yl)piperidin-4-yl)oxy)-pyridin-2-yl)-N,N-dimethyl-1H-indole-5-carboxamide;
Ethyl (1-(5-((1-(3-cyclopropyl-1,2,4-oxadiazol-5-yl)piperidin-4-yl)oxy)pyridin-2-yl)-1H-indol-5-yl)carbamate;
N-(2-hydroxyethyl)-1-(5-((1-(3-isopropyl-1,2,4-oxadiazol-5-yl)piperidin-4-yl)oxy)pyridin-2-yl)-1H-indole-5-carboxamide;
(±)-1-(5-((1-(5-Ethylpyrimidin-2-yl)pyrrolidin-3-yl)oxy) pyridin-2-yl)-N-(2-hydroxyethyl)-1H-indole-5-carboxamide;
(±)-3-Ethyl-5-(3-((6-(5-(methylsulfonyl)-1H-indol-1-yl) pyridin-3-yl)oxy)pyrrolidin-1-yl)-1,2,4-oxadiazole;
5-(Methylsulfonyl)-1-(5-((1-(4-(trifluoromethy)benzyl) piperidin-4-yl)oxy)pyridin-2-yl)-1H-indole;
tert-Butyl-4-((6-(5-methoxy-1H-indol-pyridin-3-yl)oxy)-piperidine-1-carboxylate;
(±)-3-Isopropyl-5-(3-((6-(5-(methylsulfonyl)-1H-indol-1-yl)pyridin-3-yl)oxy)pyrrolidin-1-yl)-1,2,4-oxadiazole;
1-(5-((1-(5-Ethylpyrimidin-2-yl)piperidin-4-yl)oxy)pyridin-2-yl)-5-methoxy-1H-indole;
(±)-3-Ethyl-5-((3-((6-(5-(methylsulfonyl)-1H-indol-1-yl) pyridin-3-yl)oxy)pyrrolidin-1-yl)methyl)-1,2,4-oxadiazole;
(±)-3-Isopropyl-5-((3-((6-(5-(methylsulfonyl)-1H-indol-1-yl)pyridin-3-yl)oxy)pyrrolidin-1-yl)methyl)-1,2,4-oxadiazole;
3-Isopropyl-5-((3-((6-(5-(methylsulfonyl)-1H-indol-1-yl) pyridin-3-yl)oxy)azetidin-1-yl)methyl)-1,2,4-oxadiazole;
3-Ethyl-5-((3-((6-(5-(methylsulfonyl)-1H-indol-1-yl)pyridin-3-yl)oxy)azetidin-1-yl)methyl)-1,2,4-oxadiazole;
1-(5-((1-(2-Fluoro-2-methylpropyl)piperidin-4-yl)oxy) pyridin-2-yl)-N-(2-hydroxyethyl)-1H-indole-5-carboxamide;
tert-Butyl-4-((6-(5-(2-oxooxazolidin-3-yl)-1H-indol-1-yl)pyridin-3-yl)oxy)piperidine-1-carboxylate;
Isopropyl 4-((6-(5-(2-oxooxazolidin-3-yl)-1H-indol-1-yl) pyridin-3-yl)oxy)piperidine-1-carboxylate;
tert-Butyl-4-((6-(3-methyl-5-(methylsulfonyl)-1H-indol-1-yl)pyridin-3-yl)oxy)piperidine-1-carboxylate;
1-(5-((1-(5-Ethylpyrimidin-2-yl)piperidin-4-yl)oxy)pyridin-2-yl)-3-methyl-5-(methylsulfonyl)-1H-indole;
Isopropyl 4-((6-(5-(methylsulfonyl)-1H-indol-1-yl)-pyridin-3-yl)oxy)piperidine-1-carboxylate;
Isopropyl 4-((6-(7-fluoro-5-(methylsulfonyl)-1H-indol-1-yl)pyridin-3-yl)oxy)piperidine-1-carboxylate;
1-(5-((1-(5-Ethylpyrimidin-2-yl)piperidin-4-yl)oxy)pyridin-2-yl)-7-fluoro-5-(methylsulfonyl)-1H-indole;

2,2,2-Trifluoro-1-(4-((6-(5-(methylsulfonyl)-1H-indol-1-yl)pyridin-3-yl)oxy)piperidin-1-yl)ethanone;
(4-((6-(5-(Methylsulfonyl)-1H-indol-1-yl)pyridin-3-yl)oxy)piperidin-1-yl)(1-(trifluoromethyl)cyclopropyl)methanone;
5-(4-((6-(7-Fluoro-5-(methylsulfonyl)-1H-indol-1-yl)pyridin-3-yl)oxy)piperidin-1-yl)-3-isopropyl-1,2,4-oxadiazole;
tert-Butyl-4-((6-(5-(2-oxopyrrolidin-1-yl)-1H-indol-1-yl)pyridin-3-yl)oxy)piperidine-1-carboxylate;
1-(1-(5-((1-(5-Ethylpyrimidin-2-yl)piperidin-4-yl)oxy)pyridin-2-yl)-1H-indol-5-yl)pyrrolidin-2-one;
tert-Butyl-4-((6-(5-cyano-7-fluoro-1H-indol-1-yl)pyridin-3-yl)oxy)-piperidine-1-carboxylate;
1-(5-((1-(5-((1-(5-Ethylpyrimidin-2-yl)piperidin-4-yl)oxy)pyridin-2-yl)-7-fluoro-1H-indole-5-carbonitrile;
Ethyl 4-((6-(5-(2-oxopyrrolidin-1-yl)-H-indol-1-yl)pyridin-3-yl)oxy)piperidine-1-carboxylate;
tert-Butyl-4-((6-(5-(cyclopropylsulfonyl)-1H-indol-1-yl)pyridin-3-yl)oxy)piperidine-1-carboxylate;
5-(Cyclopropylsulfonyl)-1-(5-((1-(5-ethylpyrimidin-2-yl)piperidin-4-yl)oxy)pyridin-2-yl)-1H-indole;
Ethyl-4-((6-(5-(methylsulfonyl)-1H-indol-1-yl)pyridin-3-yl)oxy)-piperidine-1-carboxylate;
tert-Butyl-4-((6-(5-(1H-tetrazol-1-yl)-1H-indol-1-yl)pyridin-3-yl)oxy)piperidine-1-carboxylate;
Ethyl-4-((6-(5-(1H-tetrazol-1-yl)-1H-indol-1-yl)pyridin-3-yl)oxy)-piperidine-1-carboxylate;
Ethyl (1-(5-((1-(5-ethylpyrimidin-2-yl)piperidin-4-yl)oxy)pyridin-2-yl)-1H-indol-5-yl)(methyl)carbamate;
tert-Buty 4-((6-(5-(1H-1,2,4-triazol-1-yl)-1H-indol-1-yl)pyridin-3-yl)oxy)piperidine-1-carboxylate;
1-(5-((1-(5-Ethylpyrimidin-2-yl)piperidin-4-yl)oxy)pyridin-2-yl)-5-(1H-1,2,4-triazol-1-yl)-1H-indole;
Isopropyl 4-((6-(5-(1H-1,2,4-triazol-1-yl)-1H-indol-1-yl)pyridin-3-yl)oxy)piperidine-1-carboxylate;
Ethyl-4-((6-(5-(1H-1,2,4-triazol-1-yl)-1H-indol-1-yl)pyridin-3-yl)oxy)piperidine-1-carboxylate;
5-(methylsulfonyl)-1-(5-((1-((1-(trifluoromethyl)cyclopropyl)methyl)-piperidin-4-yl)oxy)pyridin-2-yl)-1H-indole;
3-(1-(5-((1-(4-Ethylphenyl)piperidin-4-yl)oxy)pyridin-2-yl)-1H-indol-5-yl)oxazolidin-2-one;
5-(Methylsulfonyl)-1-(5-((1-(4-(trifluoromethyl)phenyl)piperidin-4-yl)oxy)pyridin-2-yl)-1H-indole;
1-(4-((6-(5-(Methylsulfonyl)-1H-indol-1-yl)pyridin-3-yl)oxy)-piperidin-1-yl)-2-(pyrrolidin-1-yl)ethanone;
1-(4-((6-(5-(Methylsulfonyl)-1H-indol-1-yl)pyridin-3-yl)oxy)-piperidin-1-yl)-2-(piperidin-1-yl)ethanone;
1-(4-((6-(5-(methylsulfonyl)-1H-indol-1-yl)pyridin-3-yl)oxy)-piperidin-1-yl)-2-morpholinoethanone;
5-(methylsulfonyl)-1-(5-((1-(2,2,2-trifluoroethyl)piperidin-4-yl)oxy)pyridin-2-yl)-1H-indole;
2-(4-((6-(5-(methylsulfonyl)-1H-indol-1-yl)pyridin-3yl)oxy)piperidin-1-yl)-1-(pyrrolidin-1-yl)ethanone;
2-Cyclopentyl-1-(4-((6-(5-(methylsulfonyl)-1H-indol-1-yl)pyridin-3-yl)oxy)piperidin-1-yl)ethanone;
Cyclobutyl(4-((6-(5-(methylsulfonyl)-1H-indol-1-yl)pyridin-3-yl) oxy)piperidin-1-yl)methanone;
Cyclopentyl(4-((6-(5-(methylsulfonyl)-1H-indol-1-yl)pyridin-3-yl)oxy)piperidin-1-yl)methanone;
Cyclohexyl(4-((6-(5-(methylsulfonyl)-1H-indol-1-yl)pyridin-3-yl)oxy)piperidin-1-yl)methanone;
1-(5-((1-(2,2-Difluoropropyl)piperidin-4-yl)oxy)pyridin-2-yl)-5-(methylsulfonyl)-1H-indole;
1-(5-((1-((1-Fluorocyclopentyl)methyl)piperidin-4-yl)oxy)pyridin-2-yl)-5-(methylsulfonyl)-1H-indole;
1-(5-((1-((1-Fluorocyclobutyl)methyl)piperidin-4-yl)oxy)pyridin-2-yl)-5-(methylsulfonyl)-1H-indole;
1-(5-((1-(2-Fluoro-2-methylpropyl)piperidin-4-yl)oxy)pyridin-2-yl)-5-(methylsulfonyl)-1H-indole;
1-(5-((1-((5-Fluoropyridin-2-yl)methyl)piperidin-4-yl)oxy)pyridin-2-yl)-5-(methylsulfonyl)-1H-indole;
1-(Furan-2-yl)-2-(4-((6-(5-(methylsulfonyl)-1H-indol-1-yl)pyridin-3-yl)oxy)piperidin-1-yl)ethanone;
3-((6-(5-(Methylsulfonyl)-1H-indol-1-yl)pyridin-3-yl)oxy)-6-((1-(trifluoromethyl)cyclopropyl)methyl)-6-azabicyclo[3.1.1]heptanes;
5-(Methylsulfonyl)-1-(5-((8-(2,2,2-trifluoroethyl)-8-azabicyclo[3.2.1]octan-3-yl)oxy)pyridin-2-yl)-1H-indole;
(4-((6-(5-(Methylsulfonyl)-1H-indol-1-yl)pyridin-3-yl)oxy)piperidin-1-yl)(pyrrolidin-1-yl)methanone;
N,N-Diethyl-4-((6-(5-(methylsulfonyl)-1H-indol-1-yl)pyridin-3-yl)oxy)piperidine-1-carboxamide;
5-(Methylsulfonyl)-1-(5-((1-(4,4,4-trifluoro-2-methylbutan-2-yl)piperidin-4-yl)oxy)pyridin-2-yl)-1H-indole;
1-(5-((1-(1,1-Difluoro-2-methylpropyl)piperidin-4-yl)oxy)pyridin-2-yl)-5-(methylsulfonyl)-1H-indole;
1,3-Difluoropropan-2-yl 4-((6-(5-(methylsulfonyl)-1H-indol-1-yl)pyridin-3-yl)oxy)piperidine-1-carboxylate;
3-Fluoro-3-methyl-1-(4-((6-(5-(methylsulfonyl)-1H-indol-1-yl)pyridin-3-yl)oxy)piperidin-1-yl)butan-1-one;
3-Fluoro-1-(5-((1-isobutylpiperidin-4-yl)oxy)pyridin-2-yl)-5-(methylsulfonyl)-1H-indole;
1-(5-((1-Isobutyl-2,6-dimethylpiperidin-4-yl)oxy)pyridin-2-yl)-5-(methylsulfonyl)-1H-indole;
5-(Methylsulfonyl)-1-(5-((1-(2-(pyrrolidin-1-yl)ethyl)piperidin-4-yl)oxy)pyridin-2-yl)-1H-indole;
1-(5-((1-Isopropylpiperidin-4-yl)oxy)pyridin-2-yl)-5-(methylsulfonyl)-1H-indole;
1-(5-((1-(2-Methoxyethyl)piperidin-4-yl)oxy)pyridin-2-yl)-5-(methylsulfonyl)-1H-indole;
5-(Methylsulfonyl)-1-(5-((1-propylpiperidin-4-yl)oxy)pyridin-2-yl)-1H-indole;
3-(4-((6-(5-(Methylsulfonyl)-1H-indol-1-yl)pyridin-3-yl)oxy)piperidin-1-yl)butan-2-one;
1-(5-((1-Cyclobutylpiperidin-4-yl)oxy)pyridin-2-yl)-5-(methylsulfonyl)-1H-indole;
1,1,1-Trifluoro-3-(4-((6-(5-(methylsulfonyl)-1H-indol-1-yl)pyridin-3-yl)oxy)piperidin-1-yl)propan-2-one;
5-(Methylsulfonyl)-1-(5-((1-(pentan-3-yl)piperidin-4-yl)oxy)pyridin-2-yl)-1H-indole;
Isobutyl 4-((6-(5-(methylsulfonyl)-1H-indol-1-yl)pyridin-3-yl)oxy)piperidine-1-carboxylate;
2-Methoxyethyl 4-((6-(5-(methylsulfonyl)-1H-indol-1-yl)pyridin-3-yl)oxy)piperidine-1-carboxylate;
Neopentyl 4-((6-(5-(methylsulfonyl)-1H-indol-1-yl)pyridin-3-yl)oxy)piperidine-1-carboxylate;
Cyclohexyl 4-((6-(5-(methylsulfonyl)-1H-indol-1-yl)pyridin-3-yl)oxy)piperidine-1-carboxylate;
Cyclobutyl(4-((6-(5-(methylsulfonyl)-1H-indol-1-yl)pyridin-3-yl)oxy)piperidin-1-yl)methanone;
2-(Dimethylamino)-1-(4-((6-(5-(methylsulfonyl)-1H-indol-1-yl)pyridin-3-yl)oxy)piperidin-1-yl)ethanone;
Cyclopentyl(4-((6-(5-(methylsulfonyl)-1H-indol-1-yl)pyridin-3-yl)oxy)piperidin-1-yl)methanone;
Furan-2-yl(4-((6-(5-(methylsulfonyl)-1H-indol-1-yl)pyridin-3-yl)oxy)piperidin-1-yl)methanone;
1-(5-((1-(5-Ethylpyrazin-2-yl)piperidin-4-yl)oxy)pyridin-2-yl)-5-(methylsulfonyl)-1H-indole;
3-(1-(4-((6-(5-(Methylsulfonyl)-1H-indol-1-yl)pyridin-3-yl)oxy)piperidin-1-yl)ethyl)-6-oxa-3-azabicyclo[3.1.1]heptanes;

6-(1-(4-((6-(5-(Methylsulfonyl)-1H-indol-1-yl)pyridin-3-yl)oxy)piperidin-1-yl)ethyl)-2-oxa-6-azaspiro[3.3]heptanes;
4-(2-(4-((6-(5-(Methylsulfonyl)-1H-indol-1-yl)pyridin-3-yl)oxy)piperidin-1-yl)ethyl)morpholine;
N,N-Dimethyl-2-(4-((6-(5-(methylsulfonyl)-1H-indol-1-yl)pyridin-3-yl)oxy)piperidin-1-yl)acetamide;
Cyclohexyl(4-((6-(5-(methylsulfonyl)-1H-indol-1-yl)pyridin-3-yl)oxy)piperidin-1-yl)methanone;
Cyclopropyl(4-((6-(5-(methylsulfonyl)-1H-indol-1-yl)pyridin-3-yl)oxy)piperidin-1-yl)methanone;
1-(5-((1-Cyclopentylpiperidin-4-yl)oxy)pyridin-2-yl)-5-(methylsulfonyl)-1H-indole;
1-(5-((1-Cyclohexylpiperidin-4-yl)oxy)pyridin-2-yl)-5-(methylsulfonyl)-1H-indole;
1-(5-((1-(Cyclopropylmethyl)piperidin-4-yl)oxy)pyridin-2-yl)-5-(methylsulfonyl)-1H-indole;
1-(5-((1-(Cyclohexylmethyl)piperidin-4-yl)oxy)pyridin-2-yl)-5-(methylsulfonyl)-1H-indole;
1-(5-((1-(Cyclobutylmethyl)piperidin-4-yl)oxy)pyridin-2-yl)-5-(methylsulfonyl)-1H-indole;
1-(5-((1-(4-Chlorobenzyl)piperidin-4-yl)oxy)pyridin-2-yl)-5-(methylsulfonyl)-1H-indole;
1-(5-((1-Benzylpiperidin-4-yl)oxy)pyridin-2-yl)-5-(methylsulfonyl)-1H-indole; 1-(5-((1-Cyclopropylpiperidin-4-yl)oxy)pyridin-2-yl)-5-(methylsulfonyl)-1H-indole;
Cyclopropyl 4-((6-(5-(methylsulfonyl)-1H-indol-1-yl)pyridin-3-yl)oxy)piperidine-1-carboxylate;
2-Fluoroethyl 4-((6-(5-(methylsulfonyl)-1H-indol-1-yl)pyridin-3-yl)oxy)piperidine-1-carboxylate;
Azetidin-1-yl(1-(5-((1-(cyclobutylmethyl)piperidin-4-yl)oxy)pyridin-2-yl)-1H-indol-5-yl)methanone;
Azetidin-1-yl(1-(5-((1-(1,1-difluoroethyl)piperidin-4-yl)oxy)pyridin-2-yl)-1H-indol-5-yl)methanone;
Azetidin-1-yl(1-(5-((1-((1-fluorocyclopentyl)methyl)piperidin-4-yl)oxy)pyridin-2-yl)-1H-indol-5-yl)methanone;
Azetidin-1-yl(1-(5-((1-((1-fluorocyclobutyl)methyl)piperidin-4-yl)oxy)pyridin-2-yl)-1H-indol-5-yl)methanone;
Azetidin-1-yl(1-(5-((1-(2-fluoro-2-methylpropyl)piperidin-4-yl)oxy)pyridin-2-yl)-1H-indol-5-yl)methanone;
Azetidin-1-yl(1-(5-((1-((5-fluoropyridin-2-yl)methyl)piperidin-4-yl)oxy)pyridin-2-yl)-1H-indol-5-yl)methanone;
1-(4-((6-(5-(Azetidine-1-carbonyl)-1H-indol-1-yl)pyridin-3-yl)oxy)piperidin-1-yl)-2-(furan-2-yl)ethanone;
1,3-Difluoropropan-2-yl 4-((6-(5-(azetidine-1-carbonyl)-1H-indol-1-yl)pyridin-3-yl)oxy)piperidine-1-carboxylate;
Azetidin-1-yl(1-(5-((1-(pyrrolidine-1-carbonyl)piperidin-4-yl)oxy)pyridin-2-yl)-1H-indol-5-yl)methanone;
4-((6-(5-(Azetidine-1-carbonyl)-1H-indol-1-yl)pyridin-3-yl)oxy)-N,N-diethylpiperidine-1-carboxamide;
Azetidin-1-yl(1-(5-((1-(4,4,4-trifluoro-2-methylbutan-2-yl)piperidin-4-yl)oxy)pyridin-2-yl)-1H-indol-5-yl)methanone;
Azetidin-1-yl(1-(5-((1-(1,1-difluoro-2-methylpropyl)piperidin-4-yl)oxy)pyridin-2-yl)-1H-indol-5-yl)methanone;
1-(4-((6-(5-(Azetidine-1-carbonyl)-1H-indol-1-yl)pyridin-3-yl)oxy)piperidin-1-yl)-3,3-difluorobutan-1-one;
Azetidin-1-yl(1-(5-((1-isobutylpiperidin-4-yl)oxy)pyridin-2-yl)-1H-indol-5-yl)methanone;
Azetidin-1-yl(1-(5-((1-(2-(pyrrolidin-1-yl)ethyl)piperidin-4-yl)oxy)pyridin-2-yl)-1H-indol-5-yl)methanone;
Azetidin-1-yl(1-(5-((1-isopropylpiperidin-4-yl)oxy)pyridin-2-yl)-1H-indol-5-yl)methanone;
Azetidin-1-yl(1-(5-((1-propylpiperidin-4-yl)oxy)pyridin-2-yl)-1H-indol-5-yl)methanone;
Azetidin-1-yl(1-(5-((1-cyclopropylpiperidin-4-yl)oxy)pyridin-2-yl)-1H-indol-5-yl)methanone;
Azetidin-1-yl(1-(5-((1-cyclobutylpiperidin-4-yl)oxy)pyridin-2-yl)-1H-indol-5-yl)methanone;
Azetidin-1-yl(1-(5-((1-cyclopentylpiperidin-4-yl)oxy)pyridin-2-yl)-1H-indol-5-yl)methanone;
Azetidin-1-yl(1-(5-((1-cyclohexylpiperidin-4-yl)oxy)pyridin-2-yl)-1H-indol-5-yl)methanone;
Azetidin-1-yl(1-(5-((1-(cyclohexylmethyl)piperidin-4-yl)oxy)pyridin-2-yl)-1H-indol-5-yl)methanone;
Azetidin-1-yl(1-(5-((1-(2-methoxyethyl)piperidin-4-yl)oxy)pyridin-2-yl)-1H-indol-5-yl)methanone;
2-Methoxyethyl 4-((6-(5-(azetidine-1-carbonyl)-1H-indol-1-yl)pyridin-3-yl)oxy)piperidine-1-carboxylate;
3-(4-((6-(5-(Azetidine-1-carbonyl)-1H-indol-1-yl)pyridin-3-yl)oxy)piperidin-1-yl)butan-2-one;
3-(4-((6-(5-(Azetidine-1-carbonyl)-1H-indol-1-yl)pyridin-3-yl)oxy)piperidin-1-yl)-1,1,1-trifluoropropan-2-one
Azetidin-1-yl(1-(5-((1-(cyclopropylmethyl)piperidin-4-yl)oxy)pyridin-2-yl)-1H-indol-5-yl)methanone;
Azetidin-1-yl(1-(5-((1-(cyclobutylmethyl)piperidin-4-yl)oxy)pyridin-2-yl)-1H-indol-5-yl)methanone;
Azetidin-1-yl(1-(5-((1-(pentan-3-yl)piperidin-4-yl)oxy)pyridin-2-yl)-1H-indol-5-yl)methanone;
Neopentyl 4-((6-(5-(azetidine-1-carbonyl)-1H-indol-1-yl)pyridin-3-yl)oxy)piperidine-1-carboxylate;
Cyclohexyl 4-((6-(5-(azetidine-1-carbonyl)-1H-indol-1-yl)pyridin-3-yl)oxy)piperidine-1-carboxylate;
Cyclopropyl 4-((6-(5-(azetidine-1-carbonyl)-1H-indol-1-yl)pyridin-3-yl)oxy)piperidine-1-carboxylate;
2-Fluoroethyl 4-((6-(5-(azetidine-1-carbonyl)-1H-indol-1-yl)pyridin-3-yl)oxy)piperidine-1-carboxylate;
Azetidin-1-yl(1-(5-((1-(cyclopropanecarbonyl)piperidin-4-yl)oxy)pyridin-2-yl)-1H-indol-5-yl)methanone;
Azetidin-1-yl(1-(5-((1-(cyclobutanecarbonyl)piperidin-4-yl)oxy)pyridin-2-yl)-1H-indol-5-yl)methanone;
Azetidin-1-yl(1-(5-((1-(cyclopentanecarbonyl)piperidin-4-yl)oxy)pyridin-2-yl)-1H-indol-5-yl)methanone;
Azetidin-1-yl(1-(5-((1-(5-ethylpyrazin-2-yl)piperidin-4-yl)oxy)pyridin-2-yl)-1H-indol-5-yl)methanone;
Azetidin-1-yl(1-(5-((1-(2-morpholinoethyl)piperidin-4-yl)oxy)pyridin-2-yl)-1H-indol-5-yl)methanone;
2-(4-((6-(5-(Azetidine-1-carbonyl)-1H-indol-1-yl)pyridin-3-yl)oxy)piperidin-1-yl)-N,N-dimethylacetamide;
Azetidin-1-yl(1-(5-((1-(morpholinomethyl)piperidin-4-yl)oxy)pyridin-2-yl)-1H-indol-5-yl)methanone;
(1-(5-((1-(1-(6-Oxa-3-azabicyclo[3.1.1]heptan-3-yl)ethyl)piperidin-4-yl)oxy)pyridin-2-yl)-1H-indol-5-yl)(azetidin-1-yl)methanone;
(1-(5-((1-(1-(2-Oxa-6-azaspiro[3.3]heptan-6-yl)ethyl)piperidin-4-yl)oxy)pyridin-2-yl)-1H-indol-5-yl)(azetidin-1-yl)methanone;
Azetidin-1-yl(1-(5-((1-((1S,4R)-bicyclo[2.2.1]heptan-2-yl)piperidin-4-yl)oxy)pyridin-2-yl)-1H-indol-5-yl)methanone;
Azetidin-1-yl(1-(5-((1-(isopropylsulfonyl)piperidin-4-yl)oxy)pyridin-2-yl)-1H-indol-5-yl)methanone;
Azetidin-1-yl(1-(5-((1-(cyclopropylsulfonyl)piperidin-4-yl)oxy)pyridin-2-yl)-1H-indol-5-yl)methanone;
Azetidin-1-yl(1-(5-((1-(methylsulfonyl)piperidin-4-yl)oxy)pyridin-2-yl)-1H-indol-5-yl)methanone;

Azetidin-1-yl(1-(5-((1-(ethylsulfonyl)piperidin-4-yl)oxy)pyridin-2-yl)-1H-indol-5-yl)methanone;
Azetidin-1-yl(1-(5-((1-(3,3,3-trifluoro-2,2-dimethylpropyl)piperidin-4-yl)oxy)pyridin-2-yl)-1H-indol-5-yl)methanone;
Azetidin-1-yl(1-(5-((1-((1-(trifluoromethyl)cyclopropyl)methyl)piperidin-4-yl)oxy)pyridin-2-yl)-1H-indol-5-yl)methanone;
Azetidin-1-yl(1-(5-((1-((1-(trifluoromethyl)cyclobutyl)methyl)piperidin-4-yl)oxy)pyridin-2-yl)-1H-indol-5-yl)methanone;
Azetidin-1-yl(1-(5-((1-isobutylpiperidin-4-yl)oxy)pyridin-2-yl)-1H-indol-5-yl)methanone;
Azetidin-1-yl(1-(5-((1-isobutylpiperidin-4-yl)oxy)pyridin-2-yl)-1H-indol-5-yl)methanone;
(1-(5-((1-(1,1-Difluoroethyl)piperidin-4-yl)oxy)pyridin-2-yl)-1H-indol-5-yl)(pyrrolidin-1-yl)methanone;
(1-(5-((1-((1-Fluorocyclopentyl)methyl)piperidin-4-yl)oxy)pyridin-2-yl)-1H-indol-5-yl)(pyrrolidin-1-yl)methanone;
(1-(5-((1-((1-Fluorocyclobutyl)methyl)piperidin-4-yl)oxy)pyridin-2-yl)-1H-indol-5-yl)(pyrrolidin-1-yl)methanone;
(1-(5-((1-(2-Fluoro-2-methylpropyl)piperidin-4-yl)oxy)pyridin-2-yl)-1H-indol-5-yl)(pyrrolidin-1-yl)methanone;
(1-(5-((1-((5-Fluoropyrimidin-2-yl)methyl)piperidin-4-yl)oxy)pyridin-2-yl)-1H-indol-5-yl)(pyrrolidin-1-yl)methanone;
2-(Furan-2-yl)-1-(4-((6-(5-(pyrrolidine-1-carbonyl)-1H-indol-1-yl)pyridin-3-yl)oxy)piperidin-1-yl)ethanone;
1,3-Difluoropropan-2-yl 4-((6-(5-(pyrrolidine-1-carbonyl)-1H-indol-1-yl)pyridin-3-yl)oxy)piperidine-1-carboxylate;
Pyrrolidin-1-yl(4-((6-(5-(pyrrolidine-1-carbonyl)-1H-indol-1-yl)pyridin-3-yl)oxy)piperidin-1-yl)methanone;
N,N-Diethyl-4-((6-(5-(pyrrolidine-1-carbonyl)-1H-indol-1-yl)pyridin-3-yl)oxy)piperidine-1-carboxamide;
Pyrrolidin-1-yl(1-(5-((1-(4,4,4-trifluoro-2-methylbutan-2-yl)piperidin-4-yl)oxy)pyridin-2-yl)-1H-indol-5-yl)methanone;
(1-(5-((1-(1,1-Difluoro-2-methylpropyl)piperidin-4-yl)oxy)pyridin-2-yl)-1H-indol-5-yl)(pyrrolidin-1-yl)methanone;
3,3-Difluoro-1-(4-((6-(5-(pyrrolidine-1-carbonyl)-1H-indol-1-yl)pyridin-3-yl)oxy)piperidin-1-yl)butan-1-one;
(1-(5-((1-Isobutylpiperidin-4-yl)oxy)pyridin-2-yl)-1H-indol-5-yl)(pyrrolidin-1-yl)methanone;
Pyrrolidin-1-yl(1-(5-((1-(2-(pyrrolidin-1-yl)ethyl)piperidin-4-yl)oxy)pyridin-2-yl)-1H-indol-5-yl)methanone;
(1-(5-((1-Isopropylpiperidin-4-yl)oxy)pyridin-2-yl)-1H-indol-5-yl)(pyrrolidin-1-yl)methanone;
(1-(5-((1-Cyclopropylpiperidin-4-yl)oxy)pyridin-2-yl)-1H-indol-5-yl)(pyrrolidin-1-yl)methanone;
(1-(5-((1-Cyclobutylpiperidin-4-yl)oxy)pyridin-2-yl)-1H-indol-5-yl)(pyrrolidin-1-yl)methanone;
(1-(5-((1-Cyclopentylpiperidin-4-yl)oxy)pyridin-2-yl)-1H-indol-5-yl)(pyrrolidin-1-yl)methanone;
(1-(5-((1-Cyclohexylpiperidin-4-yl)oxy)pyridin-2-yl)-1H-indol-5-yl)(pyrrolidin-1-yl)methanone;
(1-(5-((1-(Cyclohexylmethyl)piperidin-4-yl)oxy)pyridin-2-yl)-1H-indol-5-yl)(pyrrolidin-1-yl)methanone;
(1-(5-((1-(2-Methoxyethyl)piperidin-4-yl)oxy)pyridin-2-yl)-1H-indol-5-yl)(pyrrolidin-1-yl)methanone;
Pyrrolidin-1-yl(1-(5-((1-(cyclobutylmethyl)piperidin-4-yl)oxy)pyridin-2-yl)-1H-indol-5-yl)methanone;
Pyrrolidin-1-yl(1-(5-((1-(1,1-difluoroethyl)piperidin-4-yl)oxy)pyridin-2-yl)-1H-indol-5-yl)methanone;
Pyrrolidin-1-yl(1-(5-((1-((1-fluorocyclopentyl)methyl)piperidin-4-yl)oxy)pyridin-2-yl)-1H-indol-5-yl)methanone;
Pyrrolidin-1-yl(1-(5-((1-((1-fluorocyclobutyl)methyl)piperidin-4-yl)oxy)pyridin-2-yl)-1H-indol-5-yl)methanone;
Pyrrolidin-1-yl(1-(5-((1-(2-fluoro-2-methylpropyl)piperidin-4-yl)oxy)pyridin-2-yl)-1H-indol-5-yl)methanone;
Pyrrolidin-1-yl(1-(5-((1-((5-fluoropyridin-2-yl)methyl)piperidin-4-yl)oxy)pyridin-2-yl)-1H-indol-5-yl)methanone;
1-(4-((6-(5-(Azetidine-1-carbonyl)-1H-indol-1-yl)pyridin-3-yl)oxy)piperidin-1-yl)-2-(furan-2-yl)ethanone;
1,3-Difluoropropan-2-yl 4-((6-(5-(azetidine-1-carbonyl)-1H-indol-1-yl)pyridin-3-yl)oxy)piperidine-1-carboxylate;
Pyrrolidin-1-yl(1-(5-((1-(pyrrolidine-1-carbonyl)piperidin-4-yl)oxy)pyridin-2-yl)-1H-indol-5-yl)methanone;
4-((6-(5-(Azetidine-1-carbonyl)-1H-indol-1-yl)pyridin-3-yl)oxy)-N,N-diethylpiperidine-1-carboxamide;
Pyrrolidin-1-yl(1-(5-((1-(4,4,4-trifluoro-2-methylbutan-2-yl)piperidin-4-yl)oxy)pyridin-2-yl)-1H-indol-5-yl)methanone;
Pyrrolidin-1-yl(1-(5-((1-(1,1-difluoro-2-methylpropyl)piperidin-4-yl)oxy)pyridin-2-yl)-1H-indol-5-yl)methanone;
1-(4-((6-(5-(Azetidine-1-carbonyl)-1H-indol-1-yl)pyridin-3-yl)oxy)piperidin-1-yl)-3,3-difluorobutan-1-one;
Pyrrolidin-1-yl(1-(5-((1-isobutylpiperidin-4-yl)oxy)pyridin-2-yl)-1H-indol-5-yl)methanone;
Pyrrolidin-1-yl(1-(5-((1-(2-(pyrrolidin-1-yl)ethyl)piperidin-4-yl)oxy)pyridin-2-yl)-1H-indol-5-yl)methanone;
Pyrrolidin-1-yl(1-(5-((1-isopropylpiperidin-4-yl)oxy)pyridin-2-yl)-1H-indol-5-yl)methanone;
Pyrrolidin-1-yl(1-(5-((1-propylpiperidin-4-yl)oxy)pyridin-2-yl)-1H-indol-5-yl)methanone;
Pyrrolidin-1-yl(1-(5-((1-cyclopropylpiperidin-4-yl)oxy)pyridin-2-yl)-1H-indol-5-yl)methanone;
Pyrrolidin-1-yl(1-(5-((1-cyclobutylpiperidin-4-yl)oxy)pyridin-2-yl)-1H-indol-5-yl)methanone;
Pyrrolidin-1-yl(1-(5-((1-cyclopentylpiperidin-4-yl)oxy)pyridin-2-yl)-1H-indol-5-yl)methanone;
Pyrrolidin-1-yl(1-(5-((1-cyclohexylpiperidin-4-yl)oxy)pyridin-2-yl)-1H-indol-5-yl)methanone;
Pyrrolidin-1-yl(1-(5-((1-(cyclohexylmethyl)piperidin-4-yl)oxy)pyridin-2-yl)-1H-indol-5-yl)methanone;
Pyrrolidin-1-yl(1-(5-((1-(2-methoxyethyl)piperidin-4-yl)oxy)pyridin-2-yl)-1H-indol-5-yl)methanone;
2-Methoxyethyl 4-((6-(5-(azetidine-1-carbonyl)-1H-indol-1-yl)pyridin-3-yl)oxy)piperidine-1-carboxylate;
3-(4-((6-(5-(Pyrrolidin-1-carbonyl)-1H-indol-1-yl)pyridin-3-yl)oxy)piperidin-1-yl)butan-2-one;
3-(4-((6-(5-(Pyrrolidin-1-carbonyl)-1H-indol-1-yl)pyridin-3-yl)oxy)piperidin-1-yl)-1,1,1-trifluoropropan-2-one;
Pyrrolidin-1-yl(1-(5-((1-(cyclopropylmethyl)piperidin-4-yl)oxy)pyridin-2-yl)-1H-indol-5-yl)methanone;
Pyrrolidin-1-yl(1-(5-((1-(cyclobutylmethyl)piperidin-4-yl)oxy)pyridin-2-yl)-1H-indol-5-yl)methanone;
Pyrrolidin-1-yl(1-(5-((1-(pentan-3-yl)piperidin-4-yl)oxy)pyridin-2-yl)-1H-indol-5-yl)methanone;
Neopentyl 4-((6-(5-(pyrrolidine-1-carbonyl)-1H-indol-1-yl)pyridin-3-yl)oxy)piperidine-1-carboxylate;
Cyclohexyl 4-((6-(5-(pyrrolidine-1-carbonyl)-1H-indol-1-yl)pyridin-3-yl)oxy)piperidine-1-carboxylate;

Cyclopropyl 4-((6-(5-(pyrrolidin-1-carbonyl)-1H-indol-1-yl)pyridin-3-yl)oxy)piperidine-1-carboxylate;
2-Fluoroethyl 4-((6-(5-(pyrrolidin-1-carbonyl)-1H-indol-1-yl)pyridin-3-yl)oxy)piperidine-1-carboxylate;
Pyrrolidin-1-yl(1-(5-((1-(cyclopropanecarbonyl)piperidin-4-yl)oxy)pyridin-2-yl)-1H-indol-5-yl)methanone;
Pyrrolidin-1-yl(1-(5-((1-(cyclobutanecarbonyl)piperidin-4-yl)oxy)pyridin-2-yl)-1H-indol-5-yl)methanone;
Pyrrolidin-1-yl(1-(5-((1-(cyclopentanecarbonyl)piperidin-4-yl)oxy)pyridin-2-yl)-1H-indol-5-yl)methanone;
Pyrrolidin-1-yl(1-(5-((1-(5-ethylpyrazin-2-yl)piperidin-4-yl)oxy)pyridin-2-yl)-1H-indol-5-yl)methanone;
Pyrrolidin-1-yl(1-(5-((1-(2-morpholinoethyl)piperidin-4-yl)oxy)pyridin-2-yl)-1H-indol-5-yl)methanone;
2-(4-((6-(5-(Pyrrolidin-1-carbonyl)-1H-indol-1-yl)pyridin-3-yl)oxy)piperidin-1-yl)-N,N-dimethylacetamide;
Pyrrolidin-1-yl(1-(5-((1-(morpholinomethyl)piperidin-4-yl)oxy)pyridin-2-yl)-1H-indol-5-yl)methanone;
(1-(5-((1-(1-(6-Oxa-3-azabicyclo[3.1.1]heptan-3-yl)ethyl)piperidin-4-yl)oxy)pyridin-2-yl)-1H-indol-5-yl)(pyrrolidin-1-yl)methanone;
(1-(5-((1-(1-(2-Oxa-6-azaspiro[3.3]heptan-6-yl)ethyl)piperidin-4-yl)oxy)pyridin-2-yl)-1H-indol-5-yl)(pyrrolidin-1-yl)methanone;
Pyrrolidin-1-yl(1-(5-((1-((1S,4R)-bicyclo[2.2.1]heptan-2-yl)piperidin-4-yl)oxy)pyridin-2-yl)-1H-indol-5-yl)methanone;
Pyrrolidin-1-yl(1-(5-((1-(isopropylsulfonyl)piperidin-4-yl)oxy)pyridin-2-yl)-1H-indol-5-yl)methanone;
Pyrrolidin-1-yl(1-(5-((1-(cyclopropylsulfonyl)piperidin-4-yl)oxy)pyridin-2-yl)-1H-indol-5-yl)methanone;
Pyrrolidin-1-yl(1-(5-((1-(methylsulfonyl)piperidin-4-yl)oxy)pyridin-2-yl)-1H-indol-5-yl)methanone;
Pyrrolidin-1-yl(1-(5-((1-(ethylsulfonyl)piperidin-4-yl)oxy)pyridin-2-yl)-1H-indol-5-yl)methanone;
Pyrrolidin-1-yl(1-(5-((1-(3,3,3-trifluoro-2,2-dimethylpropyl)piperidin-4-yl)oxy)pyridin-2-yl)-1H-indol-5-yl)methanone;
Pyrrolidin-1-yl(1-(5-((1-((1-(trifluoromethyl)cyclopropyl)methyl)piperidin-4-yl)oxy)pyridin-2-yl)-1H-indol-5-yl)methanone;
Pyrrolidin-1-yl(1-(5-((1-((1-(trifluoromethyl)cyclobutyl)methyl)piperidin-4-yl)oxy)pyridin-2-yl)-1H-indol-5-yl)methanone;
Pyrrolidin-1-yl(1-(5-((1-isobutylpiperidin-4-yl)oxy)pyridin-2-yl)-1H-indol-5-yl)methanone;
2-Methoxyethyl 4-((6-(5-(pyrrolidine-1-carbonyl)-1H-indol-1-yl)pyridin-3-yl)oxy)piperidine-1-carboxylate;
1-(5-((1-(1-(2-Oxa-6-azaspiro[3.3]heptan-6-yl)ethyl)piperidin-4-yl)oxy)pyridin-2-yl)-N,N-dimethyl-1H-indole-5-carboxamide;
1-(5-((1-(1-(6-Oxa-3-azabicyclo[3.1.1]heptan-3-yl)ethyl)piperidin-4-yl)oxy)pyridin-2-yl)-N,N-dimethyl-1H-indole-5-carboxamide;
1-(5-((1-(2-(Dimethylamino)-2-oxoethyl)piperidin-4-yl)oxy)pyridin-2-yl)-N,N-dimethyl-1H-indole-5-carboxamide;
N,N-Dimethyl-1-(5-((1-(2-morpholinoethyl)piperidin-4-yl)oxy)pyridin-2-yl)-1H-indole-5-carboxamide;
1-(5-((1-(5-Ethylpyridin-2-yl)piperidin-4-yl)oxy)pyridin-2-yl)-N,N-dimethyl-1H-indole-5-carboxamide;
1-(5-((1-(5-Ethylpyridin-2-yl)piperidin-4-yl)oxy)pyridin-2-yl)-N,N-dimethyl-1H-indole-5-carboxamide;
1-(5-((1-(Cyclopropanecarbonyl)piperidin-4-yl)oxy)pyridin-2-yl)-N,N-dimethyl-1H-indole-5-carboxamide;
1-(5-((1-(Cyclobutanecarbonyl)piperidin-4-yl)oxy)pyridin-2-yl)-N,N-dimethyl-1H-indole-5-carboxamide;
1-(5-((1-(Cyclohexanecarbonyl)piperidin-4-yl)oxy)pyridin-2-yl)-N,N-dimethyl-1H-indole-5-carboxamide;
1-(5-((1-(Cyclopentanecarbonyl)piperidin-4-yl)oxy)pyridin-2-yl)-N,N-dimethyl-1H-indole-5-carboxamide;
1-(5-((1-(2-(Dimethylamino)acetyl)piperidin-4-yl)oxy)pyridin-2-yl)-N,N-dimethyl-1H-indole-5-carboxamide;
1-(5-((1-(Furan-2-carbonyl)piperidin-4-yl)oxy)pyridin-2-yl)-N,N-dimethyl-1H-indole-5-carboxamide;
Isobutyl 4-((6-(5-(dimethylcarbamoyl)-1H-indol-1-yl)pyridin-3-yl)oxy)piperidine-1-carboxylate;
2-Methoxyethyl 4-((6-(5-(dimethylcarbamoyl)-1H-indol-1-yl)pyridin-3-yl)oxy)piperidine-1-carboxylate;
2-Fluoroethyl 4-((6-(5-(dimethylcarbamoyl)-1H-indol-1-yl)pyridin-3-yl)oxy)piperidine-1-carboxylate;
Neopentyl 4-((6-(5-(dimethylcarbamoyl)-1H-indol-1-yl)pyridin-3-yl)oxy)piperidine-1-carboxylate;
Cyclopropyl 4-((6-(5-(dimethylcarbamoyl)-1H-indol-1-yl)pyridin-3-yl)oxy)piperidine-1-carboxylate;
Cyclohexyl 4-((6-(5-(dimethylcarbamoyl)-1H-indol-1-yl)pyridin-3-yl)oxy)piperidine-1-carboxylate;
1-(5-((1-(2-Methoxyethyl)piperidin-4-yl)oxy)pyridin-2-yl)-N,N-dimethyl-1H-indole-5-carboxamide;
N,N-Dimethyl-1-(5-((1-propylpiperidin-4-yl)oxy)pyridin-2-yl)-1H-indole-5-carboxamide;
1-(5-((1-Cyclobutylpiperidin-4-yl)oxy)pyridin-2-yl)-N,N-dimethyl-1H-indole-5-carboxamide;
1-(5-((1-Isopropylpiperidin-4-yl)oxy)pyridin-2-yl)-N,N-dimethyl-1H-indole-5-carboxamide;
N,N-Dimethyl-1-(5-((1-(3-oxobutan-2-yl)piperidin-4-yl)oxy)pyridin-2-yl)-1H-indole-5-carboxamide;
1-(5-((1-Cyclopentylpiperidin-4-yl)oxy)pyridin-2-yl)-N,N-dimethyl-1H-indole-5-carboxamide;
N,N-Dimethyl-1-(5-((1-(3,3,3-trifluoro-2-oxopropyl)piperidin-4-yl)oxy)pyridin-2-yl)-1H-indole-5-carboxamide;
1-(5-((1-Cyclohexylpiperidin-4-yl)oxy)pyridin-2-yl)-N,N-dimethyl-1H-indole-5-carboxamide;
N,N-Dimethyl-1-(5-((1-phenethylpiperidin-4-yl)oxy)pyridin-2-yl)-1H-indole-5-carboxamide;
1-(5-((1-(Cyclopropylmethyl)piperidin-4-yl)oxy)pyridin-2-yl)-N,N-dimethyl-1H-indole-5-carboxamide;
1-(5-((1-(4-Chlorobenzyl)piperidin-4-yl)oxy)pyridin-2-yl)-N,N-dimethyl-1H-indole-5-carboxamide;
1-(5-((1-Benzylpiperidin-4-yl)oxy)pyridin-2-yl)-N,N-dimethyl-1H-indole-5-carboxamide;
1-(5-((1-Cyclopropylpiperidin-4-yl)oxy)pyridin-2-yl)-N,N-dimethyl-1H-indole-5-carboxamide;
1-(5-((1-((1S,4R)-Bicyclo[2.2.1]heptan-2-yl)piperidin-4-yl)oxy)pyridin-2-yl)-N,N-dimethyl-1H-indole-5-carboxamide;
N,N-Dimethyl-1-(5-((1-(pentan-3-yl)piperidin-4-yl)oxy)pyridin-2-yl)-1H-indole-5-carboxamide;
1-(5-((1-(1-(2-Oxa-6-azaspiro[3.3]heptan-6-yl)ethyl)piperidin-4-yl)amino)pyridin-2-yl)-N,N-dimethyl-1H-indole-5-carboxamide;
1-(5-((1-(1-(6-Oxa-3-azabicyclo[3.1.1]heptan-3-yl)ethyl)piperidin-4-yl)amino)pyridin-2-yl)-N,N-dimethyl-1H-indole-5-carboxamide;
1-(5-((1-(2-(Dimethylamino)-2-oxoethyl)piperidin-4-yl)amino)pyridin-2-yl)-N,N-dimethyl-1H-indole-5-carboxamide;
N,N-Dimethyl-1-(5-((1-(2-morpholinoethyl)piperidin-4-yl)amino)pyridin-2-yl)-1H-indole-5-carboxamide;
1-(5-((1-(5-Ethylpyridin-2-yl)piperidin-4-yl)amino)pyridin-2-yl)-N,N-dimethyl-1H-indole-5-carboxamide;

1-(5-((1-(5-Ethylpyridin-2-yl)piperidin-4-yl)amino)pyridin-2-yl)-N,N-dimethyl-1H-indole-5-carboxamide;
1-(5-((1-(Cyclopropanecarbonyl)piperidin-4-yl)amino)pyridin-2-yl)-N,N-dimethyl-1H-indole-5-carboxamide;
1-(5-((1-(Cyclobutanecarbonyl)piperidin-4-yl)amino)pyridin-2-yl)-N,N-dimethyl-1H-indole-5-carboxamide;
1-(5-((1-(Cyclohexanecarbonyl)piperidin-4-yl)amino)pyridin-2-yl)-N,N-dimethyl-1H-indole-5-carboxamide;
1-(5-((1-(Cyclopentanecarbonyl)piperidin-4-yl)amino)pyridin-2-yl)-N,N-dimethyl-1H-indole-5-carboxamide;
1-(5-((1-(2-(Dimethylamino)acetyl)piperidin-4-yl)amino)pyridin-2-yl)-N,N-dimethyl-1H-indole-5-carboxamide;
1-(5-((1-(Furan-2-carbonyl)piperidin-4-yl)amino)pyridin-2-yl)-N,N-dimethyl-1H-indole-5-carboxamide;
Isobutyl 4-((6-(5-(dimethylcarbamoyl)-1H-indol-1-yl)pyridin-3-yl)amino)piperidine-1-carbaminolate;
2-Methaminoethyl 4-((6-(5-(dimethylcarbamoyl)-1H-indol-1-yl)pyridin-3-yl)amino)piperidine-1-carbaminolate;
2-Fluoroethyl 4-((6-(5-(dimethylcarbamoyl)-1H-indol-1-yl)pyridin-3-yl)amino)piperidine-1-carbaminolate;
Neopentyl 4-((6-(5-(dimethylcarbamoyl)-1H-indol-1-yl)pyridin-3-yl)amino)piperidine-1-carbaminolate;
Cyclopropyl 4-((6-(5-(dimethylcarbamoyl)-1H-indol-1-yl)pyridin-3-yl)amino)piperidine-1-carbaminolate;
Cyclohexyl 4-((6-(5-(dimethylcarbamoyl)-1H-indol-1-yl)pyridin-3-yl)amino)piperidine-1-carbaminolate;
1-(5-((1-(2-Methaminoethyl)piperidin-4-yl)amino)pyridin-2-yl)-N,N-dimethyl-1H-indole-5-carboxamide;
N,N-Dimethyl-1-(5-((1-propylpiperidin-4-yl)amino)pyridin-2-yl)-1H-indole-5-carboxamide;
1-(5-((1-Cyclobutylpiperidin-4-yl)amino)pyridin-2-yl)-N,N-dimethyl-1H-indole-5-carboxamide;
1-(5-((1-Isopropylpiperidin-4-yl)amino)pyridin-2-yl)-N,N-dimethyl-1H-indole-5-carboxamide;
N,N-Dimethyl-1-(5-((1-(3-oxobutan-2-yl)piperidin-4-yl)amino)pyridin-2-yl)-1H-indole-5-carboxamide;
1-(5-((1-Cyclopentylpiperidin-4-yl)amino)pyridin-2-yl)-N,N-dimethyl-1H-indole-5-carboxamide;
N,N-Dimethyl-1-(5-((1-(3,3,3-trifluoro-2-oxopropyl)piperidin-4-yl)amino)pyridin-2-yl)-1H-indole-5-carboxamide;
1-(5-((1-Cyclohexylpiperidin-4-yl)amino)pyridin-2-yl)-N,N-dimethyl-1H-indole-5-carboxamide;
N,N-Dimethyl-1-(5-((1-phenethylpiperidin-4-yl)amino)pyridin-2-yl)-1H-indole-5-carboxamide;
1-(5-((1-(Cyclopropylmethyl)piperidin-4-yl)amino)pyridin-2-yl)-N,N-dimethyl-1H-indole-5-carboxamide;
1-(5-((1-(4-Chlorobenzyl)piperidin-4-yl)amino)pyridin-2-yl)-N,N-dimethyl-1H-indole-5-carboxamide;
1-(5-((1-Benzylpiperidin-4-yl)amino)pyridin-2-yl)-N,N-dimethyl-1H-indole-5-carboxamide;
1-(5-((1-Cyclopropylpiperidin-4-yl)amino)pyridin-2-yl)-N,N-dimethyl-1H-indole-5-carboxamide;
1-(5-((1S,4R)-Bicyclo[2.2.1]heptan-2-yl)piperidin-4-yl)amino)pyridin-2-yl)-N,N-dimethyl-1H-indole-5-carboxamide and
N,N-Dimethyl-1-(5-((1-(pentan-3-yl)piperidin-4-yl)amino)pyridin-2-yl)-1H-indole-5-carboxamide
or pharmaceutically acceptable salt thereof.

11. A pharmaceutical composition comprising one or more compounds of Formula (II) according to claim 1, and one or more pharmaceutically acceptable excipients; wherein the pharmaceutically acceptable excipient is a carrier or a diluent.

* * * * *